(12) United States Patent
Cumming et al.

(10) Patent No.: US 10,550,089 B2
(45) Date of Patent: Feb. 4, 2020

(54) INHIBITORS OF PROTEASE-ACTIVATED RECEPTOR-2

(71) Applicant: Heptares Therapeutics Limited, Cambridge (GB)

(72) Inventors: John Graham Cumming, Basel (CH); Frank Xinhe Wu, Waltham, MA (US); Karl Henrik Edman, Mölndal (SE); Hongming Chen, Mölndal (SE); Dean Gordon Brown, Waltham, MA (US); Roland Werner Burli, Cambridge (GB); Shawn Donald Johnstone, Saint Laurent (CA); Giles Albert Brown, Cambridge (GB); Benjamin Gerald Tehan, Cambridge (GB); Barry John Teobald, Cambridge (GB); Miles Stuart Congreve, Cambridge (GB)

(73) Assignee: Heptares Therapeutics Limited, Cambridge (GB)

( * ) Notice: Subject to any disclaimer, the term of this patent is extended or adjusted under 35 U.S.C. 154(b) by 0 days.

(21) Appl. No.: 16/300,641

(22) PCT Filed: May 11, 2017

(86) PCT No.: PCT/EP2017/061409
§ 371 (c)(1),
(2) Date: Nov. 12, 2018

(87) PCT Pub. No.: WO2017/194716
PCT Pub. Date: Nov. 16, 2017

(65) Prior Publication Data
US 2019/0144394 A1 May 16, 2019

Related U.S. Application Data

(60) Provisional application No. 62/335,496, filed on May 12, 2016.

(51) Int. Cl.
*C07D 233/64* (2006.01)
*C07D 403/06* (2006.01)
(Continued)

(52) U.S. Cl.
CPC ............ *C07D 233/64* (2013.01); *A61P 17/00* (2018.01); *A61P 29/00* (2018.01); *C07D 249/08* (2013.01);
(Continued)

(58) Field of Classification Search
CPC .. C07D 233/64; C07D 249/08; C07D 403/06; C07D 403/10; C07D 405/06;
(Continued)

(56) References Cited

U.S. PATENT DOCUMENTS

| 2007/0167506 A1 | 7/2007 | Chubb et al. |
| 2007/0197621 A1* | 8/2007 | Galley ............... A61K 31/4164 514/400 |
| 2010/0041712 A1* | 2/2010 | Chubb .................. A01N 43/50 514/345 |

FOREIGN PATENT DOCUMENTS

WO      1999/37636 A1     7/1999

OTHER PUBLICATIONS

Lee; Yonsei Med J. 2010, 51, 808-822. (Year: 2010).*
(Continued)

*Primary Examiner* — Daniel R Carcanague
(74) *Attorney, Agent, or Firm* — McCarter & English, LLP; Steven G. Davis; Mei Bai

(57) ABSTRACT

The present application relates to certain substituted imidazole and triazole compounds, pharmaceutical compositions containing them, and methods of using them, including methods for treating pain, musculoskeletal inflammation, neuroinflammatory disorders, airway inflammation, itch,
(Continued)

dermatitis, colitis and related conditions. The compounds are of Formula (I) where X is N or CH, Z and Y are N or C (but both not N) and $R^1$-$R^3$ are as defined herein.

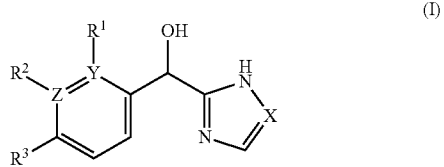

(I)

7 Claims, 3 Drawing Sheets

Specification includes a Sequence Listing.

(51) Int. Cl.
| | |
|---|---|
| C07D 403/10 | (2006.01) |
| C07D 405/06 | (2006.01) |
| C07D 409/06 | (2006.01) |
| C07D 413/10 | (2006.01) |
| C07D 417/10 | (2006.01) |
| C07D 249/08 | (2006.01) |
| C07D 471/04 | (2006.01) |
| A61P 17/00 | (2006.01) |
| A61P 29/00 | (2006.01) |
| A61K 31/4164 | (2006.01) |

(52) U.S. Cl.
CPC ......... *C07D 403/06* (2013.01); *C07D 403/10* (2013.01); *C07D 405/06* (2013.01); *C07D 409/06* (2013.01); *C07D 413/10* (2013.01); *C07D 417/10* (2013.01); *C07D 471/04* (2013.01); *A61K 31/4164* (2013.01)

(58) Field of Classification Search
CPC .. C07D 409/06; C07D 413/10; C07D 417/10; C07D 471/04; A61P 17/00; A61P 29/00
USPC ........................................................ 546/121
See application file for complete search history.

(56) References Cited

OTHER PUBLICATIONS

Lohman; Journal of Pharmacology and Experimental Therapeutics 2012, 340, 256-265. (Year: 2012).*
Rothmeier; Semin Immunopathol 2012, 34, 133-149. (Year: 2012).*
Steinhoff; The Journal of Neuroscience 2003, 23, 6176-6180. (Year: 2003).*
Yau; Expert Opinion on Therapeutic Patents 2016, 264, 471-483. (Year: 2016).*
Cheng et al., Structural insight into allosteric modulation of protease-activated receptor 2. Nature. May 4, 2017;545 (7652):112-5. with supplemental materials.
STN RN 1480040-69-4, 1H-1,2,4-Triazole-5-methanol, .alpha.[2-(trifluoromethyl)phenyl]—1 page. Nov. 24, 2013.
STN RN 1480169-52-5, 1H-1,2,4-Triazole-5-methanol, .alpha.[2-(trifluoromethyl)phenyl]—1 page. Nov. 25, 2013.
STN RN 1487125-46-1, 1H-1,2,4-Triazole-5-methanol, .alpha.-(4-fluoro-2-methylphenyl)—1 page, Dec. 5, 2013.
STN RN 1490207-25-4, 5-Isoquinolinemethanol, .alpha.-1H-1,2,4-triazol-5-yl—1 page, Dec. 8, 2013.
STN RN 1490912-03-2, 1H-1,2,4-Triazole-5-methanol, .alpha.-1-naphthalenul—1 page, Dec. 9, 2013.
STN RN 1499321-77-5, 1H-Imidazole-2-methanol, .alpha.-(2-methylphenyl)—1 page, Dec. 20, 2013.
STN RN 1500493-84-4, 5-Quinolinemethanol, .alpha.-1H-1,2,4-triazol-5-yl—1 page, Dec. 22, 2013.
STN RN 1503979-43-8, 5-Isoquinolinemethanol, .alpha.-1H-imidazol-2-yl—1 page, Dec. 26, 2013.
STN RN 1504000-29-6, 1H-Imidazole-2-methanol, .alpha.-1-naphthalenyl—1 page, Dec. 26, 2013.
STN RN 1505031-95-7, 8-Quinolinemethanol, .alpha.-1H-1,2,4-triazol-5-yl—1 page, Dec. 27, 2013.
STN RN 1511219-94-5, 1H-Imidazole-2-methanol, .alpha.[2-(trifluoremethyl)phenyl)—1 page, Jan. 5, 2014.
STN RN 1520772-28-4, 8-Quinolinemethanol, .alpha.-1H-imidazol-2-yl—1 page, Jan. 15, 2014.
STN RN 1523381-28-3, 1H-Imidazole-2-methanol, .alpha.-benzo[b]thien-7-yl—1 page, Jan. 17, 2014.
STN RN 1528571-14-3, 1H-1,2,4-Trizaole-5-methanol, .alpha.-benzo[b]thien-7-yl—1 page, Jan. 23, 2014.
STN RN 1538774-85-4, 5-Quinolinemethanol, .alpha.-1H-imidazol-2-yl—1 page, Feb. 7, 2014.
STN RN 1540925-09-4, 1H-Imidazole-2-methanol, .alpha.-(4-fluoro-2-methylphenyl)—1 page, Feb. 10, 2014.
STN RN 1592559-93-7, 1H-Imidazole-2-methanol, .alpha.-(2,3-dihydro-7-benzofuranyl)—1 page, Apr. 29, 2014.
STN RN 1601133-05-4, 1H-1,2,4-Triazole-5-methanol, .alpha.-(2,3-dihydro-7-benzofuranyl)—1 page, May 9, 2014.
STN RN 1711960-59-6, 1H-1,2,4-Triazole-5-methanol, .alpha.-(2-cyclobutylphenyl)—1 page, May 25, 2015.
STN RN 1712137-85-3, 1H-Imidazole-2-methanol, .alpha.-(2-cyclobutylphenyl)—1 page, May 25, 2015.
STN RN 1773441-60-3, 1H-Imidazole-2-methanol, .alpha.-(3-4-dihydro-2H-1-benzopyran-8-yl)—1 page, Jun. 4, 2015.
STN RN 1777564-84-7, 1H-1,2,4-Triazole-5-methanol, .alpha.-(3,4-dihydro-2F1-1-benzopyran-8-yl)—1 page, Jun. 10, 2015.
STN RN 1859845-51-4, 1H-1,2,4-Triazole-5-methanol, .alpha.-(2-propylphenyl)—1 page, Feb. 4, 2016.
STN RN 1866896-71-0, 1H-Imidazole-2-methanol, .alpha.-(2-propylphenyl)—1 page, Feb. 15, 2016.
STN RN 1873217-92-5, 1H-Imidazole-2-methanol, .alpha.-[2-(1-methylethyl)phenyl]—1 page, Feb. 24, 2016.
STN RN 1874916-48-9, 1H-Imidazole-2-methanol, .alpha.-(2-ethylphenyl)—1 page, Feb. 26, 2016.
STN RN 1879447-51-4, 1H-1,2,4-Triazole-5-methanol, .alpha.-(2-ethylphenyl)—1 page, Mar. 4, 2016.
STN RN 1880610-70-7, 1H-1,2,4-Triazole-5-methanol, .alpha.-[2-(1-methylethyl)phenyl]—1 page, Mar. 7, 2016.
STN RN 1971314-68-7, 8-Isoquinolinemethanol, .alpha.-1H-1,2,4-triazol-5-yl—1 page, Aug. 11, 2016.
STN RN 1989188-82-0, 8-Isoquinolinemethanol, .alpha.-1H-imidazol-2-yl—1 page, Sep. 8, 2016.
STN RN 1997059-82-1, 1,2-Benzisothiazole-7-methanol, .alpha.-1H-1,2,4-triazol-5-yl—1 page, Sep. 21, 2016.
STN RN 1999788-81-6, 1,2-Benzisothiazole-7-methanol, .alpha.-1H-imidazol-2-yl—1 page, Sep. 26, 2016.
Yau et al., Toward drugs for protease-activated receptor 2 (PAR2). J Med Chem. Oct. 10, 2013;56(19):7477-97.
International Search Report and Written Opinion for Application No. PCT/EP2017/061409, dated Aug. 2, 2017. 22 pages.

* cited by examiner

SEQUENCE LISTING

<160> NUMBER OF SEQ ID NOS: 4

<210> SEQ ID NO 1
<211> LENGTH: 397
<212> TYPE: PRT
<213> ORGANISM: Homo sapiens

<400> SEQUENCE: 1

```
Met Arg Ser Pro Ser Ala Ala Trp Leu Leu Gly Ala Ala Ile Leu Leu
1               5                   10                  15

Ala Ala Ser Leu Ser Cys Ser Gly Thr Ile Gln Gly Thr Asn Arg Ser
            20                  25                  30

Ser Lys Gly Arg Ser Leu Ile Gly Lys Val Asp Gly Thr Ser His Val
        35                  40                  45

Thr Gly Lys Gly Val Thr Val Glu Thr Val Phe Ser Val Asp Glu Phe
    50                  55                  60

Ser Ala Ser Val Leu Thr Gly Lys Leu Thr Thr Val Phe Leu Pro Ile
65                  70                  75                  80

Val Tyr Thr Ile Val Phe Val Gly Leu Pro Ser Asn Gly Met Ala
                85                  90                  95

Leu Trp Val Phe Leu Phe Arg Thr Lys Lys Lys His Pro Ala Val Ile
                100                 105                 110

Tyr Met Ala Asn Leu Ala Leu Ala Asp Leu Leu Ser Val Ile Trp Phe
            115                 120                 125

Pro Leu Lys Ile Ala Tyr His Ile His Gly Asn Asn Trp Ile Tyr Gly
        130                 135                 140

Glu Ala Leu Cys Asn Val Leu Ile Gly Phe Phe Tyr Gly Asn Met Tyr
145                 150                 155                 160

Cys Ser Ile Leu Phe Met Thr Cys Leu Ser Val Gln Arg Tyr Trp Val
                165                 170                 175

Ile Val Asn Pro Met Gly His Ser Arg Lys Lys Ala Asn Ile Ala Ile
                180                 185                 190

Gly Ile Ser Leu Ala Ile Trp Leu Leu Ile Leu Leu Val Thr Ile Pro
            195                 200                 205

Leu Tyr Val Val Lys Gln Thr Ile Phe Ile Pro Ala Leu Asn Ile Thr
        210                 215                 220

Thr Cys His Asp Val Leu Pro Glu Gln Leu Leu Val Gly Asp Met Phe
225                 230                 235                 240

Asn Tyr Phe Leu Ser Leu Ala Ile Gly Val Phe Leu Phe Pro Ala Phe
                245                 250                 255

Leu Thr Ala Ser Ala Tyr Val Leu Met Ile Arg Met Leu Arg Ser Ser
            260                 265                 270

Ala Met Asp Glu Asn Ser Glu Lys Lys Arg Lys Arg Ala Ile Lys Leu
        275                 280                 285

Ile Val Thr Val Leu Ala Met Tyr Leu Ile Cys Phe Thr Pro Ser Asn
    290                 295                 300

Leu Leu Leu Val Val His Tyr Phe Leu Ile Lys Ser Gln Gly Gln Ser
305                 310                 315                 320

His Val Tyr Ala Leu Tyr Ile Val Ala Leu Cys Leu Ser Thr Leu Asn
                325                 330                 335

Ser Cys Ile Asp Pro Phe Val Tyr Tyr Phe Val Ser His Asp Phe Arg
```

```
                340             345             350

Asp His Ala Lys Asn Ala Leu Leu Cys Arg Ser Val Arg Thr Val Lys
        355                 360                 365

Gln Met Gln Val Ser Leu Thr Ser Lys Lys His Ser Arg Lys Ser Ser
    370                 375                 380

Ser Tyr Ser Ser Ser Ser Thr Thr Val Lys Thr Ser Tyr
385                 390                 395

<210> SEQ ID NO 2
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ser Leu Ile Gly Lys Val
1               5

<210> SEQ ID NO 3
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Ser Leu Ile Gly Leu Arg
1               5

<210> SEQ ID NO 4
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ser Leu Ile Gly Arg Leu
1               5
```

INHIBITORS OF PROTEASE-ACTIVATED RECEPTOR-2

RELATED APPLICATION INFORMATION

This application is a 371 U.S. National Phase of International Application No. PCT/EP2017/061409, filed May 11, 2017, which claims the benefit of U.S. Provisional Application No. 62/335,496, filed May 12, 2016. The entire contents of these applications are incorporated herein by reference in their entirety.

FIELD

The present application relates to the treatment or prevention of conditions or disorders related to pain, musculoskeletal inflammation such as osteoarthritis, neuroinflammatory disorders, airway inflammation, itch, dermatitis, colitis and related conditions with substituted imidazoles compounds, compositions containing them and methods of using them.

BACKGROUND

The actions of Protease Activated Receptor-2 (PAR2) are thought to be involved in pain, musculoskeletal inflammation, neuroinflammatory disorders, airway inflammation, itch, dermatitis, colitis and related conditions. The protease activated receptors are composed of four family members (PAR1, PAR2, PAR3 and PAR4), which are G-protein coupled receptors activated by a proteolytic cleavage of the N-terminal region of the receptor (Ramachandran, Hollenberg et al, *Nature Reviews Drug Discovery*, 2012, 11 69-86). Upon proteolytic cleavage, the receptor then is activated for second messenger activation and cellular responses. Many enzymes are known to cleave the N-terminal region of PAR receptors to initiate this process such as thrombin, trypsin, mast cell tryptase, kallikreins and related enzymes in the inflammatory and coagulation cascades. Other ligands are known to activate the receptor, such as short peptides like SLIGKV-NH2 (SEQ ID NO.: 2), SLIGLR-NH2 (SEQ ID NO.: 3) or small molecule ligands such as GB-110 (Fairlie et al, *Journal of Medicinal Chemistry*, 2013, 56, 7477-7497).

PAR2 expression has been shown to be increased in synovial lining, chondrocytes, and tissues in human rheumatoid arthritis and animal models of arthritis (Amiable, N. et al, *Bone*, 44, 1143-1150). PAR2 also potentiates signaling via channels such as TRPV1 (Dai, et al *Journal of Innate Immunology*, 2010, 2, 495-504), a ligand-gated ion channel involved in inflammatory pain. PAR2 signaling is also known to sensitize TRPV1 in vivo, resulting in thermal hyperalgesia.

The inhibition of PAR2 receptors is known to be responsible for inflammatory signaling pathways. In mice lacking the PAR2 receptor, there is a delayed onset of inflammation (Linder et al, *Journal of Immunology* 2000, 165, 6504-6510). Other rodent PAR2 knockout studies have demonstrated that PAR2 plays an important role in pathophysiology of many disease conditions such as pain, musculoskeletal inflammation such as osteoarthritis, neuroinflammatory disorders, airway inflammation, itch, dermatitis, colitis and related conditions (Fairlie et al, *Journal of Medicinal Chemistry*, 2013, 56, 7477-749). PAR2 receptor antagonists such as GB88 have also been shown to block inflammatory responses in vivo such as collagen-induced arthritis model in rats (Fairlie et al, *FASEB Journal*, 2012, 26, 2877-2887).

PAR2 antagonists are thus thought likely to provide benefit to numerous people and to have a potential to alleviate pain and inflammation related conditions.

SUMMARY OF THE APPLICATION

This application provides a compound of formula (I),

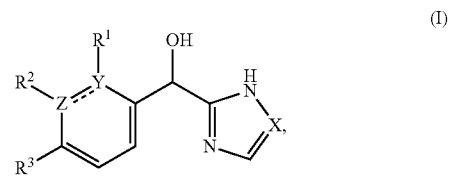

or a pharmaceutically acceptable salt thereof, wherein:
$R^3$ is —H or halogen (such as —F);
X is N or CH;
Y is C or N; and
Z is C or N, wherein Y and Z are not both N, and
(1) when both Z and Y are C, the bond "-------" is a double bond, and
$R^1$ is selected from alkyl (such as $C_{1-12}$-alkyl-, $C_{2-12}$-alkyl-, or $C_{2-6}$-alkyl-, e.g., ethyl or propyl); alkenyl (such as $C_{2-12}$-alkenyl- or $C_{2-6}$-alkenyl-, e.g.,

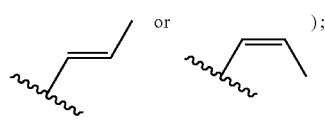

cycloalkyl (such as $C_{3-10}$-cycloalkyl- or $C_{3-6}$-cycloalkyl-, e.g., cyclobutyl, cyclopentyl, or

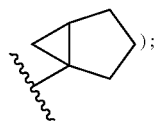 [SMILES: *C12CCCC1C2]

cycloalkenyl (such as $C_{3-10}$-cycloalkenyl- or $C_{3-6}$-cycloalkenyl-, e.g.,

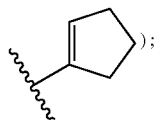 [SMILES: *C1=CCCC1]

aryl (such as $C_{6-10}$-aryl-); heterocyclyl (such as 3- to 10-membered heterocyclyl- or 3- to 6-membered heterocyclyl, e.g.,

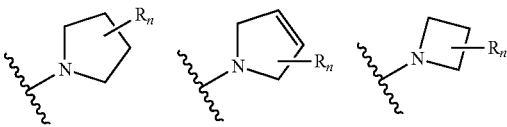

-continued

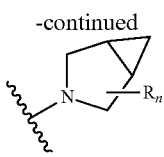

wherein n is selected from 0-3); and heteroaryl (such as 5- to 10-membered heteroaryl-, e.g.,

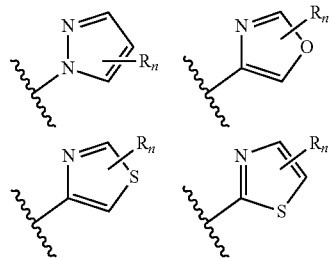

wherein n is selected from 0-3); wherein $R^1$ is substituted with 0-3 R, wherein each occurrence of R is independently selected from alkyl, such as $C_{1-4}$alkyl (e.g., methyl, ethyl, or —$CF_3$); cycloalkyl; halo, such as —F, —Cl, or —Br (e.g., —Cl); —OH; alkoxy, such as methoxy; —CN; —$NR^aR^b$; —$N(R^a)C(O)$ alkyl; —$N(R^a)CO_2$alkyl; —$N(R^a)SO_2$alkyl; —C(O)alkyl; —$CO_2H$; —$CO_2$alkyl; —$CONR^aR^b$; —$SO_2$alkyl; and —$SO_2NR^aR^b$; wherein $R^a$ and $R^b$ are independently for each occurrence H or alkyl;

$R^2$ is —H or -halogen (such as —F or —Cl); or $R^1$ and $R^2$ may be taken together with the atoms to which they are bound to form a 3- to 10-membered aromatic or non-aromatic monocyclic ring having 0-3 heteroatoms or heteroatom groups independently selected from N, NH, O, S, SO, and $SO_2$, wherein said ring is substituted with 0-3 R, and wherein said ring is optionally fused to a $C_{6-10}$aryl, 5- to 10-membered heteroaryl, $C_{3-10}$cycloalkyl, or a 3- to 10-membered heterocyclyl, wherein said $C_{6-10}$aryl, 5- to 10-membered heteroaryl, $C_{3-10}$cycloalkyl, or a 3- to 10-membered heterocyclyl is substituted with 0-3 R, wherein each occurrence of R is independently selected from alkyl, such as $C_{1-4}$alkyl (e.g., methyl, ethyl, propyl, isopropyl, —$CH_2CF_3$ or —$CF_3$); cycloalkyl (e.g., cyclopropyl or

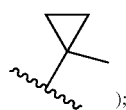 [SMILES: *C1(C)CC1]

halo, such as —F, —Cl, or —Br (e.g., —Cl); —OH; alkoxy, such as methoxy; —CN; —$NR^aR^b$; —$N(R^a)C(O)$ alkyl; —$N(R^a)CO_2$alkyl; —$N(R^a)SO_2$alkyl; —C(O)alkyl; —$CO_2H$; —$CO_2$alkyl; —$CONR^aR^b$; —$SO_2$alkyl; and —$SO_2NR^aR^b$; wherein $R^a$ and $R^b$ are independently for each occurrence H or alkyl; or (2) when one of Z and Y is N and the other is C, the bond "-----" is a single bond, and $R^1$ and $R^2$ are taken together with the atoms to which they are bound to form a 3- to 10-membered aromatic or non-aromatic monocyclic ring having 0-3 heteroatoms or heteroatom groups independently selected from N, NH, O, S, SO, and $SO_2$, wherein said ring is substituted with 0-3 R, and wherein said ring is optionally fused to a $C_{6-10}$aryl, 5- to 10-membered heteroaryl, $C_{3-10}$cycloalkyl, or a 3- to 10-membered heterocyclyl, wherein said $C_{6-10}$aryl, 5- to 10-membered heteroaryl, $C_{3-10}$cycloalkyl, or a 3- to 10-membered heterocyclyl is substituted with 0-3 R, wherein each occurrence of R is independently selected from alkyl, such as $C_{1-4}$alkyl (e.g., methyl, ethyl, propyl, isopropyl, —$CH_2CF_3$ or —$CF_3$); cycloalkyl (e.g., cyclopropyl or

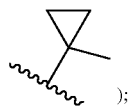

halo, such as —F, —Cl, or —Br (e.g., —Cl); —OH; alkoxy, such as methoxy; —CN; —$NR^aR^b$; —$N(R^a)C(O)$ alkyl; —$N(R^a)CO_2$alkyl; —$N(R^a)SO_2$alkyl; —C(O)alkyl; —$CO_2H$; —$CO_2$alkyl; —$CONR^aR^b$; —$SO_2$alkyl; and —$SO_2NR^aR^b$;

wherein $R^a$ and $R^b$ are independently for each occurrence H or alkyl;

provided that when $R^1$ is methyl and X is CH, $R^2$ and $R^3$ are not both —H. In some embodiments of the forgoing, when $R^1$ is methyl and X is CH, $R^3$ is —F.

In certain embodiments, $R^3$ is —H. In certain embodiments, $R^3$ is —F.

In certain embodiments, X is CH. In certain embodiments, X is N.

In certain embodiments, both Z and Y are C and the bond "-----" is a double bond. In certain embodiments, both Z and Y are C, the bond "-----" is a double bond and the compound can be represented by formula (I-A):

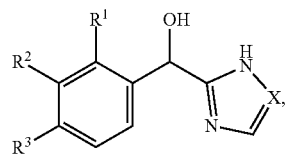

(I-A)

or a pharmaceutically acceptable salt thereof, wherein:
X is N or CH;
$R^1$ is selected from alkyl (such as $C_{1-12}$-alkyl-, $C_{2-12}$-alkyl-, or $C_{2-6}$-alkyl-, e.g., ethyl or propyl); alkenyl (such as $C_{2-12}$-alkenyl-, or $C_{2-6}$-alkenyl-, e.g.,

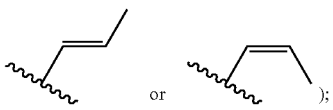

cycloalkyl (such as $C_{3-10}$-cycloalkyl- or $C_{3-6}$-cycloalkyl-, e.g., cyclobutyl, cyclopentyl, or

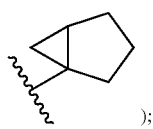 [SMILES: *C12CCCC1C2]

cycloalkenyl (such as $C_{3-10}$-cycloalkenyl- or $C_{3-6}$-cycloalkenyl-, e.g.,

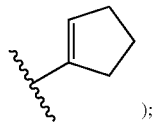 [SMILES: *C1=CCCC1]

aryl (such as $C_{6-10}$-aryl-); heterocyclyl (such as 3- to 10-membered heterocyclyl- or 3- to 6-membered heterocyclyl, e.g.,

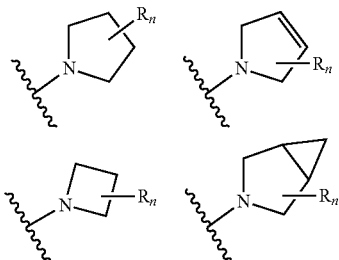

wherein n is selected from 0-3); and heteroaryl (such as 5- to 10-membered heteroaryl-, e.g.,

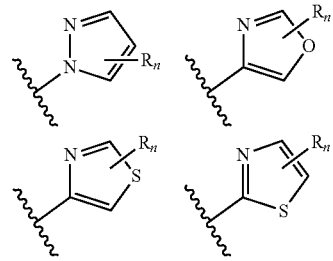

wherein n is selected from 0-3); wherein $R^1$ is substituted with 0-3 R, wherein each occurrence of R is independently selected from alkyl, such as $C_{1-4}$alkyl (e.g., methyl, ethyl, or —$CF_3$); cycloalkyl; halo, such as —F, —Cl, or —Br (e.g., —Cl); —OH; alkoxy, such as methoxy; —CN; —$NR^aR^b$; —$N(R^a)C(O)$ alkyl; —$N(R^a)CO_2$alkyl; —$N(R^a)SO_2$alkyl; —C(O)alkyl; —$CO_2H$; —$CO_2$alkyl; —$CONR^aR^b$; —$SO_2$alkyl; and —$SO_2NR^aR^b$; wherein $R^a$ and $R^b$ are independently for each occurrence H or alkyl;
$R^2$ is —H or -halogen (such as —F or —Cl); or
$R^1$ and $R^2$ may be taken together with the atoms to which they are bound to form a 3- to 10-membered aromatic or non-aromatic monocyclic ring having 0-3 heteroatoms or heteroatom groups independently selected from N, NH, O, S, SO, and $SO_2$, wherein said ring is substituted with 0-3 R, and wherein said ring is optionally fused to a $C_{6-10}$aryl, 5- to 10-membered heteroaryl, $C_{3-10}$cycloalkyl, or a 3- to 10-membered heterocyclyl, wherein said $C_{6-10}$aryl, 5- to 10-membered heteroaryl, $C_{3-10}$cycloalkyl, or a 3- to 10-membered heterocyclyl is substituted with 0-3 R, wherein each occurrence of R is independently selected from alkyl, such as $C_{1-4}$alkyl (e.g., methyl, ethyl, propyl, isopropyl, —$CH_2CF_3$ or —$CF_3$); cycloalkyl (e.g., cyclopropyl or

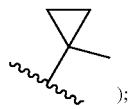 [SMILES: *C1(C)CC1]

halo, such as —F, —Cl, or —Br (e.g., —Cl); —OH; alkoxy, such as methoxy; —CN; —$NR^aR^b$; —$N(R^a)C(O)$ alkyl; —$N(R^a)CO_2$alkyl; —$N(R^a)SO_2$alkyl; —C(O)alkyl; —$CO_2H$; —$CO_2$alkyl; —$CONR^aR^b$; —$SO_2$alkyl; and —$SO_2NR^aR^b$; wherein $R^a$ and $R^b$ are independently for each occurrence H or alkyl; and
$R^3$ is —H or halogen (such as —F);
provided that when $R^1$ is methyl and X is CH, $R^2$ and $R^3$ are not both —H. In some embodiments of the forgoing, when $R^1$ is methyl and X is CH, $R^3$ is —F.

In certain embodiments wherein one of Z and Y is N and the other is C, the compound can be represented by formula (I-B):

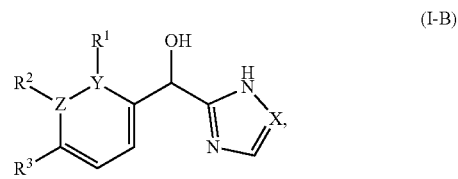

(I-B)

or a pharmaceutically acceptable salt thereof, wherein:
X is N or CH;
$R^1$ and $R^2$ are taken together with the atoms to which they are bound to form a 3- to 10-membered aromatic or non-aromatic monocyclic ring having 0-3 heteroatoms or heteroatom groups independently selected from N, NH, O, S, SO, and $SO_2$, wherein said ring is substituted with 0-3 R, and wherein said ring is optionally fused to a $C_{6-10}$aryl, 5- to 10-membered heteroaryl, $C_{3-10}$cycloalkyl, or a 3- to 10-membered heterocyclyl, wherein said $C_{6-10}$aryl, 5- to 10-membered heteroaryl, $C_{3-10}$cycloalkyl, or a 3- to 10-membered heterocyclyl is substituted with 0-3 R, wherein each occurrence of R is independently selected from alkyl, such as $C_{1-4}$alkyl (e.g., methyl, ethyl, propyl, isopropyl, —$CH_2CF_3$ or —$CF_3$); cycloalkyl (e.g., cyclopropyl or

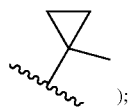 [SMILES: *C1(C)CC1]

halo, such as —F, —Cl, or —Br (e.g., —Cl); —OH; alkoxy, such as methoxy; —CN; —$NR^aR^b$; —$N(R^a)C(O)$ alkyl; —$N(R^a)CO_2$alkyl; —$N(R^a)SO_2$alkyl; —C(O)alkyl; —$CO_2H$; —$CO_2$alkyl; —$CONR^aR^b$; —$SO_2$alkyl; and —$SO_2NR^aR^b$; wherein $R^a$ and $R^b$ are independently for each occurrence H or alkyl; and
$R^3$ is —H or halogen (such as —F).

In certain embodiments, Y is C and Z is N and the bond "------" is a single bond. In certain embodiments, Y is N and Z is C and the bond "------" is a single bond.

In another aspect, the present application provides a compound that binds to an allosteric site of a PAR2 polypeptide comprising an amino acid sequence set forth in SEQ ID NO.: 1, wherein the compound interacts with one or more amino acid residues selected from the group consisting of Asp 228, Lys 131, His 135, and Tyr 82 of SEQ ID NO.: 1. In some embodiments, the compound binds to an allosteric site of a PAR2 polypeptide comprising an amino acid sequence set forth in SEQ ID NO.: 1, wherein the compound interacts with amino acid residues Asp 228, Lys 131, and His 135 of SEQ ID NO.: 1. In some embodiments, the compound binds to an allosteric site of a PAR2 polypeptide comprising an amino acid sequence set forth in SEQ ID NO.: 1, wherein the compound interacts with amino acid residues Asp 228, Lys 131, His 135, and Tyr 82 of SEQ ID NO.: 1. In some embodiments, such a compound is an antagonist of PAR2. In some embodiments, such a compound is a small molecule (e.g., a small molecule antagonist). In certain embodiments of the forgoing, the compound has a structure of formula (I), (I-A), or (I-B), or a pharmaceutically acceptable salt thereof.

In another aspect, the present application provides a compound that binds to an allosteric site of PAR2 polypeptide comprising an amino acid sequence set forth in SEQ ID NO.: 1, wherein said compound has a target dissociative half life ($t_{1/2}$) of greater than 10 minutes. In some embodiments, the compound binds to an allosteric site of PAR2 polypeptide comprising an amino acid sequence set forth in SEQ ID NO.: 1, wherein said compound has a target dissociative half life ($t_{1/2}$) selected from over 3000 minutes, 10 to 3000 minutes, 10 to 2000 minutes, 10 to 1000 minutes, 10 to 900 minutes, 10 to 800 minutes, 10 to 700 minutes, 10 to 600 minutes, 10 to 500 minutes, 10 to 400 minutes, 10 to 300 minutes, 10 to 200 minutes, 10 to 100 minutes, 10 to 50 minutes, 10 to 40 minutes, 10 to 30 minutes, and 10 to 20 minutes. In some embodiments, such a compound has a target dissociative half life of 10 to 200 minutes. In some embodiments of the forgoing, the compound binds to an allosteric site of a PAR2 polypeptide comprising an amino acid sequence set forth in SEQ ID NO.: 1, wherein the compound interacts with one or more amino acid residues selected from the group consisting of Asp 228, Lys 131, His 135, and Tyr 82 of SEQ ID NO.: 1. In some embodiments, the compound interacts with amino acid residues Asp 228, Lys 131, and His 135 of SEQ ID NO.: 1. In some embodiments, the compound interacts with amino acid residues Asp 228, Lys 131, His 135, and Tyr 82 of SEQ ID NO.: 1. In certain embodiments, the dissociative half life is determined in either a FLPR dissociation assay, surface plasmon resonance assay or radiochemical binding assay. In some embodiments, such a compound is an antagonist of PAR2. In some embodiments, such a compound is a small molecule (e.g., a small molecule antagonist). In some embodiments of the forgoing, the compound has a structure of formula (I), (I-A), or (I-B), or a pharmaceutically acceptable salt thereof.

In certain embodiments, this application provides a pharmaceutical composition, comprising at least one compound described herein, or a pharmaceutically acceptable salt thereof. Pharmaceutical compositions as described herein may further comprise a pharmaceutically acceptable excipient. In certain embodiments, this application also provides a compound described herein or a pharmaceutically acceptable salt thereof, or a composition comprising of any of the foregoing for use as a medicament.

In another aspect, this application provides methods of treating a disease or disorder mediated by PAR2 activity, such as those described herein, comprising administering to a subject in need of such treatment, such as a patient, an effective amount of at least one compound described herein or a pharmaceutically acceptable salt thereof in a dose, at a frequency, and for a duration to provide a beneficial effect to the subject.

In certain embodiments, this application provides the use of a compound described herein, or a pharmaceutically acceptable salt thereof, or a composition comprising of any of the foregoing in the preparation of a medicament for the treatment of diseases or disorders regulated by PAR2 activity, and the use of such compounds and salts for treatment of such diseases and disorders.

In certain embodiments, this application provides a method of treating a disease or disorder in a subject, such as a patient, comprising modulating PAR2, wherein the modulation of PAR2 comprises administering to the subject at least one compound described herein, or a pharmaceutically acceptable salt thereof, or a composition comprising of any of the foregoing, in a dose, at a frequency, and for a duration to provide a beneficial effect to the subject patient. In certain such embodiments, the disease or disorder is selected from the group consisting of pain, musculoskeletal inflammation (such as osteoarthritis), neuroinflammatory disorders, airway inflammation, itch, dermatitis, or colitis. In certain embodiments, the disease or disorder is osteoarthritis.

In certain embodiments, this application provides a method of modulating the activity of PAR2, comprising contacting a cell comprising the PAR2 with an effective amount of at least one compound described herein, or a pharmaceutically acceptable salt thereof, or a composition comprising any one of the foregoing.

In certain embodiments, this application describes a method of modulating the activity of a PAR2 receptor, comprising contacting a cell comprising the PAR2 receptor with an effective amount of at least one compound described herein or a pharmaceutically acceptable salt thereof, and/or with at least one compound or pharmaceutical composition as described herein. In certain embodiments of the foregoing, the contacting is in vitro, ex vivo, or in vivo.

Additional embodiments, features, and advantages of the application will be apparent from the following detailed description and through practice of the embodiments described in this application.

DETAILED DESCRIPTION OF THE FIGURES

DETAILED DESCRIPTION

Figure 1:
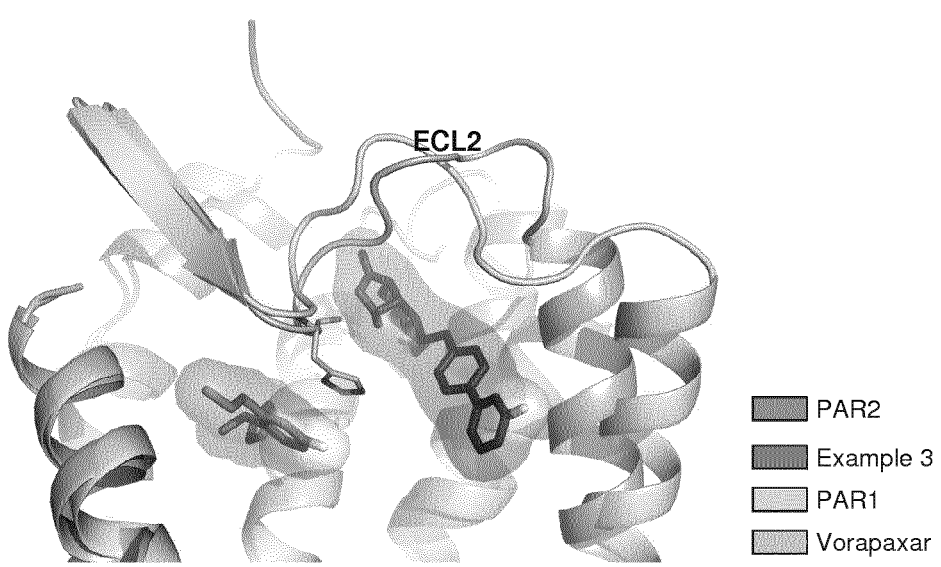
FIG. 1 shows PAR1 crystal structure bound to Vorapaxar compared to PAR2 crystal structure bound to the compound of Example 3.

The present applicant provides a compound of formula (I):

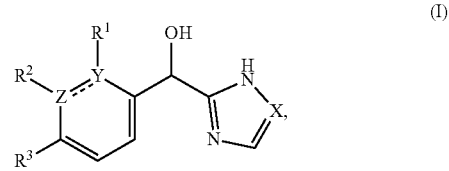

or a pharmaceutically acceptable salt thereof, wherein:

R³ is —H or halogen (such as —F);

X is N or CH;

Y is C or N; and

Z is C or N, wherein Y and Z are not both N, and (1) when both Z and Y are C, the bond "‑‑‑‑‑" is a double bond, and R¹ is selected from alkyl (such as $C_{1-12}$-alkyl-, $C_{2-12}$-alkyl-, or $C_{2-6}$-alkyl-, e.g., ethyl or propyl); alkenyl (such as $C_{2-12}$-alkenyl- or $C_{2-6}$-alkenyl-, e.g.,

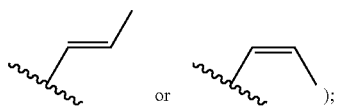

cycloalkyl (such as $C_{3-10}$-cycloalkyl- or $C_{3-6}$-cycloalkyl-, e.g., cyclobutyl, cyclopentyl, or

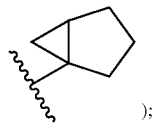 [SMILES: *C12CCCC1C2]

cycloalkenyl (such as $C_{3-10}$-cycloalkenyl- or $C_{3-6}$-cycloalkenyl-, e.g.,

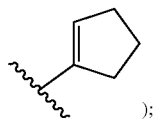 [SMILES: *C1=CCCC1]

aryl (such as $C_{6-10}$-aryl-); heterocyclyl (such as 3- to 10-membered heterocyclyl- or 3- to 6-membered heterocyclyl, e.g.,

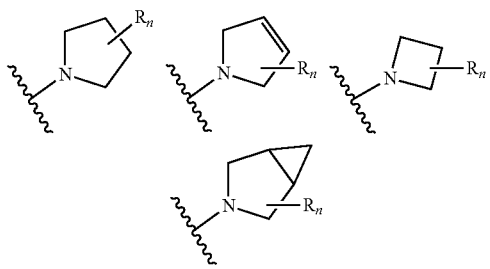

wherein n is selected from 0-3); and heteroaryl (such as 5- to 10-membered heteroaryl- or as 5- to 6-membered heteroaryl-, e.g.,

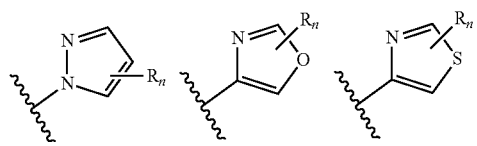

-continued

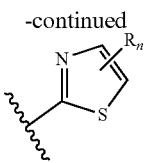

wherein n is selected from 0-3); wherein R¹ is substituted with 0-3 R, wherein each occurrence of R is independently selected from alkyl, such as $C_{1-4}$alkyl (e.g., methyl, ethyl, or —CF₃); cycloalkyl; halo, such as —F, —Cl, or —Br (e.g., —Cl); —OH; alkoxy, such as methoxy; —CN; —NRᵃRᵇ; —N(Rᵃ)C(O) alkyl; —N(Rᵃ)CO₂alkyl; —N(Rᵃ)SO₂alkyl; —C(O)alkyl; —CO₂H; —CO₂alkyl; —CONRᵃRᵇ; —SO₂alkyl; and —SO₂NRᵃRᵇ; wherein Rᵃ and Rᵇ are independently for each occurrence H or alkyl;

R² is —H or -halogen (such as —F or —Cl); or

R¹ and R² may be taken together with the atoms to which they are bound to form a 3- to 10-membered aromatic or non-aromatic monocyclic ring having 0-3 heteroatoms or heteroatom groups independently selected from N, NH, O, S, SO, and SO₂, wherein said ring is substituted with 0-3 R, and wherein said ring is optionally fused to a $C_{6-10}$aryl, 5- to 10-membered heteroaryl, $C_{3-10}$cycloalkyl, or a 3- to 10-membered heterocyclyl, wherein said $C_{6-10}$aryl, 5- to 10-membered heteroaryl, $C_{3-10}$cycloalkyl, or a 3- to 10-membered heterocyclyl is substituted with 0-3 R, wherein each occurrence of R is independently selected from alkyl, such as $C_{1-4}$alkyl (e.g., methyl, ethyl, propyl, isopropyl, —CH₂CF₃ or —CF₃); cycloalkyl (e.g., cyclopropyl or

halo, such as —F, —Cl, or —Br (e.g., —Cl); —OH; alkoxy, such as methoxy; —CN; —NRᵃRᵇ; —N(Rᵃ)C(O) alkyl; —N(Rᵃ)CO₂alkyl; —N(Rᵃ)SO₂alkyl; —C(O)alkyl; —CO₂H; —CO₂alkyl; —CONRᵃRᵇ; —SO₂alkyl; and —SO₂NRᵃRᵇ; wherein Rᵃ and Rᵇ are independently for each occurrence H or alkyl; or (2) when one of Z and Y is N and the other is C, the bond "‑‑‑‑‑" is a single bond, and R¹ and R² are taken together with the atoms to which they are bound to form a 3- to 10-membered aromatic or non-aromatic monocyclic ring having 0-3 heteroatoms or heteroatom groups independently selected from N, NH, O, S, SO, and SO₂, wherein said ring is substituted with 0-3 R, and wherein said ring is optionally fused to a $C_{6-10}$aryl, 5- to 10-membered heteroaryl, $C_{3-10}$cycloalkyl, or a 3- to 10-membered heterocyclyl, wherein said $C_{6-10}$aryl, 5- to 10-membered heteroaryl, $C_{3-10}$cycloalkyl, or a 3- to 10-membered heterocyclyl is substituted with 0-3 R, wherein each occurrence of R is independently selected from alkyl, such as $C_{1-4}$alkyl (e.g., methyl, ethyl, propyl, isopropyl, —CH₂CF₃ or —CF₃); cycloalkyl (e.g., cyclopropyl or

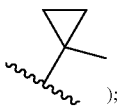 [SMILES: *C1(C)CC1]

halo, such as —F, —Cl, or —Br (e.g., —Cl); —OH; alkoxy, such as methoxy; —CN; —NR$^a$R$^b$; —N(R$^a$)C(O) alkyl; —N(R$^a$)CO$_2$alkyl; —N(R$^a$)SO$_2$alkyl; —C(O)alkyl; —CO$_2$H; —CO$_2$alkyl; —CONR$^a$R$^b$; —SO$_2$alkyl; and —SO$_2$NR$^a$R$^b$;

wherein R$^a$ and R$^b$ are independently for each occurrence H or alkyl;

provided that when R$^1$ is methyl and X is CH, R$^2$ and R$^3$ are not both —H. In certain embodiments, when R$^1$ is methyl and X is CH, R$^3$ is —F.

In certain embodiments, X is CH. In certain embodiments, X is N.

In certain embodiments, R$^3$ is —H. In certain embodiments, R$^3$ is —F.

In certain embodiments, both Z and Y are C and the bond "-----" is a double bond. In certain embodiments, both Z and Y are C, the bond "-----" is a double bond, and the compound can be represented by formula (I-A):

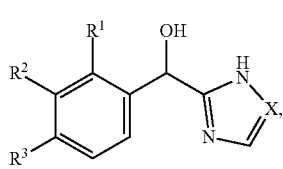

(I-A)

or a pharmaceutically acceptable salt thereof, wherein:

X is N or CH;

R$^1$ is selected from alkyl (such as C$_{1-12}$-alkyl-, C$_{2-12}$-alkyl-, or C$_{2-6}$-alkyl-, e.g., ethyl or propyl); alkenyl (such as C$_{2-12}$-alkenyl-, or C$_{2-6}$-alkenyl-, e.g.,

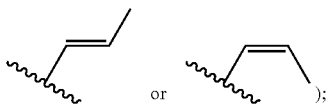

cycloalkyl (such as C$_{3-10}$-cycloalkyl- or C$_{3-6}$-cycloalkyl-, e.g., cyclobutyl, cyclopentyl, or

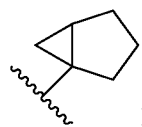

cycloalkenyl (such as C$_{3-10}$-cycloalkenyl- or C$_{3-6}$-cycloalkenyl-, e.g.,

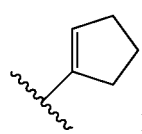

aryl (such as C$_{6-10}$-aryl-); heterocyclyl (such as 3- to 10-membered heterocyclyl- or 3- to 6-membered heterocyclyl, e.g.,

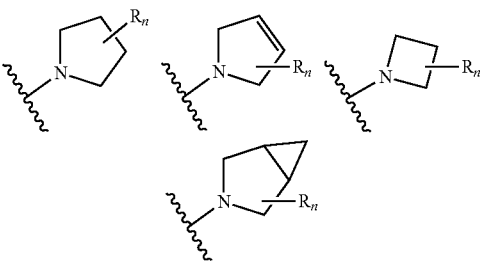

wherein n is selected from 0-3); and heteroaryl (such as 5- to 10-membered heteroaryl-, e.g.,

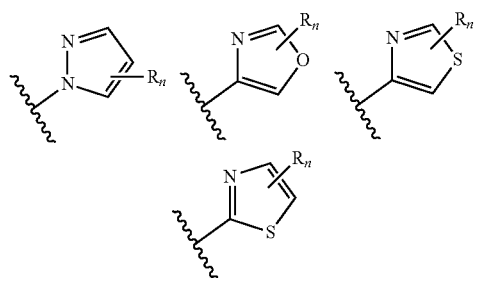

wherein n is selected from 0-3); wherein R$^1$ is substituted with 0-3 R, wherein each occurrence of R is independently selected from alkyl, such as C$_{1-4}$alkyl (e.g., methyl, ethyl, or —CF$_3$); cycloalkyl; halo, such as —F, —Cl, or —Br (e.g., —Cl); —OH; alkoxy, such as methoxy; —CN; —NR$^a$R$^b$; —N(R$^a$)C(O) alkyl; —N(R$^a$)CO$_2$alkyl; —N(R$^a$)SO$_2$alkyl; —C(O)alkyl; —CO$_2$H; —CO$_2$alkyl; —CONR$^a$R$^b$; —SO$_2$alkyl; and —SO$_2$NR$^a$R$^b$; wherein R$^a$ and R$^b$ are independently for each occurrence H or alkyl;

R$^2$ is —H or -halogen (such as —F or —Cl); or

R$^1$ and R$^2$ may be taken together with the atoms to which they are bound to form a 3- to 10-membered aromatic or non-aromatic monocyclic ring having 0-3 heteroatoms or heteroatom groups independently selected from N, NH, O, S, SO, and SO$_2$, wherein said ring is substituted with 0-3 R, and wherein said ring is optionally fused to a C$_{6-10}$aryl, 5- to 10-membered heteroaryl, C$_{3-10}$cycloalkyl, or a 3- to 10-membered heterocyclyl, wherein said C$_{6-10}$aryl, 5- to 10-membered heteroaryl, C$_{3-10}$cycloalkyl, or a 3- to 10-membered heterocyclyl is substituted with 0-3 R, wherein each occurrence of R is independently selected from alkyl, such as C$_{1-4}$alkyl (e.g., methyl, ethyl, propyl, isopropyl, —CH$_2$CF$_3$ or —CF$_3$); cycloalkyl (e.g., cyclopropyl or

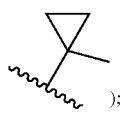 [SMILES: *C1(C)CC1]

halo, such as —F, —Cl, or —Br (e.g., —Cl); —OH; alkoxy, such as methoxy; —CN; —NR$^a$R$^b$; —N(R$^a$)C(O) alkyl; —N(R$^a$)CO$_2$alkyl; —N(R$^a$)SO$_2$alkyl; —C(O)alkyl; —CO$_2$H; —CO$_2$alkyl; —CONR$^a$R$^b$; —SO$_2$alkyl; and —SO$_2$NR$^a$R$^b$; wherein R$^a$ and R$^b$ are independently for each occurrence H or alkyl; and R³ is —H or halogen (such as —F);
provided that when R¹ is methyl and X is CH, R² and R³ are not both —H. In some embodiments of the forgoing, when R¹ is methyl and X is CH, R³ is —F.

In certain embodiments, X is CH. In certain embodiments, X is N.

In certain embodiments, R³ is —H. In certain embodiments, R³ is —F.

In certain embodiments of compounds of formula (I) or (I-A), R¹ is $C_{1-12}$ alkyl that is optionally substituted with 0-3 R. In some embodiments, R¹ is $C_{2-12}$ alkyl that is optionally substituted with 0-3 R. In some embodiments, R¹ is $C_{2-6}$ alkyl that is optionally substituted with 0-3 R. In some embodiments, R¹ is a linear or branched $C_{3-6}$ alkyl that is optionally substituted with 0-3 R. In some of the above embodiments, R¹ is unsubstituted. In some embodiments, R¹ is ethyl or propyl. In some embodiments, R¹ is propyl.

In certain embodiments of compounds of formula (I) or (I-A), R¹ is $C_{2-12}$ alkenyl that is optionally substituted with 0-3 R. In some embodiments, R¹ is $C_{2-6}$ alkenyl that is optionally substituted with 0-3 R. In some embodiments, R¹ is a linear or branched $C_{3-6}$ alkenyl that is optionally substituted with 0-3 R. In some of the above embodiments, R¹ is unsubstituted. In some embodiments, R¹ is

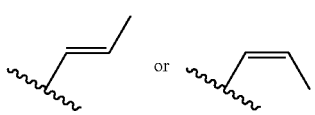

In certain embodiments of compounds of formula (I) or (I-A), R¹ is $C_{3-10}$-cycloalkyl- that is optionally substituted with 0-3 R. In some embodiments, R¹ is $C_{3-6}$-cycloalkyl- that is optionally substituted with 0-3 R. In some embodiments, R¹ is selected from cyclobutyl, cyclopentyl, and

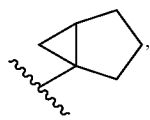

wherein R¹ is optionally substituted with 0-3 R. In some of the above embodiments, R¹ is unsubstituted.

In certain embodiments of compounds of formula (I) or (I-A), R¹ is $C_{3-10}$-cycloalkenyl- that is optionally substituted with 0-3 R. In some embodiments, R¹ is $C_{3-6}$-cycloalkenyl- that is optionally substituted with 0-3 R. In some embodiments, R¹ is

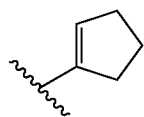 [SMILES: *C1=CCCC1]

that is optionally substituted with 0-3 R. In some of the above embodiments, R¹ is unsubstituted.

In certain embodiments of compounds of formula (I) or (I-A), R¹ is 3- to 10-membered heterocyclyl- that is optionally substituted with 0-3 R. In some embodiments, R¹ is 3- to 6-membered heterocyclyl- that is optionally substituted with 0-3 R. In some embodiments, R¹ is selected from:

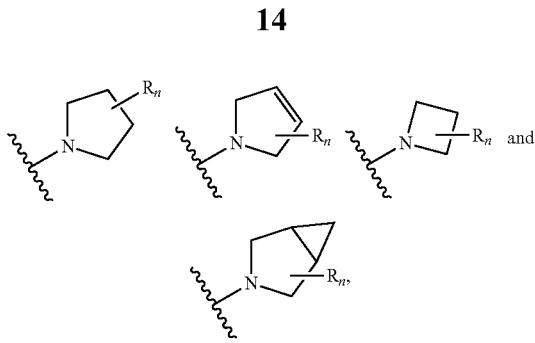

wherein n is 0-3. In some of the above embodiments, R¹ is unsubstituted. In some of the above embodiments, each occurrence of R is independently selected from: $C_{1-3}$ alkyl (such as -Me) and halogen (such as —F). In some embodiments, R¹ is selected from:

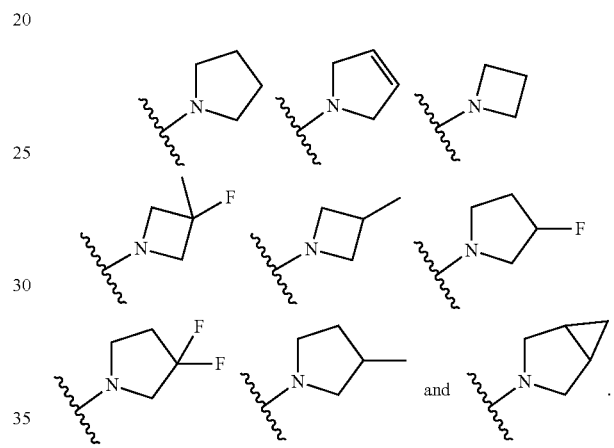

In certain embodiments of compounds of formula (I) or (I-A), R¹ is 5- to 10-membered heteroaryl- that is optionally substituted with 0-3 R. In some embodiments, R¹ is 5- or 6-membered heteroaryl- that is optionally substituted with 0-3 R. In some embodiments, R¹ is selected from:

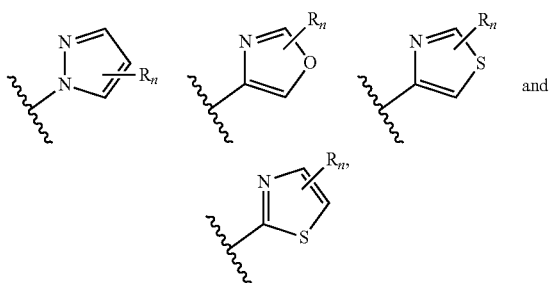

wherein n is 0-3. In some embodiments, R¹ is unsubstituted, and is selected from:

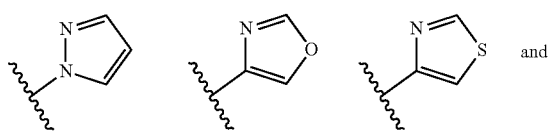

-continued

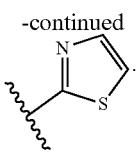

In certain embodiments of compounds of formula (I) or (I-A), $R^2$ is —H or -halogen. In some embodiments, $R^2$ is —H. In some embodiments, $R^2$ is —F or —Cl.

In certain embodiments of compounds of formula (I) or (I-A), $R^1$ and $R^2$ are taken together with the atoms to which they are bound to form a 3- to 10-membered aromatic or non-aromatic monocyclic ring having 0-3 heteroatoms or heteroatom groups independently selected from N, NH, O, S, SO, and $SO_2$, wherein said ring is substituted with 0-3 R, and wherein said ring is optionally fused to a $C_{6-10}$aryl, 5- to 10-membered heteroaryl, $C_{3-10}$cycloalkyl, or a 3- to 10-membered heterocyclyl, wherein said $C_{6-10}$aryl, 5- to 10-membered heteroaryl, $C_{3-10}$cycloalkyl, or a 3- to 10-membered heterocyclyl is substituted with 0-3 R. In some of the above embodiments, the structure

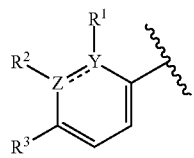

of formula (I) or the structure

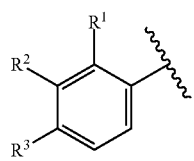

of formula (I-A) is selected from:

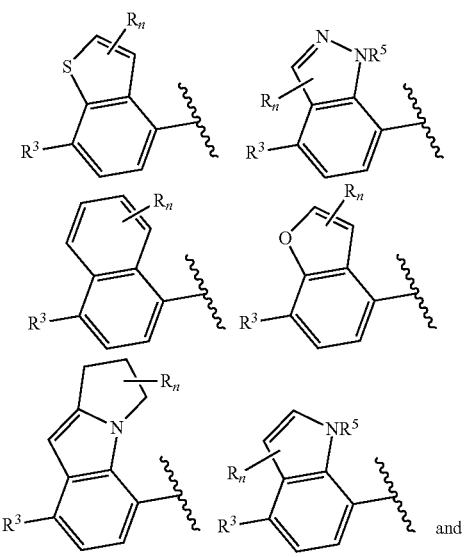

and

-continued

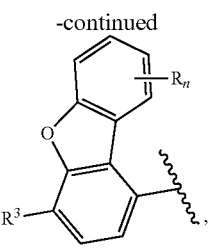

wherein $R^5$ is —H or —$C_{1-3}$alkyl, n is selected from 0-3. In some of these embodiments, $R^5$ is -Me or -Et. In some of the above embodiments, each occurrence of R is independently selected from: $C_{1-4}$alkyl, $C_{3-6}$cycloalkyl, and halo. In some of the above embodiments, each occurrence of R is independently selected from: methyl, ethyl, propyl, isopropyl, —$CH_2CF_3$, —$CF_3$, cyclopropyl,

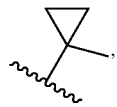

F, —Cl, and —Br, for example, methyl, ethyl, —$CH_2CF_3$, cyclopropyl, and

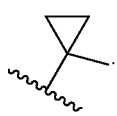

In some embodiments, the structure

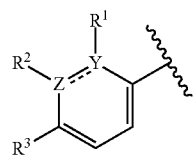

of formula (I) or the structure

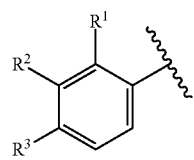

of formula (I-A) is selected from:

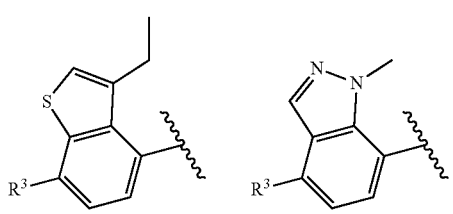

-continued

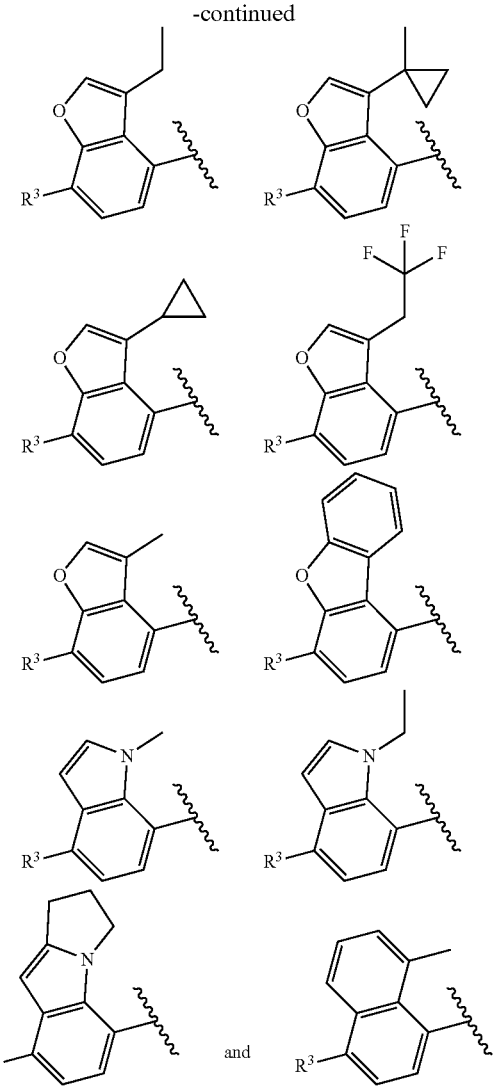

In certain embodiments wherein one of Z and Y is N and the other is C, the compound can be represented by formula (I-B):

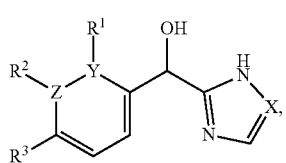

or a pharmaceutically acceptable salt thereof, wherein:
X is N or CH;
$R^1$ and $R^2$ are taken together with the atoms to which they are bound to form a 3- to 10-membered aromatic or non-aromatic monocyclic ring having 0-3 heteroatoms or heteroatom groups independently selected from N, NH, O, S, SO, and $SO_2$, wherein said ring is substituted with 0-3 R, and wherein said ring is optionally fused to a $C_{6-10}$aryl, 5- to 10-membered heteroaryl, $C_{3-10}$cycloalkyl, or a 3- to 10-membered heterocyclyl, wherein said $C_{6-10}$aryl, 5- to 10-membered heteroaryl, $C_{3-10}$cycloalkyl, or a 3- to 10-membered heterocyclyl is substituted with 0-3 R, wherein each occurrence of R is independently selected from alkyl, such as $C_{1-4}$alkyl (e.g., methyl, ethyl, propyl, isopropyl, —$CH_2CF_3$ or —$CF_3$); cycloalkyl (e.g., cyclopropyl or

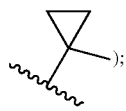 [SMILES: *C1(C)CC1]

halo, such as —F, —Cl, or —Br (e.g., —Cl); —OH; alkoxy, such as methoxy; —CN; —$NR^aR^b$; —$N(R^a)C(O)$ alkyl; —$N(R^a)CO_2$alkyl; —$N(R^a)SO_2$alkyl; —C(O)alkyl; —$CO_2H$; —$CO_2$alkyl; —$CONR^aR^b$; —$SO_2$alkyl; and —$SO_2NR^aR^b$; wherein $R^a$ and $R^b$ are independently for each occurrence H or alkyl;
$R^3$ is —H or halogen (such as —F).

In certain embodiments, Y is C and Z is N and the bond "═══" is a single bond. In certain embodiments, Y is N and Z is C and the bond "═══" is a single bond.

In certain embodiments, X is CH. In certain embodiments, X is N.

In certain embodiments, $R^3$ is —H. In certain embodiments, $R^3$ is —F.

In certain embodiments of compounds of formula (I) or (I-B), the structure

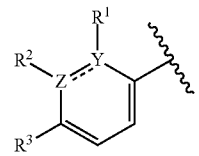

is selected from:

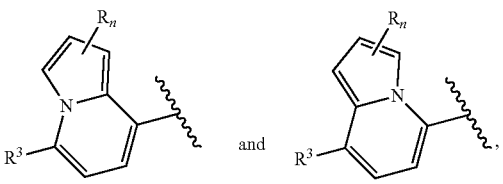

wherein n is selected from 0-3. In some of these embodiments, each occurrence of R is independently selected from: $C_{1-4}$alkyl, $C_{3-6}$cycloalkyl, and halo. In some embodiments, each occurrence of R is independently selected from: methyl, ethyl, propyl, isopropyl, —$CH_2CF_3$, —$CF_3$, cyclopropyl,

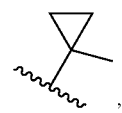

—F, —Cl, and —Br, such as methyl, ethyl, isopropyl, cyclopropyl, and —Cl. In some embodiments, the structure

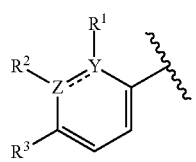
of formula (I) or (I-B) is selected from:
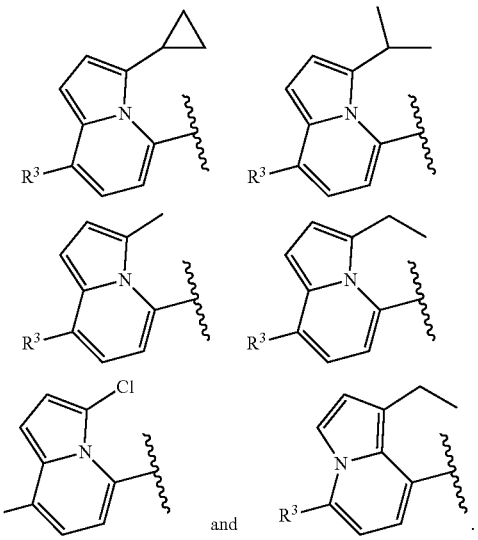
In certain embodiments, the compound of the present application is selected from:
1
2
3
4
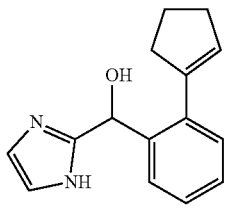
5
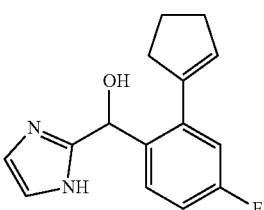
6
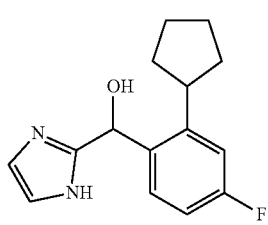
7
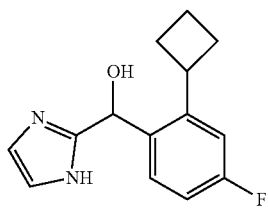
8
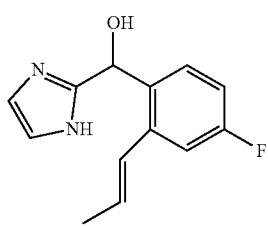
9
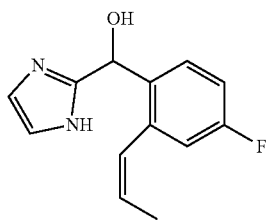
10
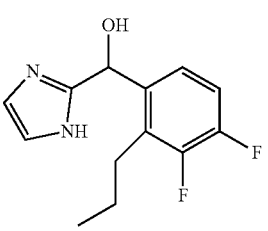

-continued
11
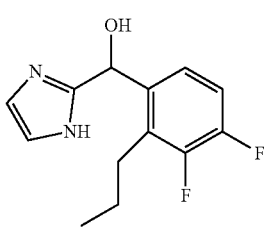
12
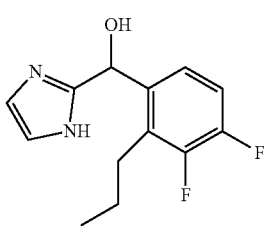
13
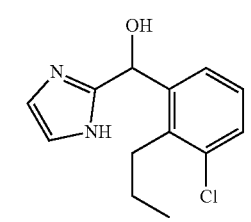
14
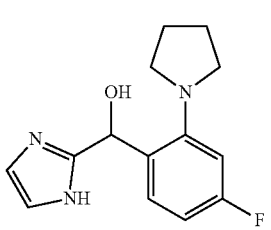
15
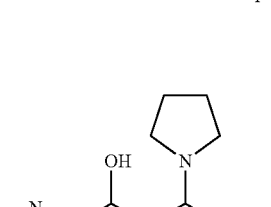
16
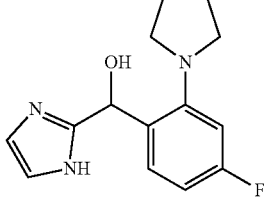
17
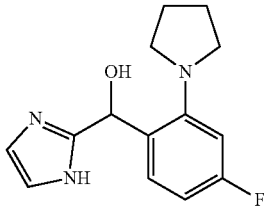
-continued
18
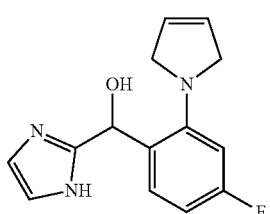
19
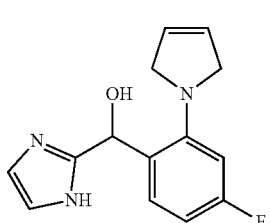
20
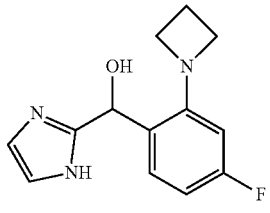
21
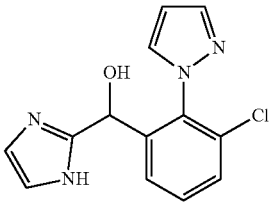
22
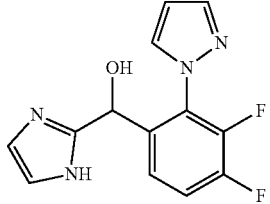
23
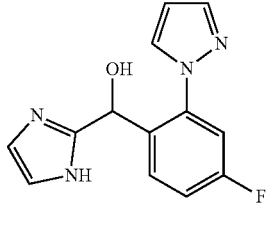
24
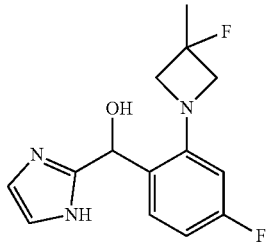

25
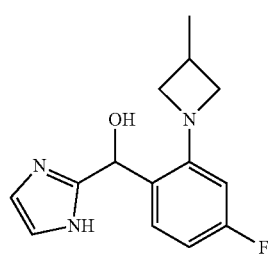
26
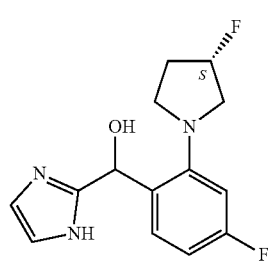
27
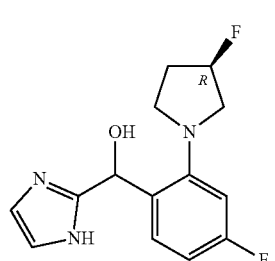
28
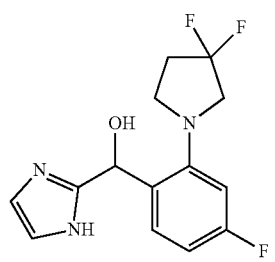
29
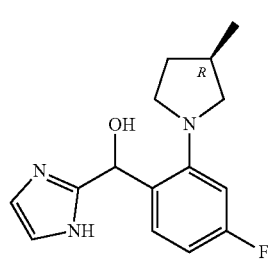
30
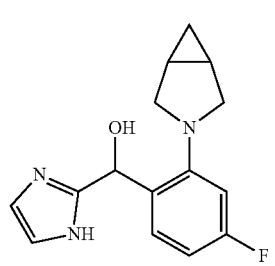
31
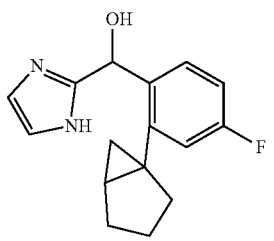
32
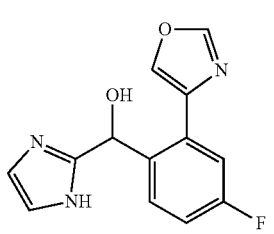
33
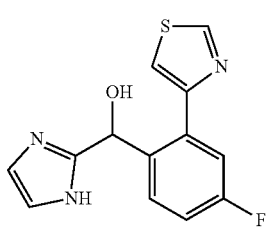
34
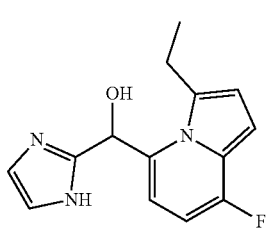
35
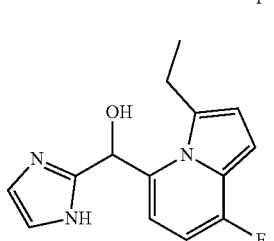
36
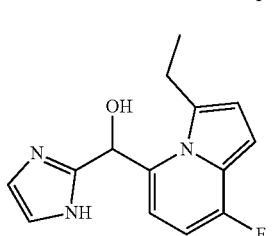
37
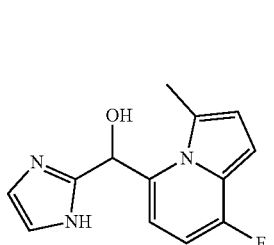

-continued

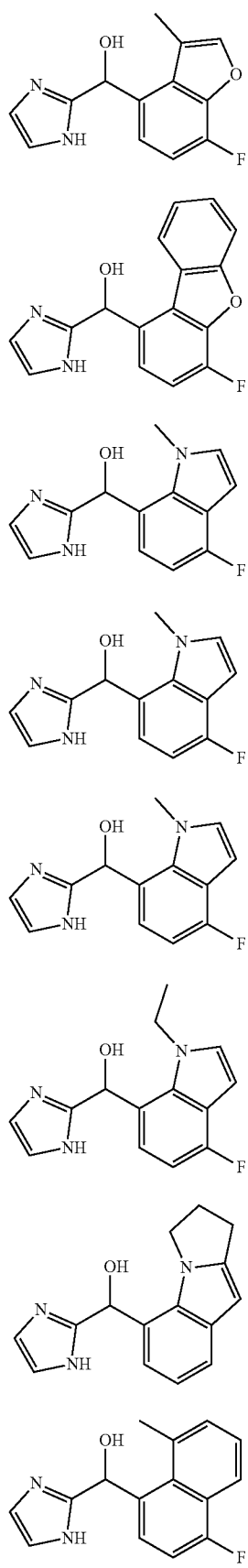
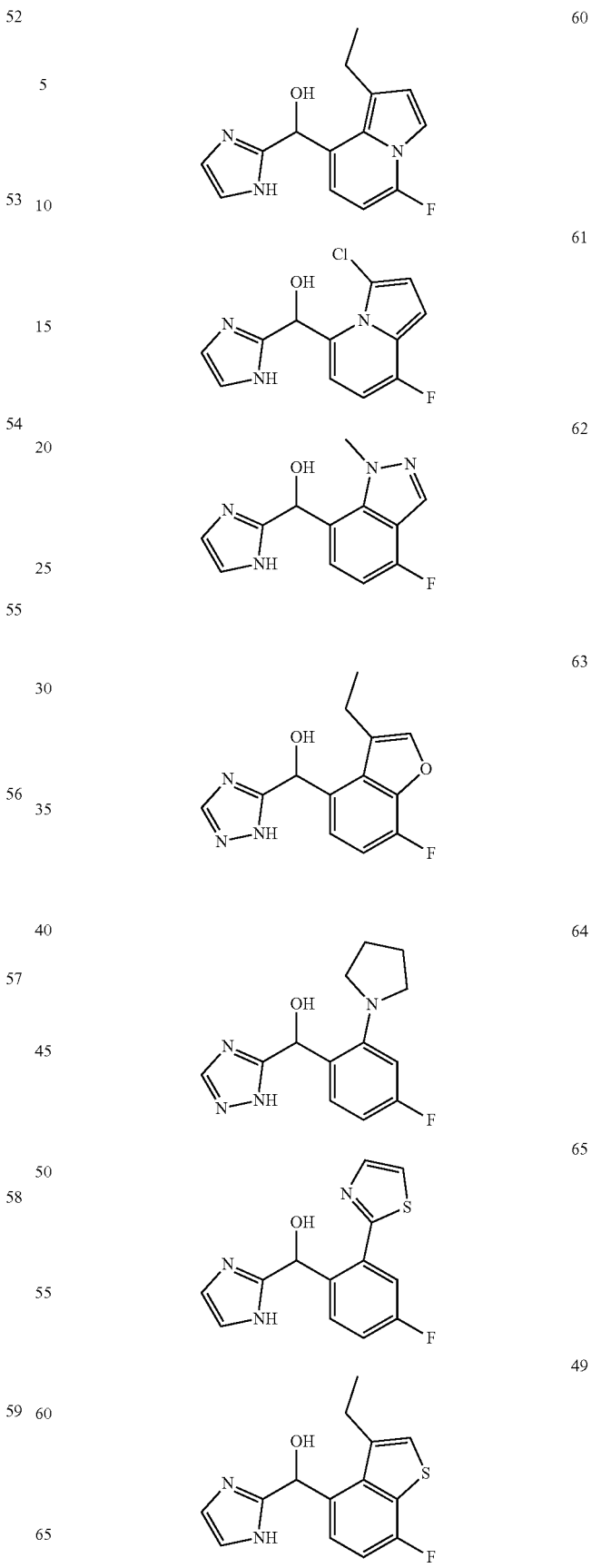

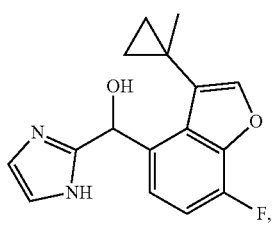

and pharmaceutically acceptable salts thereof.

An example of a compound of the specification is:
(4-Fluoro-2-propylphenyl)(1H-imidazol-2-yl)methanol;
(R)-(4-fluoro-2-propylphenyl) (1H-imidazol-2-yl)methanol;
(S)-(4-Fluoro-2-propylphenyl)(1H-imidazol-2-yl)methanol;
(2-Cyclopentenylphenyl) (1H-imidazol-2-yl)methanol;
(2-Cyclopentenyl-4-fluorophenyl)(1H-imidazol-2-yl)methanol;
(2-Cyclopentyl-4-fluorophenyl) (1H-imidazol-2-yl)methanol;
(2-Cyclobutyl-4-fluorophenyl) (1H-imidazol-2-yl)methanol;
(E)-(4-Fluoro-2-(prop-1-enyl)phenyl) (1H-imidazol-2-yl)methanol;
(Z)-(4-Fluoro-2-(prop-1-enyl)phenyl) (1H-imidazol-2-yl)methanol;
(3,4-Difluoro-2-propylphenyl) (1H-imidazol-2-yl)methanol;
(R)-(3,4-Difluoro-2-propylphenyl)(1H-imidazol-2-yl)methanol;
(S)-(3,4-Difluoro-2-propylphenyl)(1H-imidazol-2-yl)methanol;
(3-Chloro-2-propylphenyl)(1H-imidazol-2-yl)methanol;
(4-Fluoro-2-(pyrrolidin-1-yl)phenyl) (1H-imidazol-2-yl)methanol;
(R)-(4-Fluoro-2-(pyrrolidin-1-yl)phenyl)(1H-imidazol-2-yl)methanol;
(S)-(4-Fluoro-2-(pyrrolidin-1-yl)phenyl)(1H-imidazol-2-yl)methanol;
(2-(2,5-dihydro-1H-pyrrol-1-yl)-4-fluorophenyl) (1H-imidazol-2-yl)methanol;
(R)-(2-(2,5-dihydro-1H-pyrrol-1-yl)-4-fluorophenyl)(1H-imidazol-2-yl)methanol;
(S)-(2-(2,5-dihydro-1H-pyrrol-1-yl)-4-fluorophenyl)(1H-imidazol-2-yl)methanol;
(2-(Azetidin-1-yl)-4-fluorophenyl) (1H-imidazol-2-yl)methanol;
(3-Chloro-2-(1H-pyrazol-1-yl)phenyl)(1H-imidazol-2-yl)methanol;
(3,4-Difluoro-2-(1H-pyrazol-1-yl)phenyl)(1H-imidazol-2-yl)methanol;
(4-Fluoro-2-(1H-pyrazol-1-yl)phenyl)(1H-imidazol-2-yl)methanol;
(4-Fluoro-2-(3-fluoro-3-methylazetidin-1-yl)phenyl)(1H-imidazol-2-yl)methanol;
(4-Fluoro-2-(3-methylazetidin-1-yl)phenyl)(1H-imidazol-2-yl)methanol;
(4-Fluoro-2-((S)-3-fluoropyrrolidin-1-yl)phenyl) (1H-imidazol-2-yl)methanol;
(4-Fluoro-2-((R)-3-fluoropyrrolidin-1-yl)phenyl) (1H-imidazol-2-yl)methanol;
(2-(3,3-Difluoropyrrolidin-1-yl)-4-fluorophenyl)(1H-imidazol-2-yl)methanol;
(4-Fluoro-2-((R)-3-methylpyrrolidin-1-yl)phenyl) (1H-imidazol-2-yl)methanol;
(2-(3-Azabicyclo[3.1.0]hexan-3-yl)-4-fluorophenyl)(1H-imidazol-2-yl)methanol;
(2-(Bicyclo[3.1.0]hexan-1-yl)-4-fluorophenyl) (1H-imidazol-2-yl)methanol;
(4-Fluoro-2-(oxazol-4-yl)phenyl)(1H-imidazol-2-yl)methanol;
(4-Fluoro-2-(thiazol-4-yl)phenyl)(1H-imidazol-2-yl)methanol;
(3-Ethyl-8-fluoroindolizin-5-yl)(1H-imidazol-2-yl)methanol;
(R)-(3-Ethyl-8-fluoroindolizin-5-yl)(1H-imidazol-2-yl)methanol;
(S)-(3-Ethyl-8-fluoroindolizin-5-yl) (1H-imidazol-2-yl)methanol;
(8-Fluoro-3-methylindolizin-5-yl)(1H-imidazol-2-yl)methanol;
(8-Fluoro-3-isopropylindolizin-5-yl) (1H-imidazol-2-yl)methanol;
(3-Cyclopropyl-8-fluoroindolizin-5-yl)(1H-imidazol-2-yl)methanol;
(3-Ethyl-7-fluorobenzofuran-4-yl) (1H-imidazol-2-yl)methanol;
(R)-(3-Ethyl-7-fluorobenzofuran-4-yl)(1H-imidazol-2-yl)methanol;
(S)-(3-Ethyl-7-fluorobenzofuran-4-yl)(1H-imidazol-2-yl)methanol;
(3-Cyclopropyl-7-fluorobenzofuran-4-yl) (1H-imidazol-2-yl)methanol;
(R)-(3-Cyclopropyl-7-fluorobenzofuran-4-yl)(1H-imidazol-2-yl)methanol;
(S)-(3-Cyclopropyl-7-fluorobenzofuran-4-yl) (1H-imidazol-2-yl)methanol;
(7-Fluoro-3-(2,2,2-trifluoroethyl)benzofuran-4-yl) (1H-imidazol-2-yl)methanol;
(R)-(7-fluoro-3-(2,2,2-trifluoroethyl)benzofuran-4-yl)(1H-imidazol-2-yl)methanol;
(S)-(7-fluoro-3-(2,2,2-trifluoroethyl)benzofuran-4-yl)(1H-imidazol-2-yl)methanol;
(3-Ethyl-7-fluorobenzo[b]thiophen-4-yl)(1H-imidazol-2-yl)methanol;
(R)-(3-Ethyl-7-fluorobenzo[b]thiophen-4-yl)(1H-imidazol-2-yl)methanol;
(S)-(3-Ethyl-7-fluorobenzo[b]thiophen-4-yl)(1H-imidazol-2-yl)methanol;
(7-Fluoro-3-methylbenzofuran-4-yl)(1H-imidazol-2-yl)methanol;
(4-Fluorodibenzo[b,d]furan-1-yl)(1H-imidazol-2-yl)methanol;
(4-Fluoro-1-methyl-1H-indol-7-yl)(1H-imidazol-2-yl)methanol;
(R)-(4-Fluoro-1-methyl-1H-indol-7-yl)(1H-imidazol-2-yl)methanol;
(S)-(4-Fluoro-1-methyl-1H-indol-7-yl)(1H-imidazol-2-yl)methanol;
(1-Ethyl-4-fluoro-1H-indol-7-yl) (1H-imidazol-2-yl)methanol;
(2,3-Dihydro-1H-pyrrolo[1,2-a]indol-5-yl) (1H-imidazol-2-yl)methanol;
(4-Fluoro-8-methylnaphthalen-1-yl) (1H-imidazol-2-yl)methanol;
(1-Ethyl-5-fluoro-indolizin-8-yl)-(1H-imidazol-2-yl)methanol;
(3-Chloro-8-fluoro-indolizin-5-yl)-(1H-imidazol-2-yl)methanol;
(4-Fluoro-1-methyl-1H-indazol-7-yl) (1H-imidazol-2-yl)methanol;

(3-Ethyl-7-fluorobenzofuran-4-yl) (1H-1,2,4-triazol-5-yl)methanol;
(4-Fluoro-2-(pyrrolidin-1-yl)phenyl)(1H-1,2,4-triazol-5-yl)methanol;
(4-Fluoro-2-(thiazol-2-yl)phenyl)(1H-imidazol-2-yl)methanol;
[7-Fluoro-3-(1-methylcyclopropyl)benzofuran-4-yl]-(1H-imidazol-2-yl)methanol;
or a pharmaceutically acceptable salt thereof.

In another aspect, the present application provides a compound that binds to an allosteric site of a PAR2 polypeptide comprising an amino acid sequence set forth in SEQ ID NO.: 1, wherein the compound interacts with one or more amino acid residues selected from the group consisting of Asp 228, Lys 131, His 135, and Tyr 82 of SEQ ID NO.: 1. In some embodiments, the compound binds to an allosteric site of a PAR2 polypeptide comprising an amino acid sequence set forth in SEQ ID NO.: 1, wherein the compound interacts with amino acid residues Asp 228, Lys 131, and His 135 of SEQ ID NO.: 1. In some embodiments, the compound binds to an allosteric site of a PAR2 polypeptide comprising an amino acid sequence set forth in SEQ ID NO.: 1, wherein the compound interacts with amino acid residues Asp 228, Lys 131, His 135, and Tyr 82 of SEQ ID NO.: 1. In some embodiments, such a compound is an antagonist of PAR2. In some embodiments, such a compound is a small molecule (e.g., a small molecule antagonist). In certain embodiments of the forgoing, the compound has a structure of formula (I), (I-A), or (I-B), or a pharmaceutically acceptable salt thereof.

Compounds which act on their target with long mean target residence times have been shown to have potential advantages such as long duration of activity and target selectivity. This can be measured on enzymes and proteins using methods such as surface plasmon resonance spectroscopy, radiochemical binding assays or inferred from time-dependant studies in a biochemical assay. The kinetic methods can be used to determine the on-rate ($K_{on}$), the off-rate ($K_{off}$) and the $K_d$ value for a given compound (Copeland et al, *Nat. Rev. Drug Disc.* 2006, 5, 730-739). These kinetic measurements can either be reported as residence time ($\tau=1/k_{off}$), or as the dissociative half life ($t_{1/2}=0.693/k_{off}$). The value of the residence time or dissociative half-life needed to obtain a long duration of activity (e.g. PD effect) is thought to vary from one target to another and is generally influenced by the surrounding environmental factors such as local concentrations of competing ligands (such as agonists), protein turnover rate as well as the distribution and localization of the compound. Compounds with this property are also sometimes described as having slow off-rate kinetics.

In another aspect, the present application provides a compound that binds to an allosteric site of PAR2 polypeptide comprising an amino acid sequence set forth in SEQ ID NO.: 1, wherein said compound has a target dissociative half life ($t_{1/2}$) of greater than 10 minutes. In some embodiments, the present application provides a compound that binds to an allosteric site of PAR2 polypeptide comprising an amino acid sequence set forth in SEQ ID NO.: 1, wherein said compound has a target dissociative half life ($t_{1/2}$) selected from over 3000 minutes, 10 to 3000 minutes, 10 to 2000 minutes, 10 to 1000 minutes, 10 to 900 minutes, 10 to 800 minutes, 10 to 700 minutes, 10 to 600 minutes, 10 to 500 minutes, 10 to 400 minutes, 10 to 300 minutes, 10 to 200 minutes, 10 to 100 minutes, 10 to 50 minutes, 10 to 40 minutes, 10 to 30 minutes, and 10 to 20 minutes. In some embodiments, such a compound has a target dissociative half life of 10 to 200 minutes. In some embodiments of the forgoing, the compound binds to an allosteric site of a PAR2 polypeptide comprising an amino acid sequence set forth in SEQ ID NO.: 1, wherein the compound interacts with one or more amino acid residues selected from the group consisting of Asp 228, Lys 131, His 135, and Tyr 82 of SEQ ID NO.: 1. In some embodiments, the compound interacts with amino acid residues Asp 228, Lys 131, and His 135 of SEQ ID NO.: 1. In some embodiments, the compound interacts with amino acid residues Asp 228, Lys 131, His 135, and Tyr 82 of SEQ ID NO.: 1. In certain embodiments, the dissociative half life is determined in either a FLPR dissociation assay, surface plasmon resonance assay or radiochemical binding assay. In some embodiments, such a compound is an antagonist of PAR2. In some embodiments, such a compound is a small molecule (e.g., a small molecule antagonist). In some embodiments of the forgoing, the compound has a structure of formula (I), (I-A), or (I-B), or a pharmaceutically acceptable salt thereof.

In certain embodiments, this application relates to a pharmaceutical composition comprising (a) a compound described herein, or a pharmaceutically acceptable salt thereof; and (b) a pharmaceutically acceptable excipient.

In certain embodiments, this application relates to a compound described herein, or a pharmaceutically acceptable salt thereof, or a pharmaceutical composition comprising any one of the foregoing, for use as a medicament.

In certain embodiments, this application relates to a method of treating a disease or disorder mediated by PAR2 activity, comprising administering to a subject in need of such treatment an effective amount of at least one compound described herein, or a pharmaceutically acceptable salt thereof, or a pharmaceutical composition comprising any one of the foregoing. In certain such embodiments, the disease or disorder mediated by PAR2 activity is selected from the group consisting of pain, musculoskeletal inflammation (such as osteoarthritis), neuroinflammatory disorders, airway inflammation, itch, dermatitis, or colitis. In certain such embodiments, the disease or disorder mediated by PAR2 activity is osteoarthritis.

In certain embodiments, this application relates to the use of a compound described herein, or a pharmaceutically acceptable salt thereof, or a pharmaceutical composition of any one of the foregoing, in the preparation of a medicament for the treatment of diseases or disorders regulated by PAR2 activity, and the use of such compounds for treatment of such diseases and disorders. In certain such embodiments, the disease or disorder is selected from the group consisting of pain, musculoskeletal inflammation (such as osteoarthritis), neuroinflammatory disorders, airway inflammation, itch, dermatitis, or colitis. In certain such embodiments, the disease or disorder mediated by PAR2 activity is osteoarthritis.

In certain embodiments, this application relates to a method of modulating (e.g., inhibiting) the activity of a PAR2 receptor, comprising contacting a cell comprising the PAR2 with an effective amount of at least one compound described herein, or a pharmaceutically acceptable salt thereof, or a pharmaceutical composition of any one of the foregoing. In certain such embodiments, the contacting is in vitro, ex vivo, or in vivo.

In certain embodiments, this application relates to a method of treating a disease or disorder in a patient in need thereof, comprising administering a compound described herein, or a pharmaceutically acceptable salt thereof, or a pharmaceutical composition of any one of the foregoing, wherein the disease or disorder is selected from the group consisting of pain, musculoskeletal inflammation (such as osteoarthritis), neuroinflammatory disorders, airway inflammation, itch, dermatitis, or colitis. In certain such embodiments, the disease or disorder mediated by PAR2 activity is osteoarthritis.

Those skilled in the art will recognize that the species listed or illustrated herein are not exhaustive, and that additional species within the scope of these defined terms may also be selected.

The application also includes pharmaceutically acceptable prodrugs, salts, solvates, such as hydrates, of the compounds described herein, preferably of those described above and of the specific compounds exemplified herein, and pharmaceutical compositions comprising such prodrugs, salts, or solvates, such as hydrates, and methods of using such salts or hydrates.

The present application also relates to pharmaceutically active metabolites of compounds described herein, and uses of such metabolites in the methods of the application.

Definitions

The definitions set forth in this application are intended to clarify terms used throughout this application.

Unless defined otherwise, all technical and scientific terms used herein have the same meaning as is commonly understood by one of ordinary skill in the art to which this application belongs. All patents, applications, published applications and other publications referred to herein are incorporated by reference in their entireties to disclose and describe the methods and/or materials in connection with which the publications are cited. If a definition set forth in this section is contrary to or otherwise inconsistent with a definition set forth in a patent, application, or other publication that is herein incorporated by reference, the definition set forth in this section prevails over the definition incorporated herein by reference. Although any methods and materials similar or equivalent to those described herein can also be used in the practice or testing of the embodiments in the present application, the preferred methods and materials are now described.

To provide a more concise description, some of the quantitative expressions given herein are not qualified with the term "about." It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. This nomenclature has generally been derived using the commercially-available ChemBioDraw Ultra software (Cambridgesoft/Perkin Elmer), Version 12.0.

It is to be understood that the present description is not limited to particular embodiments described, as such may, of course, vary. It is also to be understood that the terminology used herein is for the purpose of describing particular embodiments only, and is not intended to be limiting, since the scope of the present application will be limited only by the appended claims.

It is appreciated that certain features of the application, which are, for clarity, described in the context of separate embodiments, may also be provided in combination in a single embodiment. Conversely, various features of the application, which are, for brevity, described in the context of a single embodiment, may also be provided separately or in any suitable subcombination. All combinations of the embodiments pertaining to the chemical groups represented by the variables are specifically embraced by the present application and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present application and are disclosed herein just as if each and every such sub-combination of chemical groups was individually and explicitly disclosed herein.

Any formula depicted herein is intended to represent a compound of that structural formula as well as certain variations or forms. E.g., a formula given herein is intended to include a racemic form, or one or more enantiomeric, diastereomeric, or geometric isomers, or tautomeric forms, or a mixture thereof. Additionally, any formula given herein is intended to refer also to a solvate, such as a hydrate, solvate, or polymorph of such a compound, or a mixture thereof. Any formula given herein is intended to refer to amorphous and/or crystalline physical forms of the compound. The compounds described herein may be analytically pure, or a mixture in which the compound comprises at least 50%, at least 70%, at least 80%, at least 90%, at least 95%, or at least 98% by weight of the mixture.

In addition, where features or aspects of the embodiments of this application are described in terms of Markush groups, those skilled in the art will recognize that embodiments described herein is also thereby described in terms of any individual member or subgroup of members of the Markush group. E.g., if X is described as selected from the group consisting of bromine, chlorine, and iodine, claims for X being bromine and claims for X being bromine and chlorine are fully described.

The term "herein" refers to the entire application.

As used herein, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

As used herein, "subject" (as in the subject of the treatment) refers to both mammals and non-mammals. Mammals include, e.g., humans; non-human primates, e.g. apes and monkeys; and non-primates, e.g. mice, rats, rabbits, dogs, cats, cattle, horses, sheep, and goats.

Non-mammals include, e.g., worms, fish and birds. In some embodiments, the subject is a human.

"Substantially" as the term is used herein refers to being completely or almost completely; e.g., a composition that is "substantially free" of a component either has none of the component or contains such a trace amount that any relevant functional property of the composition is unaffected by the presence of the trace amount, or a compound is "substantially pure" is there are only negligible traces of impurities present.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, e.g., by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive.

E.g., substitution of alkenyl groups by one or more alkyl, carbocyclyl, aryl, heterocyclyl, or heteroaryl groups is contemplated.

The term "alkynyl", as used herein, refers to an aliphatic group containing at least one triple bond and is intended to include both "unsubstituted alkynyls" and "substituted alkynyls", the latter of which refers to alkynyl moieties having substituents replacing one or more hydrogens on one or more carbons of the alkynyl group. Such substituents may occur on one or more carbons that are included or not included in one or more triple bonds. Moreover, such substituents include all those contemplated for alkyl groups, as discussed above, except where stability is prohibitive. E.g., substitution of alkynyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, such as from 1 to 12 carbon atoms, preferably from 1 to about 10, more preferably from 1 to 4, unless otherwise defined. Examples of straight chained and branched alkyl groups include methyl, ethyl, n-propyl, isopropyl, n-butyl, isobutyl, sec-butyl, tert-butyl, pentyl, isopentyl, tert-pentyl, hexyl, isohexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen or more hydrogens on one or more carbons of the hydrocarbon backbone. Such substituents, if not otherwise specified, can include, e.g., a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "(ATOM)$_{i\text{-}j}$" with j>i, when used in conjunction with a chemical moiety, such as, acyl, acyloxy, alkyl, alkenyl, alkynyl, or alkoxy is meant to include groups that contain from i to j (including i and j) atoms. E.g., the term "$C_{x\text{-}y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl refers to a hydrogen atom where the group is in a terminal position, a bond if internal. Similarly, e.g., $C_{3\text{-}6}$cycloalkyl refers to a cycloalkyl as defined herein that has 3 to 6 carbon ring atoms. The terms "$C_{2\text{-}y}$alkenyl" and "$C_{2\text{-}y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The terms "amine" and "amino" are art-recognized and refer to both unsubstituted and substituted amines and salts thereof, e.g., a moiety that can be represented by

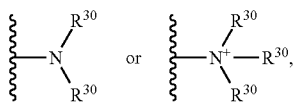

wherein each $R^{30}$ independently represents a hydrogen or a hydrocarbyl group, or two $R^{30}$ are taken together with the N atom to which they are attached complete a heterocycle having from 4 to 8 atoms in the ring structure.

The term "aminoalkyl", as used herein, refers to an alkyl group substituted with an amino group.

The term "amide", as used herein, refers to a group:

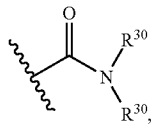

wherein each $R^{30}$ independently represent a hydrogen or hydrocarbyl group, or two $R^{30}$ are taken together with the N atom to which they are attached complete a heterocycle having from 4 to 8 atoms in the ring structure.

The term "carbamate" is art-recognized and refers to a group

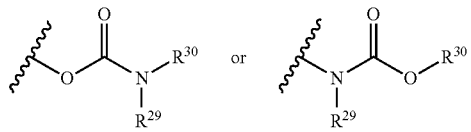

wherein $R^{29}$ and $R^{30}$ independently represent hydrogen or a hydrocarbyl group, such as an alkyl group, or $R^{29}$ and $R^{30}$ taken together with the intervening atom(s) complete a heterocycle having from 4 to 8 atoms in the ring structure.

The term "halogen," or "halide" represents chlorine, fluorine, bromine, or iodine. The term "halo" represents fluoro, chloro, bromo, or iodo.

The term "haloalkyl", as used herein, refers to an alkyl group with one or more halo substituents, or one, two, or three halo substituents. Examples of haloalkyl groups include —$CF_3$, —$CH_2F$, —$CHF_2$, —$CH_2Br$, —$CH_2CF_3$, and —$CH_2CH_2F$.

The term "heteroatom", as used herein, refers to an atom of any element other than carbon or hydrogen. Exemplary heteroatoms include but are not limited to nitrogen, oxygen, and sulfur.

The term "heteroalkyl", as used herein, refers to a saturated or unsaturated chain of carbon atoms and at least one heteroatom, wherein no two heteroatoms are adjacent.

The term "aryl", as used herein, includes substituted or unsubstituted monocyclic aromatic rings in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "aralkyl", as used herein, refers to an alkyl group substituted with an aryl group.

An "aroyl" group, as the term is used herein, refers to an aryl group bonded via an exocyclic carbonyl group, such as a benzoyl group.

The term "heteroaryl", as used herein, includes substituted or unsubstituted monocyclic aromatic ring system, preferably 5- to 7-membered aromatic rings, more preferably 5- to 6-membered rings, whose ring structures include at least one heteroatom, preferably one to four heteroatoms, more preferably one to two heteroatoms. E.g., a 5-membered heteroaryl is furan, thiophene, pyrrole, oxazole, isoxazole, thiazole, isothiazole, pyrazole, imidazole, oxadiazole, thiadiazole, triazole, or tetrazole. In another example, a 6-membered heteroaryl is pyridine, pyrazine, pyrimidine, pyridazine, or triazine. The term "heteroaryl" also include substituted or unsubstituted "polycyclic" ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls.

Illustrative examples of heteroaryl groups include but are not limited to the following entities, in the form of properly bonded moieties:

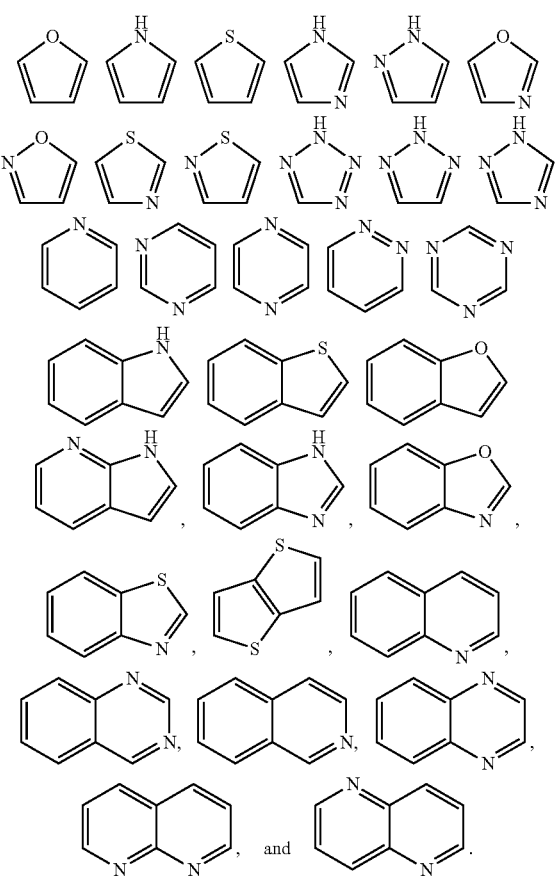

The term "heteroaralkyl" or "hetaralkyl", as used herein, refers to an alkyl group substituted with a heteroaryl group.

A "heteroaroyl" group, as the term is used herein, refers to a heteroaryl group bonded via an exocyclic carbonyl group, analogous to a benzoyl group but wherein the phenyl ring of the benzoyl group is replaced by a heteroaryl group.

The terms "heterocyclyl", "heterocycle", and "heterocyclic", as used herein, refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include substituted or unsubstituted polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, e.g., piperidine, piperazine, pyrrolidine, morpholine, lactones, lactams, and the like, such as e.g., piperidine, piperazine, pyrrolidine, morpholine, lactones, lactams, azetidines, and the like.

The term "heterocyclylalkyl", as used herein, refers to an alkyl group substituted with a heterocycle group which is optionally substituted.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be substituted at any one or more positions capable of bearing a hydrogen atom.

A "cycloalkyl" group, as used herein, refers to a substituted or unsubstituted cyclic hydrocarbon which is completely saturated. "Cycloalkyl" includes substituted or unsubstituted monocyclic and bicyclic rings. Typically, a monocyclic cycloalkyl group has from 3 to about 10 carbon atoms, more typically 3 to 8 carbon atoms unless otherwise defined. Such a monocyclic cycloalkyl group may be substituted or unsubstituted. The second ring of a bicyclic cycloalkyl may be selected from saturated, unsaturated and aromatic rings that are substituted or unsubstituted. Cycloalkyl includes substituted or unsubstituted bicyclic molecules in which one, two or three or more atoms are shared between the two rings. The term "fused cycloalkyl" refers to a substituted or unsubstituted bicyclic cycloalkyl in which each of the rings shares two adjacent atoms with the other ring. The second ring of a fused bicyclic cycloalkyl may be selected from saturated, unsaturated and aromatic rings.

The term "carbocyclylalkyl", as used herein, refers to an alkyl group substituted with a carbocycle group.

A "cycloalkenyl" group, as used herein, refers to a cyclic hydrocarbon containing one or more double bonds. A "cycloalkynyl" group is a cyclic hydrocarbon containing one or more triple bonds.

The terms "polycyclyl", "polycycle", and "polycyclic", as used herein, refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "carbonate" is art-recognized and refers to a group —OCO$_2$—R$^{30}$, wherein R$^{30}$ represents a hydrocarbyl group.

The term "carboxy", as used herein, refers to a group represented by the formula —CO$_2$H.

The term "ester", as used herein, refers to a group —C(O)OR$^{30}$ wherein R$^{30}$ represents a hydrocarbyl group.

The term "ether," as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The term "sulfate" is art-recognized and refers to the group —OSO$_3$H, or a pharmaceutically acceptable salt thereof.

The term "sulfonamide" is art-recognized and refers to the group represented by the general formulae

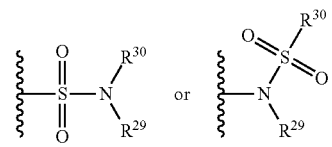

wherein R$^{29}$ and R$^{30}$ independently represents hydrogen or hydrocarbyl, such as alkyl, or R$^{29}$ and R$^{30}$ taken together with the intervening atom(s) complete a heterocycle having from 4 to 8 atoms in the ring structure.

The term "sulfoxide" is art-recognized and refers to the group —S(O)—R$^{30}$, wherein R$^{30}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{30}$, wherein R$^{30}$ represents a hydrocarbyl.

The term "thioalkyl", as used herein, refers to an alkyl group substituted with a thiol group.

The term "thioester", as used herein, refers to a group —C(O)SR$^{30}$ or —SC(O)R$^{30}$ wherein R$^{30}$ represents a hydrocarbyl.

The term "thioether", as used herein, is equivalent to an ether, wherein the oxygen is replaced with a sulfur.

The term "urea" is art-recognized and may be represented by the general formula

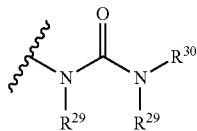

wherein $R^{29}$ and $R^{30}$ independently represent hydrogen or a hydrocarbyl, such as alkyl, or either occurrence of $R^{29}$ taken together with $R^{30}$ and the intervening atom(s) complete a heterocycle having from 4 to 8 atoms in the ring structure.

The term "substituted", as used herein, refers to moieties having substituents replacing one or more hydrogens on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this application, the heteroatoms such as nitrogen may have hydrogen substituents and/or any permissible substituents of organic compounds described herein which satisfy the valences of the heteroatoms. In some embodiments, "substituted" means that the specified group or moiety bears one, two, or three substituents. In other embodiments, "substituted" means that the specified group or moiety bears one or two substituents. In still other embodiments, "substituted" refers to the specified group or moiety bears one substituent.

Substituents can include any substituents described herein, e.g., a lower alkyl (such as $C_{1-6}$ alkyl, e.g., -methyl, -ethyl, and -propyl), a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate.

Unless specifically stated as "unsubstituted," references to chemical moieties herein are understood to include substituted variants. E.g., reference to an "aryl" group or moiety implicitly includes both substituted and unsubstituted variants. The term "unsubstituted" refers to that the specified group bears no substituents.

The term "optionally substituted", as used herein, means that substitution is optional and therefore it is possible for the designated atom or moiety to be unsubstituted.

Any disubstituent referred to herein is meant to encompass the various attachment possibilities when more than one of such possibilities are allowed. E.g., reference to a disubstituent -A-B-, where A≠B, refers herein to such disubstituent with A attached to a first substituted member and B attached to a second substituted member, and it also refers to such disubstituent with A attached to the second substituted member and B attached to the first substituted member.

"Protecting group", as used herein, refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically acceptable salt" is intended to mean a salt of a free acid or base of a compound represented herein that is non-toxic, biologically tolerable, or otherwise biologically suitable for administration to the subject. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

For a compound described herein that contains a basic group, such as an amine, a pharmaceutically acceptable salt may be prepared by any suitable method available in the art, e.g., treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

For a compound described herein that contains an acidic group, such as a carboxylic acid group, base addition salts can be prepared by any suitable method available in the art, e.g., treatment of such compound with a sufficient amount of the desired the desired base, either neat or in a suitable inert solvent. Examples of pharmaceutically acceptable base addition salts include, but are not limited to, lithium, sodium, potassium, calcium, ammonium, zinc, or magnesium salt, or other metal salts; organic amino salts, such as, alkyl, dialkyl, trialkyl, or tetra-alkyl ammonium salts.

Other examples of pharmaceutically acceptable salts include, but are not limited to, camsylate, sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17$^{th}$ Edition, Mack Publishing Company, Easton, Pa., 1985.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present application.

The term "prodrug" is intended to encompass compounds which, under physiologic conditions, are converted into the therapeutically active agents of the present application, e.g., a compound of described herein. A common method for making a prodrug is to include one or more selected moieties which are hydrolyzed under physiologic conditions to yield the desired molecule. In certain embodiments, the prodrug is converted by an enzymatic activity of the host animal. E.g., a prodrug with a nitro group on an aromatic ring could be reduced by reductase to generate the desired amino group of the corresponding active compound in vivo. In another example, functional groups such as a hydroxyl, carbonate, or carboxylic acid in the parent compound are presented as an ester, which could be cleaved by esterases. Additionally, amine groups in the parent compounds are presented in, but not limited to, carbamate, N-alkylated or N-acylated forms (Simplicio et al, "Prodrugs for Amines," Molecules, (2008), 13:519-547). In certain embodiments, some or all of the compounds described herein in a formulation represented above can be replaced with the corresponding suitable prodrug.

A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, e.g., in "Design of Prodrugs", ed. H. Bundgaard, Elsevier, 1985.

A "pharmaceutically active metabolite" or "metabolite" refers to a pharmacologically active product of metabolism/biochemical modification of a compound described herein, e.g., a compound of Formula (I), (I-A), (I-B), or salt thereof, under physiological conditions, e.g., through certain enzymatic pathway. E.g., an oxidative metabolite is formed by oxidation of the parent compound during metabolism, such as the oxidation of a pyridine ring to pyridine-N-oxide. In another example, an oxidative metabolite is formed by demethylation of a methoxy group to result in a hydroxyl group.

Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Compounds of the present application, such as compounds of formulae (I), (I-A) and (I-B), can also exist as various "solvates" or "hydrates." A "hydrate" is a compound that exists in a composition with water molecules. The composition can include water in stoichiometric quantities, such as a monohydrate or a dihydrate, or can include water in random amounts. A "solvate" is a similar composition except that a solvent other that water, such as with methanol, ethanol, dimethylformamide, diethyl ether and the like replaces the water. E.g., methanol or ethanol can form an "alcoholate,"" which can again be stoichiometric or non-stoichiometric. Mixtures of such solvates or hydrates can also be prepared. The source of such solvate or hydrate can be from the solvent of crystallization, inherent in the solvent of preparation or crystallization, or adventitious to such solvent.

The compounds of the application, including their pharmaceutically acceptable salts and prodrugs, can exist as various polymorphs, pseudo-polymorphs, or in amorphous state. The term "polymorph", as used herein, refers to different crystalline forms of the same compound and other solid state molecular forms including pseudo-polymorphs, such as hydrates, solvates, or salts of the same compound. Different crystalline polymorphs have different crystal structures due to a different packing of molecules in the lattice, as a result of changes in temperature, pressure, or variations in the crystallization process. Polymorphs differ from each other in their physical properties, such as x-ray diffraction characteristics, stability, melting points, solubility, or rates of dissolution in certain solvents. Thus crystalline polymorphic forms are important aspects in the development of suitable dosage forms in pharmaceutical industry.

The present application further embraces isolated compounds according to formula (I), (I-A) or (I-B). The term "isolated compound" refers to a preparation of a compound of formula (I), (I-A) or (I-B), or a mixture of compounds according to formula (I), (I-A) or (I-B), wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of formula (I), (I-A) or (I-B) or a mixture of compounds according to formula (I), (I-A) or (I-B), which contains the named compound or mixture of compounds according to formula (I), (I-A) or (I-B) in an amount of at least 10 percent by weight of the total weight. Preferably the preparation contains the named compound or mixture of compounds in an amount of at least 50% by weight of the total weight; more preferably at least 80% by weight of the total weight; and most preferably at least 90%, at least 95% or at least 98% by weight of the total weight of the preparation.

The compounds of the application and intermediates may be isolated from their reaction mixtures and purified by standard techniques such as filtration, liquid-liquid extraction, solid phase extraction, distillation, recrystallization or chromatography, including flash column chromatography, or HPLC.

Isomerism and Tautomerism in Described Compounds
Tautomerism

Within the present application it is to be understood that a compound described herein or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the application encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. E.g., tautomerism may be exhibited by a pyrazolyl group bonded as indicated by the wavy line. While both substituents would be termed a 4-pyrazolyl group, it is evident that a different nitrogen atom bears the hydrogen atom in each structure.

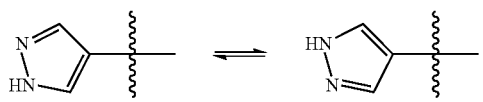

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. E.g., the equilibrium:

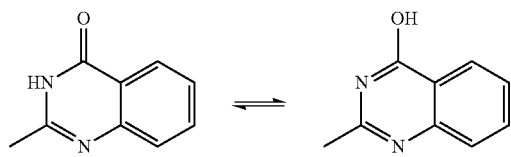

is an example of tautomerism. Accordingly, a structure depicted herein as one tautomer is intended to also include the other tautomer.

Optical Isomerism

It will be understood that when compounds of the present application contain one or more chiral centers, the compounds may exist in, and may be isolated as pure enantiomeric or diastereomeric forms or as racemic mixtures. The present application therefore includes any possible enantiomers, diastereomers, racemates in their pure forms or mixtures thereof, and salts thereof, of the compounds of the application.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

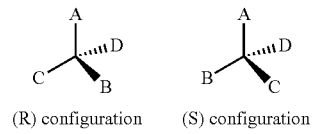

(R) configuration     (S) configuration

In certain embodiments, the therapeutic preparation may be enriched to provide predominantly one enantiomer of a compound (e.g., of formula (I), (I-A) or (I-B)). An enantiomerically enriched mixture may comprise, e.g., at least 60 mol percent of one enantiomer, or more preferably at least 75, 90, 95, or even 99 mol percent. In certain embodiments, a compound of the application may have greater than 30% ee, 40% ee, 50% ee, 60% ee, 70% ee, 80% ee, 90% ee, or even 95% or greater ee. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. E.g., if a composition or compound mixture contains 98 grams of a first enantiomer and 2 grams of a second enantiomer, it would be said to contain 98 mol percent of the first enantiomer and only 2% of the second enantiomer.

In certain embodiments, compounds of the application may have more than one stereocenter. In certain such embodiments, compounds of the application may be enriched in one or more diastereomer. E.g., a compound of the application may have greater than 30% de, 40% de, 50% de, 60% de, 70% de, 80% de, 90% de, or even 95% or greater de.

Isolated optical isomers may be purified from racemic mixtures by well-known chiral separation techniques, such as but not limited to, normal and reverse phase chromatography, and crystallization. According to one such method, a racemic mixture of a compound of the application, or a chiral intermediate thereof, is separated using a chiral salt or carried out on a Chiralcell OD column. The column is operated according to the manufacturer's instructions.

Isolated optical isomers (enantiomerically pure compounds) can also be prepared by the use of chiral intermediates or catalysts in synthesis. When a chiral synthetic intermediate is used, the optical center (chiral center) can be preserved without racemization throughout the remainder of the preparative procedure, as is well known in the art. Chiral catalyst can be used to impart at least some degree of enantiomeric purity to products of reactions catalyzed by the chiral catalyst. And, in some cases, compounds having at least some degree of enantiomeric enrichment can be obtained by physical processes such as selective crystallization of salts or complexes formed with chiral adjuvants.

A variety of compounds in the present application may exist in particular geometric or stereoisomeric forms. The present application takes into account all such compounds, including tautomers, cis- and trans-isomers, R- and S-enantiomers, diastereomers, (D)-isomers, (L)-isomers, the racemic mixtures thereof, and other mixtures thereof, as being covered within the scope of this application. All tautomeric forms are encompassed in the present application. Additional asymmetric carbon atoms may be present in a substituent such as an alkyl group. All such isomers, as well as mixtures thereof, are intended to be included in this application, unless the stereochemistry or isomeric form is specifically indicated.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (see below). It is further understood that certain structural elements, including steric bulk or substituents on the amide nitrogen, may enhance the stability of a rotamer to the extent that a compound may be isolated as, and exist indefinitely, as a single stable rotamer. The present application therefore includes any possible stable rotamers of formula (I) which are biologically active in the treatment of cancer or other proliferative disease states.

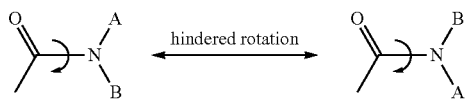

Regioisomerism

The preferred compounds of the present application have a particular spatial arrangement of substituents on the aromatic rings, which are related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

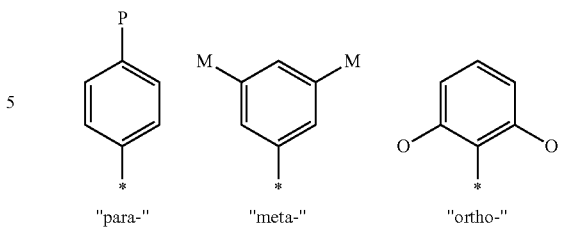

Isotopical Labeling in Described Compounds

The present application further includes all pharmaceutically acceptable isotopically labeled compound [e.g., of formula (I), (I-A) or (I-B)]. An "isotopically" or "radiolabeled" compound is a compound where one or more atoms are replaced or substituted by an atom having an atomic mass or mass number different from the atomic mass or mass number typically found in nature (i.e., naturally occurring). E.g., in certain embodiments, in compounds [e.g., of formula (I), (I-A) or (I-B)], hydrogen atoms are replaced or substituted by one or more deuterium or tritium (e.g., hydrogen atoms on a $C_{1-6}$ alkyl or a $C_{1-6}$ alkoxy are replaced with deuterium, such as $d_3$-methoxy or 1,1,2,2-$d_4$-3-methylbutyl).

Certain isotopically labeled compounds [e.g., compounds of formula (I), (I-A) or (I-B)], e.g., those incorporating a radioactive isotope, are useful in drug and/or substrate tissue distribution studies. The radioactive isotopes tritium, i.e., $^3H$, and carbon 14, i.e., $^{14}C$, are particularly useful for this purpose in view of their ease of incorporation and ready means of detection.

Such isotopically labeled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. Further, substitution with heavier isotopes such as deuterium (i.e., $^2H$) may afford certain therapeutic advantages resulting from greater metabolic stability, for example increased in vivo half-life or reduced dosage requirements.

Substitution with positron emitting isotopes, such as $^{11}C$, $^{18}F$, $^{15}O$, and $^{13}N$, can be useful in Positron Emission Tomography (PET) studies for examining substrate receptor occupancy.

Isotopically labeled compounds [e.g., of formula (I), (I-A) or (I-B)] or their corresponding prodrugs can generally be prepared by conventional techniques known to those skilled in the art or by processes analogous to those described in the accompanying examples using an appropriate isotopically labeled reagent in place of the non-labeled reagent previously employed. Suitable isotopes that may be incorporated in compounds of the present application include but are not limited to isotopes of hydrogen, carbon, nitrogen, oxygen, phosphorous, fluorine, chlorine, and iodine, such as $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, $^{131}I$, $^{31}P$, and $^{32}P$.

Isotopically labeled compounds of this application and prodrugs thereof can generally be prepared by carrying out the procedures disclosed in the schemes or in the examples and preparations described below by substituting a readily available isotopically labeled reagent for a non-isotopically labeled reagent.

Provisos may apply to any of the disclosed categories or embodiments such that specific embodiments or species may be excluded from such categories or embodiments.

In various embodiments, the compound or set of compounds, such as are used in the inventive methods, can be any one of any of the combinations and/or sub-combinations of the above-listed embodiments.

Pharmaceutical Compositions

The compositions and methods of the present application may be utilized to treat a subject, such as a mammal, e.g., human, or a non-human mammal, in need thereof. When administered to an animal, such as a human, the composition or the compound is preferably administered as a pharmaceutical composition comprising, e.g., a compound of the application and a pharmaceutically acceptable carrier. In certain embodiments, the application relates to a pharmaceutical composition comprising as active ingredient a therapeutically effective amount of a compound described herein, or a pharmaceutically acceptable salt, solvate, or prodrug thereof, in association with at least one pharmaceutically acceptable carrier, excipient, or diluent.

The term "pharmaceutically acceptable carrier", as used herein, refers to a pharmaceutically acceptable material, composition or vehicle, such as a liquid or solid filler, diluent, excipient, solvent or encapsulating material, which can act, e.g., to stabilize, increase solubility or to increase the absorption of a compound such as a compound of the application. Each carrier must be "acceptable" in the sense of being compatible with the other ingredients of the formulation and not injurious to the patient.

Pharmaceutically acceptable carriers are well known in the art. E.g., some examples of materials which can serve as pharmaceutically acceptable carriers include, but are not limited to: (1) sugars, such as lactose, glucose, sucrose or dextrans; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as glycerol or propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) antioxidants, such as ascorbic acid or glutathione; and (22) other non-toxic compatible substances employed in pharmaceutical formulations, such as chelating agents, low molecular weight proteins or other stabilizers or excipients.

The choice of a pharmaceutically acceptable carrier, including a physiologically acceptable agent, depends, e.g., on the route of administration of the composition. The pharmaceutical composition can be a self-emulsifying or a self-microemulsifying drug delivery system. The pharmaceutical composition also can be a liposome or other polymer matrix, which can have incorporated therein. Liposomes, e.g., which comprise phospholipids or other lipids, are nontoxic, physiologically acceptable and metabolizable carriers that are relatively simple to make and administer.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. Such liquid compositions may optionally contain: pharmaceutically-acceptable excipients such as suspending agents (e.g., sorbitol, methyl cellulose, sodium alginate, gelatin, hydroxyethylcellulose, carboxymethylcellulose, aluminum stearate gel and the like); non-aqueous vehicles, e.g., oil (e.g., almond oil or fractionated coconut oil), propylene glycol, ethyl alcohol, or water; preservatives (e.g., methyl or propyl p-hydroxybenzoate or sorbic acid); wetting agents such as lecithin; and, if desired, flavoring or coloring agents.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

A pharmaceutical composition can be administered to a subject by any of a number of routes of administration including, but not limited to, e.g., orally [e.g., drenches as in aqueous or non-aqueous solutions or suspensions, tablets, pills, capsules (including sprinkle capsules and gelatin capsules), boluses, powders, granules, pastes for application to the tongue]; absorption through the oral mucosa (e.g., sublingually); anally, rectally or vaginally (e.g., as a pessary, cream or foam); parenterally (including intramuscularly, intravenously, subcutaneously or intrathecally as, e.g., a sterile solution or suspension); nasally; intraperitoneally; subcutaneously; transdermally (for example as a patch applied to the skin); and topically (e.g., as a cream, ointment or spray applied to the skin, or as an eye drop). The composition or compound may also be formulated for inhalation. In certain embodiments, the composition or compound may be simply dissolved or suspended in sterile water. Details of appropriate routes of administration and compositions suitable for same can be found in, e.g., U.S. Pat. Nos. 6,110,973, 5,763,493, 5,731,000, 5,541,231, 5,427,798, 5,358,970 and 4,172,896, as well as in patents cited therein. Sterile compositions are also contemplated by the application, including compositions that are in accord with national and local regulations governing such compositions. Preferably, the compositions are formulated for intravenous or oral administration.

For oral administration, the compounds of the application may be provided in a solid form, such as a tablet, pills, dragees, powers, granules, or capsule, or as a solution, emulsion, or suspension. To prepare the oral compositions, the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, e.g., carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, e.g., cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; (11) coloring agents; (12) emulsifying and suspending agents, such as, ethoxylated isostearyl alcohols, polyoxyethylene sorbitol, sorbitan esters, microcrystalline cellulose, aluminum metahydroxide, bentonite, agar, and tragacanth; and (13) other non-toxic compatible substances employed in pharmaceutical formulations, such as, without limitation, buffering agents, perfuming and preservative agents, sweetening agents, flavoring agents.

Oral tablets may be made by compression or molding, optionally with one or more accessory ingredients, such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include hydroxypropylmethyl cellulose, starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. E.g., to prepare hard gelatin capsules, active ingredient(s) may be mixed with a solid, semi-solid, or liquid diluent. Soft gelatin capsules may be prepared by mixing the active ingredient with water, oil such as peanut oil or olive oil, liquid paraffin, a mixture of mono and di-glycerides of short chain fatty acids, polyethylene glycol 400, or propylene glycol.

The pharmaceutical compositions may also be formulated so as to provide slow or controlled release of the active ingredient therein using, e.g., hydroxypropylmethyl cellulose in varying proportions to provide the desired release profile, other polymer matrices, liposomes and/or microspheres. They may be sterilized by, e.g., filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs, or may be lyophilized or presented as a dry product for reconstitution with water or other suitable vehicle before use. In addition to the active ingredient, the liquid dosage forms may contain inert diluents commonly used in the art, such as, e.g., water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition, formulations of the pharmaceutical compositions for administration to the mouth may be presented as a mouthwash, or an oral spray, or an oral ointment.

The phrases "parenteral administration" and "administered parenterally", as used herein, means modes of administration other than enteral and topical administration, usually by injection, and includes, without limitation, intravenous, intramuscular, intraarterial, intrathecal, intracapsular, intraorbital, intracardiac, intradermal, intranasal, intrapeirtoneal, transtracheal, subcutaneous, subcuticular, intraarticular, subcapsular, subarachnoid, intraspinal, and intrasternal injection and infusion.

For parenteral use, the agents of the application may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be reconstituted into a sterile injectable formulation, such as solutions or dispersions just prior to use, which may contain antioxidants, buffers, bacteriostats, solutes which render the formulation isotonic with the blood of the intended recipient or suspending or thickening agents. Illustrative infusion doses range from about 1 to 1000 µg/kg/minute of agent admixed with a pharmaceutical carrier over a period ranging from several minutes to several days.

Examples of suitable aqueous and nonaqueous carriers that may be employed in the pharmaceutical compositions of the application include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, e.g., by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, e.g., paraben, chlorobutanol, phenol sorbic acid, and the like. It may also be desirable to include isotonic agents, such as sugars, sodium chloride, and the like into the compositions.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, e.g., to effect delayed release of an agent or to selectively target one or more cells, tissues or organs.

For rectal, vaginal, or urethral administration, formulations of the pharmaceutical compositions may be presented as a suppository, which may be prepared by mixing one or more active compounds with one or more suitable nonirritating excipients or carriers comprising, e.g., cocoa butter, polyethylene glycol, a suppository wax or a salicylate, and which is solid at room temperature, but liquid at body temperature and, therefore, will melt in the rectum or vaginal cavity and release the active compound. Formulations which are suitable for vaginal administration also include pessaries, tampons, creams, gels, pastes, foams or spray formulations containing such carriers as are known in the art to be appropriate.

For topical applications or transdermal administration, the active compounds of the present application may be mixed under sterile conditions with a pharmaceutically acceptable carrier, and with any preservatives, buffers, excipients, or propellants, such as animal and vegetable fats, oils, waxes, paraffins, starch, tragacanth, cellulose derivatives, polyethylene glycols, silicones, bentonites, silicic acid, talc and zinc oxide, or mixtures thereof. Dosage forms for the topical include powders, sprays, ointments, pastes, creams, lotions, gels, solutions, patches and inhalants. The active compounds may be mixed with a pharmaceutical carrier at a concentration of about 0.1% to about 10% of drug to vehicle.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present application to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this application. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

Alternatively or additionally, compositions can be formulated for delivery via a catheter, stent, wire, or other intraluminal device. Delivery via such devices may be especially useful for delivery to the bladder, urethra, ureter, rectum, or intestine.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

A physician or veterinarian having ordinary skill in the art can readily determine and prescribe the therapeutically effective amount of the pharmaceutical composition required. The term "therapeutically effective amount" or "dose", or "dosage", as used herein, refers to an amount or dose sufficient to generally bring about the desired therapeutic benefit or an amount sufficient to modulate the biological activity of the target receptor in subjects needing such treatment.

Effective amounts or dosages of the compounds of the application may be ascertained by routine methods, such as modeling, dose escalation, or clinical trials, taking into account routine factors. Actual dosage levels of the active ingredients in the pharmaceutical compositions may be varied. In general, a suitable daily dose of an active compound used in the compositions and methods of the application will be that amount of the compound that is the lowest dose effective to produce a therapeutic effect.

The selected dosage level will depend upon a variety of factors including the activity of the particular compound or combination of compounds employed, or the salts, solvate, and prodrug thereof, the route of administration, the time of administration, the rate of excretion of the particular compound(s) being employed, the duration of the treatment, other drugs, compounds and/or materials used in combination with particular compound(s) employed, age, sex, weight, condition, general health, prior medical history of the patient being treated, and the preference and experience of the physician or veterinarian in charge, and like factors well known in the medical arts.

E.g., in choosing a regimen for a subject, such as a patient, it can frequently be necessary to begin with a higher dosage and when the condition is under control to reduce the dosage. In another example, it is also possible to start at a dosage of the pharmaceutical composition for compound at levels lower than that required in order to achieve the desired therapeutic effect and gradually increase the dosage until the desired effect is achieved.

The compounds of the application are effective over a wide dosage range. E.g., in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day, or 25 to 200 mg per day, or 50 to 100 mg per day, or less than 100 mg per day.

In some embodiments, the compounds of the application are dispensed in unit dosage form including from about 0.05 mg to about 1000 mg of active ingredient together with a pharmaceutically acceptable carrier per unit dosage. In other embodiments, a unit dosage form includes from about 10 to about 200 mg of active ingredient. In other embodiments, dosage forms suitable for oral, nasal, pulmonal or transdermal administration include from about 125 µg to about 1250 mg, preferably from about 250 µg to about 500 mg, and more preferably from about 2.5 mg to about 250 mg, of the compounds admixed with a pharmaceutically acceptable carrier or diluent. Methods to determine efficacy and dosage are known to those skilled in the art (Isselbacher et al. (1996) Harrison's Principles of Internal Medicine 13$^{ed}$., 1814-1882, herein incorporated by reference).

Dosage forms can be administered daily or more than once a day, such as twice or thrice daily. Alternatively dosage forms can be administered less frequently than daily, such as every other day, or weekly, if found to be advisable by a prescribing physician. A larger dosage can be delivered by multiple administrations of the agent. In some embodiments, dosage forms are administered once, twice, or thrice daily. In preferred embodiments, the active compound will be administered once daily. Once improvement of the patient's disease has occurred, the dose may be adjusted for maintenance treatment. E.g., the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Methods and Uses

In various embodiments, compounds of the application can be used to modulate, such as to activate (agonist), or to block activation of (antagonist), a PAR2 receptor. Accordingly, in various embodiments, the application provides a method of modulating a PAR2 receptor comprising contacting the receptor with an effective amount or concentration of a compound of the application. In various embodiments, the compound of the application is an antagonist of a PAR2 receptor. In various embodiments, contacting can take place in vivo within tissues of a patient, such as a human patient. In various embodiments, modulation of a PAR2 receptor, for example, antagonism of PAR2, by a compound of the application can be used to treat a disease or disorder in a patient, as described herein.

In various embodiments, the application provides a method of treating a disease or disorder in a patient wherein modulation of a PAR2 receptor is medically indicating, comprising administering to the subject, such as a patient, a compound of the application in a dose, at a frequency, and for duration to provide a beneficial effect to the subject. Modulation, such as agonism or antagonism, of a PAR2 receptor can be medically indicated in treatment of a disease or disorder wherein the PAR2 receptor plays a metabolic or regulatory role. Certain such conditions can be treated by selective modulation of a PAR2 receptor, while the other protease-activated receptors such as PAR1, PAR3 and PAR4 are not influenced by administration of the compound of the application at the dose provided. In various embodiments, compounds of the application can be PAR2 antagonists, and some of those are selective PAR2 antagonists with respect to other protease-activated receptors such as PAR1, PAR3 and PAR4. By "selective" is meant that one receptor is modulated at concentrations of the compound at least 10 times lower than the concentrations at which the comparative receptor is modulated by that compound. In further embodiments, the compound of the application can further modulate other types or classes of protease-activated receptors such as PAR1, PAR3 and PAR4.

In various embodiments, the application provides a use of a compound of the application for treatment of a disease or disorder in a patient. For example, a compound of the application can be used in the preparation of a medicament for administration to a patient suffering from a disease or disorder. More specifically, the disease or disorder can comprise pain, musculoskeletal inflammation, neuroinflammatory disorders, airway inflammation, itch, dermatitis, colitis and related conditions.

In some embodiments, the application provides a use of a compound of the application for treatment of a pain, including but not limited to acute pain, chronic pain, inflammatory and neuropathic pain. The pain may be chronic, allodynia (the perception of pain from a normally innocuous stimulus), hyperalgesia (an exaggerated response to any given pain stimulus) and an expansion of the receptive field (i.e. the area that is "painful" when a stimulus is applied), phantom pain or inflammatory pain. Acute pain types comprise, but are not limited to, pain associated with tissue damage, postoperative pain, pain after trauma, pain caused by burns, pain caused by local or systemic infection, visceral pain associated with diseases comprising: pancreatitis, intestinal cystitis, dysmenorrhea, Irritable bowel syndrome, Crohn's disease, ureteral colic and myocardial infarction. Furthermore, the term "pain" comprises pain associated with CNS disorders comprising: multiple sclerosis, spinal cord injury, traumatic brain injury, Parkinson's disease and stroke. In some embodiments, "pain" relates to chronic pain types comprising headache (for example migraine disorders, episodic and chronic tension-type headache, tension-type like headache, cluster headache, and chronic paroxysmal hemicrania), low back pain, cancer pain, osteoarthritis pain and neuropathic pain, but is not limited thereto. Inflammatory pain (pain in response to tissue injury and the resulting inflammatory process) as defined herein relates to inflammatory pain associated with diseases comprising connective tissue diseases, rheumatoid arthritis, systemic lupus erythematosus, multiple sclerosis and arthritis, but is not limited thereto. Neuropathic pain (pain resulting from damage to the peripheral nerves or to the central nervous system itself) includes conditions comprising, but not limited to metabolic neuropathies (e.g., diabetic neuropathy), post-herpetic neuralgia, trigeminal neuralgia, cranial neuralgia, post-stroke neuropathic pain, multiple sclerosis-associated neuropathic pain, HIV/AIDS-associated neuropathic pain, cancer-associated neuropathic pain, carpal tunnel-associated neuropathic pain, spinal cord injury-associated neuropathic pain, complex regional pain syndrome, fibromyalgia-associated neuropathic pain, reflex sympathic dystrophy, phantom limb syndrome or peripheral nerve or spinal cord trauma, nerve transection including surgery, limb amputation and stump pain, pain caused by the side effects of anti-cancer and anti-AIDS therapies, post-surgical neuropathic pain, neuropathy-associated pain such as in idiopathic or post-traumatic neuropathy and mononeuritis, and neuropathic pain caused by connective tissue disease such as rheumatoid arthritis, Wallenberg's syndrome, systemic lupus erythematosus, multiple sclerosis, or polyarteritis *nodosa*. The neuropathy can be classified as radiculopathy, mononeuropathy, mononeuropathy multiplex, polyneuropathy or plexopathy.

In some embodiments, the application provides a use of a compound of the application for treatment of a musculoskeletal inflammatory disorder, including but not limited to low back pain, fibromyalgia, gout, osteoarthritis, rheumatoid arthritis, and tendinitis.

In some embodiments, the application provides a use of a compound of the application for treatment of a neuroinflammatory disorder, including but not limited to Multiple Sclerosis (MS), which includes, but is not limited to, for example, Relapse Remitting Multiple Sclerosis (RRMS), Secondary Progressive Multiple Sclerosis (SPMS), and Primary Progressive Multiple Sclerosis (PPMS); Parkinson's disease; Multiple System Atrophy (MSA); Corticobasal Degeneration; Progressive Supranuclear Paresis; Guillain-Barre Syndrome (GBS); and chronic inflammatory demyelinating polyneuropathy (CIDP).

In some embodiments, the application provides a use of a compound of the application for treatment of an airway inflammatory disorder, including but not limited to Kartagener syndrome, asthma (such as difficult asthma, or severe persistent asthma), vocal cord dysfunction (such as uncontrolled closing of the vocal cords while breathing), spasmodic croup, reflexive vasomotor disease, and autonomic disorders.

In some embodiments, the application provides a use of a compound of the application for treatment of itch.

In some embodiments, the application provides a use of a compound of the application for treatment of dermatitis, including but not limited to contact dermatitis, atopic dermatitis, seborrheic dermatitis, nummular dermatitis, exfoliative dermatitis, chronic dermatitis, stasis dermatitis, and perioral dermatitis.

In some embodiments, the application provides a use of a compound of the application for treatment of colitis, including but not limited to inflammatory bowel disease (IBD) colitis (Crohn's disease or ulcerative colitis), microscopic colitis, chemical colitis, ischemic colitis, infectious colitis (food poisoning caused by infections, and infections caused by parasites or bacteria).

It is believed that antagonism of PAR2, in particular, is medically indicated for the treatment of the above-listed conditions. By antagonism is meant blocking a receptor, in this case a PAR2 receptor, without causing it to transduce a signal. That is, antagonism results in blocking an endogenous or exogenous ligand from activating, or causing antagonism, of the receptor.

It is within ordinary skill to evaluate any compound disclosed and claimed herein for effectiveness in modulation of PAR2 receptor and in the various cellular assays using the procedures described above or found in the scientific literature. Accordingly, the person of ordinary skill can prepare and evaluate any of the claimed compounds without undue experimentation.

Any compound found to be an effective modulator, agonist or antagonist, can likewise be tested in animal models and in human clinical studies using the skill and experience of the investigator to guide the selection of dosages and treatment regimens.

In certain embodiments, the application comprises a method for conducting a pharmaceutical business, by determining an appropriate formulation and dosage of a compound of the application for treating or preventing any of the diseases or conditions as described herein, conducting therapeutic profiling of identified formulations for efficacy and toxicity in animals, and providing a distribution network for selling an identified preparation as having an acceptable therapeutic profile. In certain embodiments, the method further includes providing a sales group for marketing the preparation to healthcare providers.

In certain embodiments, the application relates to a method for conducting a pharmaceutical business by determining an appropriate formulation and dosage of a compound of the application for treating or preventing any of the disease or conditions as described herein, and licensing, to a third party, the rights for further development and sale of the formulation.

The term "healthcare providers" refers to individuals or organizations that provide healthcare services to a person, community, etc. Examples of "healthcare providers" include doctors, hospitals, continuing care retirement communities, skilled nursing facilities, subacute care facilities, clinics, multispecialty clinics, freestanding ambulatory centers, home health agencies, and HMO's.

Drug Combinations

The compounds of the present application may be used in pharmaceutical compositions or methods in combination with one or more additional active ingredients in the treatment of the diseases and disorders described herein. Further additional active ingredients include other therapeutics or agents that mitigate adverse effects of therapies for the intended disease targets. Such combinations may serve to increase efficacy, ameliorate other disease symptoms, decrease one or more side effects, or decrease the required dose of an inventive compound. In certain embodiments, such combination provides an additive effect, wherein an additive effect refers to the sum of each of the effects of individual administration of the compound of the application and one or more additional therapeutic agent(s). In other embodiments, such combination provides a synergistic effect, in which the therapeutic effect exceeds the sum of each of the effects of individual administration of the compound of the application and one or more additional therapeutic agent(s).

The additional active ingredients may be administered in a separate pharmaceutical composition from a compound of the present application or may be included with a compound of the present application in a single pharmaceutical composition. The additional active ingredients may be administered simultaneously with, prior to, or after administration of a compound of the present application. Actual dosage levels of the active ingredients in the pharmaceutical compositions may be varied so as to obtain an amount of the active ingredient that is effective to achieve the desired therapeutic response for a particular subject, such as a patient, composition, and mode of administration, without being toxic to the subject.

Combination agents include additional active ingredients that are known or discovered to be effective in treating the diseases and disorders described herein, including those active against another target associated with the disease. E.g., compositions and formulations of the application, as well as methods of treatment, can further comprise other drugs or pharmaceuticals, e.g., other active agents useful for treating or palliative for the target diseases or related symptoms or conditions. The pharmaceutical compositions of the any compound described herein may additionally comprise one or more of such active agents, and methods of treatment may additionally comprise administering an effective amount of one or more of such active agents.

EXAMPLES

The following examples are offered to illustrate but not to limit the application. One of skill in the art will recognize that the following synthetic reactions and schemes may be modified by choice of suitable starting materials and reagents in order to access other compounds of the application, or a pharmaceutically acceptable salt thereof.

Synthetic Protocols

Exemplary chemical entities useful in methods of the application will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Unless otherwise specified, the variables are as defined above in reference to Formula (I), (I-A), or (I-B). Isotopically labeled compounds as described herein are prepared according to the methods described below, using suitably labeled starting materials. Such materials are generally available from commercial suppliers of radiolabeled chemical reagents.

Terms and Abbreviations:
ACN acetonitrile;
aq aqueous;
Atm atmospheric pressure;
Boc t-butoxycarbonyl;
Borax di-sodium tetraborate or sodium borate or sodium tetraborate;
Cbz benzyloxycarbonyl;
CDI 1,1'-carbonyldiimidazole;
dba dibenzylideneacetone;
DCM dichloromethane;
DEA diethylamine;
DIBAL-H diisobutylaluminium hydride;
DIPEA diisopropylethylamine;
DME 1,2-dimethoxyethane;
DMF N,N-dimethyl formamide;
DMSO dimethyl sulfoxide;
Et$_2$O diethyl ether;
EtOAc ethyl acetate;
EtOH ethanol;
eq. or equiv. equivalent;
h hour(s);
HATU 2-(7-aza-1H-benzotriazole-1-yl)-1,1,3,3-tetramethyluronium hexafluorophosphate;
HBTU O-benzotriazole-N,N,N',N'-tetramethyluronium hexafluorophosphate
HPLC high performance liquid chromatography;
LCMS liquid chromatography mass spectrometry;
LDA lithium diisopropylamide;
LiHMDS lithium bis(trimethylsilyl)amide;
MeOH methanol;
min minute(s);
MS mass spectrometry;
MW microwave(s);
NH$_4$OAc ammonium acetate;
NMR nuclear magnetic resonance;
ox oxidation;
Psi pounds per square inch;
quant. quantitative;
RCM ring closing metathesis;
r.t. room temperature;
sat. saturated;
SFC supercritical fluid chromatography;
T3P propylphosphonic anhydride;
TFA trifluoroacetic acid;
THF tetrahydrofuran;
TLC thin layer chromatography;
TMEDA tetramethylethylenediamine;
UPLC ultra performance liquid chromatography.

LC-MS Conditions:
Method A:
LC-MS carried out using a Shimadzu LCMS-2020. UV detection=190-400 nm, mass spec=ESI. The column used was Ascentis express C18, 2.1 mm×50 mm, 2.7 m at 40° C. Flow rate was lml/min using a solvent gradient of 5 to 100% B over 1.8 minutes, where A=water (0.05% TFA) and B=acetonitrile (0.05% TFA). Where indicated, with designation base or modified to basic eluents or conditions, the mobile phases were made basic and replaced with A=water+ 6.5 mM NH$_4$HCO$_3$ to pH10 in A, and B=acetonitrile (no additive).

Method B:
UPLC-MS was carried out using a Waters Acquity UPLC and Waters SQD mass spectrometer. UV detection=210-400 nm, mass spec=ESI with positive/negative switching and cone voltage=10 V. The column used was Waters Acquity HSS T3, 1.8 μm, 2.1×30 mm, at temperature 30° C. Flow rate was lml/min using a solvent gradient of 2 to 98% B over 1.5 minutes (total runtime with equilibration back to starting conditions 2 min), where A=0.1% formic acid in water and B=0.1% formic acid in acetonitrile.

Method C:
Analytical HPLC chromatograms were performed using an Agilent 1100 series instrument. The mass spectra were recorded with a Waters Micromass ZQ detector at 100° C.

The mass spectrometer was equipped with an electrospray ion source (ESI) operated in a positive ion mode and was set to scan between m/z 150-750 with a scan time of 0.3 s. Products and intermediates were analyzed by HPLC/MS on a Gemini (5.0 mM, 2.10×30 mm) using a high pH buffer gradient of 5% to 100% of ACN in H$_2$O (0.03% (NH$_4$)$_2$CO$_3$/0.375% NH$_4$OH) over 3.0 min at 1.8 mL/min for a 3.5 min run and on a Kinetex EVO (5.0 mM, 2.10×50 mm) using a low pH buffer gradient of 5% to 100% of ACN in H$_2$O (0.05% HCOOH) over 2.8 min at 2.2 mL/min for a 3.5 min run.

Method D:
Instruments: Waters Acquity H Class, Photo Diode Array, SQ Detector; Column: BEH C18, 1.7 micron, 2.1×50 mm; Gradient [time (min)/solvent B in A (%)]: 0.00/5, 0.40/5, 0.8/35, 1.20/55, 2.50/100, 3.30/100 4.00/5; Solvents: solvent A=5 mM ammonium acetate and 0.1% formic acid in H$_2$O; solvent B=0.1% formic acid in MeCN; Injection volume 2 μL; UV detection 200 to 400 nM; Mass detection 100 to 1200 AMU (+ve electrospray); column at ambient temperature; Flow rate 0.5 mL/min.

1H NMR spectroscopy:
The chemical shifts are reported in part-per-million from a tetramethylsilane standard.

General Synthetic Scheme
Compounds of formula (I), (I-A) or (I-B) of the application can be prepared following the general synthetic scheme below:

General procedure 1:

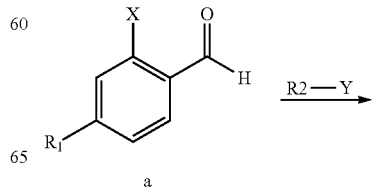

a

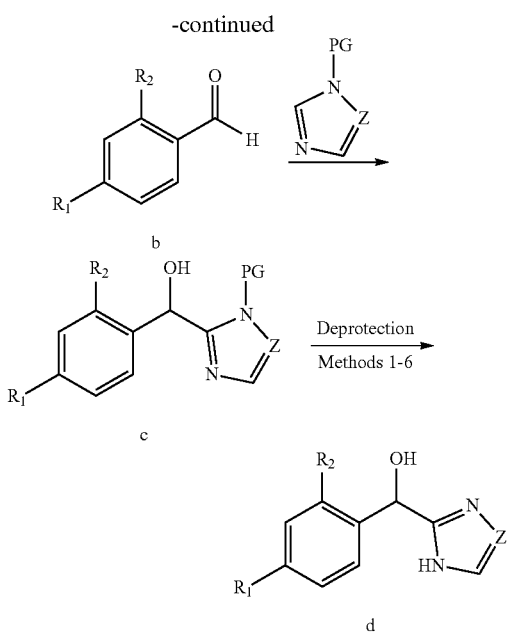

X = halogen
Y = B(OH)₂, B(OR)₂, SNBu3, NH
PG = protecting group
Z = N or C—H

General Suzuki-Type Coupling (a to b, where Y=B(OH)2 or B(OR)2:

2-Bromo-4-fluorobenzaldehyde (5 g, 24.63 mmol) is added to propylboronic acid (3.25 g, 36.94 mmol), PdCl₂ (dppf) (1.802 g, 2.46 mmol) and CS₂CO₃ (16.05 g, 49.26 mmol) in dioxane (40 mL) and water (10 mL), then warmed to 80° C. under nitrogen. The resulting suspension is stirred at 80° C. for 12 hours. The reaction mixture is diluted with EtOAc (50 mL), and washed sequentially with saturated brine (20 mL×3). The organic layer is dried over Na₂SO₄, filtered and evaporated to afford crude product. The crude product is purified by flash silica chromatography, elution gradient 0 to 5% EtOAc in petroleum ether.

General Buchwald-Type Coupling (a to b, Where Y=NH):

PdOAc₂ (553 mg, 2.46 mmol) is added to pyrrolidine (2.59 g, 36.9 mmol), BINAP (4.6 g, 7.4 mmol), CS₂CO₃ (16.05 g, 4.93 mmol) and 2-bromo-4-fluorobenzaldehyde (5 g, 24.63 mmol) in toluene (50 mL) under nitrogen. The resulting solution is stirred at 120° C. for 1 hour. The reaction mixture is filtered through celite. The solvent is removed under reduced pressure. The crude product is purified by flash silica chromatography, elution gradient 0 to 1% EtOAc in petroleum ether.

General Stille-Type Coupling (a to b, where Y=SnBu3:

4-(Tributylstannyl)thiazole (1198 mg, 3.20 mmol) is added to a stirred solution of 2-bromo-4-fluorobenzaldehyde (500 mg, 2.46 mmol) and bis(triphenylphosphine)palladium (II) chloride (104 mg, 0.15 mmol) in DMF (10 mL) under nitrogen. The resulting solution is stirred at 100° C. for 16 hours. The solution is washed with brine and KF. The aqueous layer is extracted with EtOAc (2×20 mL). The solvent is removed under reduced pressure to afford crude product. The crude product is purified by flash silica chromatography with EtOAc/petroleum ether (1:30).

General Alkylation of Aldehyde (b to c):

To the solution of 1-((2-(trimethylsilyl)ethoxy)methyl)-1H-imidazole (1.355 g, 6.83 mmol) in THF (30 mL) at −78° C. is added n-butyllithium (5.05 mL, 8.07 mmol) dropwise. The reaction mixture is stirred at −78° C. for 30 mins, then 4-fluoro-2-(pyrrolidin-1-yl)benzaldehyde (1.2 g, 6.21 mmol) is added. The reaction is warmed up to RT and stirred at RT for 1 hr. The reaction is then quenched with sat. NH₄Cl solution and extracted with EtOAc (3×60 mL). The organic layer is combined, washed with water (60 mL), brine (60 mL), dried over MgSO4, filtered and concentrated to give off-white solid.

General Deprotection Strategies:

Method 1:

To a solution of (4-fluoro-2-propylphenyl)(1-((2-(trimethylsilyl)ethoxy)methyl)-1H-imidazol-2-yl)methanol (11.6 g, 31.82 mmol) in DCM (50 mL) is added TFA (24.52 mL, 318.22 mmol). The resulting solution is refluxed for 3 hrs and evaporated. The residue is redissolved in DCM (50 ml) and the solution is treated with saturated NaHCO₃.

Method 2:

In a 125 mL pea-shaped flask is added (2-(2,5-dihydro-1H-pyrrol-1-yl)-4-fluorophenyl)(1-((2-(trimethylsilyl)ethoxy)methyl)-1H-imidazol-2-yl)methanol (3 g, 7.70 mmol) and HCl in dioxane (50 mL, 200 mmol) to give a colorless solution. The resulting mixture is stirred at rt for 30 hours. The solvent is removed under reduced pressure. The reaction mixture is quenched with saturated NaHCO₃ (150 mL), extracted with EtOAc (3×125 mL), the organic layer is dried over Na₂SO₄, filtered and evaporated to afford yellow solid. The precipitate is washed with EtOAc (20 mL) and dried under vacuum Method 3:

Hydrogen chloride/EtOAc (10 mL) is added to (4-fluoro-2-(oxazol-4-yl)phenyl)(1-((2-(trimethylsilyl)ethoxy)methyl)-1H-imidazol-2-yl)methanol (200 mg, 0.51 mmol) under nitrogen. The resulting mixture is stirred at rt for 36 hours. The solvent is removed under reduced pressure. The crude product is purified by preparative HPLC (Xselect CSH Fluoro phenyl OBD column, 5 m silica, 19 mm diameter, 100 mm length), using decreasingly polar mixtures of water (containing 0.05% Formic acid) and MeCN as eluents.

Method 4:

Combined alkylation/deprotection one-pot method: 2.50 M n-BuLi in THF (11.8 mL, 29.5 mmol) is added to a cooled solution of 1-(diethoxymethyl)imidazole (5.02 g, 29.5 mmol) in THF (75 mL) at −45° C., and the mixture is stirred for 15 m. The mixture is cooled to −78° C., and a solution of 3-ethyl-8-fluoro-indolizine-5-carbaldehyde (2.82 g, 14.8 mmol) in THF (25 mL) is added drop-wise. The mixture is stirred for 30 m at −78° C. and then warmed to 0° C. for 1 h. The mixture is diluted with 0.1M HCl (50.0 mL) and EtOAc (50.0 mL) at 0° C. The mixture is stirred at 23° C. for 15 m. More EtOAc (50.0 mL) is added, and the phases were separated. The organic phase is extracted with 0.1M HCl (3×50.0 mL), and the combined aqueous phases are cautiously diluted with sat. NaHCO₃ (50.0 mL). The aqueous phase w is as extracted with EtOAc (3×200 mL), and the combined organic phases are washed with brine (200 mL), dried over MgSO₄, filtered and concentrated under reduced pressure.

Method 5:

Perchlorostannane (130 mg, 0.50 mmol) is added to (3-cyclopropyl-8-fluoroindolizin-5-yl)(1-((2-(trimethylsilyl)ethoxy)methyl)-1H-imidazol-2-yl)methanol (200 mg, 0.50 mmol) in DCM (4 mL) under nitrogen. The resulting solution is stirred at rt for 30 hours. The solvent is removed under reduced pressure and redissolved in MeOH (2 ml). The reaction mixture is neutralized with NH₃.H₂O to pH=7-8. The crude product is purified by preparative HPLC (XSelect CSH Prep C18 OBD column, 5p silica, 19 mm diameter, 100 mm length), using decreasingly polar mixtures of water (containing 0.05% NH4HCO3) and MeCN as eluents.

Method 6:

Hydrogen chloride in dioxane (73.0 mL, 291.91 mmol) is added dropwise to (3-ethyl-7-fluorobenzofuran-4-yl) (1-((2-(trimethylsilyl)ethoxy)methyl)-1H-imidazol-2-yl)methanol (5.7 g, 14.60 mmol) in 1,4-dioxane (20 mL) in ice bath under nitrogen. The temperature is increased to room temperature naturally. The resulting solution is stirred at 40° C. overnight. The solvent is removed under reduced pressure to give a crude product. The crude product is basified with 7M $NH_3$ in MeOH, and purified by flash C18-flash chromatography, elution gradient 0 to 30% MeCN in water.

General procedure 2:

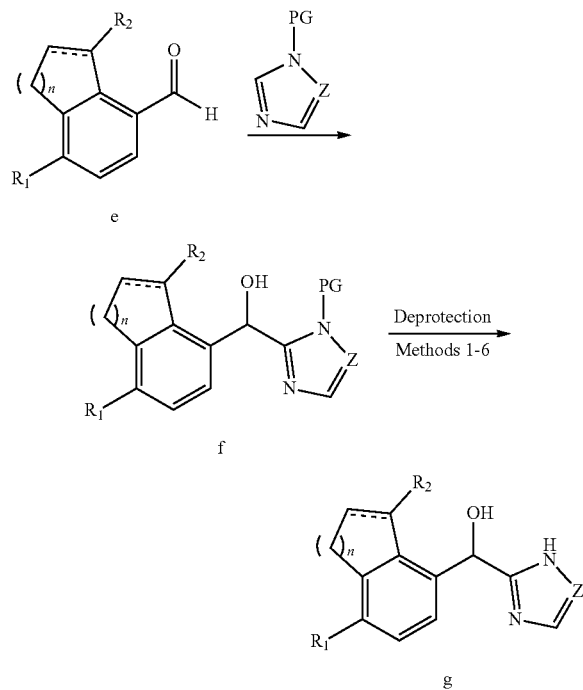

Heterocyclic aldehydes are synthesized and reacted in analgous fashion to General procedure 1 using similar protecting group and deprotection procedures.

Example 1. (4-Fluoro-2-propylphenyl)(1H-imidazol-2-yl)methanol

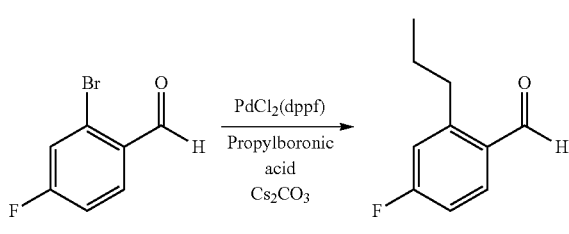

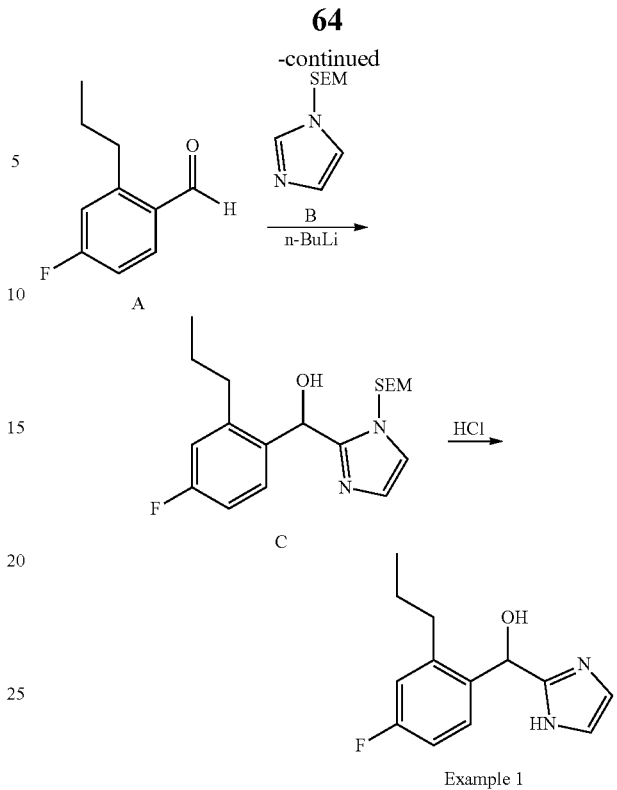

Example 1

To a solution of (4-fluoro-2-propylphenyl)(1-((2-(trimethylsilyl)ethoxy)methyl)-1H-imidazol-2-yl)methanol (11.6 g, 31.82 mmol) in DCM (50 mL) was added TFA (24.52 mL, 318.22 mmol). The resulting solution was refluxed for 3 hrs and evaporated. The residue was redissolved in DCM (50 ml) and the solution was treated with saturated $NaHCO_3$. The precipitate was filtered and dried under vacuum to give (4-fluoro-2-propylphenyl)(1H-imidazol-2-yl)methanol (5.88 g, 79%) as an off-white solid. $^1$H NMR (300 MHz, DMSO-d6) δ ppm 11.82 (br. s., 1H) 7.51 (dd, J=8.57, 6.31 Hz, 1H) 6.59-7.09 (m, 4H) 6.00 (d, J=4.33 Hz, 1H) 5.90 (d, J=4.33 Hz, 1H) 2.63-2.84 (m, 1H) 2.52-2.62 (m, 1H) 1.31-1.63 (m, 2H) 0.90 (t, J=7.25 Hz, 3H). LC-MS (Method B): m/z (ES+), [M+H]+=235; TFA, HPLC $t_R$=0.57 min.

Intermediate C: (4-Fluoro-2-propylphenyl)(1-((2-(trimethylsilyl)ethoxy)methyl)-1H-imidazol-2-yl) methanol To a stirred solution of 4-fluoro-2-propylbenzaldehyde (302 mg, 1.82 mmol) in THF (5 mL) at −78° C., was added a mixture of 1-((2-(trimethylsilyl)ethoxy)methyl)-1H-imidazole (400 mg, 2.02 mmol), n-BuLi (258 mg, 4.03 mmol) in THF (5 mL) over a period of 1 minute under nitrogen. The resulting solution was stirred at −78° C. for 1 hour. The temperature was increased to room temperature over a period of several hours. The reaction mixture was quenched with saturated $NH_4Cl$ (5 mL), extracted with DCM (3×10 mL). The organic layer was dried over $Na_2SO_4$, filtered and evaporated to afford a yellow oil. The residue was purified by preparative TLC (EtOAc: petroleum ether=1:2), to afford (4-fluoro-2-propylphenyl)(1-((2-(trimethylsilyl)ethoxy) methyl)-1H-imidazol-2-yl)methanol (C, 400 mg, 54.4%) as an orange oil. $^1$H NMR (300 MHz, $CDCl_3$-d) δ ppm 7.21 (dd, J=8.57, 5.93 Hz, 1H) 7.05 (dd, J=16.48, 1.41 Hz, 2H) 6.79-6.98 (m, 2H) 6.16 (s, 1H) 4.90-5.15 (m, 2H) 3.20-3.45 (m, 2H) 2.60-2.87 (m, 2H) 1.46-1.75 (m, 2H) 1.00 (t, J=7.25

Hz, 3H) 0.72-0.89 (m, 2H) −0.09-0.03 (m, 9H). LC-MS (Method A): m/z (ES+), [M+H]+=365; acid, HPLC $t_R$=1.062 min.

Intermediate B:
1-((2-(Trimethylsilyl)ethoxy)methyl)-1H-imidazole

Sodium hydride (0.529 g, 22.03 mmol) in THF (50 mL) was cooled to 0° C. over a period of 10 minutes under nitrogen. To this was slowly added imidazole (1 g, 14.69 mmol) in THF (30 mL) were under nitrogen. The temperature was increased to room temperature gradually. The resulting mixture was stirred at 25° C. for 30 minutes, and then (2-(chloromethoxy)ethyl)trimethylsilane (3.67 g, 22.03 mmol) was added slowly to the mixture at 0° C. over a period of 1 minute under nitrogen. The temperature was increased to room temperature gradually. The resulting mixture was stirred at 25° C. for 14 hours. The mixture was concentrated and diluted with EtOAc (200 mL), and washed sequentially with water (150 mL). The organic layer was dried over $Na_2SO_4$, filtered and evaporated to afford crude product. The crude product was purified by flash C18-flash chromatography with an elution gradient 0 to 50% MeCN in water. Pure fractions were evaporated to dryness to afford 1-((2-(trimethylsilyl)ethoxy)methyl)-1H-imidazole (B, 2.91 g, 100%) as a white oil which solidified on standing. 1H δ NMR (DMSO-d6, 300 MHz) δ −0.05-0.05 (9H, d, J=6.9 Hz), 0.83-0.97 (2H, m), 3.52-3.64 (2H, m), 5.54-5.61 (2H, s), 7.70-7.78 (1H, s), 7.84-7.91 (1H, s), 9.25-9.31 (1H, s). LC-MS (Method A): m/z (ES+), [M+H]+=199; HPLC $t_R$=1.177 min.

Intermediate A: 4-Fluoro-2-propylbenzaldehyde

2-Bromo-4-fluorobenzaldehyde (5 g, 24.63 mmol) was added to propylboronic acid (3.25 g, 36.94 mmol), $PdCl_2$(dppf) (1.802 g, 2.46 mmol) and $CS_2CO_3$ (16.05 g, 49.26 mmol) in dioxane (40 mL) and water (10 mL), then warmed to 80° C. under nitrogen. The resulting suspension was stirred at 80° C. for 12 hours. The reaction mixture was diluted with EtOAc (50 mL), and washed sequentially with saturated brine (20 mL×3). The organic layer was dried over $Na_2SO_4$, filtered and evaporated to afford crude product. The crude product was purified by flash silica chromatography, elution gradient 0 to 5% EtOAc in petroleum ether. Pure fractions were evaporated to dryness to afford 4-fluoro-2-propylbenzaldehyde (A, 3.10 g, 76%) as a pale yellow liquid. $^1$H NMR (400 MHz, DMSO-d6) δ ppm 0.93 (3H, t, J=7.3), 1.58 (2H, m), 2.96-3.05 (2H, m), 7.21-7.32 (2H, m), 7.93 (1H, dd, J=8.2, 6.3), 10.20 (1H, s).

Example 2 and 3, (R)-(4-fluoro-2-propylphenyl)(1H-imidazol-2-yl)methanol (2) and (S)-(4-Fluoro-2-propylphenyl)(1H-imidazol-2-yl)methanol (3)

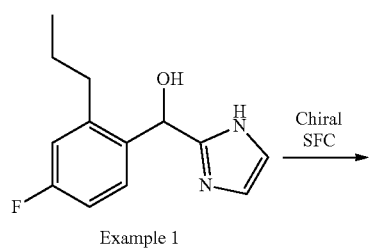

Example 1

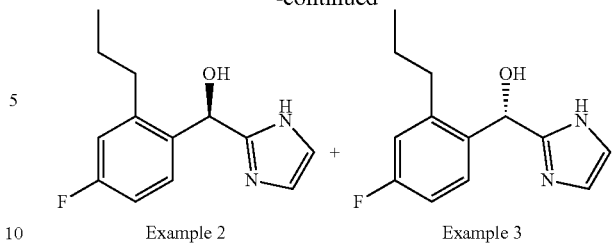

Example 2           Example 3

The racemic mixture of Example 1 was separated by chiral SFC using a chiralpak AD-H column (30×250 mm, 5 μm). The mobile phase A was supercritical $CO_2$, and Mobile phase B was isopropanol containing 0.1% dimethylamine. A gradient of up to 15% B was run at 2.8 mL/min and two peaks were isolated to give (R)-(4-fluoro-2-propylphenyl)(1H-imidazol-2-yl)methanol (Peak 1 at 3.25 min, 2.490 g, 33.4% and >99% ee, Example 2) and (S)-(4-fluoro-2-propylphenyl)(1H-imidazol-2-yl)methanol (Peak 2 at 4.54 min, 2.480 g, 33.3% and >99% ee, Example 3) as white solids. Absolute stereochemistry was assigned based on a crystal structure of the compound with PAR2 receptor.

Example 2 Analytical data: $^1$H NMR (300 MHz, DMSO-d6) δ ppm 11.83 (br. s., 1H) 7.51 (dd, J=8.48, 6.22 Hz, 1H) 6.61-7.06 (m, 4H) 6.00 (br. s., 1H) 5.90 (s, 1H) 2.64-2.78 (m, 1H) 2.52-2.62 (m, 1H) 1.35-1.63 (m, 2H) 0.90 (t, J=7.35 Hz, 3H). LC-MS (Method A): [M+H]+=235; HPLC $t_R$=0.57 min. Chiral SFC $t_R$=3.25 min.

Example 3 Analytical data: $^1$H NMR (300 MHz, DMSO-d6) δ ppm 11.83 (br. s., 1H) 7.51 (dd, J=8.57, 6.31 Hz, 1H) 6.65-7.05 (m, 4H) 5.81-6.22 (m, 2H) 2.64-2.78 (m, 1H) 2.53-2.62 (m, 1H) 1.35-1.62 (m, 2H) 0.90 (t, J=7.35 Hz, 3H). LC-MS (Method A): [M+H]+=235; HPLC $t_R$=0.57 min. Chiral SFC $t_R$=4.54 min Example 4.
(2-Cyclopentenylphenyl)(1H-imidazol-2-yl)methanol

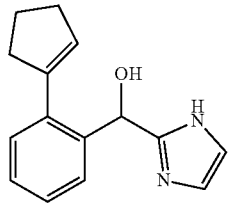

Example 4

(2-Cyclopentenylphenyl)(1H-imidazol-2-yl)methanol was made in analogous fashion to Example 1, using 2-(cyclopent-1-en-1-yl)-4,4,5,5-tetramethyl-1,3,2-dioxaborolane and 2-bromo-benzaldehyde. $^1$H NMR (400 MHz, DMSO): δ ppm 1.89-1.97 (m, 2H), 2.50-2.56 (m, 2H), 2.67-3.32 (m, 2H), 5.94-6.03 (m, 3H), 6.74-6.76 (d, 1H), 6.97 (s, 1H), 7.15-7.24 (m, 3H), 7.53-7.55 (m, 1H). LC-MS (Method A): m/z (ES+), [M+H]+=241; base, HPLC $t_R$=1.420 min.

Example 5. (2-Cyclopentenyl-4-fluorophenyl)(1H-imidazol-2-yl)methanol

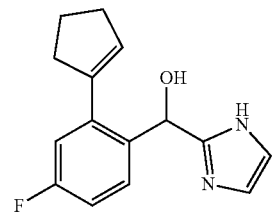

Example 5

(2-Cyclopentenyl-4-fluorophenyl)(1H-imidazol-2-yl) methanol was prepared in analogous fashion using and to Example 1 using 2-(cyclopent-1-en-1-yl)-4,4,5,5-tetramethyl-1,3,2-dioxaborolane to provide a white solid (68 mg, 68%). $^1$H NMR (400 MHz, DMSO): δ ppm 1.87-1.96 (m, 2H), 2.32-2.49 (m, 2H), 2.66-2.71 (m, 2H), 5.75 (s, 1H), 5.90-5.91 (d, 1H), 5.99-6.06 (m, 1H), 6.75 (s, 1H), 6.97-6.99 (m, 2H), 7.00-7.09 (m, 1H), 7.54-7.58 (m, 1H). LC-MS (Method A): m/z (ES+), [M+H]+=259; base, HPLC $t_R$=2.185 min.

Example 6. (2-Cyclopentyl-4-fluorophenyl)(1H-imidazol-2-yl)methanol

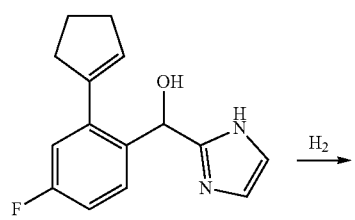

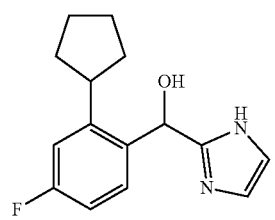

Example 6

To a stirred solution of (2-(cyclopent-1-en-1-yl)-4-fluorophenyl)(1H-imidazol-2-yl)methanol (254 mg, 0.98 mmol) in MeOH (10 mL) was stirred under an atmosphere of hydrogen (5 atm) and 70° C. for 12 hours. The reaction mixture was filtered through celite. The solvent was removed under reduced pressure. The residue was purified by preparative TLC (DCM:MeOH=10:1), to afford (2-cyclopentyl-4-fluorophenyl)(1H-imidazol-2-yl)methanol (48.6 mg, 18.99%) as a white solid. $^1$H NMR (400 MHz, DMSO): δ ppm 1.40-1.61 (m, 4H), 1.65-1.75 (m, 3H), 1.88-1.91 (m, 1H), 3.32-3.40 (m, 1H), 5.97 (s, 1H), 6.05 (s, 1H), 6.75 (s, 1H), 6.94-7.03 (m, 3H), 7.46-7.48 (m, 1H). LC-MS (Method A): m/z (ES+), [M+H]+=261; base, HPLC $t_R$=2.286 min.

Example 7. (2-Cyclobutyl-4-fluorophenyl)(1H-imidazol-2-yl)methanol

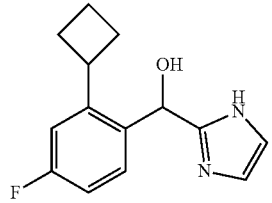

Example 7

(2-Cyclobutyl-4-fluorophenyl)(1H-imidazol-2-yl)methanol was prepared in analogous fashion using and to Example 1 using cyclobutylzinc(II) bromide to provide a white solid (55 mg, 61%). $^1$H (300 MHz, DMSO-d6) δ ppm 1.76 (1H, d, J=9.2 Hz), 1.81-1.96 (1H, m), 1.93-2.12 (3H, m), 2.30 (1H, d, J=10.7 Hz), 3.79 (1H, q, J=8.9 Hz), 5.84 (1H, d, =J 4.3 Hz), 6.00 (1H, d, J=4.4 Hz), 6.74 (1H, s), 6.94-7.03 (2H, m), 7.07 (1H, dd, J=10.9, 2.7 Hz), 7.48 (1H, dd, J=8.6, 6.3 Hz), 11.80 (1H, s). LC-MS (Method A): m/z (ES+), [M+H]+=247; $t_R$=0.79 min.

Example 8. (E)-(4-Fluoro-2-(prop-1-enyl)phenyl)(1H-imidazol-2-yl)methanol

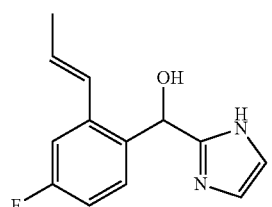

Example 8

(E)-(4-Fluoro-2-(prop-1-enyl)phenyl)(1H-imidazol-2-yl) methanol was prepared in analogous fashion using (E)-prop-1-enylboronic acid. $^1$H NMR (400 MHz, DMSO-d$_6$) δ: 1.84 (dd, J=1.5, 6.5 Hz, 3H), 5.93 (d, J=4.0 Hz, 1H), 6.11 (d, J=4.0 Hz, 1H), 6.17-6.26 (m, 1H), 6.80-6.84 (m, 2H), 6.97 (br. s, 1H), 7.03 (td, J=3.0, 8.5 Hz, 1H), 7.22 (dd, J=2.5, 11.0 Hz, 1H), 7.46 (dd, J=6.5, 8.5 Hz, 1H), 11.91 (br. s, 1H). LCMS (Method D): m/z 233 (M+H)+(ES+), $t_R$=1.53 min.

Example 9. (Z)-(4-Fluoro-2-(prop-1-enyl)phenyl)(1H-imidazol-2-yl)methanol

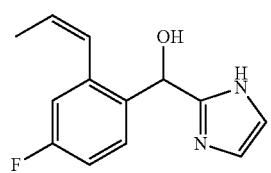

Example 9

(Z)-(4-Fluoro-2-(prop-1-enyl)phenyl)(1H-imidazol-2-yl) methanol was prepared in analogous fashion using (Z)-prop-1-enylboronic acid. $^1$H NMR (500 MHz, MeOD) δ 7.53 (dd, J=8.6, 5.9 Hz, 1H), 7.01 (td, J=8.6, 2.7 Hz, 1H), 6.95 (s, 2H), 6.89 (dd, J=9.7, 2.7 Hz, 1H), 6.47 (d, J=11.1 Hz, 1H), 5.95 (s, 1H), 5.83 (dq, J=11.5, 7.0 Hz, 1H), 1.62 (dd, J=7.0, 1.6 Hz, 3H). LC-MS (Method C): m/z (ES+), [M−H$_2$O+H]$^+$=215.3.

Example 10. (3,4-Difluoro-2-propylphenyl)(1H-imidazol-2-yl)methanol

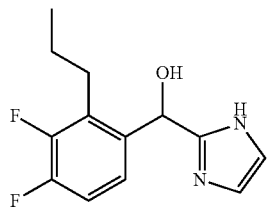

Example 10

(3,4-Difluoro-2-propylphenyl)(1H-imidazol-2-yl)methanol was prepared in analogous fashion to Example 1 using 2-bromo-3,4-difluorobenzaldehyde and propylboronic acid (750 mg, 60%). LC-MS (Method A): m/z (ES+), [M+H]+=253; HPLC t$_R$=1.416 min.

Example 11. Peak 1, Pure enantiomer of (3,4-Difluoro-2-propylphenyl)(1H-imidazol-2-yl)methanol

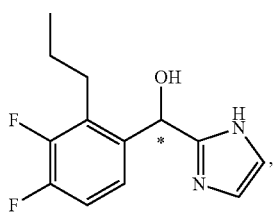

Example 11

Pure enantiomer, Peak 1

Racemic material from Example 10 was subjected to chiral SFC using EnantioCel-Cl, (21.2×250 mm) with a mobile Phase A: CO$_2$, Mobile Phase B: EtOH (0.1% IPA) at an 80:20 ratio. Flow rate: 40 mL/min. $^1$HNMR (400 MHz, Methanol-d4) δ −0.15-0.20 (3H, s), 0.93-0.98 (2H, t, J=7.3), 1.30-1.51 (2H, dtd, J=30.2, 16.4, 15.1, 6.7), 2.65-2.76 (2H, m), 5.99-6.04 (1H, s), 6.94-7.17 (3H, m), 7.26-7.34 (1H, m). Chiral SFC t$_R$=4.1 min.

Example 12. Peak 2, pure enantiomer (3,4-Difluoro-2-propylphenyl)(1H-imidazol-2-yl)methanol

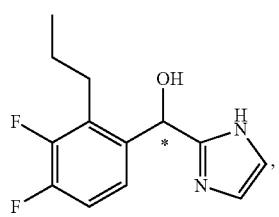

Example 12

Pure enantiomer, Peak 2

Racemic material from Example 10 was subjected to chiral SFC using EnantioCel-Cl, (21.2×250 mm) with a mobile Phase A: CO$_2$, Mobile Phase B: EtOH (0.1% IPA) at an 80:20 ratio. Flow rate: 40 mL/min. $^1$HNMR (400 MHz, Methanol-d4) δ 0.91-1.00 (3H, t, J=7.3), 1.29-1.52 (2H, m), 2.65-2.76 (2H, m), 5.99-6.04 (1H, s), 6.97-7.02 (2H, s), 7.05-7.17 (1H, m), 7.26-7.34 (1H, m). Chiral SFC t$_R$=5.5 min.

Example 13. (3-Chloro-2-propylphenyl)(1H-imidazol-2-yl)methanol

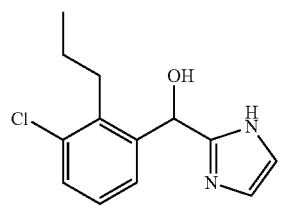

Example 13

(3-Chloro-2-propylphenyl)(1H-imidazol-2-yl)methanol was prepared in analogous fashion to Example 1 using 2-bromo-3-chlorobenzaldehyde and propylboronic acid. $^1$HNMR (300 MHz, DMSO-d6) δ 0.93 (3H, t, J=7.3), 1.35 (2H, m), 2.68 (1H, dt, J=13.1, 6.5), 2.76-2.93 (1H, m), 5.93 (1H, d, J=4.4), 6.16 (1H, d, J=4.3), 6.75 (1H, s), 6.98 (1H, s), 7.22 (1H, d, J=7.8), 7.29-7.34 (1H, m), 7.50 (1H, dd, J=7.7, 1.3), 11.90 (1H, s). LC-MS (Method A): m/z (ES+), base [M+H]+=251; HPLC t$_R$=1.53 min.

Example 14. (4-Fluoro-2-(pyrrolidin-1-yl)phenyl)(1H-imidazol-2-yl)methanol

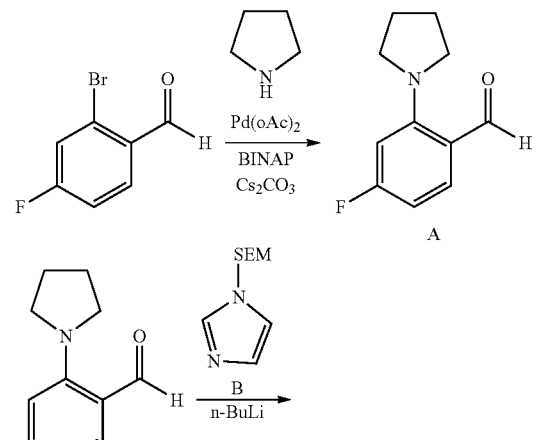

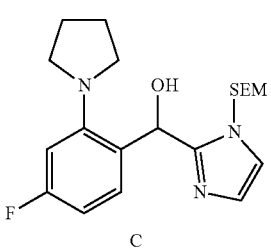

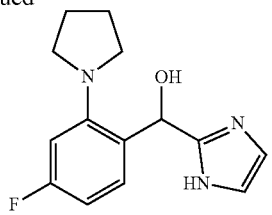

Example 14

To the solution of (4-fluoro-2-(pyrrolidin-1-yl)phenyl)(1-((2-(trimethylsilyl)ethoxy)methyl)-1H-imidazol-2-yl)methanol (2.2 g, 5.62 mmol) in DCM (30 mL) was added TFA (43.3 mL, 561.86 mmol). The reaction was stirred at RT for 6 hr. TFA was removed. The residue was partitioned between EtOAc (30 mL) and sat. NaHCO$_3$ (30 mL). The organic layer was collected, washed with water (30 mL), brine (30 mL), dried over MgSO4, filtered and concentrated. The residue was purified via combiflash (10:1 DCM/MeOH, 80 g column) to give off-white solid. $^1$H NMR (300 MHz, DMSO-d6) δ ppm 1.75-1.96 (m, 4H) 3.04-3.29 (m, 4H) 5.79-5.95 (m, 1H) 6.00-6.12 (m, 1H) 6.53-7.14 (m, 4H) 7.18-7.47 (m, 1H) 11.67-11.96 (m, 1H). LC-MS (Method B): m/z (ES+), [M+H]+=262; TFA, HPLC $t_R$=0.54 min Intermediate C: (4-Fluoro-2-(pyrrolidin-1-yl)phenyl)(1-((2-(trimethylsilyl)ethoxy)methyl)-1H-imidazol-2-yl)methanol To the solution of 1-((2-(trimethylsilyl)ethoxy)methyl)-1H-imidazole (1.355 g, 6.83 mmol) in THF (30 mL) at −78° C. was added n-butyllithium (5.05 mL, 8.07 mmol) dropwise. The reaction mixture was stirred at −78° C. for 30 mins, then 4-fluoro-2-(pyrrolidin-1-yl)benzaldehyde (1.2 g, 6.21 mmol) was added. The reaction was warmed up to RT and stirred at RT for 1 hr. The reaction was then quenched with sat. NH$_4$Cl solution and extracted with EtOAc (3×60 mL). The organic layer was combined, washed with water (60 mL), brine (60 mL), dried over MgSO4, filtered and concentrated to give off-white solid. $^1$H NMR (300 MHz, DMSO-d6) δ 0.00 (s, 10H) 0.72-1.02 (m, 2H) 1.71-1.94 (m, 4H) 2.80-3.14 (m, 4H) 3.44-3.59 (m, 2H) 5.10-5.27 (m, 1H) 5.34-5.38 (m, 1H) 5.46-5.61 (m, 1H) 5.74-5.91 (m, 1H) 6.04-6.24 (m, 1H) 6.60-6.84 (m, 3H) 7.16-7.31 (m, 1H) 7.42-7.61 (m, 1H). LC-MS (Method B): m/z (ES+), [M+H]+=392; TFA, HPLC $t_R$=0.98 min.

Intermediate B: See Example 1

Intermediate C: 4-Fluoro-2-(pyrrolidin-1-yl)benzaldehyde

PdOAc$_2$ (553 mg, 2.46 mmol) was added to pyrrolidine (2.59 g, 36.9 mmol), BINAP (4.6 g, 7.4 mmol), CS$_2$CO$_3$ (16.05 g, 4.93 mmol) and 2-bromo-4-fluorobenzaldehyde (5 g, 24.63 mmol) in toluene (50 mL) under nitrogen. The resulting solution was stirred at 120° C. for 1 hour. The reaction mixture was filtered through celite. The solvent was removed under reduced pressure. The crude product was purified by flash silica chromatography, elution gradient 0 to 1% EtOAc in petroleum ether. Pure fractions were evaporated to dryness to afford 4-fluoro-2-(pyrrolidin-1-yl)benzaldehyde (3.6 g, 76%) as a white solid. $^1$H NMR (CDCl$_3$, 400 MHz) δ 10.03 (s, 1H), 7.76-7.72 (m. 1H), 6.57-6.53 (m, 2H), 3.41-3.36 (t, 4H), 2.07-2.00 (t, 4H). m/z (ES+), [M+H]+=194.0; acid, HPLC $t_R$=0.925 min.

Example 15. Isomer 1, pure enantiomer (4-Fluoro-2-(pyrrolidin-1-yl)phenyl)(1H-imidazol-2-yl)methanol Example 15: Pure enantiomer, Isomer 1

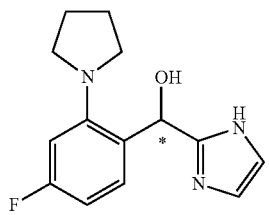

The racemic mixture of Example 14 was separated by chiral HPLC to give Peak 1 and Peak 2 as white solids. $^1$H NMR (300 MHz, DMSO-d6) δ ppm 1.75-2.01 (m, 4H) 2.97-3.33 (m, 9H) 5.69-5.95 (m, 1H) 5.99-6.09 (m, 1H) 6.48-6.80 (m, 2H) 6.78-7.00 (m, 2H) 7.17-7.47 (m, 1H) 11.65-12.13 (m, 1H). LC-MS (Method B): [M+H]+=262; TFA, HPLC $t_R$=0.55 min. Chiral purity was determined using a Lux Amylose-2 column (4.6×250 mm, 5 μm). Mobile phase A was hexane and Mobile Phase B was a 1:1 methanol:isopropanol mixture. To this was added a 0.1% diethylamine additive. The column was run at 1 ml/min with detection at 220 nM. Peak 1 eluted at 6.12 min>98% ee.

Example 16. Isomer 2, pure enantiomer (4-Fluoro-2-(pyrrolidin-1-yl)phenyl)(1H-imidazol-2-yl)methanol Example 16: Pure enantiomer, Isomer 2

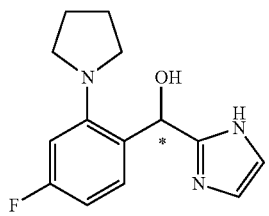

The racemic mixture of Example 14 was separated by chiral HPLC to give Peak 1 and Peak 2 as white solids. $^1$H NMR (300 MHz, DMSO-d6) δ ppm 1.72-2.05 (m, 5H) 2.98-3.32 (m, 7H) 5.67-5.96 (m, 1H) 5.98-6.16 (m, 1H) 6.52-6.79 (m, 3H) 6.73-7.03 (m, 2H) 7.17-7.38 (m, 1H) 11.67-12.12 (m, 1H). LC-MS (Method B): [M+H]+=262; TFA, HPLC $t_R$=0.55 min Chiral purity was determined using a Lux Amylose-2 column (4.6×250 mm, 5 u). Mobile phase A was hexane and Mobile Phase B was a 1:1 methanol: isopropanol mixture. To this was added a 0.1% diethylamine additive. The column was run at 1 mL/min with detection at 220 nm. Peak 2 eluted at 7.29 min with >98% ee.

Example 17. (2-(2,5-dihydro-1H-pyrrol-1-yl)-4-fluorophenyl)(1H-imidazol-2-yl)methanol

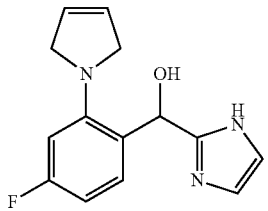

In a 125 mL pea-shaped flask was added (2-(2,5-dihydro-1H-pyrrol-1-yl)-4-fluorophenyl)(1-((2-(trimethylsilyl)ethoxy)methyl)-1H-imidazol-2-yl)methanol (3 g, 7.70 mmol) and HCl in dioxane (50 mL, 200 mmol) to give a colorless solution. The resulting mixture was stirred at rt for 30 hours. The solvent was removed under reduced pressure. The reaction mixture was quenched with saturated $NaHCO_3$ (150 mL), extracted with EtOAc (3×125 mL), the organic layer was dried over $Na_2SO_4$, filtered and evaporated to afford yellow solid. The precipitate was washed with EtOAc (20 mL) and dried under vacuum to afford (2-(2,5-dihydro-1H-pyrrol-1-yl)-4-fluorophenyl)(1H-imidazol-2-yl)methanol (1.00 g, 50.1%) as a white solid, which was used without further purification. $^1$H NMR (300 MHz, MeOD) δ ppm 4.06 (4H, s), 5.86 (2H, s), 6.25 (1H, s), 6.60 (1H, td), 6.74 (1H, dd), 6.94 (2H, s), 7.20 (1H, dd). LC-MS (Method A): m/z (ES+), [M+H]+=260; acid, HPLC $t_R$=0.592 min.

(2-(2,5-Dihydro-1H-pyrrol-1-yl)-4-fluorophenyl)(1-((2-(trimethylsilyl)ethoxy)methyl)-1H-imidazol-2-yl)methanol was prepared in analogous fashion to Example 14, using 2,5-dihydro-1H-pyrrole.

Example 18. Isomer 1, Pure Enantiomer (2-(2,5-dihydro-1H-pyrrol-1-yl)-4-fluorophenyl)(1H-imidazol-2-yl)methanol Example 18: Pure enantiomer, Isomer 1

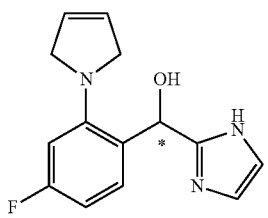

Example 17 was purified by preparative chiral-HPLC (Column: CHIRALPAK AD-H SFC, 5×25 cm, 5 m; Mobile Phase A: $CO_2$: 6%0, Mobile Phase B: EtOH (0.1% IPA)-40%; Flow rate: 160 mL/min; 215 nm detection. $^1$H NMR (300 MHz, MeOD) δ ppm 4.12 (4H, s), 5.92 (2H, s), 6.31 (1H, s), 6.66 (1H, td), 6.80 (1H, dd), 7.00 (2H, s), 7.26 (1H, dd). LC-MS (Method A): m/z (ES+), [M+H]+=260; acid, HPLC $t_R$=1.306 min. Chiral SFC $t_R$=5.45 min (peak 1). >98% ee

Example 19. Isomer 2, Pure Enantiomer (2-(2,5-dihydro-1H-pyrrol-1-yl)-4-fluorophenyl)(1H-imidazol-2-yl)methanol Example 19: Pure enantiomer, Isomer 2

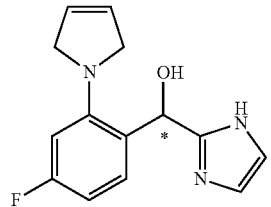 [SMILES: OC(c1ncc[nH]1)c1ccc(F)cc1N1CC=CC1]

Example 17 was purified by preparative chiral-HPLC (Column: CHIRALPAK AD-H SFC, 5×25 cm, 5 m; Mobile Phase A: $CO_2$:6%0, Mobile Phase B: EtOH (0.1% IPA)-40%; Flow rate: 160 mL/min; 215 nm detection. $^1$H NMR (300 MHz, MeOD) δ ppm 4.12 (3H, s), 5.92 (2H, s), 6.31 (1H, s), 6.66 (1H, td), 6.80 (1H, dd), 7.01 (2H, s), 7.26 (1H, dd). LC-MS (Method A): m/z (ES+), [M+H]+=260; acid, HPLC $t_R$=1.30 min Chiral SFC $t_R$=7.60 min (peak 2). >98% ee.

Example 20. (2-(Azetidin-1-yl)-4-fluorophenyl)(1H-imidazol-2-yl)methanol

Example 20

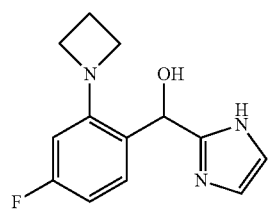

An analogous procedure to Example 14 was employed using azetidine to provide (2-(azetidin-1-yl)-4-fluorophenyl)(1H-imidazol-2-yl)methanol (17 mg, 12%). $^1$H NMR (300 MHz, $CDCl_3$) δ ppm 7.17 (dd, J=7.08, 8.59 Hz, 1H), 6.91 (s, 2H), 6.47 (dt, J=2.55, 8.45 Hz, 1H), 6.18 (dd, J=2.64, 12.09 Hz, 1H), 5.78-5.91 (m, 2H), 3.78-4.06 (m, 4H), 2.05-2.29 (m, 2H), 2.05-2.29 (m, 2H), 2.20 (quin, J=7.27 Hz, 2H). LC-MS (Method B): [M+H]+=248; TFA, HPLC $t_R$=0.35 min.

Example 21. (3-Chloro-2-(1H-pyrazol-1-yl)phenyl)(1H-imidazol-2-yl)methanol

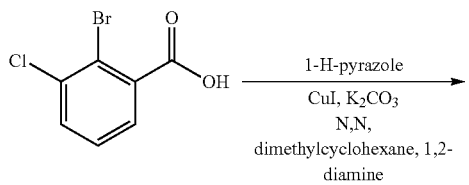

75
-continued

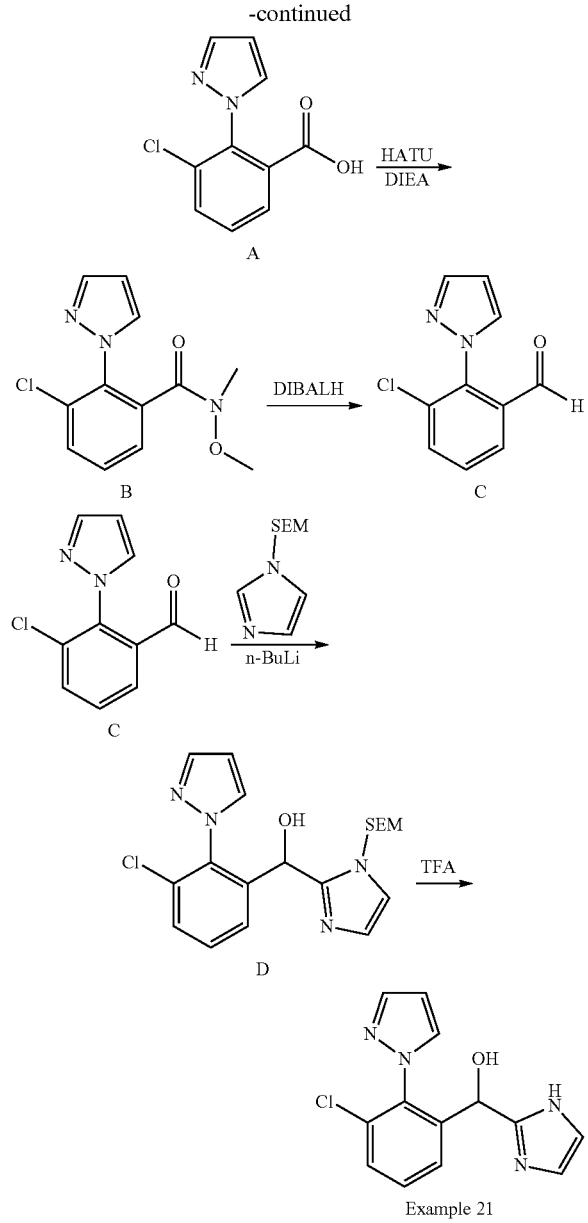

Example 21

2,2,2-Trifluoroacetic acid (2.5 mL, 32.45 mmol) was added to (3-chloro-2-(1H-pyrazol-1-yl)phenyl)(1-((2-(trimethylsilyl)ethoxy)methyl)-1H-imidazol-2-yl)methanol (200 mg, 0.49 mmol) in DCM (5 mL). The resulting solution was stirred at rt. for 18 hours. The solvent was removed under reduced pressure. The reaction mixture was neutralized with saturated NaHCO₃, extracted with EtOAc (3×5 mL), filtered and evaporated to afford white solid. The crude product was purified by flash C18-flash chromatography, elution gradient 5 to 70% MeCN in water. Pure fractions were evaporated to dryness to afford (3-chloro-2-(1H-pyrazol-1-yl)phenyl)(1H-imidazol-2-yl)methanol (45 mg, 33%) as a white solid. $^1$H NMR (300 MHz, DMSO) δ ppm 5.24-5.26 (m, 1H), 6.21-6.22 (m, 1H), 6.42-6.43 (m, 1H), 6.86 (s, 2H), 7.52-7.60 (m, 2H), 7.65-7.68 (m, 2H), 7.73 (s, 1H), 11.86 (s, 1H). LC-MS (Method A): m/z (ES+), [M+H]+=275.1; acid, HPLC $t_R$=0.477 min.

Intermediate D, (3-Chloro-2-(1H-pyrazol-1-yl)phenyl)(1-((2-(trimethylsilyl)ethoxy)methyl)-1H-imidazol-2-yl)methanol

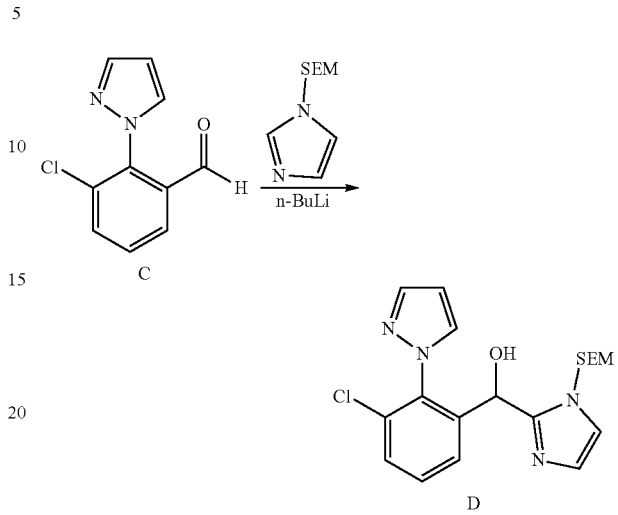

n-Butyllithium (0.774 mL, 1.94 mmol) was added slowly to 1-((2-(trimethylsilyl)ethoxy)methyl)-1H-imidazole (384 mg, 1.94 mmol) in THF (6 mL) at −78° C. under nitrogen. 0.5 hour later, was added 3-chloro-2-(1H-pyrazol-1-yl)benzaldehyde (200 mg, 0.97 mmol). The resulting solution was stirred at −78° C. for 1.5 hours. The reaction mixture was quenched with saturated NH₄Cl (5 mL), extracted with EtOAc (3×10 mL), the organic layer was dried over Na₂SO₄, filtered and evaporated to afford white liquid. The crude product was purified by flash C18-flash chromatography, elution gradient 5 to 70% MeCN in water. Pure fractions were evaporated to dryness to afford (3-chloro-2-(1H-pyrazol-1-yl)phenyl)(1-((2-(trimethylsilyl)ethoxy)methyl)-1H-imidazol-2-yl)methanol (380 mg, 97%) as a white liquid. $^1$H NMR (400 MHz, DMSO) δ −0.05-0.02 (m, 24H), 0.70-0.78 (m, 1H), 0.81-0.85 (m, 4H), 3.18-3.24 (m, 2H), 3.43-3.47 (m, 3H), 5.01-5.03 (m, 1H), 5.27-5.29 (m, 1H), 5.32 (s, 3H), 5.52-5.54 (m, 1H), 6.23-6.24 (m, 1H), 6.29 (s, 1H), 6.72 (s, 1H), 6.93 (s, 2H), 7.14 (s, 1H), 7.26 (s, 2H), 7.59-7.60 (m, 2H), 7.67 (s, 1H), 7.77 (s, 2H), 7.81-7.82 (m, 1H).

Intermediate C,
3-Chloro-2-(1H-pyrazol-1-yl)benzaldehyde

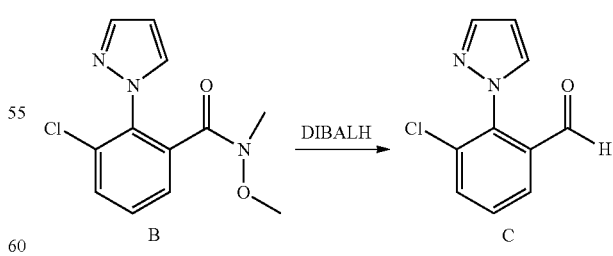

DIBAL-H (3.39 mL, 3.39 mmol) was added slowly to 3-chloro-N-methoxy-N-methyl-2-(1H-pyrazol-1-yl)benzamide (600 mg, 2.26 mmol) in THF (10 mL) at −78° C. under nitrogen. The resulting solution was stirred at −40° C. for 2 hours. The reaction mixture was poured into water (10 mL), extracted with EtOAc (3×15 mL), the organic layer was dried over Na$_2$SO$_4$, filtered and evaporated to afford white solid. The crude product was purified by flash silica chromatography, elution gradient 0 to 10% EtOAc in petroleum ether. Pure fractions were evaporated to dryness to afford 3-chloro-2-(1H-pyrazol-1-yl)benzaldehyde (345 mg, 73.9%) as a white solid. $^1$H NMR (300 MHz, DMSO) δ 6.63-6.64 (m, 1H), 7.66-7.75 (m, 1H), 7.84-7.91 (m, 2H), 8.01-8.04 (m, 1H), 8.24-8.25 (m, 1H), 9.21 (s, 1H). LC-MS (Method A): m/z (ES+), [M+H]+=207; acid, HPLC t$_R$=0.788 min.

Intermediate B, 3-Chloro-N-methoxy-N-methyl-2-(1H-pyrazol-1-yl)benzamide

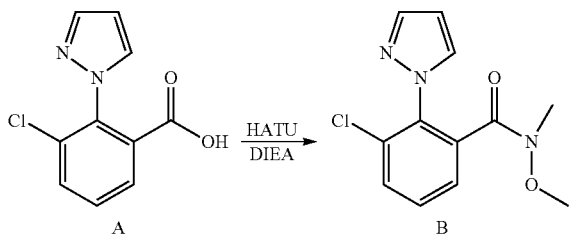

DIEA (0.941 mL, 5.39 mmol) was added slowly to 3-chloro-2-(1H-pyrazol-1-yl)benzoic acid (200 mg, 0.90 mmol), HATU (512 mg, 1.35 mmol) and N,O-dimethylhydroxylamine hydrochloride (219 mg, 2.25 mmol) in DMF (5 mL) at 0° C. over a period of 6 minutes under nitrogen. The temperature was increased to room temperature naturally. The resulting solution was stirred at rt. for 2 hours. The reaction mixture was diluted with water, extracted with EtOAc (3×10 mL), washed with saturated brine (15 mL), the organic layer was dried over Na$_2$SO$_4$, filtered and evaporated to afford white solid. The crude product was purified by flash silica chromatography, elution gradient 0 to 50% EtOAc in petroleum ether. Pure fractions were evaporated to dryness to afford 3-chloro-N-methoxy-N-methyl-2-(1H-pyrazol-1-yl)benzamide (210 mg, 88%) as a white solid. $^1$H NMR (300 MHz, DMSO) δ 2.95-3.01 (m, 3H), 3.45 (m, 3H), 6.46 (s, 1H), 7.51-7.60 (m, 2H), 7.68-7.77 (m, 2H), 7.91-7.95 (m, 3H). LC-MS (Method A): m/z (ES+), [M+H]+=266; acid, HPLC t$_R$=0.717 min.

Intermediate A,
3-Chloro-2-(1H-pyrazol-1-yl)benzoic acid

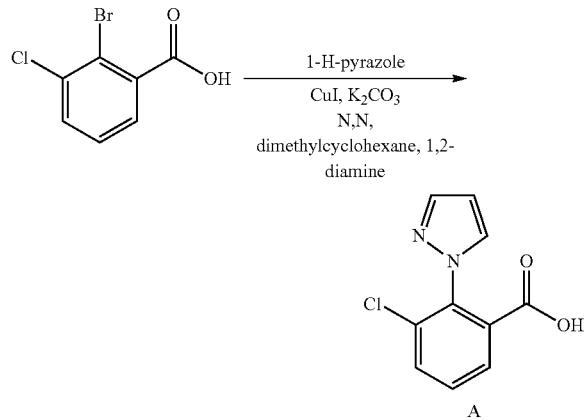

2-Bromo-3-chlorobenzoic acid (500 mg, 2.12 mmol), 1H-pyrazole (145 mg, 2.12 mmol), N1,N2-dimethylcyclohexane-1,2-diamine (15.1 mg, 0.11 mmol), copper(I) iodide (60.7 mg, 0.32 mmol), K$_2$CO$_3$ (734 mg, 5.31 mmol) and L-proline (73.3 mg, 0.64 mmol) were added to DMSO (6 mL) at 25° C. under nitrogen. The resulting mixture was stirred at 100° C. for 1 hour. The reaction mixture was diluted with water (10 mL), extracted with EtOAc (2×10 mL), the organic layer was dried over Na$_2$SO$_4$, filtered and evaporated to afford white liquid. The crude product was purified by flash silica chromatography, elution gradient 0 to 10% EtOAc in petroleum ether. Pure fractions were evaporated to dryness to afford 3-chloro-2-(1H-pyrazol-1-yl)benzoic acid (250 mg, 52.8%) as a white oil. $^1$H NMR (400 MHz, DMSO) δ ppm 6.46 (s, 1H), 7.41-7.50 (m, 1H), 7.58-7.62 (m, 1H), 7.66-7.67 (m, 1H), 7.75-7.77 (m, 1H), 7.81-7.83 (m, 1H), 7.96 (s, 1H). LC-MS (Method A): m/z (ES+), [M+H]+=222.9; acid, HPLC t$_R$=0.54 min.

Example 22. (3,4-Difluoro-2-(1H-pyrazol-1-yl)phenyl)(1H-imidazol-2-yl)methanol

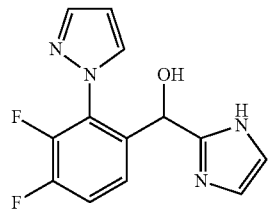

Example 22

Example 22 was prepared in an analogous fashion to Example 21, using 2-bromo-3,4-difluorobenzoic acid and 1H-pyrazole. $^1$H NMR (300 MHz, DMSO-d6) δ ppm 5.47-5.49 (m, 1H), 6.27-6.29 (m, 1H), 6.48-6.50 (m, 1H), 6.73 (s, 1H), 6.96 (s, 1H), 7.49-7.54 (m, 1H), 7.60-7.68 (m, 1H), 7.78-7.79 (m, 1H), 7.93-7.94 (m, 1H) 11.91 (s, 1H). LC-MS (Method A): m/z (ES+), [M+H]+=277; acid, HPLC t$_R$=0.656 min.

Example 23. (4-Fluoro-2-(1H-pyrazol-1-yl)phenyl)(1H-imidazol-2-yl)methanol

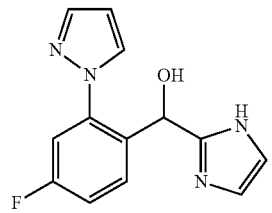

Example 23

Example 23 was prepared in analogous fashion to Example 21, using 2-bromo, 4-fluorbenzoic acid ester and 1H-pyrazole. (In this case, resultant DIBAL-H reduction on the ester led to the alcohol and not the aldehyde. An additional step was needed to oxidize the benzyl alcohol to the aldehyde using 20 equivalents of MnO$_2$ in DCM) $^1$H NMR (400 MHz, DMSO-d6) δ ppm 5.80 (1H, s), 6.53 (1H, t), 6.89 (2H, d), 7.25-7.35 (2H, m), 7.69 (1H, dd), 7.78 (1H, d), 8.41 (1H, d), 12.05 (1H, s). LC-MS (Method A): m/z (ES+), [M+H]+=259; HPLC $t_R$=0.609 min.

The following examples were made by analogous routes to Example 14, using chiral separation methods as indicated where employed:

| Example | Structure | Name | NMR | LC-MS |
|---|---|---|---|---|
| 24 | 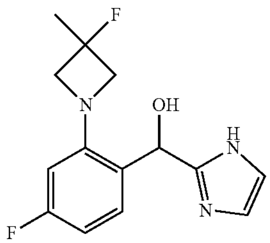 [SMILES: CC1(F)CN(c2cc(F)ccc2C(O)c2ncc[nH]2)C1] | (4-Fluoro-2-(3-fluoro-3-methylazetidin-1-yl)phenyl)(1H-imidazol-2-yl)methanol | 1H NMR(400 MHZ, DMSO-d6) δ ppm 1.56-1.62 (m, 3H), 4.01-4.06 (m, 4H), 5.75-5.76 (m, 1H), 5.89-5.91 (m, 1H), 6.28-6.31 (m, 1H), 6.53-6.58 (m, 1H), 6.78 (s, 1H), 6.99 (s, 1H), 7.21-7.25 (m, 1H), 11.84 (s, 1H). | LC-MS (Method A): m/z (ES+), [M + H]+ = 280; acid, HPLC $t_R$ = 0.745 min |
| 25 | 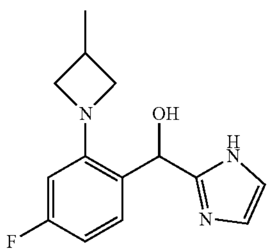 [SMILES: CC1CN(c2cc(F)ccc2C(O)c2ncc[nH]2)C1] | (4-Fluoro-2-(3-methylazetidin-1-yl)phenyl)(1H-imidazol-2-yl)methanol | ¹H NMR (300 MHz, DMSO-d6) δ ppm 7.19 (s, 1H), 7.16 (s, 1H), 6.87 (br. s., 2H), 6.45 (d, J = 2.64 Hz, 1H), 6.15 (dd, J = 2.55, 11.99 Hz, 1H), 4.06 (d, J = 15.49 Hz, 2H), 3.50 (d, J = 3.59 Hz, 2H), 2.66 (s, 1H), 2.58-2.77 (m, 1H), 1.17 (d, J = 6.61 Hz, 3H) | LC-MS (Method B): m/z (ES+), [M + H]+ = 262; acid, HPLC $t_R$ = 0.48 min |
| 26 | 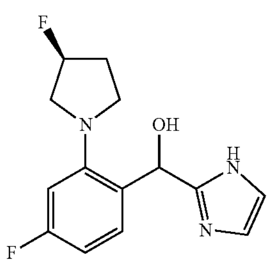 [SMILES: OC(c1ncc[nH]1)c1ccc(F)cc1N1CC[C@H](F)C1] | (4-Fluoro-2-((S)-3-fluoropyrrolidin-1-yl)phenyl)(1H-imidazol-2-yl)methanol | ¹H NMR (300 MHz, DMS0-d6) δ ppm 7.25-7.44 (m, 1H), 6.53-7.07 (m, 4H), 5.85-6.11 (m, 2H), 5.17-5.51 (m, 1H), 3.06-3.69 (m, 6H), 2.13 (d, J = 5.85 Hz, 2H) | LC-MS (Method B): m/z (ES+), [M + H]+ = 280; acid, HPLC $t_R$ = 0.33 min |
| 27 | 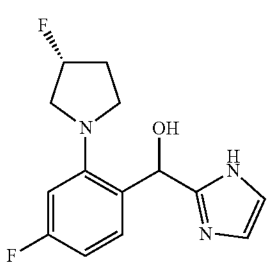 [SMILES: OC(c1ncc[nH]1)c1ccc(F)cc1N1CC[C@@H](F)C1] | (4-Fluoro-2-((R)-3-fluoropyrrolidin-1-yl)phenyl)(1H-imidazol-2-yl)methanol | ¹H NMR (300 MHz, DMSO-d6) δ ppm 7.24-7.49 (m, 1H), 6.54-7.09 (m, 4H), 5.88-6.12 (m, 2H), 5.20-5.50 (m, 1H), 3.33-3.79 (m, 2H), 3.14-3.27 (m, 1H), 1.89-2.40 (m, 2H) | LC-MS (Method B): m/z (ES+), [M + H]+ = 280; acid, HPLC $t_R$ = 0.36 min |
| 28 | 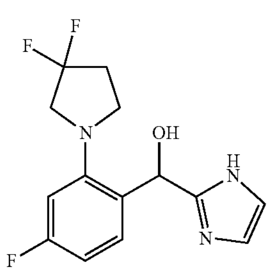 [SMILES: OC(c1ncc[nH]1)c1ccc(F)cc1N1CCC(F)(F)C1] | (2-(3,3-Difluoropyrrolidin-1-yl)-4-fluorophenyl)(1H-imidazol-2-yl)methanol | ¹H NMR (300 MHz, DMSO-d6) δ ppm 7.47 (dd, J = 7.08, 8.59 Hz, 1H), 6.61-7.06 (m, 5H), 5.84-6.16 (m, 2H), 3.38 (d, J = 6.99 Hz, 4H), 3.07-3.23 (m, 1H), 2.20-2.48 (m, 2H) | LC-MS (Method B): m/z (ES+), [M + H]+ = 298; acid, HPLC $t_R$ = 0.60 min |

| Example | Structure | Name | NMR | LC-MS |
|---|---|---|---|---|
| 29 | 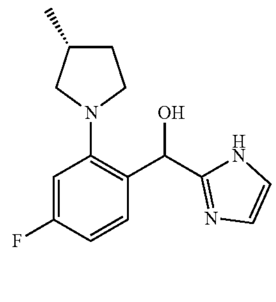 [SMILES: C[C@@H]1CCN(c2cc(F)ccc2C(O)c2ncc[nH]2)C1] | (4-Fluoro-2-((R)-3-methylpyrrolidin-1-yl)phenyl)(1H-imidazol-2-yl)methanol | $^1$H NMR (300 MHz, DMSO-d6) δ ppm 1.04 (dd, J = 6.61, 4.15 Hz, 3 H) 1.28-1.65 (m, 1 H) 1.77-2.44 (m, 2 H) 2.63-3.02 (m, 1 H) 5.67-6.16 (m, 2 H) 6.45-6.85 (m, 2 H) 6.80-7.02 (m, 2 H) 7.12-7.48 (m, 1 H) 11.60- 12.55 (m, 1 H) | LC-MS (Method B): m/z (ES+), [M + H]+ = 276; acid, HPLC $t_R$ = 0.63 min |
| 30 | 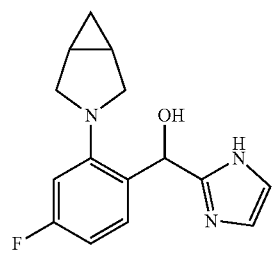 [SMILES: OC(c1ncc[nH]1)c1ccc(F)cc1N1CC2CC2C1] | (2-(3-Azabicyclo[3.1.0]hexan-3-yl)-4-fluorophenyl)(1H-imidazol-2-yl)methanol | $^1$H NMR (300 MHz, DMSO-d6) δ ppm 0.28-0.81 (m, 2 H) 1.29-1.61 (m, 2 H) 2.66-2.92 (m, 1 H) 3.29 (s, 5 H) 5.61-6.04 (m, 2 H) 6.63-7.09 (m, 4 H) 7.24-7.57 (m, 1 H) 11.45-12.00 (m, 1 H) | LC-MS (Method B): m/z (ES+), [M + H]+ = 274; acid, HPLC $t_R$ = 0.58 min |

Example 31. (2-(Bicyclo[3.1.0]hexan-1-yl)-4-fluorophenyl)(1H-imidazol-2-yl)methanol

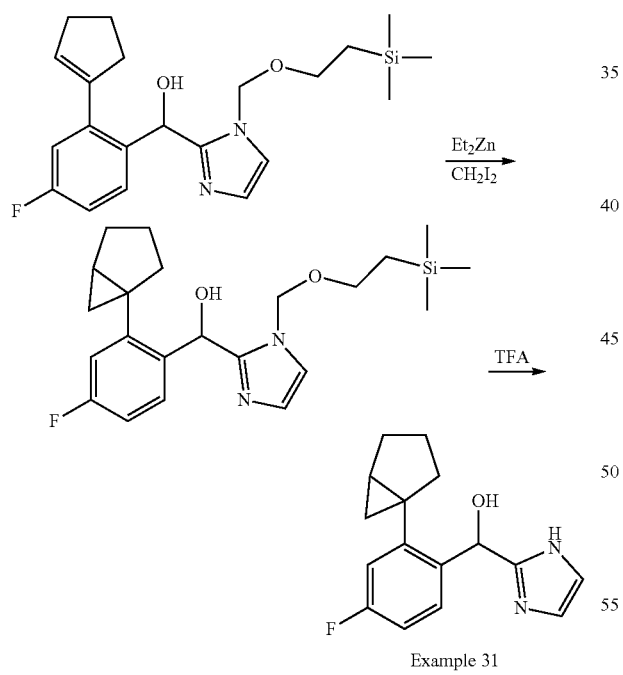

Example 31

To the solution of (2-(bicyclo[3.1.0]hexan-1-yl)-4-fluorophenyl)(1-((2-(trimethylsilyl)ethoxy)methyl)-1H-imidazol-2-yl)methanol (43 mg, 0.11 mmol) in DCM (3 mL) was added TFA (0.823 mL, 10.68 mmol). The reaction was stirred at RT for 6 hr. TFA was removed. The residue was partitioned between EtOAc (30 mL) and sat. NaHCO$_3$ (30 mL). The organic layer was collected, washed with water (30 mL), brine (30 mL), dried over MgSO$_4$, filtered and concentrated. The residue was purified via combiflash (10:1 DCM/MeOH, 24 g column) to give a white solid. 1H NMR (300 MHz, DMSO-d6) δ ppm 0.43-0.93 (m, 2H) 1.13-1.46 (m, 1H) 1.53-2.19 (m, 6H) 5.78-6.00 (m, 1H) 6.07-6.25 (m, 1H) 6.62-7.14 (m, 4H) 6.93-6.95 (m, 1H) 7.37-7.61 (m, 1H) 11.74-12.03 (m, 1H). LC-MS (Method B): m/z (ES+), [M+H]+=273; acid, HPLC $t_R$=0.65 min.

A solution of diethylzinc (1.153 mL, 1.15 mmol) in DCM (2.5 mL) was cooled to −40° C. TFA (0.089 mL, 1.15 mmol) was then added dropwise. After an additional 20 min, diiodomethane (0.093 mL, 1.15 mmol) was added dropwise. After an additional 20 min, (2-(cyclopent-1-en-1-yl)-4-fluorophenyl)(1-((2-(trimethylsilyl)ethoxy)methyl)-1H-imidazol-2-yl)methanol (Intermediate from Example 5, 80 mg, 0.21 mmol) was added. The reaction was warmed up to rt, After an additional 30 min, the reaction was quenched with sat. aqueous NH$_4$Cl (20 ml) and the layers were separated. The aqueous layer was extracted with DCM (3×20 ml). The combined organic layers were dried over Na$_2$SO$_4$, filtered, and concentrated. The crude product was purified with combiflash. (ethyl acetate in hexanes) to yield product as a yellow oil.

Example 32. (4-Fluoro-2-(oxazol-4-yl)phenyl)(1H-imidazol-2-yl)methanol

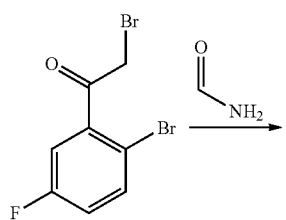

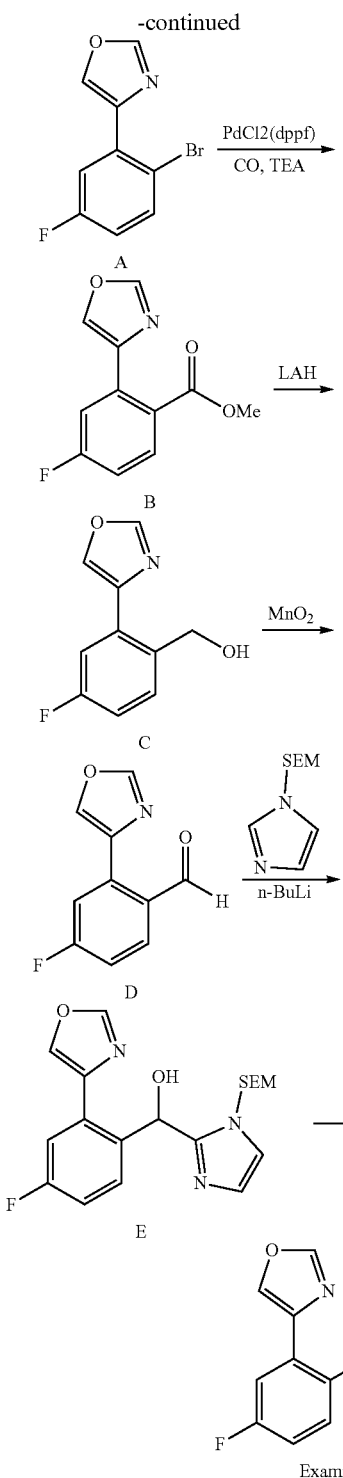

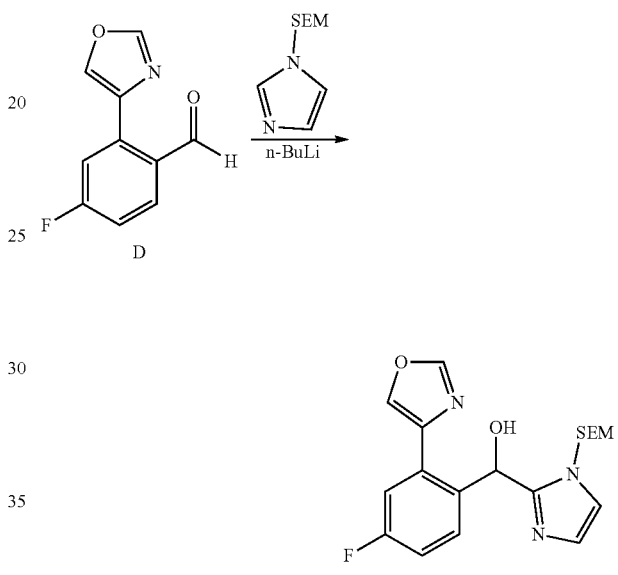

Hydrogen chloride/EtOAc (10 mL) was added to (4-fluoro-2-(oxazol-4-yl)phenyl)(1-((2-(trimethylsilyl)ethoxy)methyl)-1H-imidazol-2-yl)methanol (200 mg, 0.51 mmol) under nitrogen. The resulting mixture was stirred at rt for 36 hours. The solvent was removed under reduced pressure. The crude product was purified by preparative HPLC (Xselect CSH Fluoro phenyl OBD column, 5 μm silica, 19 mm diameter, 100 mm length), using decreasingly polar mixtures of water (containing 0.05% Formic acid) and MeCN as eluents. Fractions containing the desired compound were evaporated to dryness to afford (4-fluoro-2-(oxazol-4-yl)phenyl)(1H-imidazol-2-yl)methanol (100 mg, 75%) as a white solid. $^1$H NMR (400 MHz, DMSO) δ ppm 6.05 (1H, s), 6.91 (2H, s), 7.24 (1H, td), 7.46 (1H, dd), 7.71 (1H, dd), 8.26 (1H, s), 8.56 (1H, d), 8.78 (1H, d). LC-MS (Method A): m/z (ES+), [M+H]+=259; base, HPLC $t_R$=1.50 min.

Intermediate E, (4-Fluoro-2-(oxazol-4-yl)phenyl)(1-((2-(trimethylsilyl)ethoxy)methyl)-1H-imidazol-2-yl)methanol Butyllithium (349 mg, 5.45 mmol) was added dropwise to 1-((2-(trimethylsilyl)ethoxy)methyl)-1H-imidazole (865 mg, 4.36 mmol) in THF (10 mL) cooled to −78° C. under nitrogen. The resulting mixture was stirred at −78° C. for 1 hour. 4-fluoro-2-(oxazol-4-yl)benzaldehyde (417 mg, 2.08 mmol) in THF (10 mL) was added. The resulting mixture was stirred at −78° C. for 30 minutes.

The reaction mixture was quenched with saturated NH$_4$Cl (10 mL), extracted with EtOAc (2×15 mL), the organic layer was dried over Na$_2$SO$_4$, filtered and evaporated to afford white solid.

The crude product was purified by flash C18-flash chromatography, elution gradient 0 to 100% MeCN in water. Pure fractions were evaporated to dryness to afford (4-fluoro-2-(oxazol-4-yl)phenyl)(1-((2-(trimethylsilyl)ethoxy)methyl)-1H-imidazol-2-yl)methanol (500 mg, 58%) as a white solid. $^1$H NMR δ ppm −0.07 (3H, m), 0.83 (15H, m), 1.18 (5H, m), 1.36 (1H, dd), 1.55 (1H, dd), 1.92 (1H, s), 2.00 (4H, s), 3.46 (15H, m), 4.04 (3H, q), 5.32 (12H, m), 5.55 (3H, m), 5.79 (1H, m), 6.19 (4H, m), 6.75 (3H, m), 6.94 (4H, m), 7.25 (11H, m), 7.42 (4H, m), 7.75 (7H, m), 7.90 (2H, d), 8.48 (2H, d), 11.97 (1H, s). LC-MS (Method A): m/z (ES+), [M+H]+=390.10; acid, HPLC $t_R$=1.285 min.

Intermediate D:
4-Fluoro-2-(oxazol-4-yl)benzaldehyde

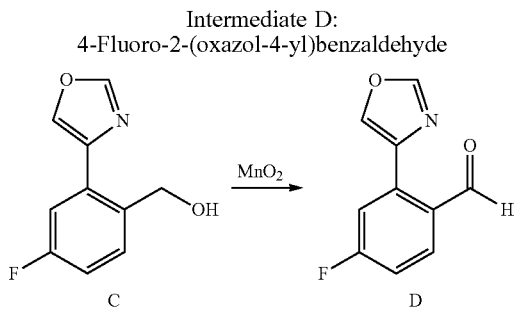

Manganese(IV) oxide (7201 mg, 82.83 mmol) was added to (4-fluoro-2-(oxazol-4-yl)phenyl)methanol (400 mg, 2.07 mmol) in DCM (10 mL) under nitrogen. The resulting mixture was stirred at rt for 24 hours. The mixture was filtered through a Celite pad to afford 4-fluoro-2-(oxazol-4-yl)benzaldehyde (300 mg, 76%) as a white solid. $^1$H NMR δ ppm 0.85 (2H, m), 1.24 (1H, s), 1.57 (9H, d), 5.42 (1H, t), 5.55 (2H, s), 5.69 (3H, q), 7.44 (7H, m), 7.66 (12H, m), 7.94 (7H, m), 8.34 (1H, t), 8.64 (3H, d), 8.76 (4H, d), 10.18 (1H, d), 10.36 (4H, d). LC-MS (Method A): m/z (ES+), [M+H]+=192.1; acid, HPLC $t_R$=0.998 min.

Intermediate C:
(4-Fluoro-2-(oxazol-4-yl)phenyl)methanol

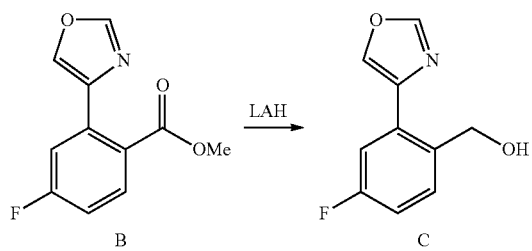

LiAlH$_4$ (64.3 mg, 1.70 mmol) was added to methyl 4-fluoro-2-(oxazol-4-yl)benzoate (250 mg, 1.13 mmol) in THF (5 mL) cooled to −20° C. under nitrogen. The resulting mixture was stirred at −20° C. for 30 minutes. The reaction mixture was quenched with water (1 mL), extracted with EtOAc (2×15 mL), the organic layer was dried over Na$_2$SO$_4$, filtered and evaporated to afford (4-fluoro-2-(oxazol-4-yl)phenyl)methanol (120 mg, 55.0%) as a white solid. LC-MS (Method A): m/z (ES+), [M+H]+=193.95; acid, HPLC $t_R$=0.684 min.

Intermediate B: Methyl 4-fluoro-2-(oxazol-4-yl)benzoate

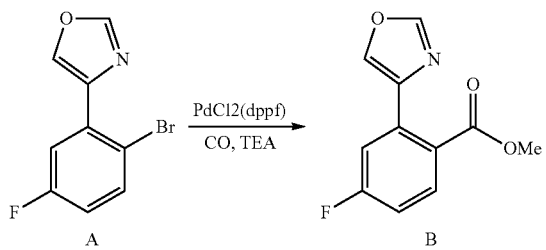

CO (excess) was added to PdCl$_2$(dppf) (159 mg, 0.22 mmol), TEA (0.806 mL, 5.78 mmol) and 4-(2-bromo-5-fluorophenyl)oxazole (350 mg, 1.45 mmol) in MeOH (5 mL). The resulting mixture was stirred at 130° C. for 20 hours. The solvent was removed under reduced pressure. The crude product was purified by flash silica chromatography, elution gradient 0 to 10% EtOAc in petroleum ether. Pure fractions were evaporated to dryness to afford methyl 4-fluoro-2-(oxazol-4-yl)benzoate (251 mg, 78%) as a white solid. $^1$H NMR δ ppm (400 MHz, CDCl3) 0.88 (5H, dd), 0.98 (1H, m), 1.29 (9H, m), 1.46 (5H, m), 1.85 (5H, s), 2.07 (2H, s), 2.55 (7H, s), 2.74 (1H, s), 3.13 (5H, s), 3.49 (1H, d), 3.90 (20H, d), 4.15 (2H, q), 7.14 (11H, m), 7.31 (3H, td), 7.53 (4H, dd), 7.91 (12H, m), 8.08 (5H, d). LC-MS (Method A): m/z (ES+), [M+H]+=222.1; acid, HPLC $t_R$=1.024 min.

Intermediate A, 4-(2-bromo-5-fluorophenyl)oxazole

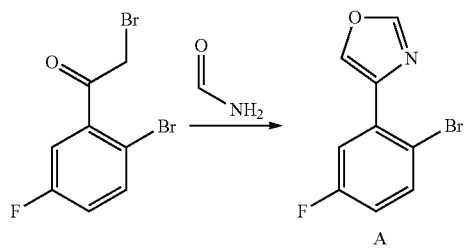

2-Bromo-1-(2-bromo-5-fluorophenyl)ethanone (1 g, 3.38 mmol) was added to formamide (0.152 g, 3.38 mmol) under nitrogen and sealed into a microwave tube. The reaction was heated to 120° C. for 2 days in the microwave reactor and cooled to RT. The reaction mixture was diluted with EtOAc (25 mL), and washed with saturated brine (15 mL×3). The organic layer was dried over Na$_2$SO$_4$, filtered and evaporated to afford crude product. The crude product was purified by flash silica chromatography, elution gradient 0 to 4% EtOAc in petroleum ether. Pure fractions were evaporated to dryness to afford 4-(2-bromo-5-fluorophenyl)oxazole (0.30 g, 36. %) as a pale yellow solid.

Example 33. (4-Fluoro-2-(thiazol-4-yl)phenyl)(1H-imidazol-2-yl)methanol

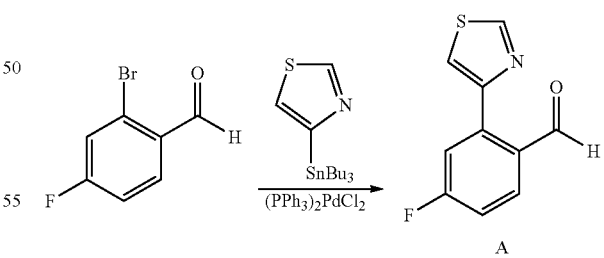

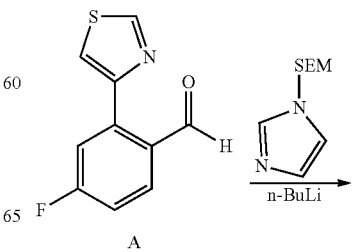

-continued

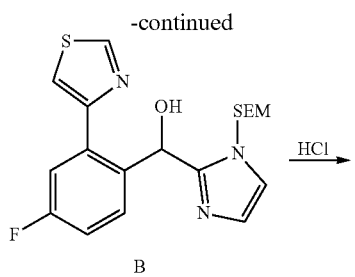

B

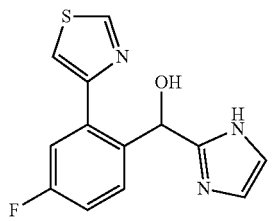

Example 33

Hydrogen chloride (excess) in EtOAc was added to (4-fluoro-2-(thiazol-4-yl)phenyl)(1-((2-(trimethylsilyl)ethoxy)methyl)-1H-imidazol-2-yl)methanol (100 mg, 0.25 mmol) in EtOAc (6 mL) under nitrogen. The resulting solution was stirred at rt for 14 hours. The solvent was removed under reduced pressure. The crude product was purified by preparative HPLC (XSelect CSH Prep C18 OBD column, 5 μm silica, 19 mm diameter, 150 mm length), using decreasingly polar mixtures of water (containing 0.05% formic acid) and MeCN as eluents. Fractions containing the desired compound were evaporated to dryness to afford (4-fluoro-2-(thiazol-4-yl)phenyl)(1H-imidazol-2-yl)methanol (29.0 mg, 34.2%) as a white solid. $^1$H NMR (300 MHz, CD$_3$OD) δ 6.21-6.22 (m, 1H), 7.13-7.25 (m, 3H), 7.37-7.41 (m, 1H), 7.58-7.62 (m, 1H), 7.84 (s, 1H), 8.33 (s, 1.5H), 9.11-9.12 (m, 1H). LC-MS (Method A): m/z (ES+), [M+H]+=276.2; acid, HPLC t$_R$=1.207 min.

Intermediate B, (4-fluoro-2-(thiazol-4-yl)phenyl)(1-((2-(trimethylsilyl)ethoxy)methyl)-1H-imidazol-2-yl)methanol

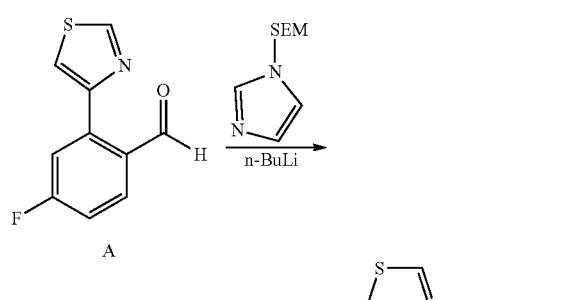

n-Butyllithium (0.386 mL, 0.97 mmol) was added to a stirred solution of 1-((2-(trimethylsilyl)ethoxy)methyl)-1H-imidazole (191 mg, 0.97 mmol) in THF (10 mL) at −78° C. under nitrogen. The resulting solution was stirred at −78° C. for 1 hour. A solution of 4-fluoro-2-(thiazol-4-yl)benzaldehyde (100 mg, 0.48 mmol) in THF (3 mL) was added to a stirred solution at −78° C. under nitrogen. The resulting solution was stirred at −78° C. for 2 hours. The reaction mixture was quenched with saturated NH4Cl (10 mL), extracted with EtOAc (3×20 mL), the organic layer was dried over Na2SO4, filtered and evaporated to afford yellow oil. The crude product was purified by flash C18-flash chromatography, elution gradient 0 to 70% MeCN in water. Pure fractions were evaporated to dryness to afford (4-fluoro-2-(thiazol-4-yl)phenyl)(1-((2-(trimethylsilyl)ethoxy)methyl)-1H-imidazol-2-yl)methanol (100 mg, 51%) as a yellow oil. LC-MS (Method A): m/z (ES+), [M+H]+=406.2; acid, HPLC t$_R$=0.721 min.

Intermediate A, 4-fluoro-2-(thiazol-4-yl)benzaldehyde

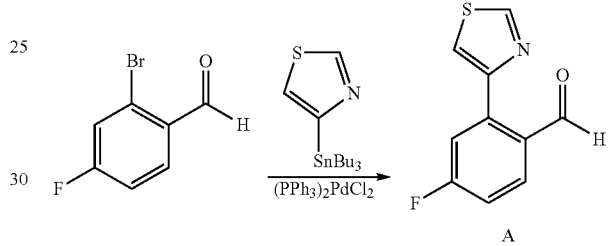

4-(Tributylstannyl)thiazole (1198 mg, 3.20 mmol) was added to a stirred solution of 2-bromo-4-fluorobenzaldehyde (500 mg, 2.46 mmol) and bis(triphenylphosphine)palladium(II) chloride (104 mg, 0.15 mmol) in DMF (10 mL) under nitrogen. The resulting solution was stirred at 100° C. for 16 hours. The solution was washed with brine and KF. The aqueous layer was extracted with EtOAc (2×20 mL). The solvent was removed under reduced pressure to afford crude product. The crude product was purified by flash silica chromatography with EtOAc/petroleum ether (1:30). Pure fractions were evaporated to dryness to afford 4-fluoro-2-(thiazol-4-yl)benzaldehyde (150 mg, 29.4%) as a white solid. LC-MS (Method A): m/z (ES+), [M+H]+=208; acid, HPLC t$_R$=0.802 min.

Example 34. (3-Ethyl-8-fluoroindolizin-5-yl)(1H-imidazol-2-yl)methanol

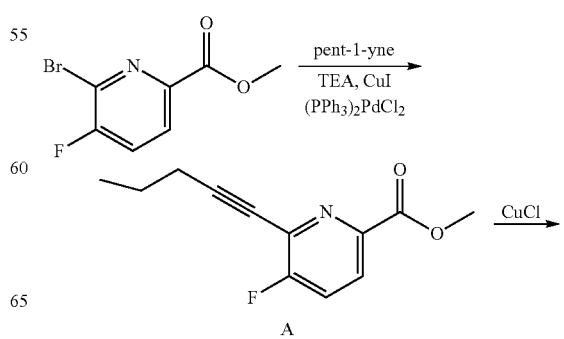

89

-continued

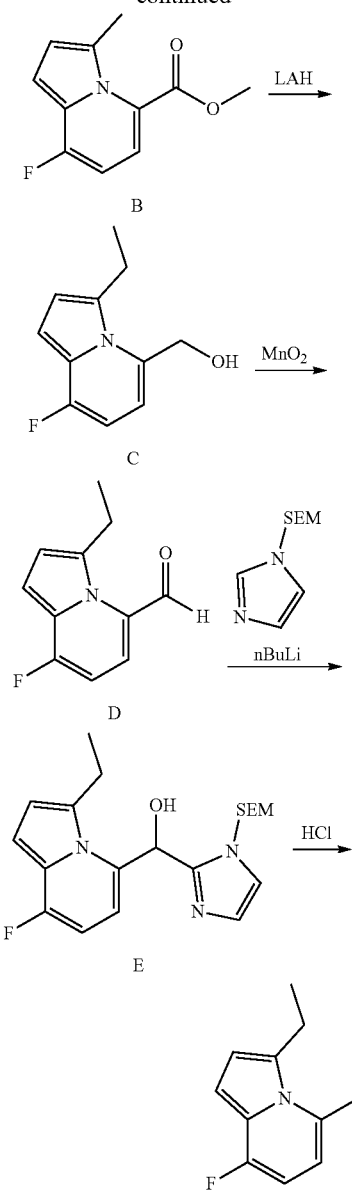

Example 34

HCl (0.125 mL, 4.11 mmol) was added to (3-ethyl-8-fluoroindolizin-5-yl)(1-((2-(trimethylsilyl)ethoxy)methyl)-1H-imidazol-2-yl)methanol (160 mg, 0.41 mmol) in EtOAc (5 mL) under nitrogen. The resulting solution was stirred at rt for 30 hours. The solvent was removed under reduced pressure and redissolved in MeOH (2 ml). The reaction mixture was neutralized with $NH_3 \cdot H_2O$ to pH=7-8. The crude product was purified by flash C18-flash chromatography, elution gradient 0 to 100% MeCN in water. Pure fractions were evaporated to dryness to afford (3-ethyl-8-fluoroindolizin-5-yl)(1H-imidazol-2-yl)methanol (90 mg, 85%) as a off-white solid. $^1$H NMR (400 MHz, DMSO) δ ppm 1.29 (3H, t), 2.52 (1H, s), 3.20 (1H, dq), 6.42 (4H, m), 6.61 (2H, h), 6.85 (1H, s), 7.10 (2H, m), 12.08 (1H, s). LC-MS (Method A): m/z (ES+), [M+H]+=260.1; base, HPLC $t_R$=2.528 min.

90

Intermediate E, (3-Ethyl-8-fluoroindolizin-5-yl)(1-((2-(trimethylsilyl)ethoxy)methyl)-1H-imidazol-2-yl)methanol

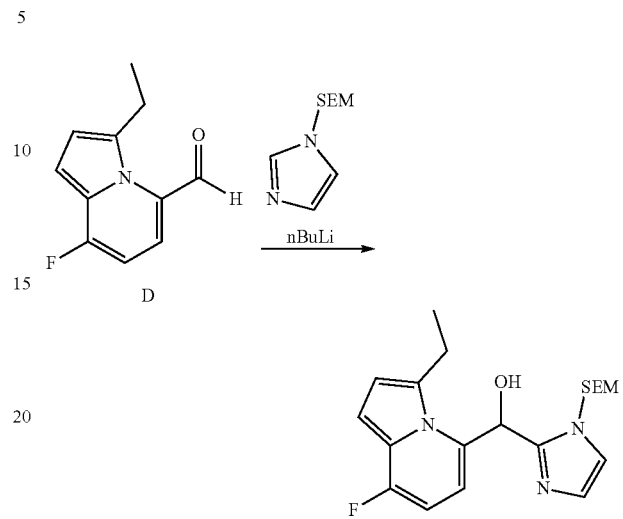

Butyllithium (317 mg, 4.94 mmol) was added portionwise to 1-((2-(trimethylsilyl)ethoxy)methyl)-1H-imidazole (840 mg, 4.24 mmol) in THF (5 mL) cooled to −78° C. over a period of 5 minutes under nitrogen. The resulting mixture was stirred at −78° C. for 30 minutes. 3-Ethyl-8-fluoroindolizine-5-carbaldehyde (270 mg, 1.41 mmol) in THF (5 mL) was added portionwise to the resulting mixture under nitrogen. The resulting mixture stirred at −78° C. for 30 minutes. The reaction mixture was quenched with saturated $NH_4Cl$ (5 mL), extracted with EtOAc (2×15 mL), the organic layer was dried over $Na_2SO_4$, filtered and evaporated to afford (3-ethyl-8-fluoroindolizin-5-yl)(1-((2-(trimethylsilyl)ethoxy)methyl)-1H-imidazol-2-yl)methanol (400 mg, 72.7%) as a colorless oil. $^1$HNMR (400 MHz, CDCl$_3$) δ −0.06 (2H, d), 0.08 (m), 0.71 (qdd), 1.29 (t), 1.48 (t), 2.07 (1H, s), 3.38 (m), 4.15 (q), 5.10 (m), 5.81 (dd), 6.11 (dd), 6.63 (s), 6.73 (q), 7.10 (dd). LC-MS (Method A): m/z (ES+), [M+H]+=390.15; acid, HPLC $t_R$=1.585 min.

Intermediate D, 3-Ethyl-8-fluoroindolizine-5-carbaldehyde

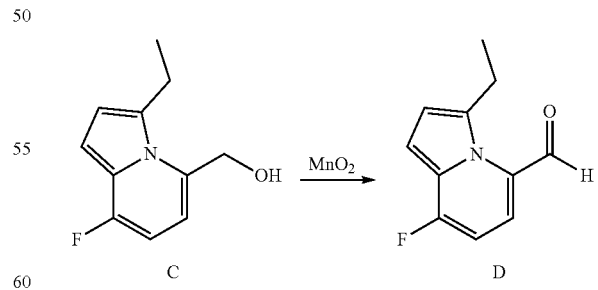

Manganese(IV) oxide (4500 mg, 51.76 mmol) was added to compound C (~400 mg) and DCM (2 mL) under nitrogen. The resulting mixture was stirred at rt for 48 hours. The reaction mixture was filtered through celite. The solvent was removed under reduced pressure. The crude product was purified by flash silica chromatography, elution gradient 0 to 1% EtOAc in petroleum ether. Pure fractions were evaporated to dryness to afford 3-ethyl-8-fluoroindolizine-5-carbaldehyde (160 mg, 32.3%) as a yellow oil. $^1$H NMR (300 MHz, CDCl$_3$-d) δ 9.93 (s, 1H), 7.47-7.36 (m, 1H), 6.99 (d, J=4.4 Hz, 1H), 6.82 (d, J=4.4 Hz, 1H), 6.57-6.44 (m, 1H), 2.99 (q, J=7.6 Hz, 2H), 1.33 (t, J=9.4, 8.4 Hz, 3H). LC-MS (Method A): m/z (ES+), [M+H]+=191.95; acid, HPLC t$_R$=1.004 min.

Intermediate C,
(3-Ethyl-8-fluoroindolizin-5-yl)methanol

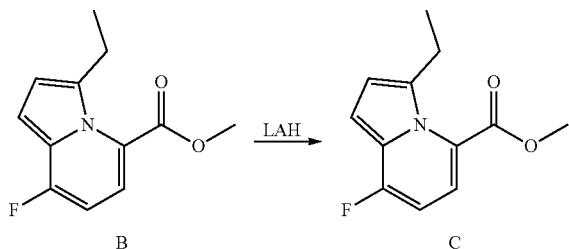

Lithium aluminum hydride (172 mg, 4.52 mmol) was added slowly to methyl 3-ethyl-8-fluoroindolizine-5-carboxylate (500 mg, 2.26 mmol) in THF (8 mL) under nitrogen. The resulting mixture was stirred at 0° C. for 1 hour. The reaction mixture was quenched with water (5 mL), extracted with EtOAc (3×15 mL), the organic layer was dried over Na$_2$SO$_4$, filtered and evaporated to afford white solid. The crude product was purified by flash C18-flash chromatography, elution gradient 0 to 60% MeCN in water. Pure fractions were evaporated to dryness to afford (3-ethyl-8-fluoroindolizin-5-yl)methanol (260 mg, 59.5%) as a grey solid. $^1$H NMR (400 MHz, CDCl$_3$) δ ppm 6.73-6.63 (m, 2H), 6.44 (dd, J=7.4, 5.6 Hz, 1H), 6.24 (dd, J=9.9, 7.4 Hz, 1H), 4.94 (s, 2H), 3.30 (q, J=7.4 Hz, 2H), 1.42 (t, J=7.4 Hz, 3H). LC-MS (Method A): m/z (ES+), [M+H]+=194.05; acid, HPLC t$_R$=1.498 min.

Intermediate B, Methyl
3-ethyl-8-fluoroindolizine-5-carboxylate

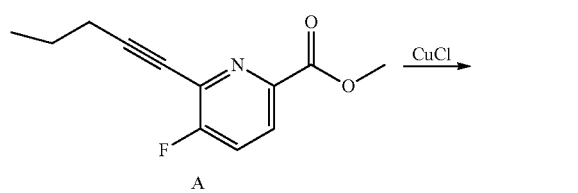

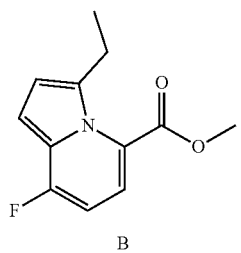

Copper(I) chloride (0.483 g, 4.88 mmol) was added to methyl 5-fluoro-6-(pent-1-yn-1-yl)picolinate (1.08 g, 4.88 mmol) in triethylamine (1.000 mL) and DMA (3.5 mL) under nitrogen. The resulting mixture was stirred at 120° C. for 16 hours. The reaction mixture was diluted with EtOAc (25 mL), and washed sequentially with water (15 mL×3), saturated brine (15 mL×2), and saturated NH$_4$Cl (10 mL×2). The organic layer was dried over Na$_2$SO$_4$, filtered and evaporated to afford crude product. The crude product was purified by flash silica chromatography, elution gradient 0 to 0% EtOAc in petroleum ether. The crude product was purified by flash C18-flash chromatography, elution gradient 0 to 60% MeCN in water. Pure fractions were evaporated to dryness to afford methyl 3-ethyl-8-fluoroindolizine-5-carboxylate (0.550 g, 50.9%) as a yellow solid. $^1$H NMR (400 MHz, CDCl$_3$) δ ppm 7.56 (d, J=7.0 Hz, 1H), 7.17 (dd, J=7.8, 5.5 Hz, 2H), 6.87 (d, J=4.2 Hz, 2H), 6.75 (d, J=4.1 Hz, 2H), 6.61 (s, 1H), 6.46 (td, J=7.1, 5.1 Hz, 1H), 6.41-6.29 (m, 3H), 3.99 (s, 5H), 2.85 (q, J=7.5 Hz, 2H), 2.76-2.66 (m, 4H), 1.41 (t, J=7.5 Hz, 3H), 1.31 (t, J=7.4 Hz, 6H). LC-MS (Method A): m/z (ES+), [M+H]+=222.0; acid, HPLC t$_R$=1.072 min.

Intermediate A, Methyl
5-fluoro-6-(pent-1-ynyl)picolinate

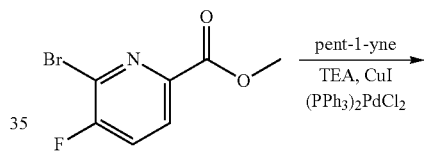

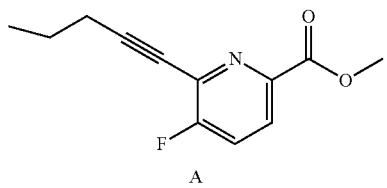

Pent-1-yne (0,524 g, 7.69 mmol) and bis(triphenylphosphine)palladium(II) chloride (0.450 g, 0.64 mmol) was added to copper(I) iodide (0.122 g, 0.64 mmol), TEA (1.787 mL, 12.82 mmol) and methyl 6-bromo-5-fluoropicolinate (1.5 g, 6.41 mmol) in acetonitrile (20 mL) under nitrogen. The resulting mixture was stirred at 80° C. for 3 hours. The solvent was removed under reduced pressure. The crude product was purified by flash silica chromatography, elution gradient 0 to 10% EtOAc in petroleum ether. Pure fractions were evaporated to dryness to afford methyl 5-fluoro-6-(pent-1-yn-1-yl)picolinate (1.28 g, 90%) as a orange solid. $^1$H NMR (400 MHz, CDCl$_3$) δ ppm 8.20-8.06 (m, 2H), 7.52 (dd, J=8.6, 8.0 Hz, 2H), 4.14 (q, J=7.1 Hz, 1H), 4.01 (s, 7H), 2.50 (td, J=7.1, 1.0 Hz, 4H), 2.07 (s, 1H), 1.71 (h, J=7.3 Hz, 4H), 1.28 (t, J=7.1 Hz, 1H), 1.09 (t, J=7.4 Hz, 6H). LC-MS (Method A): m/z (ES+), [M+H]+=222.2; acid, HPLC t$_R$=1.140 min.

Example 35. Pure Enantiomer, Isomer 1 of (3-Ethyl-8-fluoroindolizin-5-yl)(1H-imidazol-2-yl) methanol

Alternative Synthesis to Example 34, 35 and 36. (3-Ethyl-8-fluoroindolizin-5-yl)-(1H-imidazol-2-yl) methanol and Pure Enantiomers

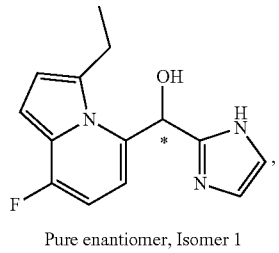

Pure enantiomer, Isomer 1

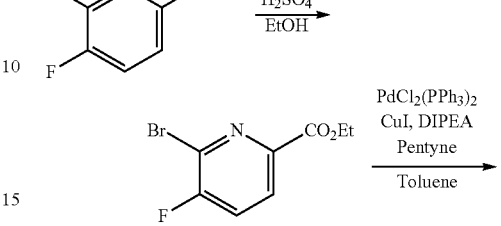

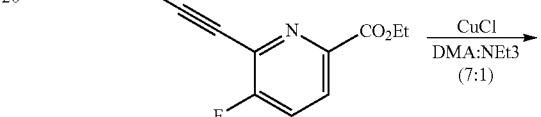

A

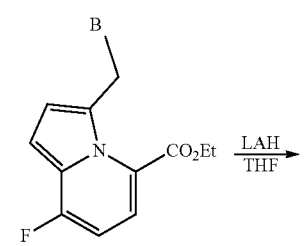

B

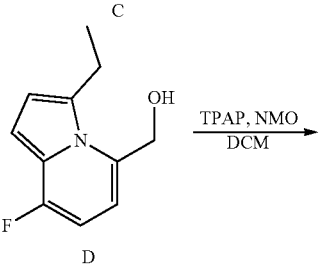

C

The product was purified by preparative chiral-HPLC on a Chiralpak IA column, eluting isocratically with 10% EtOH in heptane (modified with 0.1% DEA) as eluent. The fractions containing the desired compound were evaporated to dryness to afford P1-(3-ethyl-8-fluoroindolizin-5-yl)(1H-imidazol-2-yl)methanol (60.0 mg, 37.5%) as a brown solid (Example 35) and P2-(3-ethyl-8-fluoroindolizin-5-yl)(1H-imidazol-2-yl)methanol (60.0 mg, 37.5%) as a brown solid (Example 36). $^1$H NMR (400 MHz, DMSO) δ 1.32 (3H, t), 3.22 (1H, dt), 6.21 (1H, s), 6.46 (2H, m), 6.65 (2H, m), 6.77 (2H, s), 7.20 (2H, s), 13.20 (1H, s). m/z (ES+), [M+H]+=260.4; acid, HPLC $t_R$=2.478 min. Analytical chiral HPLC was completed using AmChemteq ACI Am-1 column, 0.46×15 cm, 5 μm. The mobile phase A was hexanes (with 0.1% DEA) and mobile phase B was ethanol (70/30 mixture A:B). Uv-vis detection at 220 nm. Flow=1.0 ml/min. $t_R$=2.95 min; Purity 99%.

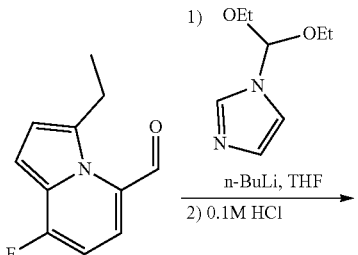

D

Example 36. Pure Enantiomer, Isomer 2 of (3-Ethyl-8-fluoroindolizin-5-yl)(1H-imidazol-2-yl) methanol

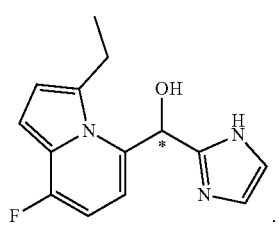

Pure enantiomer, Isomer 2

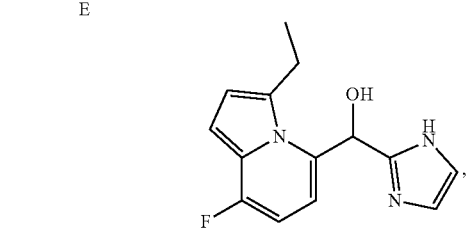

Example 34
racemic mixture

See example 35. $^1$H NMR (300 MHz, DMSO) δ ppm 1.28 (3H, t), 3.19 (2H, qd), 6.44 (4H, m), 6.60 (2H, m), 6.99 (2H, s), 12.21 (1H, s). LC-MS (Method A): m/z (ES+), [M+H]+=260.3; acid, HPLC tR=2,213 min. Chiral HPLC using methods described in Example 35. $t_R$=3.76 min; Purity 99% ee.

2.50 M n-BuLi in THF (11.8 mL, 29.5 mmol) was added to a cooled solution of 1-(diethoxymethyl)imidazole (5.02 g, 29.5 mmol) in THF (75 mL) at −45° C., and the mixture was stirred for 15 m. The mixture was cooled to −78° C., and a solution of 3-ethyl-8-fluoroindolizine-5-carbaldehyde (2.82 g, 14.8 mmol) in THF (25 mL) was added drop-wise. The mixture was stirred for 30 m at −78° C. and then warmed to 0° C. for 1 h. The mixture was diluted with 0.1M HCl (50.0 mL) and EtOAc (50.0 mL) at 0° C. The mixture was stirred at 23° C. for 15 m. More EtOAc (50.0 mL) was added, and the phases were separated. The organic phase was extracted with 0.1M HCl (3×50.0 mL), and the combined aqueous phases were cautiously diluted with sat. NaHCO$_3$ (50.0 mL). The aqueous phase was extracted with EtOAc (3×200 mL), and the combined organic phases were washed with brine (200 mL), dried over MgSO$_4$, filtered and concentrated under reduced pressure. The compound was identical to material made by the other descried route, and could be purified by chiral SFC chromatography to provide pure enantiomers as previously described.

Alternate Synthesis Example 34, Intermediate E.
3-Ethyl-8-fluoroindolizine-5-carbaldehyde NMO (8.23 g, 70.3 mmol) was added to a mixture of (3-ethyl-8-fluoroindolizin-5-yl)methanol (6.79 g, 35.1 mmol) and 4 Å molecular sieves in DCM (100 mL). The mixture was stirred at 23° C. for 30 m. The mixture was cooled to 0° C., and TPAP (1.23 g, 3.51 mmol) was added in portions. The mixture was warmed to 23° C. for 1 h and filtered through a pad of Florisil. The filtrate was concentrated under reduced pressure, and the product was purified by silica gel chromatography (120 g cartridge) eluting with hexane and EtOAc (0-30%) to provide the title compound as a solid (2.82 g, 42%). $^1$H NMR (500 MHz, CDCl$_3$) δ 9.90 (s, 1H), 7.38 (dd, J=7.9, 5.6 Hz, 1H), 6.96 (d, J=4.2 Hz, 1H), 6.79 (d, J=4.2 Hz, 1H), 6.47 (dd, J=9.3, 7.9 Hz, 1H), 2.96 (q, J=7.4 Hz, 2H), 1.31 (t, J=7.4 Hz, 3H); LC_MS (Method C) m/z (ES+), No ionization. t$_R$=1.76 min.

Alternate Synthesis Example 34, Intermediate D.
(3-Ethyl-8-fluoroindolizin-5-yl)methanol 2M LAH in THF (20.5 mL, 40.9 mmol) was added to a cooled solution of ethyl 3-ethyl-8-fluoroindolizine-5-carboxylate (9.63 g, 40.9 mmol) in THF (90.0 mL) under nitrogen at 0° C. The mixture was stirred at 0° C. for 15 m and then diluted with acetone (10.0 mL) and a sat. solution of K/Na tartrate (100 mL). Water (100 mL) was added, and the product was extracted from the aqueous phase with EtOAc (3×200 mL). The combined organic phases were washed with brine (200 mL), dried (MgSO$_4$), filtered, and concentrated under reduced pressure. The product was purified by silica gel chromatography (120 g cartridge) with hexane and EtOAc (5-60%) to provide the title compound as a solid (6.79 g, 86%). $^1$H NMR (500 MHz, CDCl$_3$) δ 6.68 (d, J=4.1 Hz, 1H), 6.64 (d, J=4.1 Hz, 1H), 6.41 (dd, J=7.4, 5.6 Hz, 1H), 6.22 (dd, J=9.8, 7.4 Hz, 1H), 4.91 (d, J=6.2 Hz, 2H), 3.27 (q, J=7.4 Hz, 2H), 1.68 (t, J=6.2 Hz, 1H), 1.40 (t, J=7.4 Hz, 3H). LC-MS (Method C) m/z (ES+), [M+H]$^+$=193.8. HPLC t$_R$=1.51 min.

Alternate Synthesis Example 34, Intermediate C.
Ethyl 3-ethyl-8-fluoroindolizine-5-carboxylate A solution of ethyl 5-fluoro-6-pent-1-ynyl-pyridine-2-carboxylate (14.5 g, 61.6 mmol) in degassed DMA (193 mL) was added to CuCl (3.05 g, 30.8 mmol) under nitrogen. Degassed NEt$_3$ (27.5 mL, 197 mmol) was added, and the mixture was stirred at 130° C. for 20 h. The mixture was cooled and filtered through Celite, washing with EtOAc. The filtrate was concentrated under reduced pressure. Water (400 mL) was added to the residue, and the aqueous phase was extracted with EtOAc (3×500 mL). The combined organic phases were washed with brine (500 mL), dried (MgSO$_4$), filtered, and concentrated under reduced pressure. The product was purified by silica gel chromatography (220 g cartridge) with hexane and EtOAc (0-20%) to provide the title compound as an oil (9.63 g, 66%). $^1$H NMR (500 MHz, CDCl$_3$) δ 7.14 (dd, J=7.7, 5.5 Hz, 1H), 6.83 (d, J=4.2 Hz, 1H), 6.72 (d, J=4.2 Hz, 1H), 6.33 (dd, J=9.7, 7.8 Hz, 1H), 4.43 (q, J=7.1 Hz, 2H), 2.71 (q, J=7.4 Hz, 2H), 1.42 (t, J=7.1 Hz, 3H), 1.28 (t, J=7.4 Hz, 3H). LC-MS (Method C): m/z (ES+), [M+H]$^+$=235.9. HPLC t$_R$=2.18 m.

Alternate Synthesis Example 34, Intermediate B.
Ethyl 5-fluoro-6-pent-1-ynyl-pyridine-2-carboxylate 1-Pentyne (12.1 mL, 123 mmol) was added to a mixture of ethyl 6-bromo-5-fluoro-pyridine-2-carboxylate (20.4 g, 82.0 mmol), CuI (2.34 g, 12.3 mmol), and PdCl$_2$(PPh$_3$)$_2$ (5.76 g, 8.20 mmol) in degassed toluene (500 mL) at 23° C. under nitrogen. DIPEA (28.6 mL, 164 mmol) was added, and the mixture was stirred in the dark (covered with aluminum foil) for 18 h. The mixture was diluted with a sat. solution of NaHCO$_3$ (400 mL). The aqueous phase was extracted with EtOAc (3×400 mL), and the combined organic phases were washed with brine (400 mL), dried (MgSO$_4$), filtered, and concentrated under reduced pressure. The product was purified by silica gel chromatography (330 g cartridge) with hexane and EtOAc (0-50%) to provide the title compound as an oil (16.8 g, 87%). $^1$H NMR (500 MHz, CDCl$_3$) δ 8.05 (dd, J=8.6, 4.0 Hz, 1H), 7.54-7.43 (m, 1H), 4.45 (q, J=7.1 Hz, 2H), 2.47 (td, J=7.1, 0.7 Hz, 2H), 1.68 (h, J=7.3 Hz, 2H), 1.42 (t, J=7.1 Hz, 3H), 1.06 (t, J=7.4 Hz, 3H). LC-MS (Method C): m/z (ES+), [M+H]$^+$=235.9. HPLC t$_R$=1.92 m.

Alternate Synthesis Example 34, Intermediate A.
Ethyl 6-bromo-5-fluoro-pyridine-2-carboxylate 6-Bromo-5-fluoro-pyridine-2-carboxylic acid (24.0 g, 109 mmol) was dissolved in a mixture of EtOH (400 mL) and conc. H$_2$SO$_4$ (17.5 mL, 328 mmol). The mixture was heated at 90° C. for 2.5 h. After cooling to 0° C., a solution of 3.50 M NaOH (90.0 mL, 315 mmol) was slowly added with vigorous stirring (pH adjusted to approx. 4), followed by a sat. solution of NaHCO$_3$ until pH was approx. 8. The slurry was filtered through a pad of Celite, and the filtrate was concentrated under reduced pressure. The residue was suspended in cold water (300 mL) and stirred at 0° C. for 5 m. The mixture was filtered, washing with water, and the solid was dried under vacuum to provide the title compound as a solid (20.4 g, 75%). $^1$H NMR (500 MHz, CDCl$_3$) δ 8.12 (dd, J=8.3, 3.6 Hz, 1H), 7.53 (dd, J=8.3, 7.0 Hz, 1H), 4.47 (q, J=7.1 Hz, 2H), 1.43 (t, J=7.1 Hz, 3H). LC-MS (Method C): m/z (ES+), [M+H]$^+$=247.8. HPLC t$_R$=1.74 m.

Example 37. (8-Fluoro-3-methylindolizin-5-yl)(1H-imidazol-2-yl)methanol

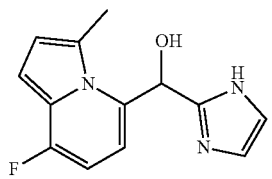

Example 37

Made in analogous fashion to Example 34. $^1$H NMR (300 MHz, DMSO-d6) δ ppm 12.08 (s, 1H), 7.08 (s, 1H), 6.86 (s, 1H), 6.53 (t, J=3.7 Hz, 2H), 6.47-6.35 (m, 2H), 6.30 (d, J=7.1 Hz, 1H), 2.71 (s, 3H). LC-MS (Method A): m/z (ES+), [M+H]+=246.2; alkali, HPLC $t_R$=1.357 min.

Example 38. (8-Fluoro-3-isopropylindolizin-5-yl)(1H-imidazol-2-yl)methanol

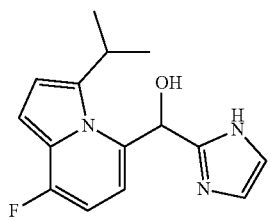

Example 38

Example 38 was made by analogous fashion to Example 34. $^1$H NMR (300 MHz, DMSO-d6) δ ppm 12.12 (s, 1H), 7.10 (s, 1H), 6.86 (s, 1H), 6.74 (d, J=4.2 Hz, 1H), 6.63 (d, J=4.2 Hz, 1H), 6.56-6.26 (m, 4H), 3.77 (p, J=6.6 Hz, 1H), 1.35-1.21 (m, 6H). LC-MS (Method A modified to basic conditions): m/z (ES+), [M+H]+=274.2; alkali, HPLC $t_R$=1.559 min.

Example 39. (3-Cyclopropyl-8-fluoroindolizin-5-yl)(1H-imidazol-2-yl)methanol

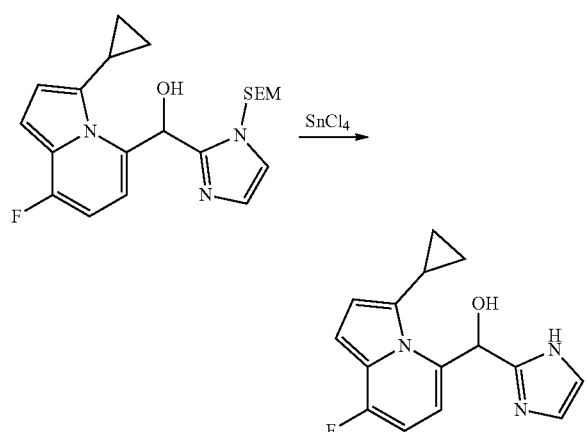

Example 39

Example 38 was made by analogous fashion to Example 34. The following modifications were made for the final deprotection step. Perchlorostannane (130 mg, 0.50 mmol) was added to (3-cyclopropyl-8-fluoroindolizin-5-yl)(1-((2-(trimethylsilthyl)-1H-imidazol-2-yl)methanol (200 mg, 0.50 mmol) in DCM (4 mL) under nitrogen. The resulting solution was stirred at rt for 30 hours. The solvent was removed under reduced pressure and redissolved in MeOH (2 ml). The reaction mixture was neutralized with NH$_3$.H$_2$O to pH=7-8. The crude product was purified by preparative HPLC (XSelect CSH Prep C18 OBD column, 5 silica, 19 mm diameter, 100 mm length), using decreasingly polar mixtures of water (containing 0.05% NH$_4$HCO$_3$) and MeCN as eluents. Fractions containing the desired compound were evaporated to dryness to afford (3-cyclopropyl-8-fluoroindolizin-5-yl)(1H-imidazol-2-yl)methanol (10.00 mg, 7.40%) as a off-white solid. $^1$H NMR (400 MHz, MeOD) ppm 0.78 (1H, tt), 0.91 (1H, tt), 1.03 (2H, s), 1.31 (1H, s), 2.42 (1H, ddd), 5.11 (5H, s), 6.27 (2H, m), 6.54 (2H, m), 7.08 (2H, s), 7.37 (1H, s). LC-MS (Method A, modified to basic conditions): m/z (ES+), [M+H]+=272.0; base, HPLC $t_R$=1.511 min.

Example 40. (3-Ethyl-7-fluorobenzofuran-4-yl)(1H-imidazol-2-yl)methanol

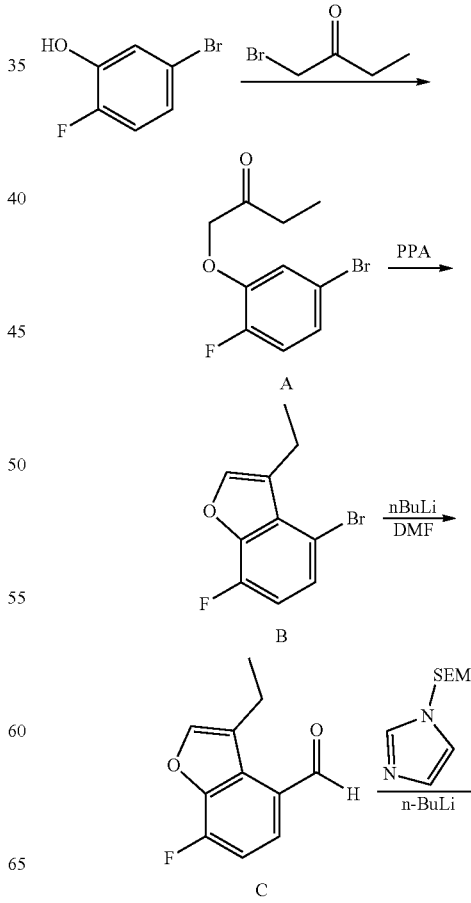

-continued

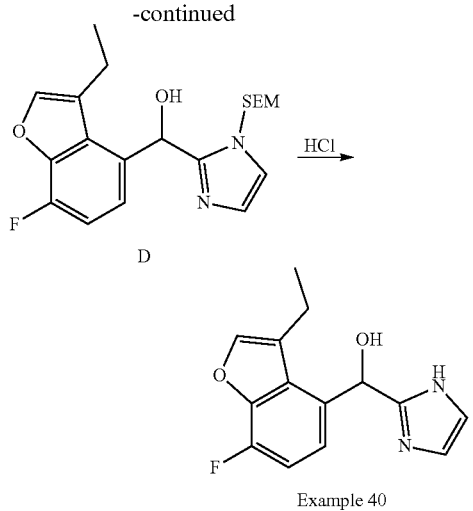

Example 40

Hydrogen chloride in dioxane (73.0 mL, 291.91 mmol) was added dropwise to (3-ethyl-7-fluorobenzofuran-4-yl)(1-((2-(trimethylsilyl)ethoxy)methyl)-1H-imidazol-2-yl)methanol (5.7 g, 14.60 mmol) in 1,4-dioxane (20 mL) in ice bath under nitrogen. The temperature was increased to room temperature naturally. The resulting solution was stirred at 40° C. overnight. The solvent was removed under reduced pressure to give a crude product. The crude product was basified with 7M NH₃ in MeOH, and purified by flash C18-flash chromatography, elution gradient 0 to 30% MeCN in water. Pure fractions were evaporated to dryness to afford (3-ethyl-7-fluorobenzofuran-4-yl)(1H-imidazol-2-yl)methanol (2.500 g, 65.8%) as a white solid. ¹HNMR (300 MHz, DMSO-d6) ppm 1.11-1.29 (3H, t, J 7.4), 2.63-2.98 (2H, m), 6.18-6.32 (2H, m), 6.84-6.93 (2H, s), 7.12-7.22 (1H, dd, J 10.7, 8.5), 7.23-7.33 (1H, dd, J 8.5, 4.7), 7.77-7.84 (1H, s), 12.01-12.13 (1H, s). LC-MS (Method A): m/z (ES+), [M+H]+=261.4; acid, HPLC $t_R$=1.539 min.

Intermediate D, (3-Ethyl-7-fluorobenzofuran-4-yl)(1-((2-(trimethylsilyl)ethoxy)methyl)-1H-imidazol-2-yl)methanol

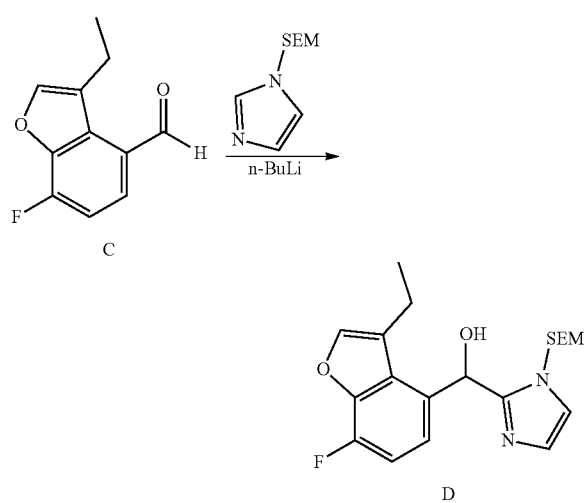

Butyllithium (13.05 mL, 32.62 mmol) was added dropwise to 1-((2-(trimethylsilyl)ethoxy)methyl)-1H-imidazole (7.06 g, 35.59 mmol), in THF (150 mL) cooled to −70° C. over a period of 5 minutes under nitrogen. 3-ethyl-7-fluorobenzofuran-4-carbaldehyde (5.7 g, 29.66 mmol) in THF (15 mL) was added dropwise after the reaction had been stirred for 1.5 hour at −70° C. The reaction was incomplete so the mixture was left to stir for 1 hour at −70° C. The reaction mixture was quenched with saturated NH₄Cl (200 mL), extracted with EtOAc (3×200 mL), the organic layer was dried over Na₂SO₄, filtered and evaporated to afford yellow oil. The crude product was purified by flash C18-flash chromatography, elution gradient 0 to 50% MeCN in water. Pure fractions were evaporated to dryness to afford (3-ethyl-7-fluorobenzofuran-4-yl)(1-((2-(trimethylsilyl)ethoxy)methyl)-1H-imidazol-2-yl)methanol (5.72 g, 49.4%) as a white solid. ¹H NMR (300 MHz, DMSO-d6) ppm −0.07--0.01 (9H, s), 0.69-0.94 (2H, dddd, J=35.8, 13.8, 9.7, 6.9), 1.06-1.18 (3H, t, J=7.4), 2.22-2.42 (1H, m), 2.52-2.67 (1H, m), 3.36-3.56 (2H, ddq, J=9.5, 6.7, 3.0), 5.26-5.36 (1H, d, J=10.7), 5.60-5.71 (1H, d, J=10.7), 6.18-6.25 (1H, d, J=6.0), 6.29-6.38 (1H, d, J=6.0), 6.69-6.76 (1H, d, J=1.1), 7.12-7.22 (1H, dd, J=10.8, 8.5), 7.27-7.38 (2H, m), 7.73-7.79 (1H, s). LC-MS (Method A): m/z (ES+), [M+H]+=391.4; acid, HPLC $t_R$=2.323 min.

Intermediate C, 3-Ethyl-7-fluorobenzofuran-4-carbaldehyde

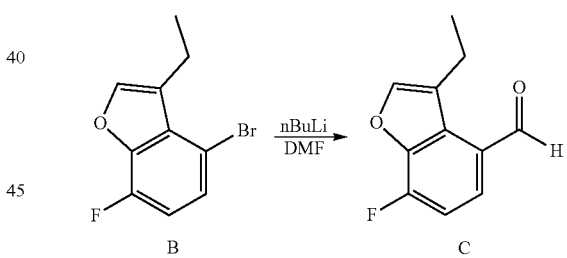

DMF (0.637 mL, 8.23 mmol) was added slowly to 4-bromo-3-ethyl-7-fluorobenzofuran (1 g, 4.11 mmol) and butyllithium (2.468 mL, 6.17 mmol) in THF (20 mL) at −78° C. over a period of 1 hour under nitrogen. The resulting solution was stirred at −78° C. for 1 hour. The reaction mixture was quenched with saturated NH₄Cl (20 mL), extracted with EtOAc (2×25 mL), the organic layer was dried over Na₂SO₄, filtered and evaporated to afford white solid. The crude product was purified by flash silica chromatography, elution gradient 0 to 20% EtOAc in petroleum ether. Pure fractions were evaporated to dryness to afford 3-ethyl-7-fluorobenzofuran-4-carbaldehyde (0.570 g, 72.1%) as a white solid. LC-MS (Method A): m/z (ES+), [M+H]+=193; acid, HPLC $t_R$=1.652 min.

Intermediate B,
4-Bromo-3-ethyl-7-fluorobenzofuran

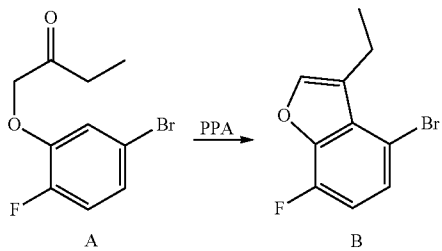

Polyphosphoric acid (11.76 g, 49.03 mmol) was added to 1-(5-bromo-2-fluorophenoxy)butan-2-one (6.4 g, 24.51 mmol) in toluene (50 mL) under nitrogen. The resulting mixture was stirred at 120° C. for 14 hours. The reaction mixture was poured into water (50 mL), extracted with EtOAc (2×75 mL), the organic layer was dried over $Na_2SO_4$, filtered and evaporated to afford white liquid. The crude product was purified by flash silica chromatography, elution gradient 0 to 1% EtOAc in petroleum ether. Pure fractions were evaporated to dryness to afford 4-bromo-3-ethyl-7-fluorobenzofuran (2.20 g, 36.9%) as a white solid use as is without further purification.

Intermediate A,
1-(5-bromo-2-fluorophenoxy)butan-2-one

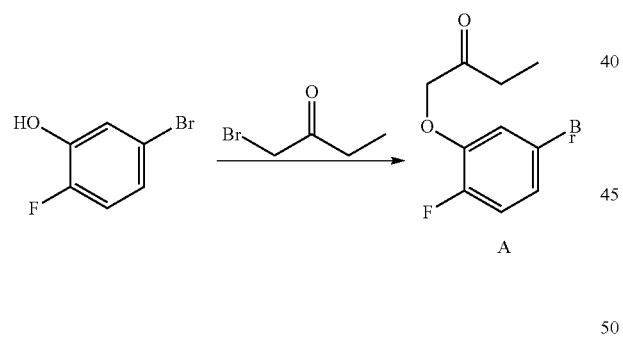

1-Bromobutan-2-one (26.1 g, 172.78 mmol) was added to 5-bromo-2-fluorophenol (30 g, 157.07 mmol) and $K_2CO_3$ (54.3 g, 392.67 mmol) in MeCN (500 mL) at 25° C. over a period of 0.5 hour under nitrogen. The resulting solution was stirred at 60° C. for 3 hours. The solvent was removed under reduced pressure. The crude product was purified by flash silica chromatography, elution gradient 0 to 10% EtOAc in petroleum ether. Pure fractions were evaporated to dryness to afford 1-(5-bromo-2-fluorophenoxy)butan-2-one (31.0 g, 76%) as a white solid. $^1$H NMR (300 MHz, Methanol-d4) δ ppm 1.02-1.14 (t, J=7.3 Hz, 3H), 2.54-2.67 (q, J=7.3 Hz, 2H), 4.78-4.85 (s, 2H), 7.00-7.13 (m, 2H), 7.14-7.22 (dd, J=7.6, 2.0 Hz, 1H). LC-MS (Method A): m/z (ES+), [M+H]+=unknown; acid, HPLC $t_R$=1.574 min.

Example 41. Pure Enantiomer, Peak 2, (R)-(3-Ethyl-7-fluorobenzofuran-4-yl)(1H-imidazol-2-yl)methanol

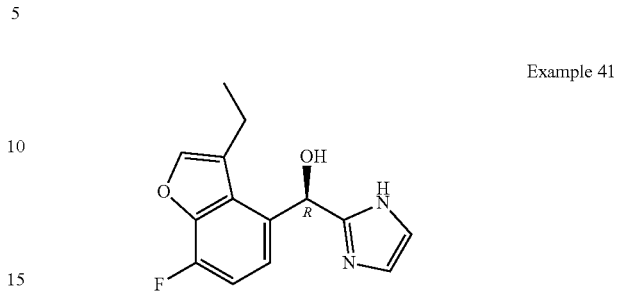

Example 41

Example 40 was purified by preparative chiral-HPLC on a CHIRALPAK AD-H SFC, 5×25 cm, 5 m with 30% MeOH in other solvent (modified with 0.1% IPAmine) as eluent. The fractions containing the desired compound were evaporated to dryness to afford (3-ethyl-7-fluorobenzofuran-4-yl)(1H-imidazol-2-yl)methanol (0.850 g, 38.2%) as a white solid. Mobile Phase A: $CO_2$: Mobile Phase B: MeOH (0.1% IPAmine) (70:30 ratio). Flow rate: 170 mL/min; 254 nm; Peak 2 $t_R$=5.66 min $^1$HNMR (300 MHz, Methanol-d4) δ ppm 1.20-1.37 (3H, t, J 7.4), 2.62-2.86 (2H, m), 6.31-6.38 (1H, s), 6.95-7.08 (3H, m), 7.08-7.18 (1H, dd, J 8.4, 4.5), 7.55-7.62 (1H, t, J 1.4). LC-MS (Method A): m/z (ES+), [M+H]+=260.95; acid, HPLC $t_R$=1.263 min.

Example 42. Pure Enantiomer, Peak 1, (S)-(3-Ethyl-7-fluorobenzofuran-4-yl)(1H-imidazol-2-yl)methanol

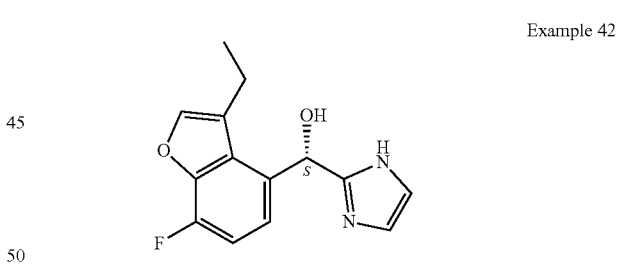

Example 42

Example 40 was purified by preparative chiral-HPLC on a CHIRALPAK AD-H SFC, 5×25 cm, 5 μm with 30% MeOH in other solvent (modified with 0.1% IPAmine) as eluent. The fractions containing the desired compound were evaporated to dryness to afford (3-ethyl-7-fluorobenzofuran-4-yl)(1H-imidazol-2-yl)methanol (0.850 g, 38.2%) as a white solid. Mobile Phase A: $CO_2$: Mobile Phase B: MeOH (0.1% IPAmine) (70:30 ratio). Flow rate: 170 mL/min; 254 nm; Peak 1, $t_R$=:4.29 min. Absolute stereochemistry established by X-ray crystal structure in Par2 protein. $^1$HNMR (300 MHz, DMSO-d6) δ ppm 1.17-1.29 (3H, t, J 7.4), 2.64-2.98 (2H, m), 6.18-6.25 (1H, s), 6.85-6.92 (2H, s), 7.10-7.34 (2H, m), 7.77-7.83 (1H, s), 8.11-8.17 (1H, s), 11.81-12.88 (1H, s). LC-MS (Method A): m/z (ES+), [M+H]+=260.95; acid, HPLC $t_R$=1.263 min.

Example 43. (3-Cyclopropyl-7-fluorobenzofuran-4-yl)(1H-imidazol-2-yl)methanol

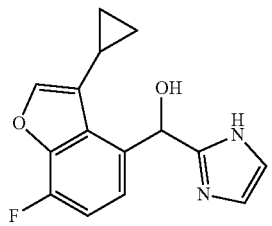

Example 43

Example 43 was prepared in analogous fashion to example 40, utilizing 2-bromo-1-cyclopropylethanone. ¹HNMR (400 MHz, DMSO-d6) δ ppm 0.55 (1H, q), 0.64 (1H, m), 0.78 (2H, m), 1.98 (1H, s), 6.79 (1H, d), 7.11 (1H, m), 7.28 (2H, m), 7.60 (2H, s), 7.93 (1H, d), 14.23 (2H, s). LC-MS (Method A): m/z (ES+), [M+H]+=273.1; base, HPLC $t_R$=2.552 min.

Example 44. Pure Enantiomer, Isomer 1, (3-Cyclopropyl-7-fluorobenzofuran-4-yl)(1H-imidazol-2-yl)methanol

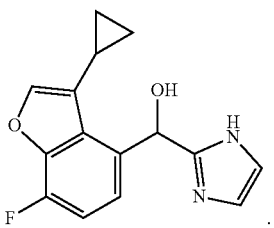

Example 44

Pure enantiomer, Isomer 1

Example 43 was purified by preparative chiral-HPLC on a Chiralpak IA column, eluting isocratically with 10% IPA hexane (modified with 0.1% DEA) as eluent. The fractions containing the desired compound were evaporated to dryness to afford P1-(3-cyclopropyl-7-fluorobenzofuran-4-yl)(1H-imidazol-2-yl)methanol (40.0 mg, 40.0%, Example 44) and P2-(3-cyclopropyl-7-fluorobenzofuran-4-yl)(1H-imidazol-2-yl)methanol (40.0 mg, 40.0%, Example 45) as a off-white solid. ¹HNMR (400 MHz, DMSO-d6) δ ppm 0.51 (1H, q), 0.81 (3H, m), 2.16 (1 H, p), 6.26 (1H, d), 6.62 (1H, d), 6.76 (1H, s), 7.00 (1H, s), 7.18 (1H, dd), 7.33 (1H, dd), 7.79 (1H, d), 11.96 (1H, s). LC-MS (Method A, modified to basic conditions): m/z (ES+), [M+H]+=273.2; base, HPLC $t_R$=1.814 min. Analytical chiral HPLC methods: ODH column, (0.46×10 cm, 5 μM), mobile phase A: Hexanes, mobile phase B: ethanol (90:10 ratio), detection at 254 nm. $t_R$=3.75.

Example 45. Pure Enantiomer, Isomer 2, (3-Cyclopropyl-7-fluorobenzofuran-4-yl)(1H-imidazol-2-yl)methanol

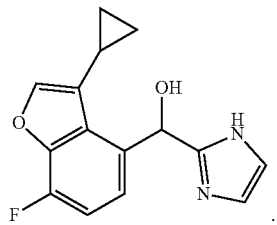

Example 45

Pure enantiomer, Isomer 2

Example 45 was purified by preparative chiral-HPLC on a Chiralpak IA column, eluting isocratically with 10% IPA hexane (modified with 0.1% DEA) as eluent. The fractions containing the desired compound were evaporated to dryness to afford P1-(3-cyclopropyl-7-fluorobenzofuran-4-yl)(1H-imidazol-2-yl)methanol (40.0 mg, 40.0%, Example 45) and P2-(3-cyclopropyl-7-fluorobenzofuran-4-yl)(1H-imidazol-2-yl)methanol (40.0 mg, 40.0%, Example 45) as a off-white solid. ¹HNMR (400 MHz, DMSO-d6) δ ppm 0.53 (1H, m), 0.80 (3H, m), 2.15 (1H, q), 6.26 (1H, d), 6.62 (1H, d), 6.76 (1H, s), 7.00 (1H, s), 7.18 (1H, dd), 7.33 (1H, dd), 7.79 (1H, d), 11.96 (1H, s). LC-MS (Method A, modified to basic conditions): m/z (ES+), [M+H]+=273.2; base, HPLC $t_R$=1.903 min. Analytical chiral HPLC methods: ODH column, (0.46×10 cm, 5 μM), mobile phase A: Hexanes, mobile phase B: ethanol (90:10 ratio), detection at 254 nm. $t_R$=5.43.

Example 46, (7-Fluoro-3-(2,2,2-trifluoroethyl)benzofuran-4-yl)(1H-imidazol-2-yl)methanol

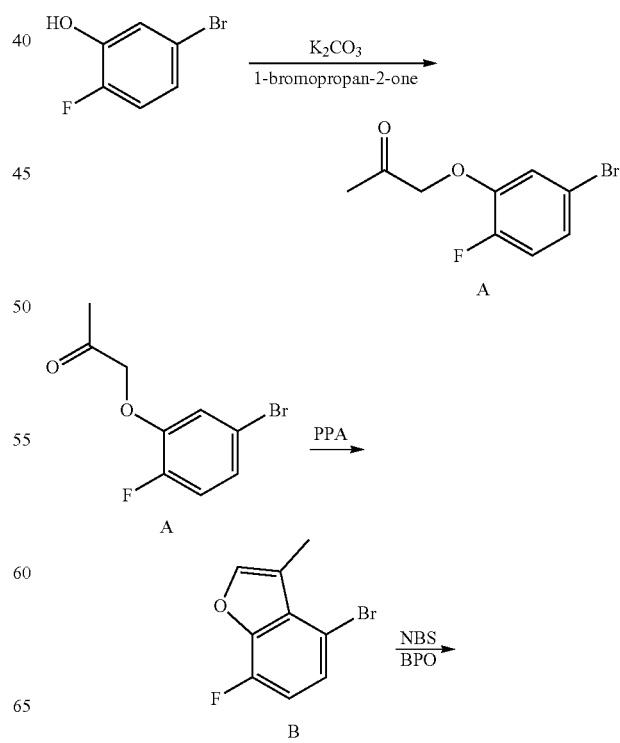

-continued

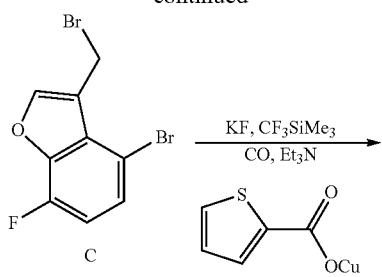

C

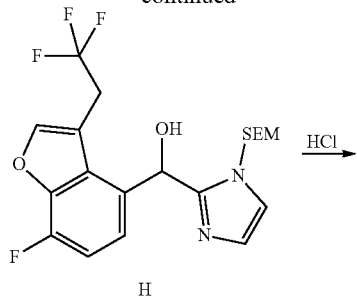

H

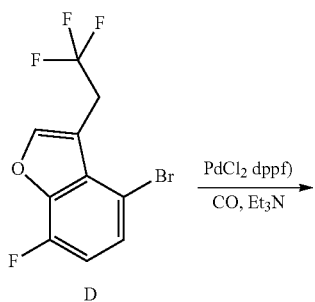

D

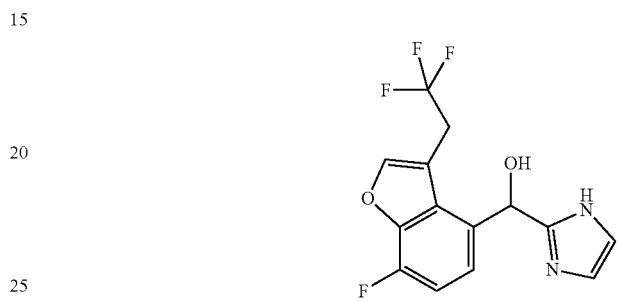

Example 46

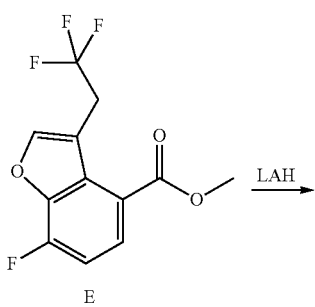

E (7-Fluoro-3-(2,2,2-trifluoroethyl)benzofuran-4-yl)(1-((2-(trimethylsilyl)ethoxy)methyl)-1H-imidazol-2-yl)methanol (100 mg, 0.22 mmol) was added EtOAc/HCl (2 mL) at rt under nitrogen. The resulting solution was stirred at rt for 16 hours. The solvent was removed under reduced pressure. The crude product was purified by preparative HPLC (XSelect CSH Prep C18 OBD column, 5 μm silica, 19 mm diameter, 150 mm length), using decreasingly polar mixtures of water (containing 0.1% Formic acid) and MeCN as eluents. Fractions containing the desired compound were evaporated to dryness to afford (7-fluoro-3-(2,2,2-trifluoroethyl)benzofuran-4-yl)(1H-imidazol-2-yl)methanol (20.00 mg, 24.30%) as a white solid. $^1$H NMR (400 MHz, Methanol-d4) δ 3.43-3.61 (1H, m), 3.91 (1H, dtd), 6.28 (1H, s), 7.06-7.18 (4H, m), 7.85-7.93 (1H, m), 8.46 (1H, s). LC-MS (Method A): m/z (ES+), [M.+]=315.2; acid, HPLC $t_R$=2.21 min. F NMR (400 MHz, Methanol-d4, 23° C.) δ −140.3 (1F), −67.2 (3F).

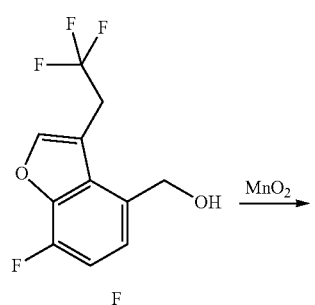

F

Intermediate H, (7-Fluoro-3-(2,2,2-trifluoroethyl)benzofuran-4-yl)(1-((2-(trimethylsilyl)ethoxy)methyl)-1H-imidazol-2-yl)methanol

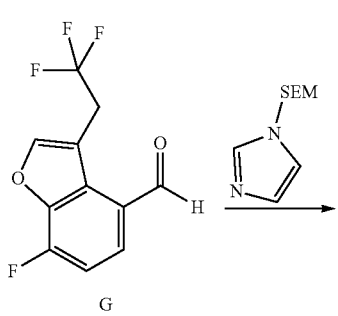

G

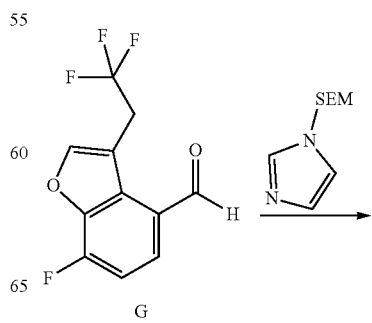

G

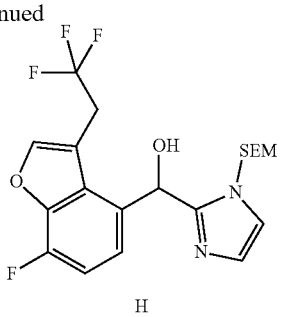

BuLi (0.471 mL, 1.18 mmol) was added dropwise to 1-((2-(trimethylsilyl)ethoxy)methyl)-1H-imidazole (234 mg, 1.18 mmol) in THF (5 mL) cooled to −78° C. under nitrogen. The resulting solution was stirred at −78° C. for 1 hour. 7-fluoro-3-(2,2,2-trifluoroethyl)benzofuran-4-carbaldehyde (145 mg, 0.59 mmol) in THF (1 mL) was added dropwise. The resulting solution was stirred at −78° C. for another 1 hour. The reaction mixture was quenched with saturated NH$_4$Cl (10 mL), extracted with EtOAc (3×5 mL), the organic layer was dried over Na$_2$SO$_4$, filtered and evaporated to afford colorless residue. The crude product was purified by flash C18-flash chromatography, elution gradient 0 to 100% MeCN in water. Pure fractions were evaporated to dryness to afford (7-fluoro-3-(2,2,2-trifluoroethyl)benzofuran-4-yl)(1-((2-(trimethylsilyl)ethoxy)methyl)-1H-imidazol-2-yl)methanol (138 mg, 52.7%) as a colorless gum. LC-MS (Method A): m/z (ES+), [M+H]+=445.2; acid, HPLC t$_R$=0.82 min.

Intermediate G, 7-Fluoro-3-(2,2,2-trifluoroethyl)benzofuran-4-carbaldehyde

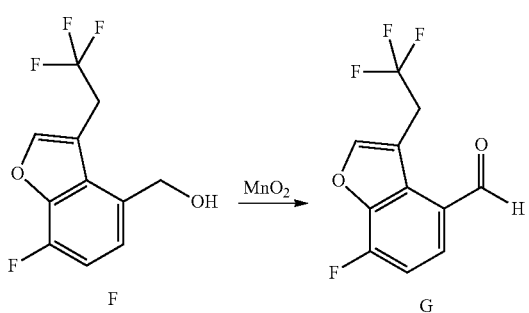

Manganese dioxide (10.51 mg, 0.12 mmol) was added to a stirred mixture of (7-fluoro-3-(2,2,2-trifluoroethyl)benzofuran-4-yl)methanol (30 mg, 0.12 mmol) in DCM (5 mL) under nitrogen. The resulting mixture was stirred at rt for 16 hours. The reaction mixture was filtered through celite. The solvent was removed under reduced pressure. This resulted in 7-fluoro-3-(2,2,2-trifluoroethyl)benzofuran-4-carbaldehyde (20.00 mg, 67.2%) as a white solid. $^1$H NMR (300 MHz, CDCl$_3$) δ ppm 4.14 (2H, qd), 7.27 (1H, dd), 7.75-7.88 (2H, m), 10.08 (1H, s).

Intermediate F, (7-Fluoro-3-(2,2,2-trifluoroethyl)benzofuran-4-yl)methanol

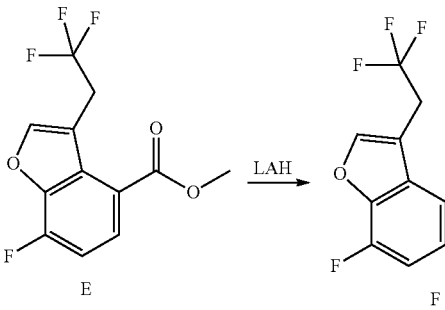

LiAlH$_4$ (5.50 mg, 0.14 mmol) was added to methyl 7-fluoro-3-(2,2,2-trifluoroethyl)benzofuran-4-carboxylate (40 mg, 0.14 mmol) in THF (5 mL) cooled to −20° C. under nitrogen. The resulting solution was warmed to 0° C. and stirred at 0° C. for 30 minutes. The reaction mixture was quenched with saturated NH$_4$Cl (5 mL), extracted with EtOAc (2×5 mL), the organic layer was dried over Na$_2$SO$_4$, filtered and evaporated to afford (7-fluoro-3-(2,2,2-trifluoroethyl)benzofuran-4-yl)methanol (35.0 mg, 97%) as a light yellow solid.

Intermediate E, Methyl 7-fluoro-3-(2,2,2-trifluoroethyl)benzofuran-4-carboxylate

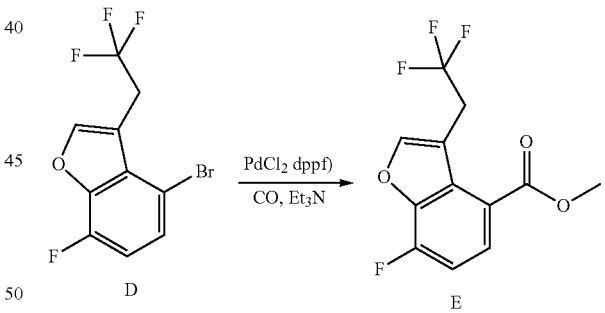

4-Bromo-7-fluoro-3-(2,2,2-trifluoroethyl)benzofuran (100 mg, 0.34 mmol), PdCl$_2$(dppf)-CH$_2$Cl$_2$Adduct (275 mg, 0.34 mmol) and Et$_3$N (0.047 mL, 0.34 mmol) in MeOH (10 mL) were stirred under an atmosphere of carbon monoxide at 40 atm and 130° C. for 16 hours. The solvent was removed under reduced pressure. The crude product was purified by flash silica chromatography, elution gradient 0 to 1% EtOAc in petroleum ether. Pure fractions were evaporated to dryness to afford methyl 7-fluoro-3-(2,2,2-trifluoroethyl)benzofuran-4-carboxylate (40.0 mg, 43.0%) as a white solid. $^1$H NMR (300 MHz, CDCl$_3$) δ ppm 3.88-4.06 (5H, m), 7.11 (1H, dd), 7.77 (1H, s), 7.89 (1H, dd).

Intermediate D, 4-Bromo-7-fluoro-3-(2,2,2-trifluoroethyl)benzofuran

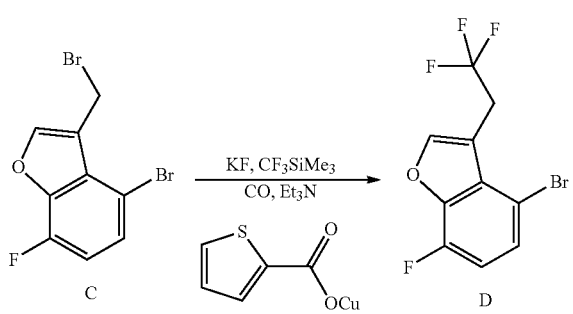

Trimethyl(trifluoromethyl)silane (942 mg, 6.62 mmol) was added to ((thiophene-2-carbonyl)oxy)copper (211 mg, 1.10 mmol), potassium fluoride (385 mg, 6.62 mmol) and 4-bromo-3-(bromomethyl)-7-fluorobenzofuran (340 mg, 1.10 mmol) in THF (10 mL) under nitrogen. The resulting mixture was stirred at 75° C. for 4 hours. The reaction mixture was quenched with water (10 mL), extracted with EtOAc (2×20 mL), the organic layer was dried over $Na_2SO_4$, filtered and evaporated to afford orange residue. The crude product was purified by flash silica chromatography, elution gradient 0 to 1% EtOAc in petroleum ether. Pure fractions were evaporated to dryness to afford 4-bromo-7-fluoro-3-(2,2,2-trifluoroethyl)benzofuran (120 mg, 36.6%) as a colorless liquid. $^1$HNMR (300 MHz, $CDCl_3$) δ ppm 4.13 (2H, q), 6.98 (1H, dd), 7.36 (1H, dd), 7.72 (1H, q).

Intermediate C, 4-Bromo-3-(bromomethyl)-7-fluorobenzofuran

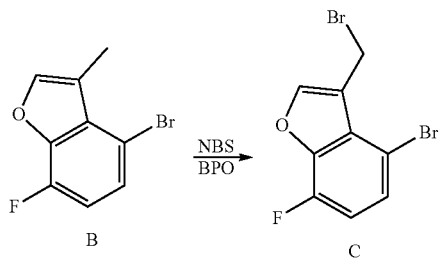

NBS (31.1 mg, 0.17 mmol) was added to 4-bromo-7-fluoro-3-methylbenzofuran (40 mg, 0.17 mmol) and benzoic peroxyanhydride (42.3 mg, 0.17 mmol) in $CCl_4$ (2 mL) at 25° C. under nitrogen. The resulting mixture was stirred at 85° C. for 16 hours. The residue was purified by preparative TLC (petroleum ether:EtOAc=50:1), to afford 4-bromo-3-(bromomethyl)-7-fluorobenzofuran (20.00 mg, 37.2%) as a yellow solid.

Intermediate B, 4-Bromo-7-fluoro-3-methylbenzofuran

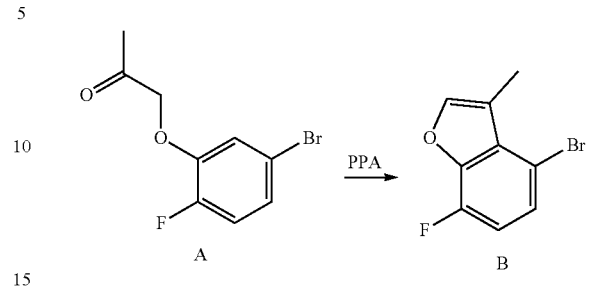

Polyphosphoric acid (5 mL, 14.17 mmol) was added to 1-(5-bromo-2-fluorophenoxy)propan-2-one (3.5 g, 14.17 mmol) at 25° C. under nitrogen. The resulting solution was stirred at 110° C. for 16 hours. The reaction mixture was quenched with water (25 mL), extracted with EtOAc (3×100 mL), the organic layer was dried over Na2SO4, filtered and evaporated to afford dark residue. The crude product was purified by flash silica chromatography, elution gradient 0 to 5% EtOAc in petroleum ether. Pure fractions were evaporated to dryness to afford 4-bromo-7-fluoro-3-methylbenzofuran (1.370 g, 42.2%) as a white solid. $^1$HNMR (400 MHz, $CDCl_3$) δ ppm 2.45 (3H, d), 6.91 (1H, dd), 7.29 (1H, dd), 7.48 (1H, q).

Intermediate A, 1-(5-Bromo-2-fluorophenoxy)propan-2-one

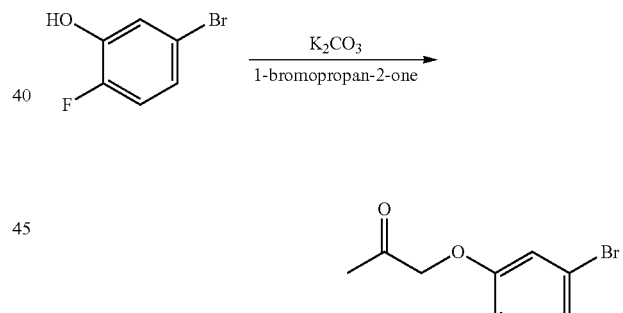

1-Bromopropan-2-one (8.61 g, 62.83 mmol) was added dropwise to 5-bromo-2-fluorophenol (10 g, 52.36 mmol) and $K_2CO_3$ (10.85 g, 78.53 mmol) in acetone (200 mL) at 60° C. over a period of 30 minutes under nitrogen. The resulting mixture was stirred at 60° C. for 2 hours. The reaction mixture was filtered through celite. The reaction mixture was diluted with EtOAc (300 mL), and washed with water (200 mL×3). The organic layer was dried over $Na_2SO_4$, filtered and evaporated to afford crude product. The crude product was purified by flash silica chromatography, elution gradient 0 to 10% EtOAc in petroleum ether. Pure fractions were evaporated to dryness to afford 1-(5-bromo-2-fluorophenoxy)propan-2-one (10.90 g, 84%) as a white solid. $^1$H NMR (400 MHz, DMSO-d6) δ 7.34-7.09 (m, 3H), 5.00 (s, 2H), 2.16 (s, 3H).

Example 47. Pure Enantiomer, Isomer 1, (7-fluoro-3-(2,2,2-trifluoroethyl)benzofuran-4-yl)(1H-imidazol-2-yl)methanol

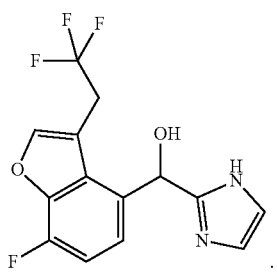

Example 47

Pure enantiomer, Isomer 1

The crude product (7-fluoro-3-(2,2,2-trifluoroethyl)benzofuran-4-yl)(1H-imidazol-2-yl)methanol (200 mg, 0.64 mmol) was purified by preparative chiral-HPLC on a Chiralpak IB column, eluting isocratically with 30% EtOH in heptane (modified with diethylamine) as eluent. The fractions containing the desired compound were evaporated to dryness to afford (7-fluoro-3-(2,2,2-trifluoroethyl)benzofuran-4-yl)(1H-imidazol-2-yl)methanol (50 mg, 25%) Peak 1 as a white solid. and (7-fluoro-3-(2,2,2-trifluoroethyl)benzofuran-4-yl)(1H-imidazol-2-yl)methanol (40 mg, 20%) Peak 2 as a white solid. $^1$HNMR (400 MHz, DMSO-d6) δ ppm 3.98-4.26 (2H, m), 6.19 (1H, d), 6.48 (1H, d), 6.80 (1H, s), 7.02 (1H, s), 7.21-7.39 (2H, m), 8.09 (1H, s), 11.99 (1H, s). LC-MS (Method A): m/z (ES+), [M+H]+=315.3; acid, HPLC $t_R$=1.44 min. Chiral analytical HPLC. Chiral Amylose-SA column, 0.46×15 cm, 5 μM, Mobile Phase A hexanes (0.2% IPA), Mobile Phase B ethanol (70:30). Flow rate 1.0 mL/min, UV-vis detection 254 nm. $t_R$=2.71 min.

Example 48, Pure enantiomer, Isomer 2, (7-fluoro-3-(2,2,2-trifluoroethyl)benzofuran-4-yl)(1H-imidazol-2-yl)methanol

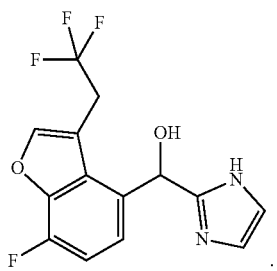

Example 48

Pure enantiomer, Isomer 2

The crude product (7-fluoro-3-(2,2,2-trifluoroethyl)benzofuran-4-yl)(1H-imidazol-2-yl)methanol (200 mg, 0.64 mmol) was purified by preparative chiral-HPLC on a Chiralpak IB column, eluting isocratically with 30% EtOH in heptane (modified with diethylamine) as eluent. The fractions containing the desired compound were evaporated to dryness to afford (7-fluoro-3-(2,2,2-trifluoroethyl)benzofuran-4-yl)(1H-imidazol-2-yl)methanol (50 mg, 25%) Peak 1 as a white solid. and (7-fluoro-3-(2,2,2-trifluoroethyl)benzofuran-4-yl)(1H-imidazol-2-yl)methanol (40 mg, 20%) Peak 2 as a white solid. $^1$H NMR (400 MHz, DMSO-d6) δ ppm 4.03-4.21 (2H, m), 6.19 (1H, d), 6.48 (1H, d), 6.80 (1H, s), 7.02 (1H, s), 7.21-7.39 (2H, m), 8.09 (1H, s), 11.99 (1H, s). LC-MS (Method A): m/z (ES+), [M+H]+=acid, HPLC $t_R$=1.99 min. Chiral analytical HPLC. Chiral Amylose-SA column, 0.46×15 cm, 5 jm, Mobile Phase A hexanes (0.2% IPA), Mobile Phase B ethanol (70:30). Flow rate 1.0 mL/min, UV-vis detection 254 nm. $t_R$=4.44 min.

Example 49, (3-Ethyl-7-fluorobenzo[b]thiophen-4-yl)(1H-imidazol-2-yl)methanol

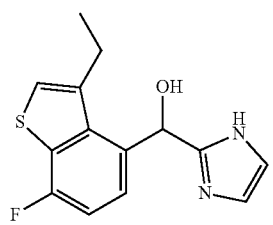

Example 49

Example 49 was made in analogous fashion to Example 40 using 5-bromo-2-fluorobenzenethiol and 1-bromobutan-2-one.). LC-MS (Method A): m/z (ES+), [M+H]+=277; acid, HPLC $t_R$=1.487 min.

Example 50. Pure Enantiomer, Isomer 1, (3-Ethyl-7-fluorobenzo[b]thiophen-4-yl)(1H-imidazol-2-yl)methanol

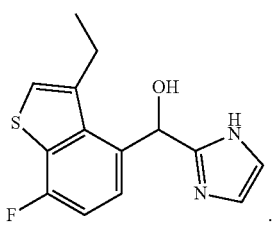

Example 50

Pure enantiomer, Isomer 1

Example 49 was purified by preparative chiral-HPLC on a Chiralpak IA column, eluting isocratically with 6% EtOH in heptane (modified with TEAA) as eluent. The fractions containing the desired compound were evaporated to dryness to afford (3-ethyl-7-fluorobenzo[b]thiophen-4-yl)(1H-imidazol-2-yl)methanol (44.0 mg, 32.4%) as a white solid (Example 51, peak 1). $^1$H NMR (400 MHz, DMSO) δ 1.29-1.33 (m, 3H), 3.06-3.22 (m, 2H), 6.27-6.28 (m, 1H), 6.52-6.53 (m, 1H), 6.89 (s, 2H), 7.19-7.23 (m, 1H), 7.49-7.52 (m, 2H), 11.97 (s, 1H). LC-MS (Method A): m/z (ES+), [M+H]+=277; acid, HPLC $t_R$=1.484 min. Chiral analytical HPLC. ODH column, 0.46×10 cm, 5 jm, Mobile Phase A hexanes (0.1% DEA), Mobile Phase B ethanol (85:15). Flow rate 1.0 mL/min, UV-vis detection 254 nm. $t_R$=2.59 min.

113

Example 51. Pure Enantiomer, Isomer 2, (3-Ethyl-7-fluorobenzo[b]thiophen-4-yl)(1H-imidazol-2-yl)methanol

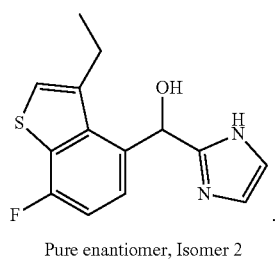

Pure enantiomer, Isomer 2

Example 49 was purified by preparative chiral-HPLC on a Chiralpak IA column, eluting isocratically with 6% EtOH in heptane (modified with TEAA) as eluent. The fractions containing the desired compound were evaporated to dryness to afford (3-ethyl-7-fluorobenzo[b]thiophen-4-yl)(1H-imidazol-2-yl)methanol (44.0 mg, 32.4%) as a white solid (Example 51, peak 2). $^1$H NMR (400 MHz, DMSO) δ ppm 1.30-1.33 (m, 3H), 3.09-3.24 (m, 2H), 6.27-6.28 (m, 1H), 6.52-6.53 (m, 1H), 6.89 (s, 2H), 7.19-7.23 (m, 1H), 7.49-7.52 (m, 2H), 11.97 (s, 1H). LC-MS (Method A): m/z (ES+), [M+H]+=277; acid, HPLC $t_R$=1,487 min. Chiral analytical HPLC. ODH column, 0.46×10 cm, 5 m, Mobile Phase A hexanes (0.1% DEA), Mobile Phase B ethanol (85:15). Flow rate 1.0 mL/min, UV-vis detection 254 nm. $t_R$=3.96 min.

Example 52. (7-Fluoro-3-methylbenzofuran-4-yl)(1H-imidazol-2-yl)methanol

Example 52 was made in analogous fashion to example 40, using 1-bromopropan-2-one. $^1$H NMR (400 MHz, DMSO-d6) δ ppm 2.26 (s, 3H), 6.27-6.24 (s, 2H), 6.84-6.95 (m, 2H), 7.13-7.18 (m, 1H), 7.25-7.28 (m, 1H), 7.80 (s, 1H), 8.21 (s, 0.5H).

Example 53. (4-Fluorodibenzo[b,d]furan-1-yl)(1H-imidazol-2-yl)methanol

114

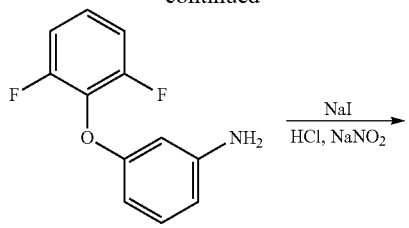

HCl/EtOAc (10 mL) was added to (4-fluorodibenzo[b,d]furan-1-yl)(1-((2-(trimethylsilyl)ethoxy)methyl)-1H-imidazol-2-yl)methanol (300 mg, 0.73 mmol). The resulting mixture was stirred at rt for 12 hours. The solvent was removed under reduced pressure. The crude product was purified by preparative HPLC (XSelect CSH Prep C18 OBD column, 5 μm silica, 19 mm diameter, 150 mm length), using decreasingly polar mixtures of water (containing 0.1% Formic acid) and MeCN as eluents. Fractions containing the desired compound were evaporated to dryness to afford (4-fluorodibenzo[b,d]furan-1-yl)(1H-imidazol-2-yl)methanol (130 mg, 50.7%) as a white solid. $^1$H NMR (300 MHz, Methanol-d4) δ ppm 6.55 (s, 1H), 7.16 (d, 2H), 7.34 (dd, 3H), 7.54 (t, 1H), 7.67 (d, 1H), 7.98 (d, 1H), 8.22 (s, 1.5H). LC-MS (method A): m/z (ES+), [M+H]+=283; base, HPLC $t_R$=1.46 min.

Intermediate E, (4-Fluorodibenzo[b,d]furan-1-yl)(1-((2-(trimethylsilyl)ethoxy)methyl)-1H-imidazol-2-yl)methanol

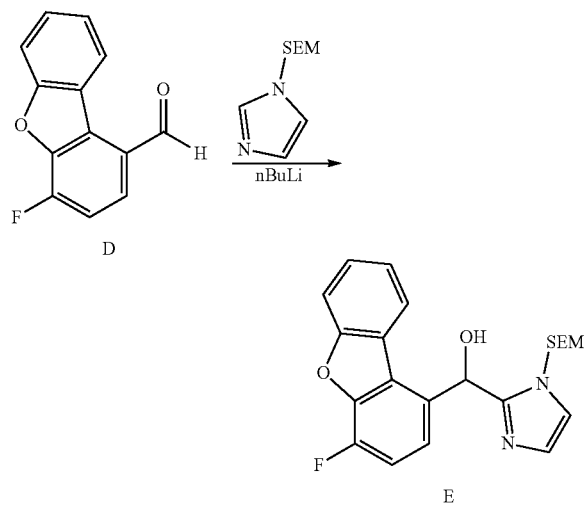

BuLi (747 μL, 1.87 mmol) was added dropwise to 1-((2-(trimethylsilyl)ethoxy)methyl)-1H-imidazole (370 mg, 1.87 mmol) in THF (10 mL) at −78° C. over a period of 0.5 hour under nitrogen. 4-fluorodibenzo[b,d]furan-1-carbaldehyde (200 mg, 0.93 mmol) in (1 mL) was added The resulting mixture was stirred at −78° C. for 1 hour. The reaction mixture was quenched with water (10 mL), extracted with EtOAc (3×10 mL), the organic layer was evaporated. The crude product was purified by flash C18-flash chromatography, elution gradient 0 to 100% water in MeCN. Pure fractions were evaporated to dryness to afford (4-fluorodibenzo[b,d]furan-1-yl)(1-((2-(trimethylsilyl)ethoxy)methyl)-1H-imidazol-2-yl)methanol (320 mg, 83%) as a pale yellow oil. LC-MS (Method A): m/z (ES+), [M+H]+=413; base, HPLC $t_R$=1.543 min.

Intermediate D, 4-Fluorodibenzo[b,d]furan-1-carbaldehyde

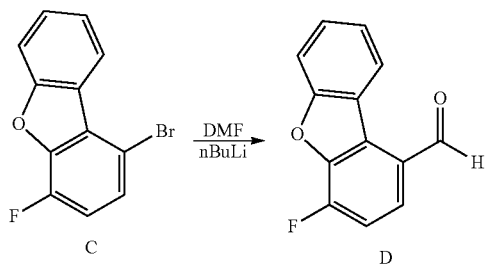

BuLi (1.132 mL, 2.83 mmol) was added dropwise to 1-bromo-4-fluorodibenzo[b,d]furan (500 mg, 1.89 mmol) in THF (10 mL) at −78° C. over a period of 0.5 hour under nitrogen. DMF (551 mg, 7.54 mmol) was added. The resulting mixture was stirred at −78° C. for 1 hour. The reaction mixture was quenched with water (10 mL), extracted with EtOAc (3×10 mL), the organic layer was dried over Na$_2$SO$_4$, filtered and evaporated. The crude product was purified by flash silica chromatography, elution gradient 0 to 2% petroleum ether in EtOAc. Pure fractions were evaporated to dryness to afford 4-fluorodibenzo[b,d]furan-1-carbaldehyde (360 mg, 89%) as a white solid.

Intermediate C, 1-Bromo-4-fluorodibenzo[b,d]furan

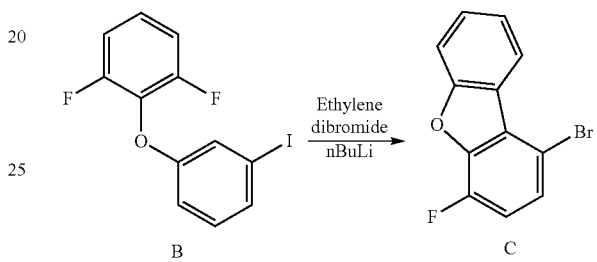

BuLi (0.482 mL, 1.20 mmol) was added dropwise to 1,3-difluoro-2-(2-iodophenoxy)benzene (100 mg, 0.30 mmol) in THF (10 mL) at −78° C. over a period of 0.5 hour under nitrogen. The resulting mixture was allowed to warm to 0° C. and stirred for 30 min. After cooling to −78° C., ethylene dibromide (85 mg, 0.45 mmol) was added dropwise, and stirring continued at low temperature for further 30 menthe warm to rt. The reaction mixture was quenched with water (10 mL), extracted with EtOAc (3×10 mL), the organic layer was dried over Na$_2$SO$_4$, filtered and evaporated. The residue was purified by preparative TLC (petroleum ether), to afford 1-bromo-4-fluorodibenzo[b,d]furan (55.0 mg, 68.9%) as a white solid. $^1$H NMR (300 MHz, DMSO-d6) δ ppm 7.43-7.72 (m, 4H), 7.83-7.90 (m, 1H), 8.47 (d, 1H).

Intermediate B, 1,3-difluoro-2-(3-iodophenoxy)benzene

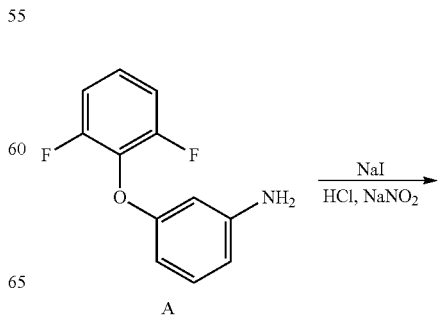

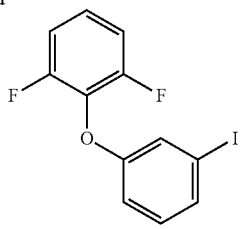

B

Sodium nitrite (206 mg, 2.94 mmol) in water (5 mL) was added dropwise to 2-(2,6-difluorophenoxy)aniline (500 mg, 2.26 mmol) in HCl (6781 μL, 6.78 mmol) at 0° C. The resulting mixture was stirred at 0° C. for 1 hour. Sodium iodide (847 mg, 5.65 mmol) in water (5 mL) was added dropwise. After 0.5 h the mixture was warmed to 100° C. for 1 h. Cooled to rt and extracted with EtOAc (10 mL×3). The combined organic layer was washed with Na$_2$S$_2$O$_3$.5H$_2$O (30 mL) and dried with Na$_2$SO$_4$. The crude product was purified by flash silica chromatography, elution gradient 0 to 2% petroleum ether in EtOAc. Pure fractions were evaporated to dryness to afford 1,3-difluoro-2-(2-iodophenoxy)benzene (530 mg, 70.6%) as a white solid. $^1$H NMR (400 MHz, DMSO-d6) δ ppm 6.68 (dq, 1H), 6.92 (td, 1H), 7.28-7.47 (m, 4H), 7.91 (dd, 1H).

Intermediate A, 3-(2,6-Difluorophenoxy)aniline

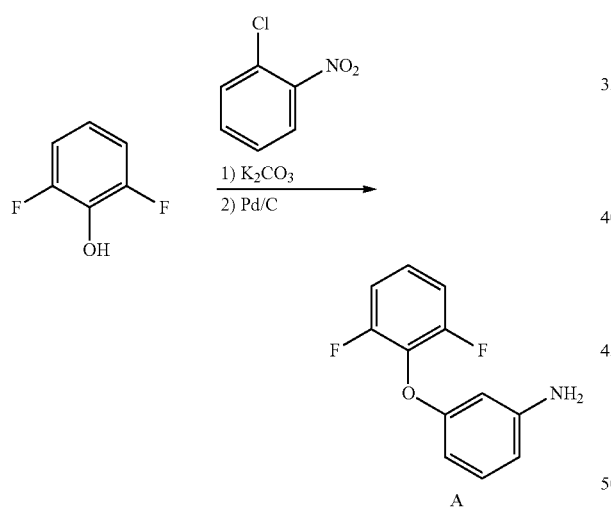

A

1-Fluoro-2-nitrobenzene (6.51 g, 46.12 mmol) was added to 2,6-difluorophenol (5 g, 38.43 mmol) and K$_2$CO$_3$ (15.94 g, 115.30 mmol) in DMF (50 mL) at 25° C. under nitrogen. The resulting mixture was stirred at 100° C. for 12 hours. The reaction mixture was quenched with water (50 mL), extracted with EtOAc (3×50 mL), the organic layer was washed with water (100 mL×3) and dried over Na$_2$SO$_4$, filtered and evaporated. The crude product was purified by flash silica chromatography, elution gradient 0 to 10% petroleum ether in EtOAc. Pure fractions were evaporated to dryness to afford 1,3-difluoro-2-(2-nitrophenoxy)benzene (9.50 g, 98%) as a yellow solid. Pd/C (4.02 g, 3.78 mmol) was added to 1,3-difluoro-2-(2-nitrophenoxy)benzene (9.5 g, 37.82 mmol) in ethanol (100 mL) at 25° C. under hydrogen. The resulting mixture was stirred at rt for 2 hours. The mixture was filtered through a Celite pad. The solvent was removed under reduced pressure. 2-(2,6-difluorophenoxy)aniline (7.50 g, 90%) as a brown oil was used in the next step directly without further purification. $^1$H NMR (300 MHz, DMSO-d6) δ ppm 5.09 (s, 2H), 6.32-6.48 (m, 2H), 6.70-6.85 (m, 2H), 7.18-7.40 (m, 3H).

Example 54. (4-Fluoro-1-methyl-1H-indol-7-yl)(1H-imidazol-2-yl)methanol

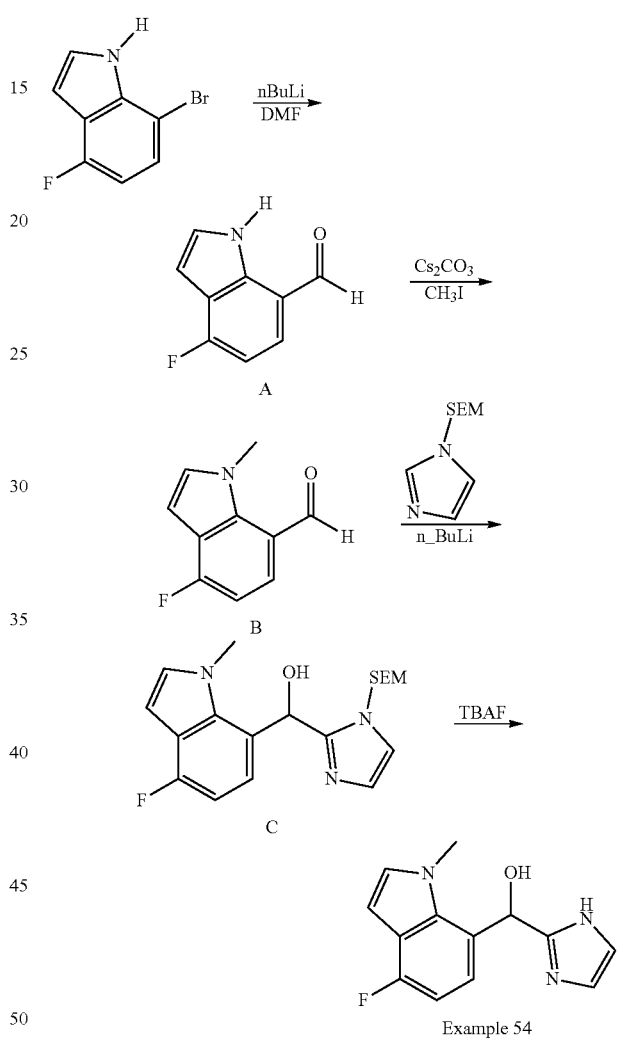

Example 54

TBAF (0.799 mL, 0.80 mmol) was added slowly to (4-fluoro-1-methyl-1H-indol-7-yl)(1-((2-(trimethylsilyl)ethoxy)methyl)-1H-imidazol-2-yl)methanol (200 mg, 0.53 mmol) in THF (7 mL) under nitrogen. The resulting solution was stirred at 50° C. for 6 hours. The solvent was removed under reduced pressure. The crude product was purified by flash C18-flash chromatography, elution gradient 0 to 70% MeCN in water. Pure fractions were evaporated to dryness to afford (4-fluoro-1-methyl-1H-indol-7-yl)(1H-imidazol-2-yl)methanol (36.9 mg, 28.2%) as a white solid. $^1$H NMR (300 MHz, DMSO) δ ppm 4.00 (s, 3H), 6.28-6.29 (m, 1H), 6.41-6.43 (m, 1H), 6.46-6.47 (m, 1H), 6.71-6.75 (m, 1H), 6.92-7.00 (m, 2H), 7.02-7.04 (m, 1H), 7.27 (s, 1H), 11.96 (s, 1H). LC-MS (Method A): m/z (ES+), [M+H]+=246; acid, HPLC t$_R$=0.544 min.

Intermediate C, (4-Fluoro-1-methyl-1H-indol-7-yl)(1-((2-(trimethylsilyl)ethoxy)methyl)-1H-imidazol-2-yl)methanol n-Butyllithium (1.255 mL, 3.14 mmol) was added slowly to 1-((2-(trimethylsilyl)ethoxy)methyl)-1H-imidazole (467 mg, 2.35 mmol) in THF (8 mL) at −78° C. under nitrogen. 1 hours later, added 1-ethyl-4-fluoro-1H-indole-7-carbaldehyde (300 mg, 1.57 mmol). The resulting solution was stirred at −78° C. for 3 hours. The reaction mixture was quenched with saturated $NH_4Cl$ (5 mL), extracted with EtOAc (2×10 mL), the organic layer was dried over $Na_2SO_4$, filtered and evaporated to afford white solid. The crude product was purified by flash silica chromatography, elution gradient 0 to 100% EtOAc in petroleum ether. Pure fractions were evaporated to dryness to afford (1-ethyl-4-fluoro-1H-indol-7-yl)(1-((2-(trimethylsilyl)ethoxy)methyl)-1H-imidazol-2-yl)methanol (525 mg, 86%) as a white solid. $^1$H NMR (300 MHz, DMSO) δ ppm −0.04-0.00 (m, 12H), 0.81-0.85 (m, 2H), 1.16-1.18 (m, 1H), 1.20-1.26 (m, 2H), 1.99 (s, 1H), 3.35-3.47 (m, 3H), 4.19 (s, 1H), 4.32 (s, 1H), 5.25-5.28 (m, 1H), 5.58-5.60 (m, 1H), 6.25-6.27 (m, 1H), 6.40-6.41 (m, 1H), 5.52-5.53 (m, 1H), 6.71-6.76 (m, 1H), 6.80 (s, 1H), 7.02-7.05 (m, 1H), 7.31-7.34 (m, 2H). LC-MS (Method A): m/z (ES+), [M+H]+=390.1; acid, HPLC $t_R$=0.58 min.

Intermediate B, 4-Fluoro-1-methyl-1H-indole-7-carbaldehyde $Cs_2CO_3$ (1997 mg, 6.13 mmol) was added to 4-fluoro-1H-indole-7-carbaldehyde (500 mg, 3.06 mmol) in acetonitrile (8 mL) warmed to 70° C. under nitrogen. 0.5 hour later, cooled to rt., added iodomethane (870 mg, 6.13 mmol). The resulting mixture was stirred at 70° C. for 2 hour. The reaction mixture was filtered, the solvent was removed under reduced pressure. The crude product was purified by flash silica chromatography, elution gradient 0 to 10% EtOAc in petroleum ether. Pure fractions were evaporated to dryness to afford 4-fluoro-1-methyl-1H-indole-7-carbaldehyde (337 mg, 62.1%) as a white liquid. $^1$H NMR (300 MHz, DMSO) δ ppm 4.08-4.11 (m, 3H), 6.66-6.67 (m, 1H), 7.01-7.07 (m, 1H), 7.49 (s, 1H), 7.80-7.83 (m, 1H), 10.32 (s, 1H). LC-MS (Method A): m/z (ES+), [M+H]+=177.95; acid, HPLC $t_R$=1.407 min.

Intermediate A, 4-Fluoro-1H-indole-7-carbaldehyde n-Butyllithium (14.39 mL, 35.98 mmol) was added slowly to 7-bromo-4-fluoro-1H-indole (2.2 g, 10.28 mmol) in THF (30 mL) at −78° C. under nitrogen, stirred for 15 minutes. Then slowly warmed to 5° C., stirred for 30 minutes. Cooled to −78° C., added DMF (3.98 mL, 51.39 mmol), slowly warmed to 25° C., stirred for 2 hours. The reaction mixture was quenched with water (50 mL), extracted with $Et_2O$ (3×50 mL), the organic layer was dried over $Na_2SO_4$, filtered and evaporated to afford white solid. The crude product was purified by flash silica chromatography, elution gradient 0 to 10% EtOAc in petroleum ether. Pure fractions were evaporated to dryness to afford 4-fluoro-1H-indole-7-carbaldehyde (1.370 g, 82%) as a white solid. $^1$H NMR (300 MHz, DMSO) δ ppm 6.64-6.66 (m, 1H), 7.02-7.08 (m, 1H), 7.44-7.46 (m, 1H), 7.79-7.84 (m, 1H), 10.13 (s, 1H), 11.90 (s, 1H). LC-MS (Method A): m/z (ES+), [M+H]+=164; acid, HPLC $t_R$=1.052 min.

Example 55. Pure Enantiomer, Isomer 1, (4-Fluoro-1-methyl-1H-indol-7-yl)(1H-imidazol-2-yl)methanol

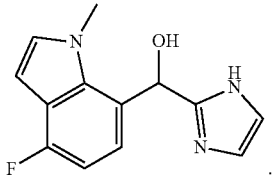

Example 55

Pure enantiomer, Isomer 1

Example 54, (4-fluoro-1-methyl-1H-indol-7-yl)(1H-imidazol-2-yl)methanol (0.22 g, 0.90 mmol), was purified by preparative chiral-HPLC on a Chiralpak IA column, eluting isocratically with 10% heptane in IPA (modified with $Et_3N$) as eluent. The fractions containing the desired compound were evaporated to dryness to afford (4-fluoro-1-methyl-1H-indol-7-yl)(1H-imidazol-2-yl)methanol (0.090 g, 40.9%, Peak 1, Example 55) as a white solid and (4-fluoro-1-methyl-1H-indol-7-yl)(1H-imidazol-2-yl)methanol (0.110 g, 50.0%, Peak 2, Example 56) as a white solid. $^1$H NMR (300 MHz, $CDCl_3$) δ ppm 3.75 (s, 3H), 6.44 (s, 1H), 6.56 (d, 1H), 6.67 (dt, 1H), 6.88-6.96 (m, 3H), 6.96-7.07 (m, 1H). LC-MS (Method A): m/z (ES+), [M+H]+=246; acid, HPLC $t_R$=1.26 min. Chiral analytical HPLC. CHIRALPAK AS-3, 0.46×5 cm, 5 μM, Mobile Phase A hexanes (0.2% DEA), Mobile Phase B isopropyl alcohol (90:10). Flow rate 1.0 mL/min, UV-vis detection 254 nm. $t_R$=2.72 min.

Example 56. Pure Enantiomer, Isomer 2, (4-Fluoro-1-methyl-1H-indol-7-yl)(1H-imidazol-2-yl)methanol

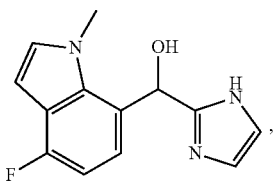

Example 56

Pure enantiomer, Isomer 2

Example 54, (4-fluoro-1-methyl-1H-indol-7-yl)(1H-imidazol-2-yl)methanol (0.22 g, 0.90 mmol), was purified by preparative chiral-HPLC on a Chiralpak IA column, eluting isocratically with 10% heptane in IPA (modified with $Et_3N$) as eluent. The fractions containing the desired compound were evaporated to dryness to afford (4-fluoro-1-methyl-1H-indol-7-yl)(1H-imidazol-2-yl)methanol (0.090 g, 40.9%, Peak 1, Example 55) as a white solid and (4-fluoro-1-methyl-1H-indol-7-yl)(1H-imidazol-2-yl)methanol (0.110 g, 50.0%, Peak 2, Example 56) as a white solid. $^1$H NMR (300 MHz, $CDCl_3$) δ ppm 3.73 (s, 3H), 6.45 (s, 1H), 6.56 (d, 1H), 6.68 (dt, 1H), 6.86-6.96 (m, 3H), 6.96-7.08 (m, 1H). LC-MS (Method A): m/z (ES+), [M+H]+=246; acid, HPLC $t_R$=1.26 min. Chiral analytical HPLC. CHIRALPAK AS-3, 0.46×5 cm, 5 μm, Mobile Phase A hexanes (0.2% DEA), Mobile Phase B isopropyl alcohol (90:10). Flow rate 1.0 mL/min, UV-vis detection 254 nm. $t_R$=4.82 min.

Example 57. (1-Ethyl-4-fluoro-1H-indol-7-yl)(1H-imidazol-2-yl)methanol

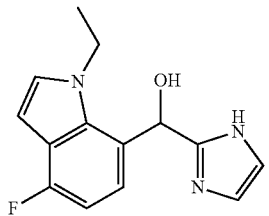

Example 57

Example 55 was prepared in analogous fashion to Example 54. $^1$H NMR (300 MHz, DMSO) δ ppm 1.22-1.29 (m, 3H), 4.37-4.46 (m, 1H), 4.55-4.67 (m, 1H), 6.27 (s, 2H), 6.50-6.51 (m, 1H), 6.71-6.78 (m, 2H), 7.01-7.08 (m, 2H), 7.35-7.36 (m, 1H), 11.93 (s, 1H). LC-MS (Method A): m/z (ES+), [M+H]+=259.9; acid, HPLC $t_R$=1.375 min.

Example 58. (2,3-Dihydro-1H-pyrrolo[1,2-a]indol-5-yl)(1H-imidazol-2-yl)methanol (2,3-Dihydro-1H-pyrrolo[1,2-a]indol-5-yl)(1-((2-(trimethylsilyl)ethoxy)methyl)-1H-imidazol-2-yl)methanol (120 mg, 0.31 mmol) was added to HCl/EtOAc (5 ml, 64.90 mmol) under nitrogen. The resulting solution was stirred at rt for 8 hours. The mixture was evaporated to afford the crude product as a purple solid. The crude product was purified by flash C18-flash chromatography, elution gradient 0 to 100% MeCN in water. Pure fractions were evaporated to dryness to afford (2,3-dihydro-1H-pyrrolo[1,2-a]indol-5-yl)(1H-imidazol-2-yl)methanol (35.0 mg, 38.6%) as a purple solid. $^1$H NMR (300 MHz, DMSO) δ ppm: 2.54-2.59 (2H, m), 2.94-2.99 (2H, m) 3.96-4.04 (1H, m), 4.32-4.40 (1H, m), 6.25 (1H, s), 6.60 (1H, s), 6.23 (1H, s), 6.94-6.99 (1H, m), 7.51-7.54 (1H, m), 7.62 (2H, s). LC-MS (Method A): m/z (ES+), [M+H]+=254.4; acid, HPLC $t_R$=1.30 min.

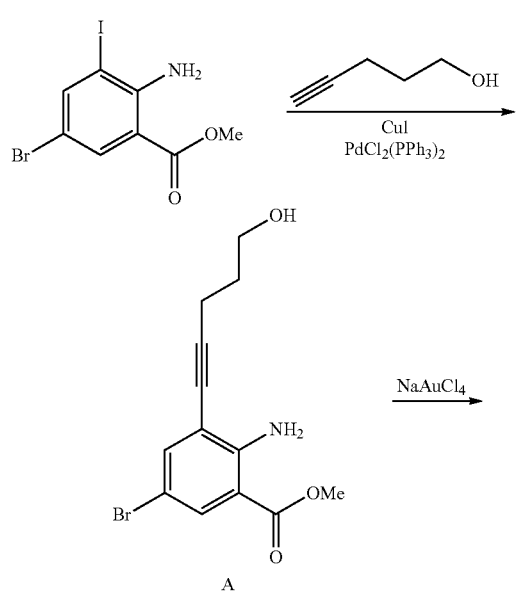

A

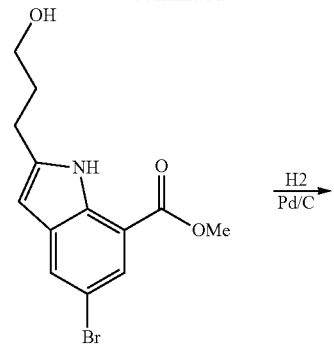

B

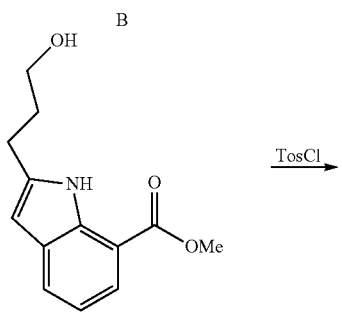

C

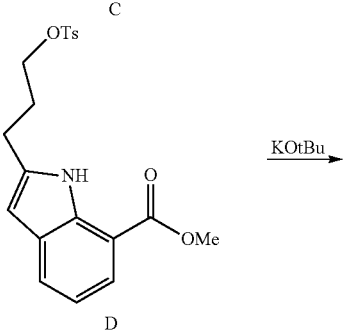

D

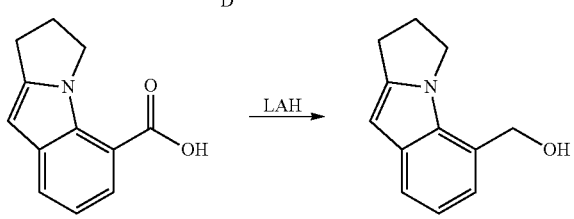

E  F

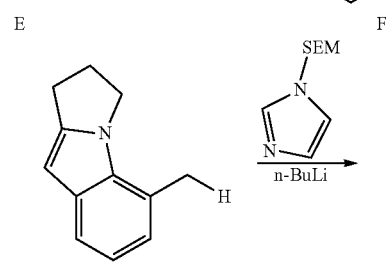

G

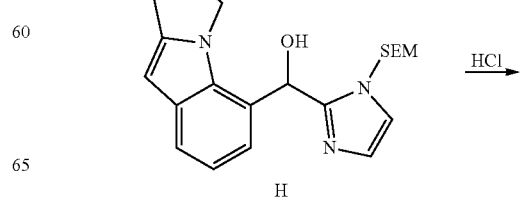

H

123

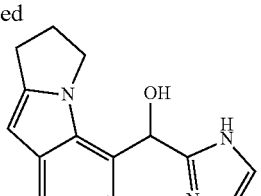

Example 58

Intermediate H, (2,3-Dihydro-1H-pyrrolo[1,2-a]indol-5-yl)(1-((2-(trimethylsilyl)ethoxy)methyl)-1H-imidazol-2-yl)methanol

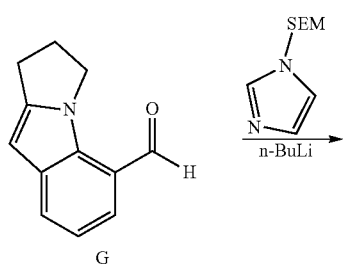

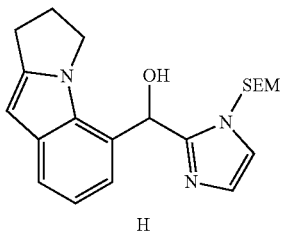

BuLi (112 mg, 1.75 mmol) was added to 1-((2-(trimethylsilyl)ethoxy)methyl)-1H-imidazole (209 mg, 1.05 mmol) in THF (10 mL) dropwise at −78° C. under nitrogen. The resulting solution was stirred at −78° C. for 1 hour. 2,3-dihydro-1H-pyrrolo[1,2-a]indole-5-carbaldehyde (130 mg, 0.70 mmol) was added dropwise. The resulting solution was stirred at −78° C. for 2 hours. The reaction mixture was quenched with saturated NH4Cl (10 mL), extracted with EtOAc (2×15 mL), the organic layer was dried over Na2SO4, filtered and evaporated to afford colorless residue. The crude product was purified by flash C18-flash chromatography, elution gradient 0 to 100% MeCN in water. Pure fractions were evaporated to dryness to afford (2,3-dihydro-1H-pyrrolo[1,2-a]indol-5-yl)(1-((2-(trimethylsilyl)ethoxy)methyl)-1H-imidazol-2-yl)methanol (150 mg, 55.7%) as a colorless gum. LC-MS (Method A): m/z (ES+), [M+H]+=384; acid, HPLC $t_R$=0.84 min.

124

Intermediate G, 2,3-Dihydro-1H-pyrrolo[1,2-a]indole-5-carbaldehyde

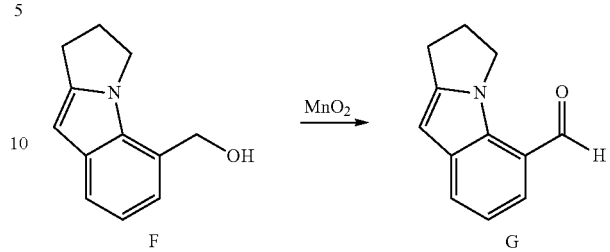

Manganese dioxide (65.0 mg, 0.75 mmol) was added to (2,3-dihydro-1H-pyrrolo[1,2-a]indol-5-yl)methanol (140 mg, 0.75 mmol) in DCM (10 mL) under nitrogen. The resulting solution was stirred at rt for 16 hours. The solid was filtered out. The filtrate was evaporated to afford 2,3-dihydro-1H-pyrrolo[1,2-a]indole-5-carbaldehyde (130 mg, 94%) as a white solid. LC-MS (Method A): m/z (ES+), [M+H]+=186.0; acid, HPLC $t_R$=0.97 min.

Intermediate F, (2,3-Dihydro-1H-pyrrolo[1,2-a]indol-5-yl)methanol

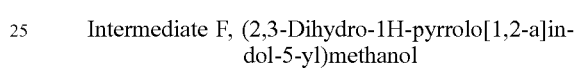
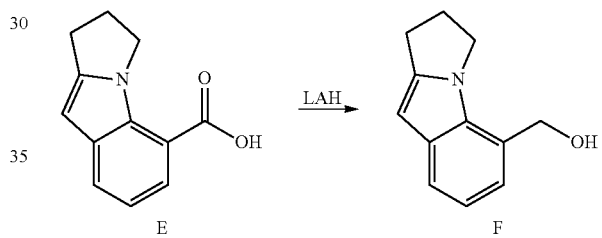

LiAlH4 (11.32 mg, 0.30 mmol) was added to 2,3-dihydro-1H-pyrrolo[1,2-a]indole-5-carboxylic acid (60 mg, 0.30 mmol) in THF (5 mL) cooled to 0° C. under nitrogen. The resulting solution was stirred at rt for 2 hours. The reaction mixture was quenched with saturated NH4Cl (10 mL), extracted with EtOAc (2×10 mL), the organic layer was dried over Na2SO4, filtered and evaporated to afford (2,3-dihydro-1H-pyrrolo[1,2-a]indol-5-yl)methanol (42.0 mg, 75%) as a white solid. LC-MS (Method A): m/z (ES+), [M+H]+=188.2; acid, HPLC $t_R$=0.81 min.

Intermediate E, 2,3-Dihydro-1H-pyrrolo[1,2-a]indole-5-carboxylic acid

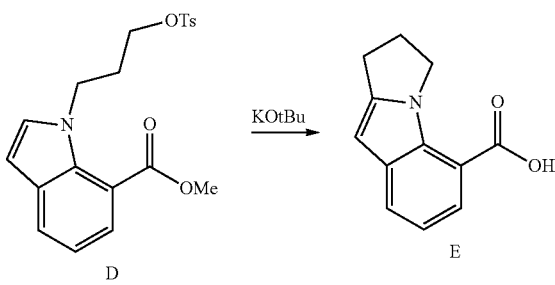

Potassium 2-methylpropan-2-olate (46.3 mg, 0.41 mmol) was added to methyl 2-(3-(tosyloxy)propyl)-1H-indole-7-carboxylate (160 mg, 0.41 mmol) in BuOH (5 mL) at 25° C. under nitrogen. The resulting solution was stirred at 100° C. for 30 minutes. The reaction mixture was acidified with 2M HCl. The reaction mixture was diluted with EtOAc (20 mL), and washed sequentially with saturated brine (10 mL). The organic layer was dried over $Na_2SO_4$, filtered and evaporated to afford 2,3-dihydro-1H-pyrrolo[1,2-a]indole-5-carboxylic acid (62.0 mg, 74.6%) as a white solid. LC-MS (Method A): m/z (ES+), [M+H]+=202.2; acid, HPLC $t_R$=0.86 min.

Intermediate D, Methyl 2-(3-(tosyloxy)propyl)-1H-indole-7-carboxylate

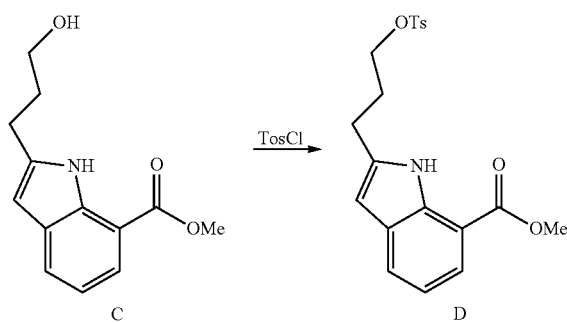

4-Methylbenzene-1-sulfonyl chloride (147 mg, 0.77 mmol) was added to methyl 2-(3-hydroxypropyl)-1H-indole-7-carboxylate (180 mg, 0.77 mmol) and Et3N (0.108 mL, 0.77 mmol) in DCM (10 mL) at 25° C. under nitrogen. The resulting solution was stirred at rt for 4 hours. The crude product was purified by flash silica chromatography, elution gradient 0 to 50% EtOAc in petroleum ether. Pure fractions were evaporated to dryness to afford methyl 2-(3-(tosyloxy)propyl)-1H-indole-7-carboxylate (260 mg, 87%) as a white solid. LC-MS (Method A): m/z (ES+), [M+H]+=388.0; acid, HPLC $t_R$=1.09 min.

Intermediate C, Methyl 2-(3-hydroxypropyl)-1H-indole-7-carboxylate

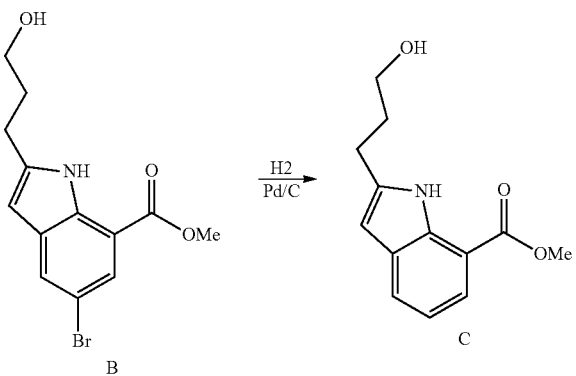

Pd/C (157 mg, 0.15 mmol) and methyl 5-bromo-2-(3-hydroxypropyl)-1H-indole-7-carboxylate (230 mg, 0.74 mmol) in MeOH (10 mL) was stirred under an atmosphere of nitrogen at 1 atm and rt for 4 hours. The solvent was removed. The crude product was purified by flash C18-flash chromatography, elution gradient 0 to 80% MeCN in water. Pure fractions were evaporated to dryness to afford methyl 2-(3-hydroxypropyl)-1H-indole-7-carboxylate (100 mg, 58.2%) as a colorless gum. $^1$H NMR (300 MHz, DMSO) δ ppm: 1.17 (2H, m), 2.85 (2H, m), 3.48 (2H, m), 3.92 (3H, s), 4.59 (1H, m), 6.28 (1H, m), 7.05 (1H, m), 7.66-7.73 (2H, m), 10.85 (1H, s). LC-MS (Method A): m/z (ES+), [M+H]+=234.2; acid, HPLC $t_R$=0.83 min.

Intermediate B, Methyl 5-bromo-2-(3-hydroxypropyl)-1H-indole-7-carboxylate

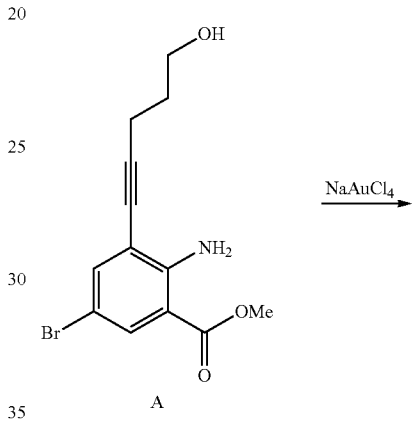

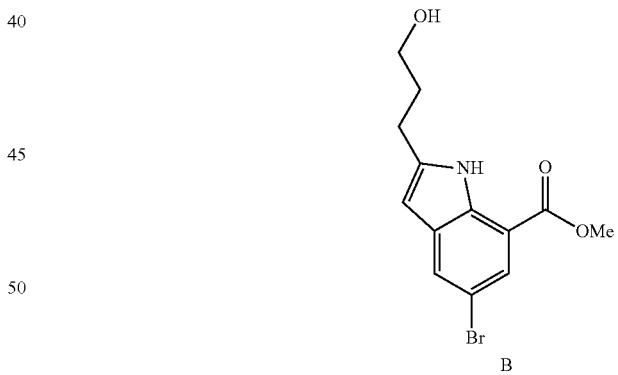

NaAuCl$_4$.2H$_2$O (49.3 mg, 0.13 mmol) was added to methyl 2-amino-5-bromo-3-(5-hydroxypent-1-yn-1-yl)benzoate (400 mg, 1.28 mmol) in ethanol (2 mL) at 25° C. The resulting solution was stirred at 25° C. for 16 hours. The crude product was purified by flash silica chromatography, elution gradient 0 to 80% EtOAc in petroleum ether. Pure fractions were evaporated to dryness to afford methyl 5-bromo-2-(3-hydroxypropyl)-1H-indole-7-carboxylate (230 mg, 57.5%) as an orange solid. LC-MS (Method A): m/z (ES+), [M+H]+=312.0; acid, HPLC $t_R$=1.11 min

127

Intermediate A, methyl 2-amino-5-bromo-3-(5-hydroxypent-1-ynyl)benzoate

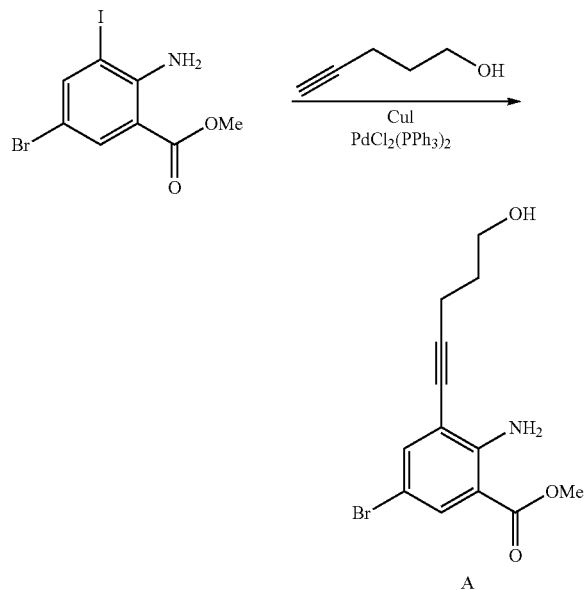

Pent-4-yn-1-ol (35.4 mg, 0.42 mmol), methyl 2-amino-5-bromo-3-iodobenzoate (100 mg, 0.28 mmol), PdCl$_2$(PPh$_3$)$_2$ (45.9 mg, 0.06 mmol), DIEA (0.098 mL, 0.56 mmol) and copper(I) iodide (10.70 mg, 0.06 mmol) were suspended in THF (2 mL) under nitrogen. The reaction was stirred at rt for 2 hours. The solvent was removed. The crude product was purified by flash silica chromatography, elution gradient 0 to 80% EtOAc in petroleum ether. Pure fractions were evaporated to dryness to afford methyl 2-amino-5-bromo-3-(5-hydroxypent-1-yn-1-yl)benzoate (80 mg, 91%) as a brown solid (80 mg, 91%). $^1$H NMR (300 MHz, CDCl$_3$-d6) δ ppm 1.67-1.76 (2H, m), 2.50-2.57 (2H, m), 3.50-3.82 (2H, m), 3.82 (3H, s), 4.58 (1H, tr), 6.76 (2H, brs), 7.52 (1H, d), 7.79 (1H, d). LC-MS (Method A): m/z (ES+), [M+H]+=312.2; acid, HPLC t$_R$=1.54 min.

Example 59, (4-Fluoro-8-methylnaphthalen-1-yl)(1H-imidazol-2-yl)methanol

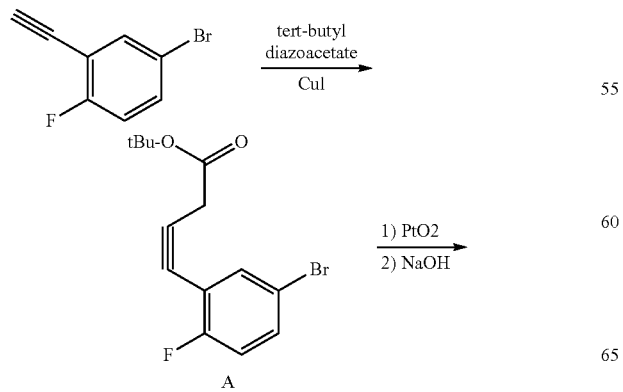

128

-continued

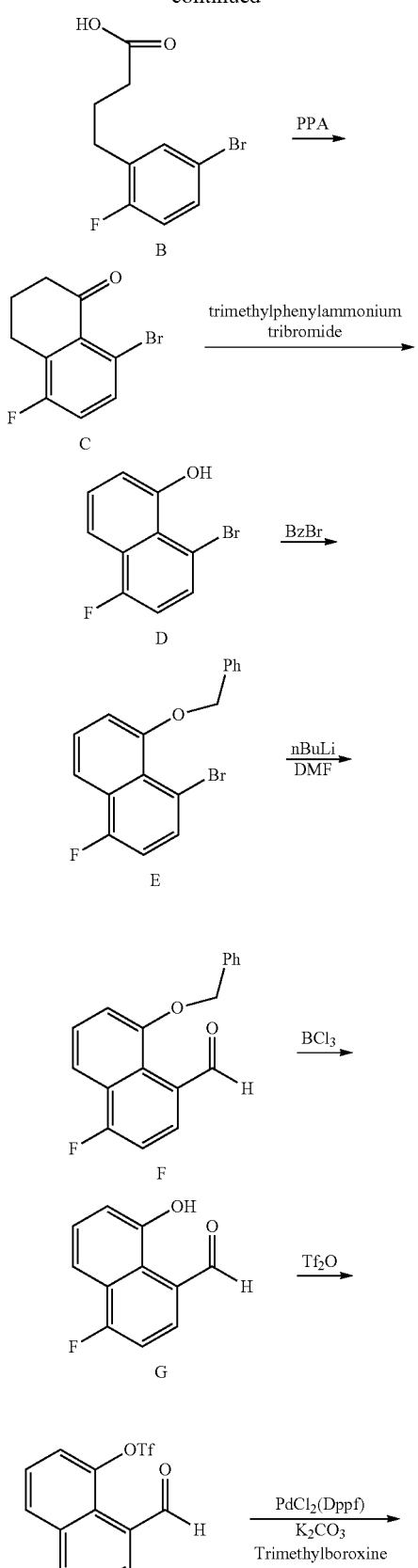

-continued

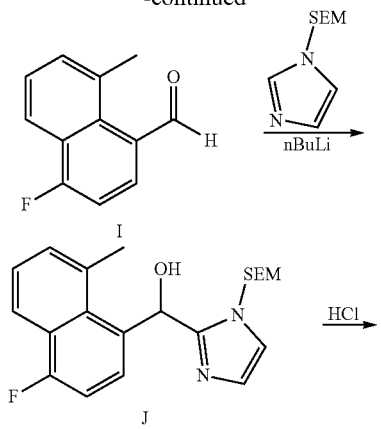

Example 59

HCl/EtOAc (15 mL) was added to (4-fluoro-8-methyl-naphthalen-1-yl)(1-((2-(trimethylsilyl)ethoxy)methyl)-1H-imidazol-2-yl)methanol (250 mg, 0.65 mmol) at rt. The resulting mixture was stirred at rt for 12 hours. The solvent was removed under reduced pressure. The crude product was purified by preparative HPLC (XSelect CSH Prep C18 OBD column, 5 silica, 19 mm diameter, 150 mm length), using decreasingly polar mixtures of water (containing 0.1% Formic acid) and MeCN as eluents. Fractions containing the desired compound were evaporated to dryness to afford (4-fluoro-8-methylnaphthalen-1-yl)(1H-imidazol-2-yl)methanol (70.0 mg, 35.7%) as a white solid. $^1$H NMR (400 MHz, Methanol-d4) δ ppm 3.01 (3H, s), 7.08 (1H, s), 7.12-7.25 (3H, m), 7.34 (1H, t), 7.45-7.54 (2H, m), 8.07 (1H, dt), 8.33 (1H, s). LC-MS (Method A): m/z (ES+), [M+H]+=257; base, HPLC $t_R$=1.411 min.

Intermediate J, (4-Fluoro-8-methylnaphthalen-1-yl)(1-((2-(trimethylsilyl)ethoxy)methyl)-1H-imidazol-2-yl)methanol

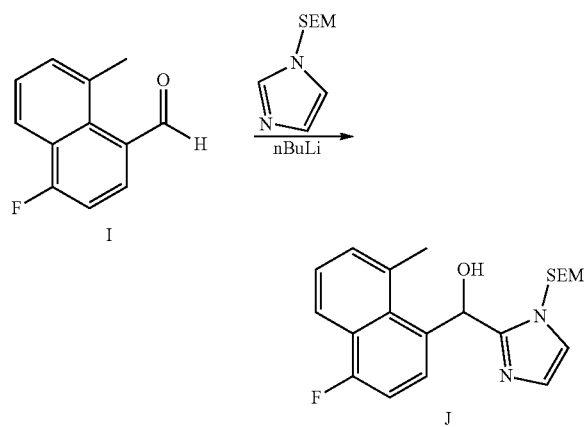

BuLi (0.638 mL, 1.59 mmol) was added dropwise to 1-((2-(trimethylsilyl)ethoxy)methyl)-1H-imidazole (316 mg, 1.59 mmol) in THF (10 mL) at −78° C. over a period of 0.5 hour under nitrogen. 4-fluoro-8-methyl-1-naphthaldehyde (150 mg, 0.80 mmol) was added at −78° C. The resulting mixture was stirred at −78° C. for 1 hour. The reaction mixture was quenched with water (10 mL), extracted with EtOAc (3×10 mL), the organic layer was dried over Na$_2$SO$_4$, filtered and evaporated. The crude product was purified by flash C18-flash chromatography, elution gradient 0 to 100% water in MeCN. Pure fractions were evaporated to dryness to afford (4-fluoro-8-methyl-naphthalen-1-yl)(1-((2-(trimethylsilyl)ethoxy)methyl)-1H-imidazol-2-yl)methanol (270 mg, 88%) as a brown solid. LC-MS (Method A): m/z (ES+), [M+H]+=387; acid, HPLC $t_R$=0.888 min.

Intermediate I, 4-Fluoro-8-methyl-1-naphthaldehyde

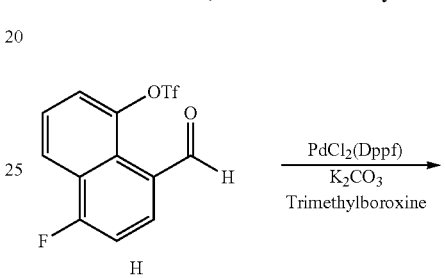

PdCl$_2$(dppf)-CH$_2$Cl$_2$adduct (25.3 mg, 0.03 mmol) was added to 5-fluoro-8-formylnaphthalen-1-yl trifluoromethanesulfonate (50 mg, 0.16 mmol), trimethylboroxine (97 mg, 0.78 mmol) and K$_2$CO$_3$ (64.3 mg, 0.47 mmol) in DME (2 mL) and water (1 mL) under nitrogen. The resulting mixture was stirred at 85° C. for 2 hours. The reaction mixture was diluted with EtOAc (10 mL), and washed with water (5 mL×3). The organic layer was dried over Na$_2$SO$_4$, filtered and evaporated. The residue was purified by preparative TLC (EtOAc: petroleum ether=1:10), to afford 4-fluoro-8-methyl-1-naphthaldehyde (20.00 mg, 68.5%) as a pale yellow solid.

Intermediate H, 5-Fluoro-8-formylnaphthalen-1-yl trifluoromethanesulfonate

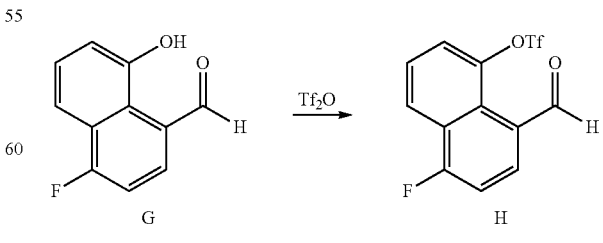

Tf$_2$O (1.237 mL, 7.32 mmol) was added to 4-fluoro-8-hydroxy-1-naphthaldehyde (1.16 g, 6.10 mmol) and pyridine (0.740 mL, 9.15 mmol) in DCM (20 mL) at 0° C. under nitrogen. The resulting mixture was stirred at rt for 2 hours. The reaction mixture was quenched with water (10 mL), extracted with DCM (3×10 mL), the organic layer was dried over Na2SO4, filtered and evaporated. The crude product was purified by flash silica chromatography, elution gradient 0 to 2% EtOAc in petroleum ether. Pure fractions were evaporated to dryness to afford 5-fluoro-8-formylnaphthalen-1-yl trifluoromethanesulfonate (1.100 g, 56.0%) as a orange solid. $^1$HNMR (300 MHz, DMSO-d6) δ ppm 7.73 (1H, m), 7.92 (1H, m), 7.99-8.09 (1H, m), 8.24 (1H, m), 8.37 (1H, m), 10.69 (1H, s).

Intermediate G,
4-Fluoro-8-hydroxy-1-naphthaldehyde

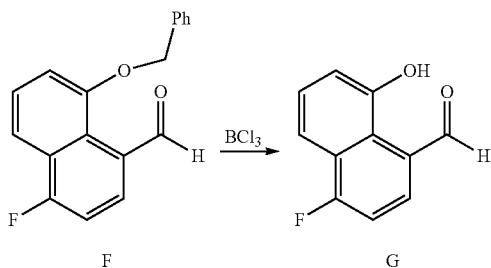

Boron trichloride (2.283 mL, 2.28 mmol) was added dropwise to 8-(benzyloxy)-4-fluoro-1-naphthaldehyde (320 mg, 1.14 mmol) in DCM (10 mL) at 0° C. under nitrogen. The resulting mixture was stirred at 0° C. for 50 minutes. The reaction mixture was quenched with 2M HCl (5 mL), extracted with DCM (3×5 mL), the organic layer was dried over Na$_2$SO$_4$, filtered and evaporated. The crude product was purified by flash silica chromatography, elution gradient 0 to 2% petroleum ether in EtOAc. Pure fractions were evaporated to dryness to afford 4-fluoro-8-hydroxy-1-naphthaldehyde (200 mg, 92%) as a orange solid.

Intermediate F,
8-(Benzyloxy)-4-fluoro-1-naphthaldehyde

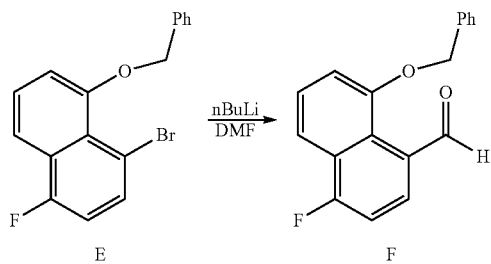

BuLi (49.3 mg, 0.77 mmol) was added dropwise to 5-(benzyloxy)-4-bromo-1-fluoronaphthalene (170 mg, 0.51 mmol) in THF (10 mL) at −78° C. over a period of 0.5 hour under nitrogen. DMF (0.159 mL, 2.05 mmol) was added. The resulting solution was stirred at −78° C. for 1 hour. The reaction mixture was quenched with water (10 mL), extracted with EtOAc (3×5 mL), the organic layer was dried over Na$_2$SO$_4$, filtered and evaporated to afford 8-(benzyloxy)-4-fluoro-1-naphthaldehyde (130 mg, 90%) as a yellow solid. The product was used in the next step directly without further purification.

Intermediate E,
5-(Benzyloxy)-4-bromo-1-fluoronaphthalene

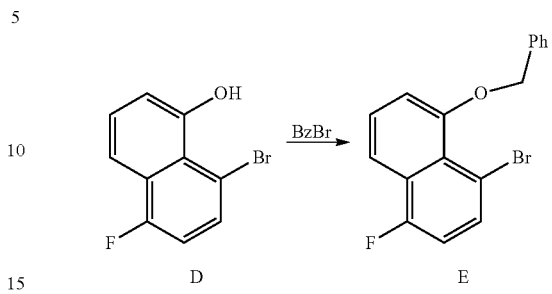

alpha-Bromotoluene (180 mg, 1.05 mmol) was added dropwise to 8-bromo-5-fluoronaphthalen-1-ol (230 mg, 0.95 mmol) and Cs$_2$CO$_3$ (622 mg, 1.91 mmol) in acetone (5 mL) at 25° C. under nitrogen. The resulting mixture was stirred at rt for 1 hour. The reaction mixture was quenched with water (10 mL), extracted with EtOAc (3×5 mL), the organic layer was dried over Na$_2$SO$_4$, filtered and evaporated to afford pale yellow solid. The crude product was purified by flash silica chromatography, elution gradient 0 to 10% petroleum ether in EtOAc. Pure fractions were evaporated to dryness to afford 5-(benzyloxy)-4-bromo-1-fluoronaphthalene (170 mg, 53.8%) as a pale yellow solid.

Intermediate D, 8-Bromo-5-fluoronaphthalen-1-ol

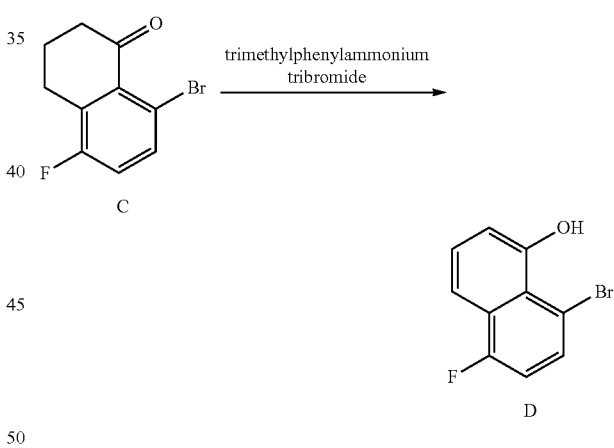

Trimethylphenylammonium tribromide (155 mg, 0.41 mmol) was added slowly to 8-bromo-5-fluoro-3,4-dihydronaphthalen-1(2H)-one (100 mg, 0.41 mmol) in THF (5 mL) at 25° C. The resulting mixture was stirred at rt for 45 minutes. The reaction mixture was quenched with water (5 mL), extracted with EtOAc (3×5 mL), the organic layer was washed with water (20 mL) and dried over Na$_2$SO$_4$, filtered and evaporated to afford pale yellow oil. The residue was dissolved in DMF (5 mL) and lithium bromide (71.5 mg, 0.82 mmol) and lithium carbonate (97 mg, 1.32 mmol) was added. The suspension was heated at 130° C. for 1 h, cooled to rt, and the solid was removed by filtration (EtOAc (20 mL)), the filtrate was washed with water (3×10 mL) and dried by Na$_2$SO$_4$. The solvent was removed under reduced pressure. The crude product was purified by flash silica chromatography, elution gradient 0 to 5% petroleum ether in EtOAc. Pure fractions were evaporated to dryness to afford 8-bromo-5-fluoronaphthalen-1-ol (63.0 mg, 63.5%) as a pale yellow solid.

Intermediate C, 8-Bromo-5-fluoro-3,4-dihydronaphthalen-1(2H)-one

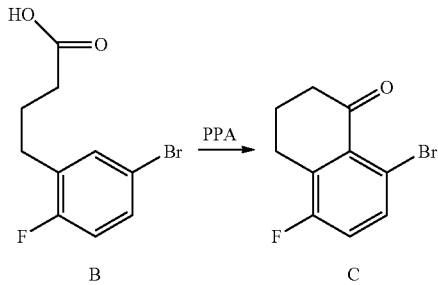

PPA (20 mL, 10.72 mmol) was added to 4-(5-bromo-2-fluorophenyl)butanoic acid (2.8 g, 10.72 mmol). The resulting mixture was stirred at 120° C. for 2 hours. The reaction mixture was poured into ice water (100 mL), extracted with EtOAc (3×30 mL), the organic layer was dried over Na2SO4, filtered and evaporated to afford pale yellow solid. The residue was purified by preparative TLC (EtOAc: petroleum ether=1:20), to afford 8-bromo-5-fluoro-3,4-dihydronaphthalen-1(2H)-one (0.50 g, 19.1%) as a orange solid.

Intermediate B, 4-(5-Bromo-2-fluorophenyl)butanoic acid

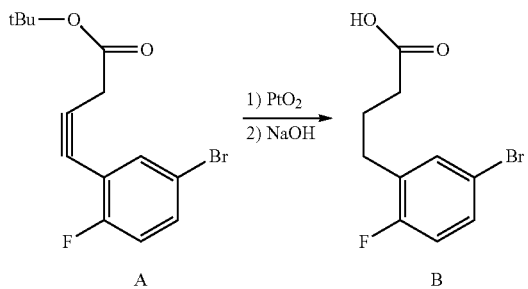

Platinum(IV) oxide (1.08 mg, 4.79 µmol) was added to tert-butyl 4-(5-bromo-2-fluorophenyl)but-3-ynoate (50 mg, 0.16 mmol), Ammonium hydroxide (0.056 mg, 1.60 µmol) in MeOH (5 mL) at 25° C. under hydrogen. The resulting mixture was stirred at rt for 12 hours. The mixture was filtered through a Celite pad. The solvent was removed under reduced pressure. tert-Butyl 4-(5-bromo-2-fluorophenyl)butanoate (45.0 mg, 89%) as a pale yellow oil was used in the next step directly without further purification. NaOH (10 mL, 10.00 mmol) was added to tert-butyl 4-(5-bromo-2-fluorophenyl)butanoate (140 mg, 0.44 mmol) in MeOH (5 mL) at 25° C. The resulting mixture was stirred at 50° C. for 4 hours. The reaction mixture was adjusted to pH=3-4 with 2M HCl. The reaction mixture was extracted with EtOAc (10 mL×2). The organic layer was dried over Na2SO4, filtered and evaporated to afford 4-(5-bromo-2-fluorophenyl)butanoic acid (100 mg, 87%) as a yellow oil.

Intermediate A, tert-Butyl 4-(5-bromo-2-fluorophenyl)but-3-ynoate

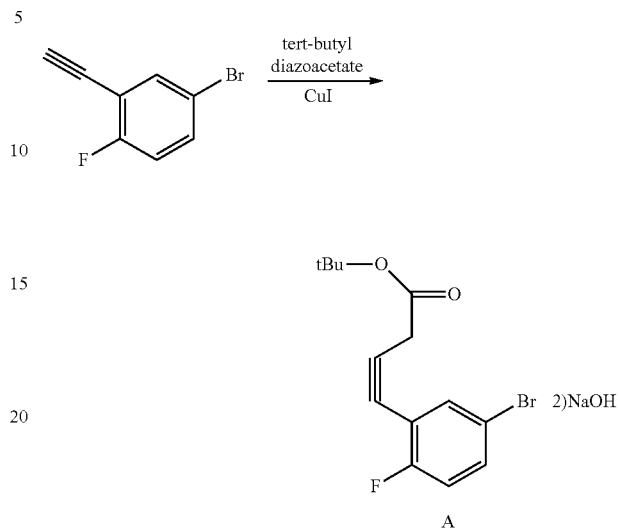

Copper(I) iodide (7.18 mg, 0.04 mmol) was added to 4-bromo-2-ethynyl-1-fluorobenzene (150 mg, 0.75 mmol) and tert-butyl 2-diazoacetate (107 mg, 0.75 mmol) in acetonitrile (10 mL) at rt. The resulting mixture was stirred at rt for 1 hour. The reaction mixture was diluted with EtOAc (25 mL), and washed sequentially with water (10 mL×3), saturated brine (10 mL×2). The organic layer was dried over Na$_2$SO$_4$, filtered and evaporated to afford crude product. The crude product was purified by flash silica chromatography, elution gradient 100 to 1% petroleum ether in EtOAc. Pure fractions were evaporated to dryness to afford tert-butyl 4-(5-bromo-2-fluorophenyl)but-3-ynoate (100 mg, 42.4%) as a yellow oil.

Example 60. (1-Ethyl-5-fluoro-indolizin-8-yl)-(1H-imidazol-2-yl)methanol

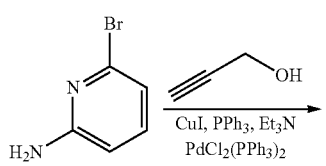

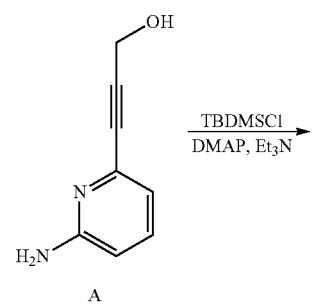

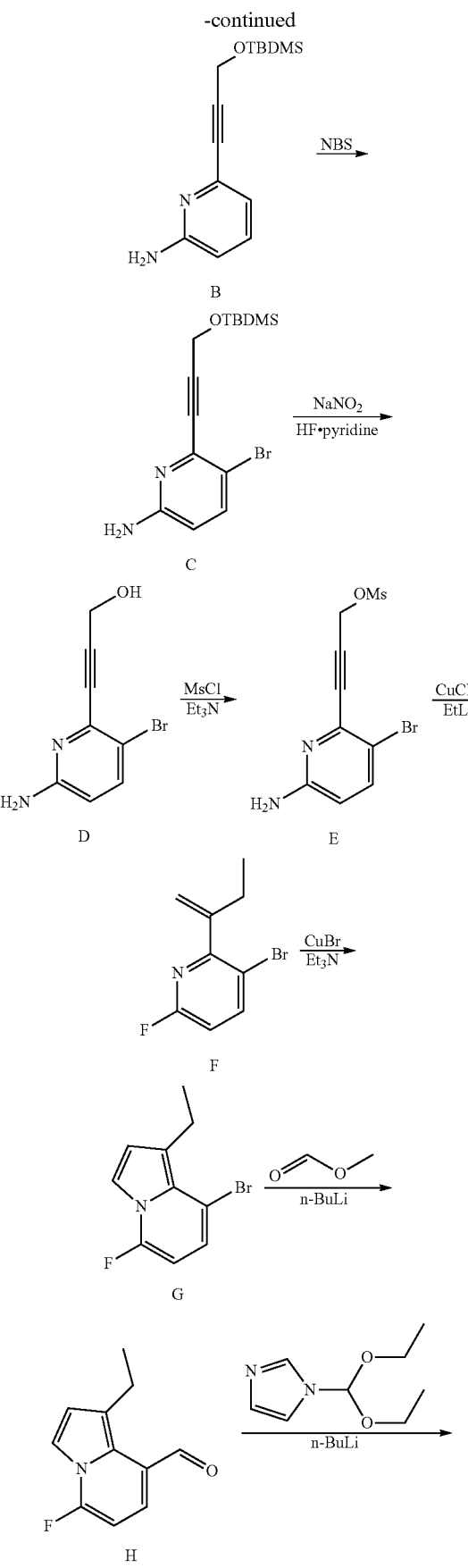

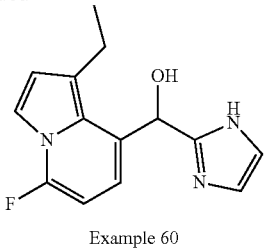

Example 60 n-BuLi (0.0960 mL, 0.241 mmol, 2.50 M solution in hexanes) was added to a mixture of 1-(diethoxymethyl)imidazole (41.0 mg, 0.241 mmol) in THF (0.500 mL) at −45° C. The mixture was stirred for 15 m and then cooled to −60° C. A solution of 1-ethyl-5-fluoro-indolizine-8-carbaldehyde (23.0 mg, 0.120 mmol) in THF (0.500 mL) was added. The mixture was stirred for 10 m at −60° C. and then warmed to 0° C. over 1 h. The mixture was diluted with 0.100 M HCl and EtOAc, and the organic phase was extracted with 0.100 M HCl (4×10.0 mL). The combined aqueous phases were cautiously diluted with sat. NaHCO₃, and the aqueous mixture was extracted with EtOAc (4×10.0 mL). The combined organic phases were dried (MgSO₄) and concentrated under reduced pressure. The product was purified by silica gel chromatography, eluting with DCM and MeOH (0-10%) to provide the title compound as a solid (12.2 mg, 38%). $^1$H NMR (500 MHz, MeOD) δ ppm 1.17 (t, J=7.5 Hz, 3H), 2.81 (ddd, J=15.0, 7.5, 3.0 Hz, 2H), 6.15 (dd, J=7.4, 6.1 Hz, 1H), 6.33 (s, 1H), 6.62 (t, J=6.8 Hz, 1H), 6.73 (d, J=2.9 Hz, 1H), 7.00 (s, 2H), 7.37 (d, J=2.8 Hz, 1H); LC-MS (Method C): m/z (ES+), [M+H]+=260.27; HPLC $t_R$=2.10 m.

Intermediate H,
1-Ethyl-5-fluoro-indolizine-8-carbaldehyde n-BuLi (0.061 mL, 0.152 mmol, 2.50 M solution in hexanes) was added to a cooled solution of 8-bromo-1-ethyl-5-fluoro-indolizine (35.0 mg, 0.145 mmol) in THF (1.40 mL) at −78° C. The resulting solution was stirred for 20 min at −78° C., and methyl formate (0.0180 mL, 0.289 mmol) was added. The mixture was stirred for 10 m at −78° C. and then warmed to 23° C. The mixture was diluted with water, and the aqueous phase was extracted with EtOAc (3×10.0 mL). The combined organic phases were dried (MgSO₄), filtered, and concentrated under reduced pressure. The product was purified by silica gel chromatography, eluting with hexanes and EtOAc (0-60%) to provide the title compound as a solid (16.0 mg, 58%). $^1$H NMR (500 MHz, CDCl₃) δ 1.29 (t, J=5.5 Hz, 3H), 3.09 (q, J=7.5 Hz, 2H), 6.23 (dd, J=7.5, 5.4 Hz, 1H), 6.86 (d, J=2.8 Hz, 1H), 7.39 (dd, J=7.5, 6.2 Hz, 1H), 7.42 (d, J=2.9 Hz, 1H), 10.14 (s, 1H); LC-MS (Method C): m/z (ES+), [M+H]+ 192.21; (A05), HPLC $t_R$=2.69 min.

Intermediate G,
8-Bromo-1-ethyl-5-fluoro-indolizine

CuBr (7.90 mg, 0.0560 mmol) and Et₃N (0.0260 mL, 0.186 mmol) were added to a mixture of 3-bromo-2-(1-ethylpropa-1,2-dienyl)-6-fluoro-pyridine (45.0 mg, 0.186 mmol) in DMA (2.10 mL). The mixture was stirred for 5 h at 130° C. with protection from light. The mixture was cooled to 23° C. and diluted with sat. NH₄Cl. The aqueous phase was extracted with EtOAc (3×10 mL), and the combined organic phases were washed with brine, dried (MgSO$_4$), filtered, and concentrated under reduced pressure. The product was purified by silica gel chromatography, eluting with hexanes and EtOAc (0-40%) to provide the title compound as an oil (36.0 mg, 80%). $^1$H NMR (500 MHz, CDCl$_3$) δ 1.29 (t, J=7.5 Hz, 3H), 3.13 (q, J=7.5 Hz, 2H), 5.94 (dd, J=7.6, 5.6 Hz, 1H), 6.75 (d, J=2.8 Hz, 1H), 6.78 (dd, J=7.6, 5.5 Hz, 1H), 7.29 (d, J=2.8 Hz, 1H); m/z: no ionization.

Intermediate F, 3-Bromo-2-(1-ethylpropa-1,2-dienyl)-6-fluoro-pyridine

A suspension of CuCN (317 mg, 3.54 mmol) in dry THF (7.00 mL) was cooled to −50° C. under nitrogen. To this was added EtLi (7.08 mL, 3.54 mmol, 0.500 M in benzene), and the suspension was stirred for 30 m at −50° C. A cooled solution of 3-(3-bromo-6-fluoro-2-pyridyl)prop-2-ynyl methanesulfonate (436 mg, 1.42 mmol) in dry THF (7.00 mL) at −50° C. was transferred with a cannula. The mixture was stirred for 2 h at −78° C. and warmed to 23° C. The mixture was diluted with a 10:1 mixture of NH$_4$Cl and NH$_4$OH. (15.0 mL). The aqueous phase was extracted with EtOAc (3×15.0 mL), and the combined organic phases were dried (MgSO$_4$), filtered, and concentrated under reduced pressure. The product was purified by silica gel chromatography, eluting with hexanes and EtOAc (0-40%) to provide the title compound as an oil (217 mg, 63%). $^1$H NMR (500 MHz, CDCl3) δ 1.01 (t, J=7.4 Hz, 3H), 2.40 (ddq, J=10.9, 7.3, 3.5 Hz, 2H), 4.99 (t, J=3.5 Hz, 2H), 6.62 (dd, J=8.5, 3.8 Hz, 1H), 7.84 (dd, J=8.5, 7.3 Hz, 1H); LC-MS (Method C): m/z (ES+), [M+H]+=242.12, 244.17; HPLC t$_R$=2.83 m.

Intermediate E, 3-(3-Bromo-6-fluoro-2-pyridyl)prop-2-ynyl methanesulfonate

DIPEA (0.315 mL, 1.81 mmol) and methanesulfonyl chloride (0.140 mL, 1.81 mmol) were added to a mixture of 3-(3-bromo-6-fluoro-2-pyridyl)prop-2-yn-1-ol (104 mg, 0.452 mmol) in DCM (1.90 mL) at 0° C. under nitrogen. The mixture was stirred at 23° C. for 1 h, and then diluted with aqueous 1N HCl. The aqueous phase was extracted with EtOAc (3×10.0 mL), and the combined organic phases were washed with brine, dried (MgSO$_4$), filtered, and concentrated under reduced pressure. The product was purified by silica gel chromatography, eluting with hexanes and EtOAc (0-60%) to provide the title compound as an oil (108 mg, 77%). $^1$H NMR (500 MHz, CDCl$_3$) δ 3.24 (s, 3H), 5.17 (s, 2H), 6.91 (dd, J=8.7, 3.4 Hz, 1H), 8.00 (dd, J=8.7, 6.9 Hz, 1H); LC-MS (Method C): m/z (ES+), [M+H]+=308.09, 310.10; HPLC t$_R$=2.17 m.

Intermediate D, 3-(3-Bromo-6-fluoro-2-pyridyl)prop-2-yn-1-ol

NaNO$_2$ (63.1 mg, 0.914 mmol) was added to a solution of (dimethyl)silyl]oxyprop-1-ynyl]pyridin-2-amine (208 mg, 0.609 mmol) in HF. Pyridine (0.900 mL) at −10 OC. The mixture was stirred for 1 h at −10° C. and then diluted with water. The aqueous phase was extracted with DCM (3×10 mL), and the combined organic phases were washed with brine, dried (MgSO$_4$), filtered, and concentrated under reduced pressure. The product was purified by silica gel chromatography, eluting with hexanes and EtOAc (0-60%) to provide the title compound as a solid (104.0 mg, 74%). $^1$H NMR (500 MHz, CDCl$_3$) δ 2.07 (t, J=6.4 Hz, 1H), 4.59 (d, J=6.3 Hz, 2H), 6.85 (dd, J=8.6, 3.4 Hz, 1H), 7.97 (dd, J=8.6, 7.0 Hz, 1H); LC-MS (Method C): m/z (ES+), [M+H]+=230.15, 232.15; HPLC t$_R$=1.59 min.

Intermediate C, 5-Bromo-6-[3-[tert-butyl(dimethyl)silyl]oxyprop-1-ynyl]pyridin-2-amine NBS (20.7 mg, 0.117 mmol) was added to a solution of 6-[3-[tert-butyl(dimethyl)silyl]oxyprop-1-ynyl]pyridin-2-amine (30.0 mg, 0.114 mmol) in MeOH (0.350 mL) at 0° C. The mixture was stirred for 20 m at 23° C. and then diluted with water. The aqueous phase was extracted with DCM (3×10 mL), and the combined organic phases were washed with brine (50.0 mL), dried (MgSO$_4$), filtered, and concentrated under reduced pressure to provide the title compound as a solid (208 mg, 100%). The product was used in the next step without further purification. $^1$H NMR (500 MHz, CDCl3) δ 0.19 (s, 6H), 0.94 (s, 9H), 4.60 (s, 4H), 6.36 (d, J=8.7 Hz, 1H), 7.55 (d, J=8.7 Hz, 1H); LC-MS (Method C): m/z (ES+), [M+H]+=341.20, 343.21; HPLC t$_R$=3.00 m.

Intermediate B, 6-[3-[tert-Butyl(dimethyl)silyl]oxyprop-1-ynyl]pyridin-2-amine

Et$_3$N (0.223 mL, 1.604 mmol), tert-butyldimethylsilyl chloride (174.6 mg, 1.158 mmol) and 4-dimethylaminopyridine (10.9 mg, 0.0890 mmol) were added to a mixture of 3-(6-amino-2-pyridyl)prop-2-yn-1-ol (132 mg, 0.891 mmol) in DCM (7.20 mL) at 0° C. under nitrogen. The mixture was stirred at 23° C. for 6 h and then diluted with water. The aqueous phase was extracted with DCM (3×10.0 mL), and the combined organic phases were washed with brine, dried (MgSO$_4$), filtered, and concentrated under reduced pressure. The product was purified by silica gel chromatography, eluting with hexanes and EtOAc (0-100%) to provide the title compound as a solid (168.0 mg, 72%). $^1$H NMR (500 MHz, CDCl3) δ 0.14 (s, 6H), 0.91 (s, 9H), 4.52 (s, 2H), 4.55 (s, 2H), 6.43 (dd, J=8.3, 0.6 Hz, 1H), 6.80 (dd, J=7.4, 0.6 Hz, 1H), 7.35 (dd, J=8.3, 7.4 Hz, 1H); m/z (ES+), [M+H]+=263.34; (B05), HPLC tR=2.84 min.

Intermediate A, 3-(6-Amino-2-pyridyl)prop-2-yn-1-ol

Propargyl alcohol (0.101 mL, 1.73 mmol) was added to a mixture of PdCl$_2$(PPh$_3$)$_2$ (40.6 mg, 0.0580 mmol), PPh$_3$ (33.4 mg, 0.127 mmol), CuI (22.0 mg, 0.115 mmol), and 2-amino-6-bromopyridine (200.0 mg, 1.16 mmol) in THF (4.20 mL) and Et$_3$N (0.242 mL, 1.73 mmol). The mixture was stirred for 2 days at 23° C. The mixture was diluted with saturated NH$_4$Cl, and the aqueous phase was extracted with EtOAc (2×10.0 mL). The combined organic phases were dried (MgSO$_4$), filtered, and concentrated under reduced pressure. The product was purified by silica gel chromatography, eluting with DCM and MeOH (0-10%) to provide the title compound as a solid (112 mg, 65%). $^1$H NMR (500 MHz, MeOD) δ 4.38 (s, 2H), 6.53 (d, J=8.4 Hz, 1H), 6.72 (d, J=7.2 Hz, 1H), 7.40 (dd, J=8.4, 7.3 Hz, 1H); LC-MS (Method C) m/z (ES+), [M+H]+=149.14; HPLC tR=0.56 min.

Example 61. (3-Chloro-8-fluoro-indolizin-5-yl)-(1H-imidazol-2-yl)methanol

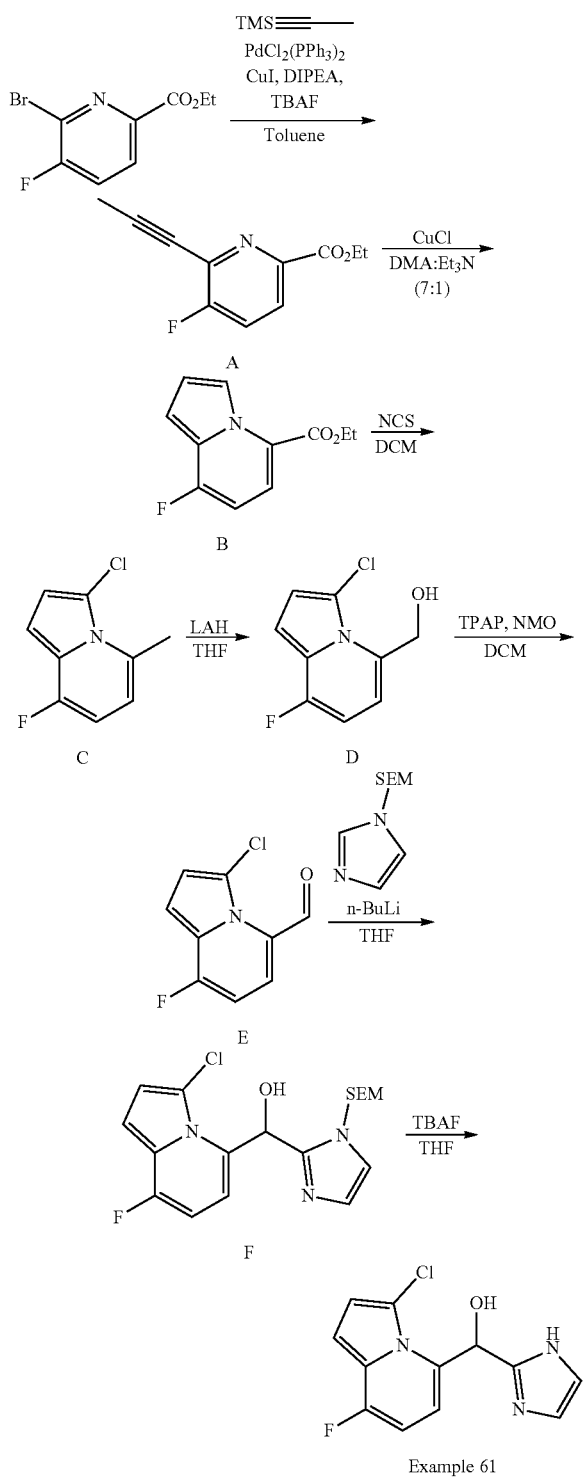

Example 61

1.00 μM TBAF in THF (0.260 mL, 0.260 mmol) was added to a mixture of (3-chloro-8-fluoro-indolizin-5-yl)-[1-(2-trimethylsilylethoxymethyl)imidazol-2-yl]methanol (34.0 mg, 0.0900 mmol) in THF (2.50 mL) at 23° C. under nitrogen. The mixture was refluxed for 3 h, and diluted with sat. NaHCO$_3$ (10.0 mL). The aqueous phase was extracted with EtOAc (3×25.0 mL), and the combined organic phases were washed with brine (25.0 mL), dried (MgSO$_4$), filtered, and concentrated under reduced pressure. The product was purified by silica gel chromatography (12 g cartridge) with hexane and EtOAc (0-100%) to provide the title compound as a solid (11.0 mg, 48%). $^1$H NMR (500 MHz, MeOD) δ 7.14 (s, 1H), 7.06 (s, 2H), 6.72 (d, J=4.3 Hz, 1H), 6.69 (d, J=4.3 Hz, 1H), 6.42 (d, J=9.2 Hz, 2H). LC-MS (Method C): m/z (ES+), [M+H]$^+$=266.0. HPLC $t_R$=2.23 m.

Intermediate F. (3-Chloro-8-fluoro-indolizin-5-yl)-[1-(2-trimethylsilylethoxymethyl)imidazol-2-yl]methanol 2.50 M n-BuLi in THF (0.260 mL, 0.640 mmol) was added to a mixture of 2-(imidazol-1-ylmethoxy)ethyl-trimethyl-silane (127 mg, 0.640 mmol) in THF (4.00 mL) at −78° C. under nitrogen. The mixture was stirred at −78° C. for 1 h, and added dropwise to a cooled solution of 3-chloro-8-fluoro-indolizine-5-carbaldehyde (97.0 mg, 0.490 mmol) in THF (2 mL) at −78° C. The mixture was stirred at −78° C. for 20 m, and warmed to 0° C. for 20 m. The mixture was diluted with NH$_4$Cl (10.0 mL). The aqueous phase was extracted with EtOAc (3×25.0 mL), and the combined organic phases were washed with brine (50.0 mL), dried (MgSO$_4$), filtered, and concentrated under reduced pressure. The product was purified by silica gel chromatography (24 g cartridge) with hexane and EtOAc (0-70%) to provide the title compound as a solid (36.0 mg, 19%). $^1$H NMR (500 MHz, CDCl$_3$) δ 7.19 (s, 1H), 7.05 (d, J=2.9 Hz, 2H), 6.72-6.66 (m, 2H), 6.36-6.24 (m, 2H), 5.27 (q, J=10.8 Hz, 2H), 3.95 (s, 1H), 3.56-3.35 (m, 2H), 0.79 (ddd, J=10.3, 6.4, 5.4 Hz, 3H), −0.04 (s, 9H). LC-MS (Method C): m/z (ES+), [M+H]$^+$=396.0. HPLC $t_R$=3.05 min.

Intermediate E. 3-Chloro-8-fluoro-indolizine-5-carbaldehyde

4 Å Molecular sieves were added to a mixture of NMO (144 mg, 1.23 mmol) and (3-chloro-8-fluoro-indolizin-5-yl)methanol (123 mg, 0.620 mmol) in DCM (5.00 mL) at 23° C. under nitrogen. The mixture was stirred for 20 m. TPAP (10.8 mg, 0.0300 mmol) was added, and the mixture was stirred for 10 m then filtered through a pad of Florisil. The filtrate was concentrated under reduced pressure, and the product was purified by silica gel chromatography (24 g cartridge) with hexane and EtOAc (0-30%) to provide the title compound as a solid (97.0 mg; 80%). $^1$H NMR (500 MHz, CDCl$_3$) δ 10.86 (d, J=0.5 Hz, 1H), 7.47 (dd, J=8.0, 5.6 Hz, 1H), 6.91 (d, J=4.4 Hz, 1H), 6.84 (d, J=4.4 Hz, 1H), 6.51 (dd, J=9.3, 8.0 Hz, 1H). LC-MS (Method C): m/z (ES+), [M+H]$^+$=198.1. HPLC $t_R$=2.67 min.

Intermediate D. (3-Chloro-8-fluoro-indolizin-5-yl)methanol 1.00 M LAH in THF (0.620 mL, 0.620 mmol) was added to a mixture of ethyl 3-chloro-8-fluoro-indolizine-5-carboxylate (150 mg, 0.620 mmol) in THF (10.0 mL) at 0° C. under nitrogen. The mixture was stirred at 23° C. for 20 m then diluted with water (1.00 mL), 1M NaOH (2.00 mL) and water (1.00 mL). The mixture was filtered through Celite, and the solid was washed with EtOAc (10.0 mL). The filtrate was concentrated under reduced pressure to provide the title compound as a solid (123 mg; 99%). $^1$H NMR (500 MHz, CDCl$_3$) δ 6.72 (d, J=4.3 Hz, 1H), 6.68 (d, J=4.3 Hz, 1H), 6.52 (dd, J=7.6, 5.4 Hz, 1H), 6.33 (dd, J=9.8, 7.6 Hz, 1H), 5.16 (s, 2H). LC-MS (Method C): m/z (ES+), [M+H]$^+$=200.2. $t_R$=2.53 min.

Intermediate C. Ethyl 3-chloro-8-fluoro-indolizine-5-carboxylate

A solution of NCS (419 mg, 3.14 mmol) in DCM (10.0 mL) was added drop-wise to a mixture of ethyl 8-fluoroindolizine-5-carboxylate (591 mg, 2.85 mmol) in DCM (20.0 mL) at 0° C. under nitrogen. The mixture was stirred in the dark at 0° C. for 3.5 h and then diluted with 1M $Na_2S_2O_3$ (50.0 mL). The aqueous phase was extracted with DCM (3×50.0 mL), and the combined organic phases were washed with brine (50.0 mL), dried ($MgSO_4$), filtered, and concentrated under reduced pressure. The product was purified by silica gel chromatography (40 g cartridge) with hexane (100%) to provide the title compound as solid (656 mg, 95%). $^1$H NMR (500 MHz, $CDCl_3$) δ 7.02 (dd, J=7.7, 5.2 Hz, 1H), 6.82 (d, J=4.3 Hz, 1H), 6.79 (d, J=4.4 Hz, 1H), 6.40 (dd, J=9.7, 7.7 Hz, 1H), 4.45 (q, J=7.2 Hz, 2H), 1.41 (t, J=7.2 Hz, 4H). LC-MS (Method C): m/z (ES+), [M+H]$^+$=242.0. HPLC $t_R$=3.04 m.

Intermediate B. Ethyl 8-fluoroindolizine-5-carboxylate

CuCl (0.760 g, 7.67 mmol) was added to a solution of ethyl 5-fluoro-6-prop-1-ynyl-pyridine-2-carboxylate (3.18 g, 15.4 mmol) in a 7:1 mixture of degassed DMA (48.0 mL) and $NEt_3$ (6.85 mL, 49.1 mmol) at 23° C. under nitrogen. The mixture was stirred at 130° C. for 17 h, and filtered through Celite. The filtrate was diluted with EtOAc (250 mL) and water (250 mL). The aqueous phase was extracted with EtOAc (3×250 mL), and the combined organic phases were washed with brine (250 mL), dried ($MgSO_4$), filtered, and concentrated under reduced pressure. The product was purified by silica gel chromatography (80 g cartridge) with hexane and EtOAc (0-20%) to provide the title compound as a solid (1.68 g, 53%). $^1$H NMR (500 MHz, $CDCl_3$) δ 8.74 (ddd, J=3.9, 2.8, 1.4 Hz, 1H), 7.61 (dd, J=8.0, 5.5 Hz, 1H), 6.91 (dd, J=4.1, 2.8 Hz, 1H), 6.83 (dd, J=4.1, 1.4 Hz, 1H), 6.40 (dd, J=9.7, 8.0 Hz, 1H), 4.43 (q, J=7.1 Hz, 2H), 1.43 (t, J=7.1 Hz, 3H). LC-MS (Method C): m/z (ES+), No ionization. HPLC $t_R$=1.96 m.

Intermediate A. Ethyl 5-fluoro-6-prop-1-ynyl-pyridine-2-carboxylate

DIPEA (8.37 mL, 48.1 mmol) and 1M TBAF in THF (28.8 mL, 28.8 mmol) were added to a mixture of ethyl 6-bromo-5-fluoro-pyridine-2-carboxylate (5.96 g, 24.0 mmol), 1-(trimethylsilyl)-1-propyne (4.27 mL, 28.8 mmol), CuI (0.690 g, 3.60 mmol), and $PdCl_2(PPh_3)_2$ (1.69 g, 2.40 mmol) in degassed toluene (225 mL) at 23° C. under nitrogen. The mixture was stirred for 16 h, and then diluted with $Et_2O$ (250 mL) and saturated $NH_4Cl$ (150 mL). The aqueous phase was extracted with $Et_2O$ (3×250 mL), and the combined organic phases were dried ($MgSO_4$), filtered, and concentrated under reduced pressure. The product was purified by silica gel chromatography (120 g cartridge) with hexane and EtOAc (0-30%) to provide the title compound as a solid (3.21 g, 65%). $^1$H NMR (500 MHz, $CDCl_3$) δ 8.06 (dd, J=8.6, 4.0 Hz, 1H), 7.54-7.42 (m, 1H), 4.46 (q, J=7.1 Hz, 2H), 2.14 (d, J=0.9 Hz, 3H), 1.42 (t, J=7.1 Hz, 3H). LC-MS (Method C): m/z (ES+), [M+H]$^+$=208.1. HPLC $t_R$=2.60 min.

Example 62. (4-Fluoro-1-methyl-1H-indazol-7-yl)(1H-imidazol-2-yl)methanol

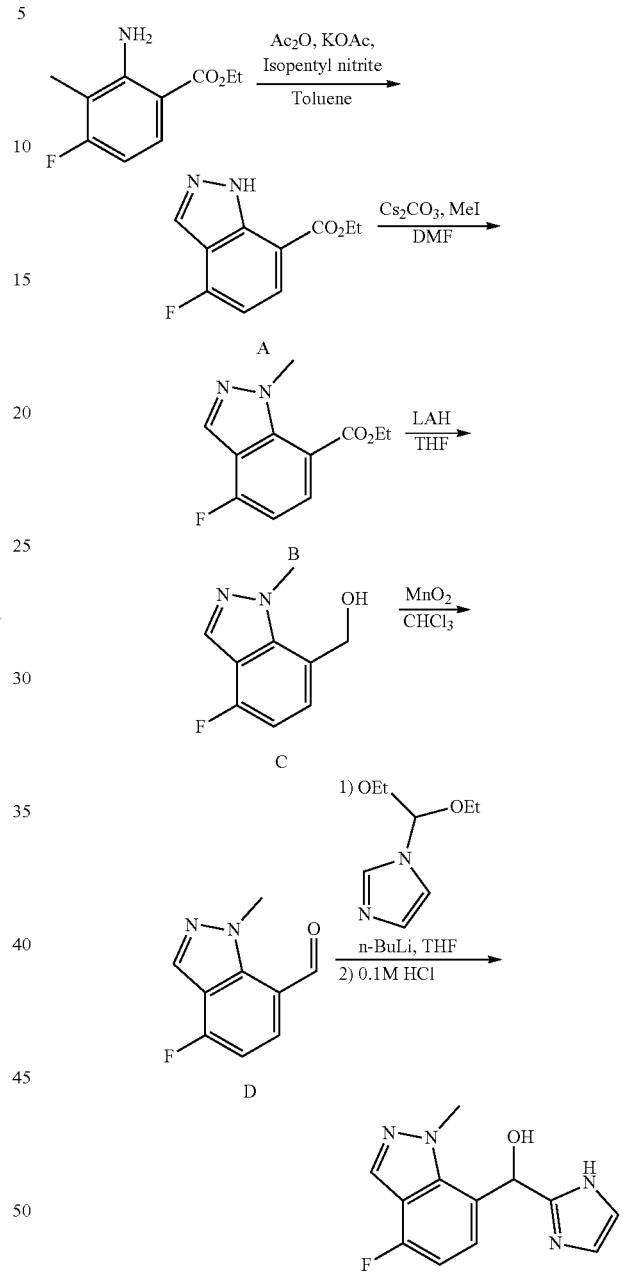

Example 62

2.50 M nBuLi in THF (0.260 mL, 0.640 mmol) was added to a mixture of 1-(diethoxymethyl)imidazole (109 mg, 0.640 mmol) in THF (1.00 mL) at −45° C., and the mixture was stirred for 15 m maintaining the temperature between −45° C. to −40° C. The mixture was cooled to −60° C., and a solution of 4-fluoro-1-methyl-indazole-7-carbaldehyde (57.0 mg, 0.320 mmol) in THF (1.00 mL) was added. The mixture was stirred for 10 m at −60° C. and warmed to 0° C. over 1 h. The mixture was diluted with 0.25 M HCl (5.00 mL) and EtOAc (5.00 mL) at 0° C. and stirred at 23° C. for 10 m. The organic phase was extracted with 0.250 M HCl (3×10.0 mL), and the combined aqueous phases were diluted with sat. NaHCO₃ (20.0 mL) and extracted with EtOAc (3×50.0 mL). The combined organic phases were washed with brine (50.0 mL), dried over MgSO₄, filtered, and concentrated under reduced pressure. The product was purified by silica gel chromatography (4 g cartridge) eluting with DCM and MeOH (0-10%) to provide the title compound as a solid (4.35 mg, 6%): ¹H NMR (500 MHz, DMSO) δ 12.10 (s, 1H), 8.13 (s, 1H), 7.29 (dd, J=8.0, 5.3 Hz, 1H), 6.94 (br, 1H), 6.86 (dd, J=9.8, 8.0 Hz, 2H), 6.51 (d, J=4.5 Hz, 1H), 6.35 (d, J=4.5 Hz, 1H), 4.11 (s, 3H). LC-MS (Method C): m/z (ES+), [M–H₂O+H]⁺=229.0. HPLC t_R=1.26 min.

Intermediate D.
4-Fluoro-1-methyl-indazole-7-carbaldehyde

A solution of (4-fluoro-1-methyl-indazol-7-yl)methanol (50.0 mg, 0.280 mmol) in CHCl₃ (1.00 mL) was added drop-wise to a mixture of MnO₂ (121 mg, 1.39 mmol) in CHCl₃ (1.00 mL) at 0° C. The mixture was refluxed for 3.5 h, and filtered through a pad of celite. The solid was washed with DCM, and the filtrate was concentrated under reduced pressure. The product was purified by silica gel chromatography (4 g cartridge) eluting with hexane and EtOAc (0-30%) to provide the title compound as a solid (40.0 mg, 81%): ¹H NMR (500 MHz, CDCl₃) δ ppm 10.09 (s, 1H), 8.15 (s, 1H), 7.86 (dd, J=8.1, 5.1 Hz, 1H), 6.92 (dd, J=8.8, 8.1 Hz, 1H), 4.50 (s, 3H). LC-MS (Method C): m/z (ES+), No ionization. HPLC t_R=1.58 min.

Intermediate C.
(4-Fluoro-1-methyl-indazol-7-yl)methanol 2.00M LAH in THF (0.220 mL, 0.440 mmol) was added to a mixture of ethyl 4-fluoro-1-methyl-indazole-7-carboxylate (98.0 mg, 0.440 mmol) in THF (2.50 mL) at 0° C. under nitrogen. The mixture was warmed to 23° C. and stirred for 20 m. The mixture was diluted with acetone (1.00 mL) and saturated Na/K tartrate (10.0 mL) at 0° C. and stirred for 5 m. The aqueous phase was extracted with EtOAc (3×20.0 mL), and the combined organic phases were dried over MgSO₄, filtered, and concentrated under reduced pressure to provide the title compound as a solid (78.0 mg, 98%). ¹H NMR (500 MHz, CDCl₃) δ 8.04 (s, 1H), 7.19 (dd, J=7.8, 5.0 Hz, 1H), 6.69 (dd, J=9.5, 7.8 Hz, 1H), 4.98 (d, J=5.4 Hz, 2H), 4.39 (s, 3H), 1.74 (t, J=5.8 Hz, 1H). LC-MS (Method C): m/z (ES+), No ionization. HPLC t_R=1.31 min.

Intermediate B. Ethyl
4-fluoro-1-methyl-indazole-7-carboxylate

Iodomethane (20.1 uL, 0.320 mmol) was added to a suspension of Cs₂CO₃ (105 mg, 0.320 mmol) and ethyl 4-fluoro-1H-indazole-7-carboxylate (56.0 mg, 0.270 mmol) in DMF (1.00 mL), and the mixture was stirred at 23° C. for 2.5 h. Water (10.0 mL) was added, and the aqueous phase was extracted with EtOAc (3×10.0 mL). The combined organic phases were washed with brine (20.0 mL), dried (MgSO₄), filtered, and concentrated under reduced pressure. The product was purified by silica gel chromatography (12 g cartridge) with hexane and EtOAc (0-50%) to provide the title compound as a solid (36 mg, 60%). ¹H NMR (500 MHz, CDCl₃) δ 8.11 (s, 1H), 7.94 (dd, J=8.2, 5.2 Hz, 1H), 6.77 (dd, J=8.9, 8.2 Hz, 1H), 4.43 (q, J=7.1 Hz, 2H), 4.28 (s, 3H), 1.43 (t, J=7.1 Hz, 3H). LC-MS (Method C): m/z (ES+), [M+H]⁺=222.9. HPLC t_R=1.98 m.

Intermediate A. Ethyl
4-fluoro-1H-indazole-7-carboxylate

Ethyl 2-amino-4-fluoro-3-methyl-benzoate (505 mg, 2.56 mmol) and KOAc (131 mg, 1.33 mmol) were added to anhydrous toluene (15.0 mL) under nitrogen. The mixture was heated to reflux, and Ac₂O (0.730 mL, 7.68 mmol) was added. The mixture was stirred at reflux for 10 m, and isopentyl nitrite (0.570 mL, 4.23 mmol) was added over 1 h. Stirring was continued at reflux for 15 h. The mixture was cooled and filtered. The filtrate was concentrated under reduced pressure, and the residue was washed with hexanes, water, and finally with hexanes to afford the title compound as a solid (347 mg, 65%). ¹H NMR (500 MHz, CDCl₃) δ 11.30 (s, 1H), 8.20 (d, J=1.7 Hz, 1H), 8.07 (dd, J=8.2, 4.8 Hz, 1H), 6.87 (dd, J=9.4, 8.2 Hz, 1H), 4.48 (q, J=7.1 Hz, 2H), 1.47 (t, J=7.1 Hz, 3H). LC-MS (Method C): m/z (ES+), [M+H]⁺=208.9. HPLC t_R=1.86 mmin.

Example 63. (3-Ethyl-7-fluorobenzofuran-4-yl)(1H-1,2,4-triazol-5-yl)methanol

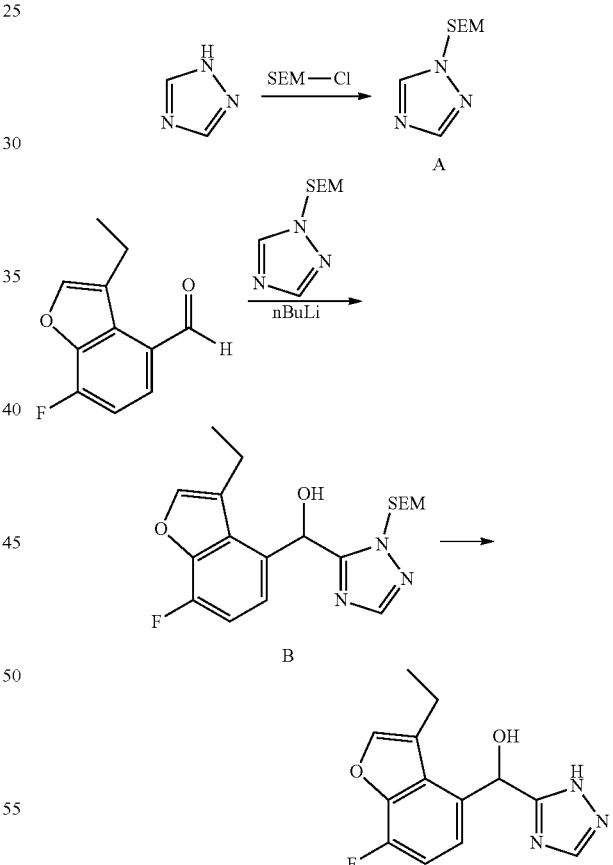

Example 63

Hydrogen chloride in EtOAc (excess) was added to (3-ethyl-7-fluorobenzofuran-4-yl)(1-((2-(trimethylsilyl)ethoxy)methyl)-1H-1,2,4-triazol-5-yl)methanol (150 mg, 0.38 mmol) in EtOAc (10 mL) under nitrogen. The resulting solution was stirred at rt. for 16 hours. The solvent was removed under reduced pressure. The crude product was purified by flash C18-flash chromatography, elution gradient 5 to 80% MeCN in water. Pure fractions were evaporated to dryness to afford (3-ethyl-7-fluorobenzofuran-4-yl)(1H-1,2,4-triazol-5-yl)methanol (30.0 mg, 30.0%) as a white solid. ¹H NMR (400 MHz, CD₃OD) δ ppm 1.26-1.35 (m, 3H), 2.05 (s, 0.1H), 2.76-2.94 (m, 2H), 6.46 (s, 1H), 7.03-7.07 (m, 1H), 7.20-7.23 (m, 1H), 7.63 (s, 1H), 8.17 (s, 1H). LC-MS (Method A): m/z (ES+), [M+H]+=262.3; acid, HPLC $t_R$=1.560 min.

Intermediate B. (3-Ethyl-7-fluorobenzofuran-4-yl)(1-((2-(trimethylsilyl)ethoxy)methyl)-1H-1,2,4-triazol-5-yl)methanol

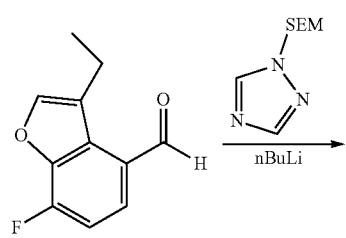

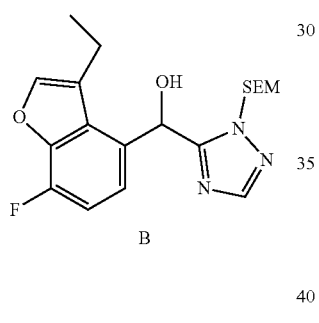

B

3-Ethyl-7-fluorobenzofuran-4-carbaldehyde (450 mg, 2.34 mmol) was added to 1-((2-(trimethylsilyl)ethoxy)methyl)-1H-1,2,4-triazole (933 mg, 4.68 mmol) and n-butyllithium (1,967 mL, 4.92 mmol) in THF (10 mL) at −78° C. over a period of 1 hour under nitrogen. The resulting mixture was stirred at −78° C. for 30 minutes. The reaction mixture was quenched with saturated NH₄Cl (5 mL), extracted with EtOAc (2×10 mL), the organic layer was dried over Na₂SO₄, filtered and evaporated to afford white liquid. The crude product was purified by flash C18-flash chromatography, elution gradient 5 to 100% MeCN in water. Pure fractions were evaporated to dryness to afford (3-ethyl-7-fluorobenzofuran-4-yl)(1-((2-(trimethylsilyl)ethoxy)methyl)-1H-1,2,4-triazol-5-yl)methanol (150 mg, 16.36%) as a white liquid. ¹H NMR (400 MHz, DMSO-d6) δ ppm 8.66 (s, 1H), 7.82 (d, J=1.4 Hz, 1H), 7.36 (dd, J=8.4, 4.5 Hz, 1H), 7.22 (dd, J=10.8, 8.4 Hz, 1H), 6.56 (d, J=5.8 Hz, 1H), 6.41 (d, J=5.8 Hz, 1H), 5.65 (d, J=10.8 Hz, 1H), 5.43 (d, J=10.8 Hz, 1H), 3.55-3.38 (m, 2H), 3.18 (d, J=5.2 Hz, 1H), 2.58 (ddt, J=15.7, 8.4, 6.8 Hz, 1H), 2.41 (dtt, J=14.6, 8.9, 7.3 Hz, 1H), 1.15 (t, J=7.4 Hz, 3H), 0.81 (dddd, J=45.9, 13.7, 10.6, 6.1 Hz, 2H). LC-MS (Method A): m/z (ES+), [M+H]+=392; acid, HPLC $t_R$=0.987 min.

Intermediate A. 1-((2-(trimethylsilyl)ethoxy)methyl)-1H-1,2,4-triazole

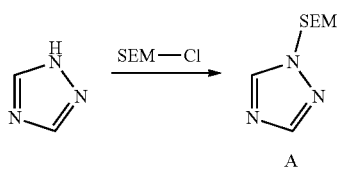

A

SEM-Cl (6.93 mL, 39.09 mmol) was added dropwise to 1H-1,2,4-triazole (3 g, 43.44 mmol) and NaH (2.085 g, 52.12 mmol) in THF (100 mL) at 0° C. over a period of 20 minutes under nitrogen. The resulting mixture was stirred at rt. for 16 hours. The reaction mixture was quenched with ice (25 mL), extracted with EtOAc (2×25 mL), the organic layer was dried over Na₂SO₄, filtered and evaporated to afford white solid. The crude product was purified by flash silica chromatography, elution gradient 0 to 10% MeOH in DCM. Pure fractions were evaporated to dryness to afford 1-((2-(trimethylsilyl)ethoxy)methyl)-1H-1,2,4-triazole (2.00 g, 23.1%) as a white solid. ¹H NMR (300 MHz, DMSO-d6) δ ppm 8.68 (s, 1H), 5.43 (s, 1H), 3.56-3.43 (m, 1H), 0.92-0.77 (m, 1H).

Example 64. (4-Fluoro-2-(pyrrolidin-1-yl)phenyl)(1H-1,2,4-triazol-5-yl)methanol

Example 64

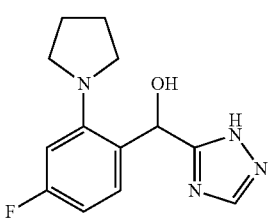

Example 64 was prepared in analogy to Example 63 using 4-fluoro-2-(pyrrolidin-1-yl)benzaldehyde and 1-((2-(trimethylsilyl)ethoxy)methyl)-1H-1,2,4-triazole. ¹H NMR (300 MHz, CDCl₃) δ ppm 8.01 (s, 1H), 7.24-7.33 (m, 1H), 6.94 (dd, J=2.54, 10.64 Hz, 1H), 6.84 (dt, J=2.64, 8.19 Hz, 1H), 6.26 (s, 1H), 3.00-3.28 (m, 4H), 1.92-2.10 (m, 4H). LC-MS (Method B): LC-MS (Method A): m/z (ES+), [M+H]+=263; acid, HPLC $t_R$=0.43 min.

Example 65. (4-Fluoro-2-(thiazol-2-yl)phenyl)(1H-imidazol-2-yl)methanol

Example 65

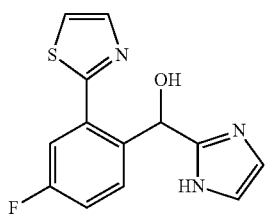

Prepared in analogous fashion to Example 33. ¹H NMR (400 MHz, CD₃OD) δ ppm 6.45-6.50 (m, 1H), 7.17-7.23 (m, 2H), 7.32-7.37 (m, 1H), 7.53-7.56 (m, 1H), 7.76-7.77 (m, 2H), 7.96-7.97 (m, 1H), 8.35 (s, 1H). LC-MS (Method A): m/z (ES+), [M+H]+=276.3; acid, HPLC $t_R$=1.312 min.

Example 66. [7-Fluoro-3-(1-methylcyclopropyl)benzofuran-4-yl]-(1H-imidazol-2-yl)methanol

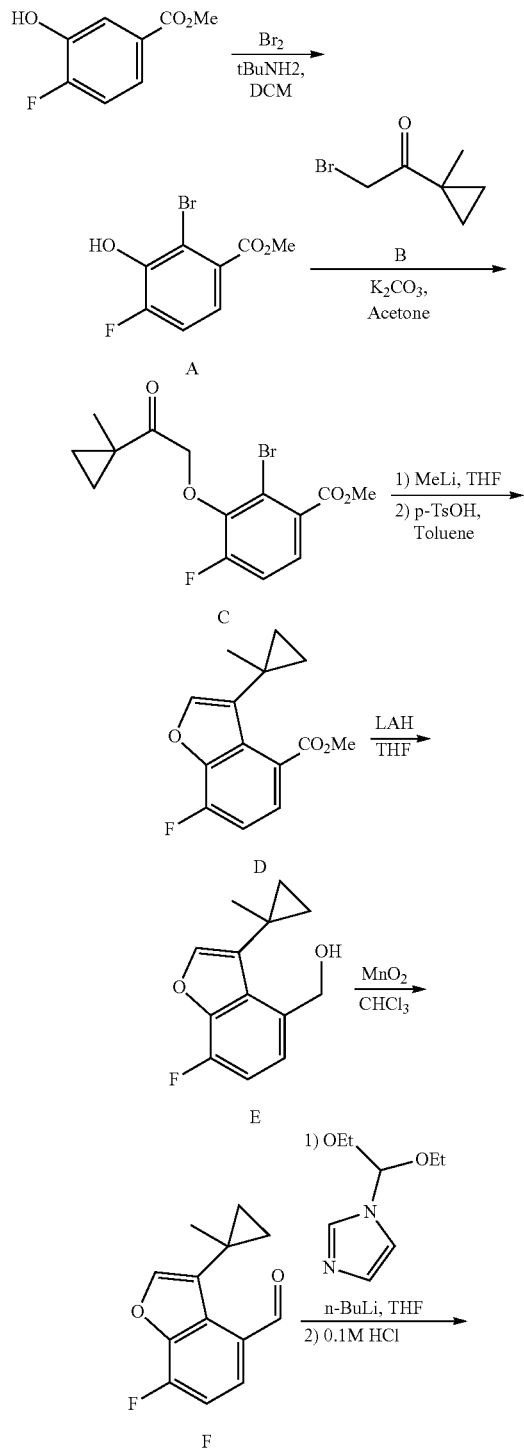

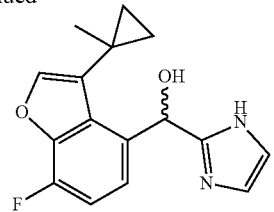

Example 66

1-(Diethoxymethyl)imidazole (81.9 mg, 0.480 mmol) in THF (1.00 mL) was cooled to −45° C. and 2.5M n-BuLi in THF (0.190 mL, 0.480 mmol) was added drop-wise. The mixture was stirred at −45° C. for 20 m. The mixture was cooled to −60° C., and a solution of 7-fluoro-3-(1-methylcyclopropyl)benzofuran-4-carbaldehyde (50.0 mg, 0.230 mmol) in THF (1.00 mL) was added drop-wise. The solution was warmed to 0° C. over 1 h. 0.1M HCl (5.00 mL) was added, and the mixture was warmed to 23° C. and stirred for 10 m. EtOAc (5.00 mL) was added. The organic phase was extracted with 0.1M HCl (2×5.00 mL), and the combined aqueous phases were diluted with sat. NaHCO₃ (10.0 mL). The aqueous mixture was extracted with EtOAc (3×25.0 mL), and the combined organic phases were washed with brine (25.0 mL), dried over MgSO₄, filtered and concentrated under reduced pressure. The product was purified by Waters HPLC (Gemini NX, 150×30, 5 micron, C-18 column), eluting isocratically with a mixture of water and MeCN (50%), containing 0.1% of (NH₄)₂CO₃ to provide the title compound as a solid (37 mg, 56%). ¹H NMR (500 MHz, DMSO) δ 12.03 (s, 1H), 7.94 (s, 1H), 7.28 (dd, J=8.5, 4.6 Hz, 1H), 7.19 (dd, J=10.7, 8.5 Hz, 1H), 7.02 (s, 1H), 6.73 (s, 1H), 6.68 (d, J=4.2 Hz, 1H), 6.13 (d, J=4.2 Hz, 1H), 1.42 (s, 3H), 1.01-0.87 (m, 1H), 0.87-0.79 (m, 1H), 0.79-0.72 (m, 1H), 0.72-0.59 (m, 1H). LC-MS (Method C): m/z (ES+), [M+H]⁺=287.1. HPLC $t_R$=1.57 m.

Intermediate F. 7-Fluoro-3-(1-methylcyclopropyl)benzofuran-4-carbaldehyde

MnO₂ (114 mg, 1.31 mmol) was added to a mixture of [7-fluoro-3-(1-methylcyclopropyl)benzofuran-4-yl]methanol (72.0 mg, 0.330 mmol) in CHCl₃ (2.00 mL) at 23° C. under nitrogen. The mixture was refluxed for 18 h, and filtered through a pad of Celite. The solid was washed with DCM, and the filtrate was concentrated under reduced pressure. The product was purified by silica gel chromatography (12 g cartridge) eluting with hexane and EtOAc (0-15%) to provide the title compound as a solid (52.0 mg, 73%). ¹H NMR (500 MHz, CDCl₃) δ 10.87 (d, J=0.6 Hz, 1H), 7.95 (dd, J=8.6, 4.6 Hz, 1H), 7.67 (s, 1H), 7.20-7.06 (m, 1H), 1.45 (s, 3H), 0.99-0.89 (m, 2H), 0.89-0.79 (m, 2H). LC-MS (Method C): m/z (ES+), No ionization. HPLC $t_R$=2.54 m.

Intermediate E. [7-Fluoro-3-(1-methylcyclopropyl)benzofuran-4-yl]methanol 1.00 M LAH in THF (0.370 mL, 0.370 mmol) was added to a cooled solution of methyl 7-fluoro-3-(1-methylcyclopropyl)benzofuran-4-carboxylate (92.0 mg, 0.370 mmol) in THF (1.00 mL) at 0° C. under nitrogen. The mixture was stirred at 0° C. for 15 m and diluted with acetone (0.500 mL) and a sat. solution of K/Na tartrate (10.0 mL). Water (10.0 mL) was added, and the aqueous phase was extracted with EtOAc (3×25.0 mL). The combined organic phases were washed with brine (30.0 mL), dried (MgSO$_4$), filtered, and concentrated under reduced pressure to afford the title compound as an oil (72.0 mg; 88%). $^1$H NMR (500 MHz, CDCl$_3$) δ 7.51 (s, 1H), 7.29 (dd, J=8.3, 4.4 Hz, 1H), 7.03 (dd, J=10.3, 8.3 Hz, 1H), 5.17 (s, 2H), 1.71 (br, 1H), 1.44 (s, 3H), 0.91-0.83 (m, 2H), 0.79-0.72 (m, 2H). LC_MS (Method C): m/z (ES+), No ionization. HPLC t$_R$=2.29 m.

Intermediate D. Methyl 7-fluoro-3-(1-methylcyclopropyl)benzofuran-4-carboxylate 1.60 M MeLi in Et$_2$O (0.700 mL, 1.11 mmol) was added drop-wise to a cooled solution of methyl 2-bromo-4-fluoro-3-[2-(1-methylcyclopropyl)-2-oxo-ethoxy]benzoate (320 mg, 0.930 mmol) in THF (92.0 mL) at −78° C. The mixture was stirred at −78° C. for 30 m. Additional 1.60 M MeLi in Et$_2$O (0.280 mL, 0.440 mmol) was added at −78° C. The mixture was warmed to 0° C. and diluted with sat. NH$_4$Cl (30 mL). The mixture was partially concentrated under reduced pressure to remove THF, and water (20.0 mL) was added. The aqueous phase was extracted with EtOAc (3×50.0 mL), and the combined organic phases were washed with brine (50.0 mL), dried over MgSO$_4$, filtered and concentrated under reduced pressure. The residue was dissolved in toluene (9.00 mL), and 4 Å molecular sieves and p-TSA monohydrate (44.1 mg, 0.230 mmol) were added. The mixture was heated at reflux for 45 m. After cooling to room temperature, the mixture was filtered, and the filtrate was concentrated under reduced pressure. The product was purified by silica gel chromatography (12 g cartridge), eluting with hexane and EtOAc (0-15%) to provide the title compound as an oil (99.0 mg, 43%). $^1$H NMR (500 MHz, CDCl$_3$) δ 7.70 (dd, J=8.5, 4.6 Hz, 1H), 7.61 (s, 1H), 7.04 (dd, J=9.8, 8.5 Hz, 1H), 3.96 (s, 3H), 1.38 (s, 3H), 0.88-0.76 (m, 2H), 0.74-0.66 (m, 2H). LC-MS (Method C): m/z (ES+), No ionization. HPLC t$_R$=2.60 m.

Intermediate C. Methyl 2-bromo-4-fluoro-3-[2-(1-methylcyclopropyl)-2-oxo-ethoxy]benzoate 2-Bromo-1-(1-methylcyclopropyl)ethanone (206 mg, 1.16 mmol) and K$_2$CO$_3$ (210 mg, 1.52 mmol) were added to a solution of methyl 2-bromo-4-fluoro-3-hydroxy-benzoate (252 mg, 1.01 mmol) in acetone (5.00 mL). The mixture was heated to 60° C. for 18 h. The mixture was filtered through Celite, and the solid was washed with EtOAc. The filtrate was concentrated under reduced pressure. The product was purified by silica gel chromatography (25 g cartridge), eluting with EtOAc and hexanes (0-25%) to provide the title compound as an oil (0.332 g, 95%). $^1$H NMR (500 MHz, CDCl$_3$) δ 7.52 (dd, J=8.7, 5.3 Hz, 1H), 7.09 (dd, J=10.2, 8.7 Hz, 1H), 4.95 (d, J=1.1 Hz, 2H), 3.92 (s, 3H), 1.39 (s, 3H), 1.38-1.35 (m, 2H), 0.81-0.77 (m, 2H). LC-MS (Method C): m/z (ES+), [M+H]$^+$=345.0. HPLC t$_R$=2.31 min.

Intermediate B. 2-Bromo-1-(1-methylcyclopropyl)ethanone

A solution of bromine (0.780 mL, 15.3 mmol) in DCM (7.50 mL) was added drop-wise to a cooled solution of methyl 1-methylcyclopropyl ketone (1.68 mL, 15.3 mmol) in MeOH (12.0 mL) at 0° C. The mixture was stirred for 1 h and poured onto ice. The aqueous phase was extracted with DCM (4×20.0 ml), and the combined organic phases were dried over Na$_2$SO$_4$, filtered, and concentrated under reduced pressure to provide the title compound (2.55 g, 94%) as an oil. $^1$H NMR (500 MHz, CDCl$_3$) δ 4.01 (s, 2H), 1.45 (d, J=0.6 Hz, 3H), 1.37-1.32 (m, 2H), 0.86-0.82 (m, 2H). LC_MS (Method C): m/z (ES+), No ionization. HPLC t$_R$=2.02 min.

Intermediate A. Methyl 2-bromo-4-fluoro-3-hydroxy-benzoate

A solution of bromine (0.510 mL, 10.0 mmol) in DCM (5.00 mL) was added drop-wise to a cooled solution of tert-butylamine (2.10 mL, 20.0 mmol) in DCM (20.0 mL) at −78° C. The mixture was stirred at −78° C. covered with aluminum foil for 1 h. A solution of methyl 4-fluoro-3-hydroxy-benzoate (1.70 g, 10.0 mmol) in DCM (20.0 mL) was added drop-wise at −78° C. The mixture was stirred at −78° C., covered with aluminum foil, and slowly warmed to 23° C. for 18 h. The mixture was filtered, and 1N HCl (30.0 mL) was added to the filtrate. The aqueous phase was extracted with DCM (2×25.0 mL). The combined organic phases were washed with brine (30.0 mL), dried over MgSO$_4$, filtered, and concentrated under reduced pressure. The residue was diluted with 1N HCl (25.0 mL), and the aqueous phase was extracted with DCM (3×25.0 mL). The combined organic phases were washed with brine (25.0 mL), dried over MgSO$_4$, filtered, and concentrated under reduced pressure to provide the title compound as a solid (1.45 g; 58%). $^1$H NMR (500 MHz, CDCl$_3$) δ 7.49 (dd, J=8.7, 5.4 Hz, 1H), 7.18-7.05 (m, 1H), 5.90 (d, J=1.7 Hz, 1H), 3.93 (s, 3H). LC_MS (Method C): m/z (ES+), No ionization. HPLC t$_R$=1.89 m.

Assay Methods:

IPone Assay:

Protocol for Testing Compounds for PAR2 Antagonist Activity Using an IP-One HTRF Assay Inositol monophosphate (IP1) production were measured in 1321N1 cells stably expressing human PAR2 using an IP-One HTRF assay kit (Cisbio). 80 nl of compound in 100% DMSO were added in white small-volume 384-well plates using an Echo 555 (Labcyte) and were incubate for 30 min at 37° C. with 4 µl of cells (15,000 cells per well) in stimulation buffer (HBSS with 20 mM HEPES, pH 7.4). IP1 production was initiated by addition of 4 µl of 140 µM SLIGRL-NH$_2$ (SEQ ID NO.: 4) in stimulation buffer supplemented with 100 mM LiCl. After 60 min at 37° C. cells were lysed and IP1 concentrations were detected according to the manufacturers protocol (Cisbio). Data were normalized to IP1 concentrations using a IP1 standard curve according to the manufacturers protocol (Cisbio).

Trypin Activated FLPR Assay:

Protocol for Testing Compounds for PAR2 Antagonist Activity Using a Ca2+ Mobilization Assay Calcium mobilization was measured using 1321N1 cells stably expressing human PAR2. Cells were seeded in 384-well plates at 4,000 cells per well in 20 µl DMEM with Glutamax supplemented with 10% FBS and incubated for 18-24 h at 37° C., 5% CO$_2$ and 95% humidity. Cells were loaded with 20 µl Fluo-8 NW calcium dye (Cat: 36316, AAT Bioquest) and kept at 37° C. for 30 min prior to addition of 10 µl compound prepared in 20 mM HEPES pH 7.4, HBSS, 2.5% DMSO, 0.1% BSA and 6 µM Vorapaxar (to block Trypsin induced activity of PAR1). The addition was done using a FLIPR$^{TETRA}$ (384-well head, Molecular Devices) and the response was read simultaneously to detect any agonist activity. The cells were incubated for 30 min at room temperature with the compounds and were then evaluated for antagonist activity by addition of 10 µl 234 nM Trypsin prepared in 20 mM HEPES pH 7.4, HBSS and 0.1% BSA and simultaneous detection of calcium mobilization using the FLIPR$^{TETRA}$.

TABLE 1

IPone and FLPR (Trypsin) assay data

| Example | hPAR2 IPpone IC$_{50}$ (μM) | hPAR2 FLPR (Trypsin) IC$_{50}$ (μM) |
|---|---|---|
| 1 | 2.93 | nm |
| 2 | >100 | >41 |
| 3 | 1.29 | 3.92 |
| 4 | 6.27 | 16.57 |
| 5 | 5.18 | 13.7 |
| 6 | 5.0 | 9.57 |
| 7 | 11.5 | 7.85 |
| 8 | 5.64 | 5.10 |
| 9 | 9.66 | 6.26 |
| 10 | 1.66 | 5.90 |
| 11 | >41 | >77 |
| 12 | 4.0 | 4.9 |
| 13 | 5.45 | 12.4 |
| 14 | 1.52 | 16.9 |
| 15 | >100 | >41 |
| 16 | 0.96 | 10.1 |
| 17 | 1.05 | 8.75 |
| 18 | 0.90 | 4.28 |
| 19 | 93 | >100 |
| 20 | 4.5 | 18.6 |
| 21 | 6.40 | 40.3 |
| 22 | 4.60 | 20 |
| 23 | 7.21 | 25.4 |
| 24 | 6.73 | 16.3 |
| 25 | 6.88 | 22.0 |
| 26 | 3.87 | nm |
| 27 | 6.96 | >41.6 |
| 28 | 4.91 | 30.3 |
| 29 | 13.1 | >41.6 |
| 30 | 4.67 | 11.6 |
| 31 | 4.32 | >41 |
| 32 | 14.3 | 30.6 |
| 33 | 3.6 | 16.8 |
| 34 | 0.30 | 1.90 |
| 35 | 0.2 | 1.61 |
| 36 | >100 | >41 |
| 37 | 0.97 | 3.27 |
| 38 | 1.91 | 13.9 |
| 39 | 13.2 | nm |
| 40 | 0.75 | 4.90 |
| 41 | 26 | 2.19 |
| 42 | 0.33 | 3.09 |
| 43 | 0.86 | 4.58 |
| 44 | 6.54 | >41 |
| 45 | 0.63 | 6.07 |
| 46 | 2.17 | 14.5 |
| 47 | 2.12 | 4.91 |
| 48 | >33.3 | >41.6 |
| 49 | nm | nm |
| 50 | >33.3 | >41 |
| 51 | 0.60 | 1.50 |
| 52 | 0.97 | 3.27 |
| 53 | 1.63 | 5.42 |
| 54 | 1.45 | 6.15 |
| 55 | 1.39 | 2.64 |
| 56 | >100 | >41.6 |
| 57 | 1.65 | 9.03 |
| 58 | 7.21 | >41.6 |
| 59 | 9.23 | 6.73 |
| 60 | 0.9 | 8.13 |
| 61 | 1.90 | 3.1 |
| 62 | 3.38 | nm |
| 63 | 1.23 | 15.6 |
| 64 | 4.06 | 20 |
| 65 | 7.79 | 18.3 |
| 66 | nm | nm |

Binding Studies

In some embodiments, the application provides compounds that bind to a site distinct from the PAR1 Vorapaxar site using crystallography techniques on a mutant form of the PAR2 receptor.

The structure of PAR1 in complex with Vorapaxar showed that the ligand binds in a peripheral pocket close to the extracellular surface of PAR1 (Zhang, C. et al. *Nature* 2012, 492, 387-392. Whilst vorapaxar exhibit high selectivity against PAR2 nearly all residues involved in the interactions are conserved. Mutational studies have shown Glu260 and Asp256 of extra cellular loop 2 (ECL2) to be important for binding the activating peptide. Both of these residues are conserved in PAR2 (Glu232 and Asp228). The Vorapaxar pocket is therefore believed to be the orthosteric site for related protease activated receptors.

Figure 2:
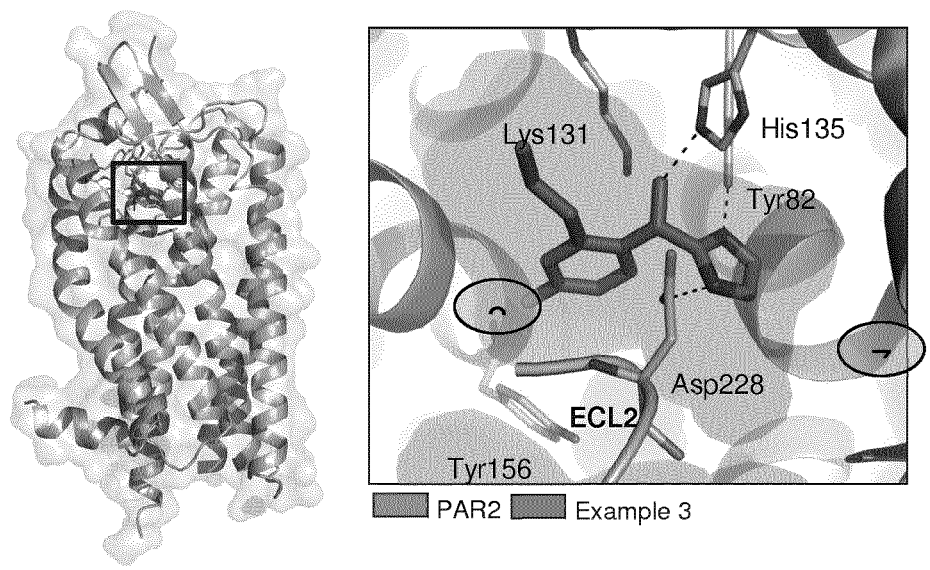
FIG. 2 shows PAR2 crystal structure in complex with the compound of Example 3.
Figure 3:
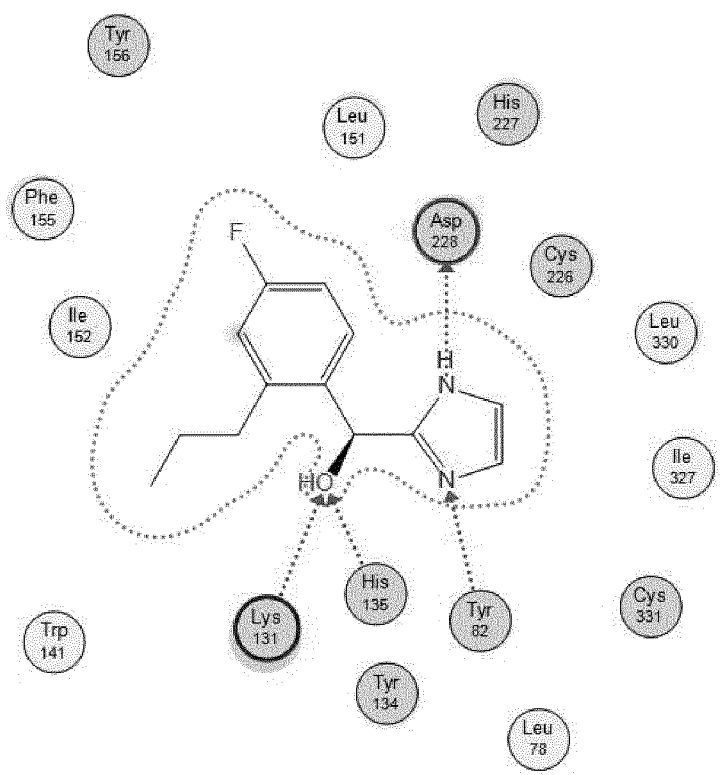
FIG. 3 shows Protein-ligand interactions with the compound Example 3 based on PAR2 crystal structure.

A crystal structure with Example 3 in complex with PAR2, revealed that the ligand binds in a novel allosteric pocket, 8 Å away from the Vorapaxar binding site identified in the PAR1 structure (FIG. 1). The pocket is completely buried in the receptor (FIG. 2) which is consistent with the long dissociation rates of the compounds in this series. The ligand is situated in a relatively rigid part of the protein near the disulphide bridge in between transmembrane 3 (TM3) and ECL2. It makes polar interactions with Asp228, Tyr 82 and His135 (FIG. 3). Based on structural data, the allosteric and the orthosteric pockets in PAR2 are clearly separated. None of the ligands tested in the Example 3 series have demonstrated activity against PAR1 (β-arrestin type assay by DiscoverX, Example 3 IC$_{50}$>50 μM, Example 35 >50 μM).

FLPR Dissociation Rate Assay: Protocol for Testing Compounds for PAR2 Mean Residence Time The FLPR assay outlined above utilized the same cell line and cell-handling protocols, but was modified in the following ways: The cells were incubated with compound at various time points (60 min, 120 min, 180 min and 240 min) at which point the cells were washed. Fluo-8 NW calcium dye (Cat: 36316, AAT Bioquest) was added similar to the protocol described above, one hour before the addition of agonist. The peptide agonist SLIGLR-NH$_2$ (ECso) was used in place of trypsin.

TABLE 2

FLPR dissociation rate assay data

| Example | FLPR Residence time t$_{1/2}$ (min) |
|---|---|
| 3 | 62 |
| 16 | 161 |
| 42 | 119 |
| 47 | 31 |

SEQ IDs

SEQ ID No.: 1 PAR2 [Homo sapiens] NCBI Reference Sequence: NP_005233.3
MRSPSAAWLLGAAILLAASLSCSGTIQGTNRSSKGRSLIGKVDGTSHVTG

KGVTVETVFSVDEFSASVLTGKLTTVFLPIVYTIVFVVGLPSNGMALWVF

LFRTKKKHPAVIYMANLALADLLSVIWFPLKIAYHIHGNNWIYGEALCNV

LIGFFYGNMYCSILFMTCLSVQRYWVIVNPMGHSRKKANIAIGISLAIWL

LILLVTIPLYVVKQTIFIPALNITTCHDVLPEQLLVGDMFNYFLSLAIGV

FLFPAFLTASAYVLMIRMLRSSAMDENSEKKRKRAIKLIVTVLAMYLICF

TPSNLLLVVHYFLIKSQGQSHVYALYIVALCLSTLNSCIDPFVYYFVSHD

FRDHAKNALLCRSVRTVKQMQVSLTSKKHSRKSSSYSSSSTTVKTSY

The invention claimed is:

1. A compound which is selected from the group consisting of:

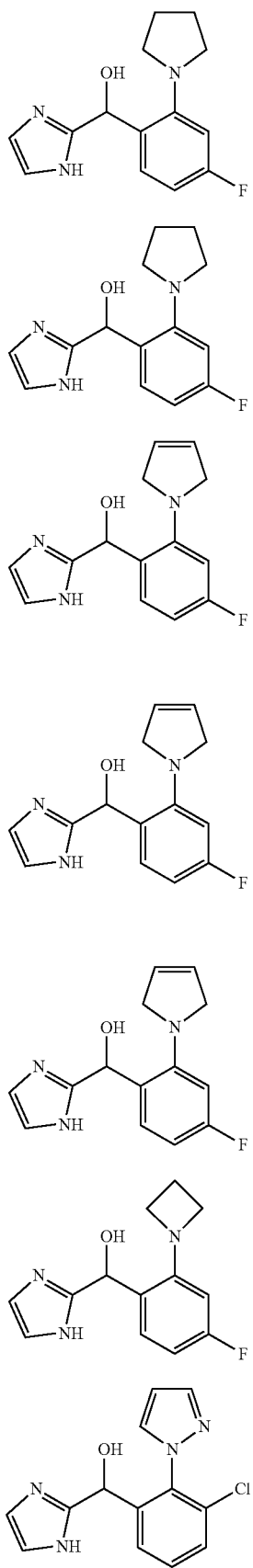
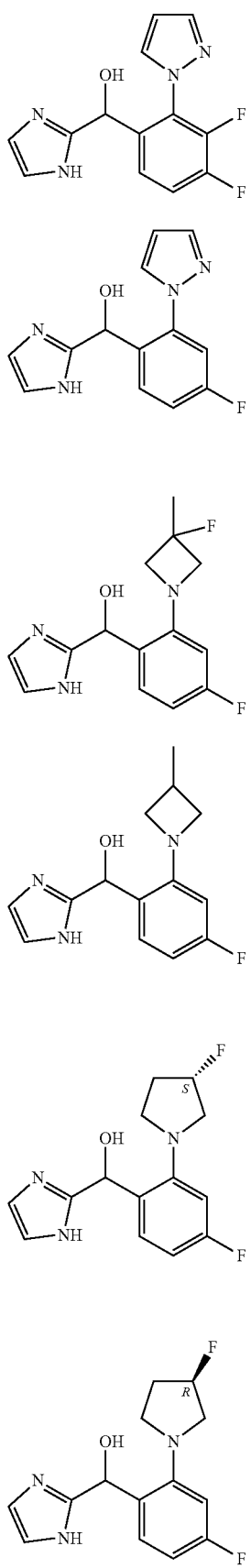

-continued

41 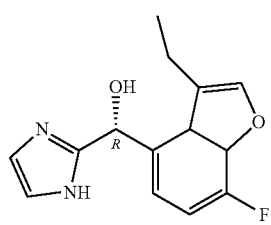
42 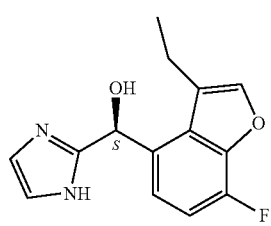
43 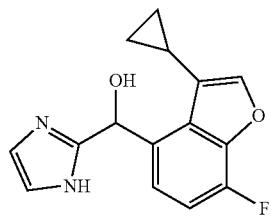
44 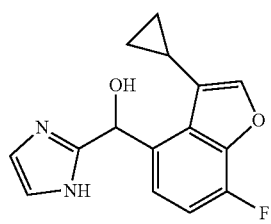
45 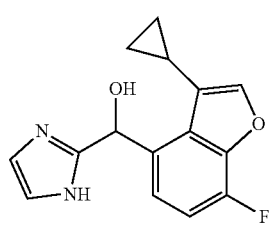
46 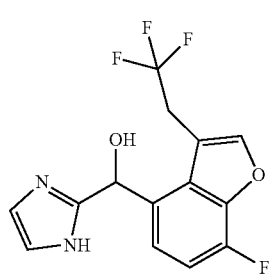
47 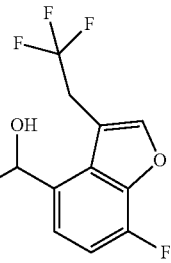
48 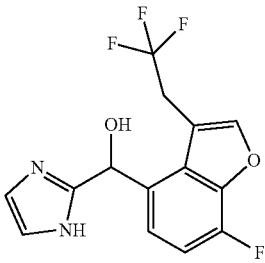
50 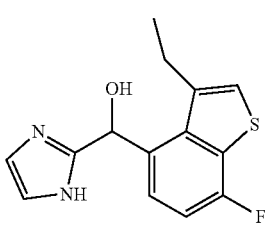
51 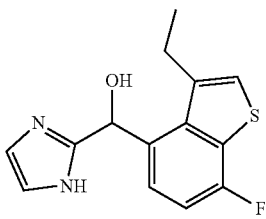
52 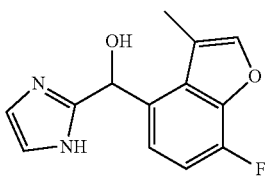
53 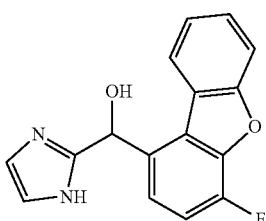
54 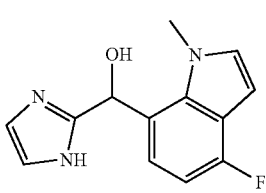

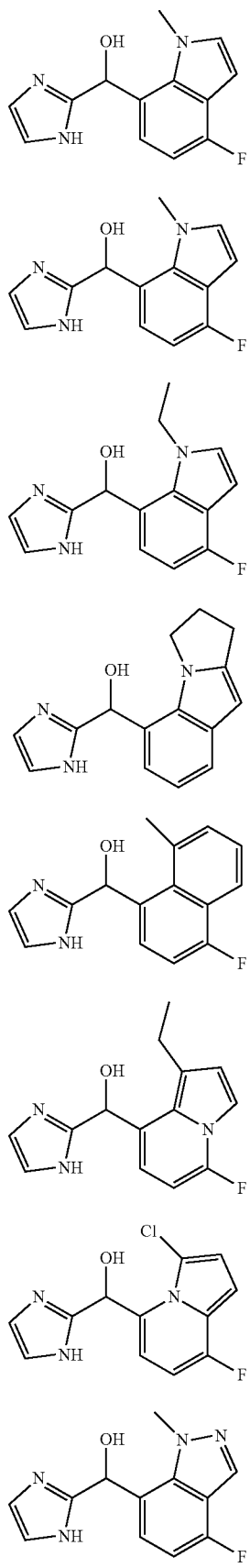
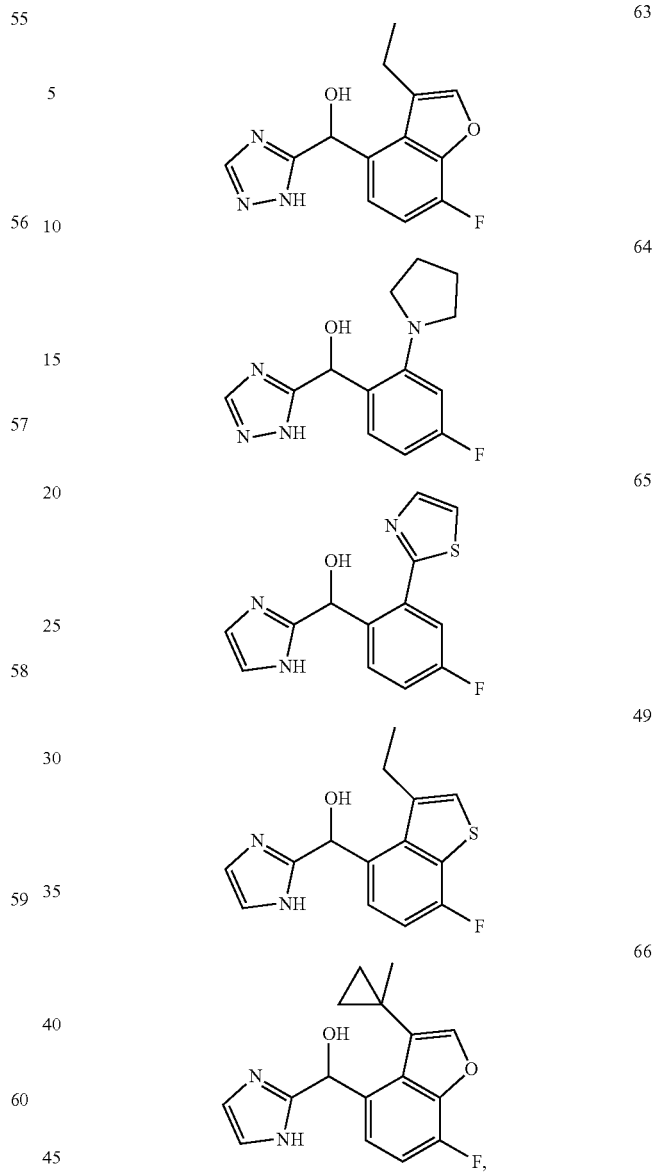

and pharmaceutically acceptable salts thereof.

2. A pharmaceutical composition comprising (a) a compound of claim 1 and (b) a pharmaceutically acceptable excipient.

3. A method of treating a disease or disorder mediated by PAR2 activity, comprising administering to a subject in need of such treatment an effective amount of at least one compound of claim 1.

4. The method of claim 3, wherein the disease or disorder is pain, musculoskeletal inflammation, neuroinflammatory disorders, airway inflammation, itch, dermatitis, or colitis.

5. A method of modulating the activity of PAR2, comprising contacting a cell comprising the PAR2 with an effective amount of at least one compound of claim 1.

6. A method of treating a disease or disorder in a patient in need thereof, comprising administering a compound of claim 1, wherein the disease or disorder is pain, musculoskeletal inflammation, neuroinflammatory disorders, airway inflammation, itch, dermatitis, or colitis.

7. The compound of claim 1, wherein the compound is selected from the group consisting of:
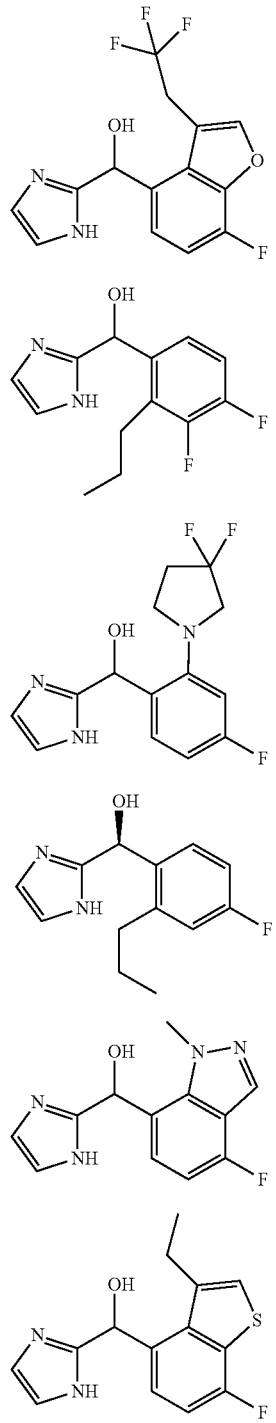
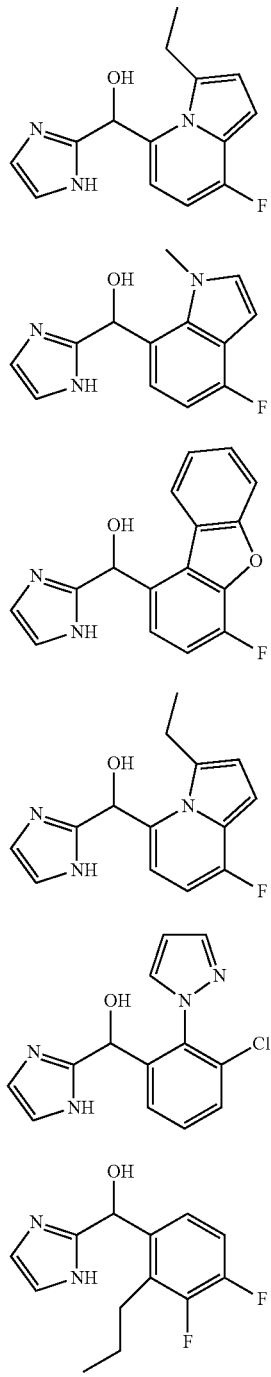
and pharmaceutically acceptable salts thereof.